US011234775B2

(12) United States Patent
Shiels et al.

(10) Patent No.: US 11,234,775 B2
(45) Date of Patent: Feb. 1, 2022

(54) END EFFECTORS, SYSTEMS, AND METHODS FOR IMPACTING PROSTHETICS GUIDED BY SURGICAL ROBOTS

(71) Applicant: MAKO Surgical Corp., Ft. Lauderdale, FL (US)

(72) Inventors: Paul Shiels, Albuquerque, NM (US); David Gene Bowling, Los Ranchos De Albuquerque, NM (US); Larry D. O'Cull, Westfield, IN (US); Patrick C. Kelly, Portage, MI (US); Christopher W. Jones, Kokomo, IN (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 317 days.

(21) Appl. No.: 16/257,594

(22) Filed: Jan. 25, 2019

(65) Prior Publication Data

US 2019/0231446 A1    Aug. 1, 2019

Related U.S. Application Data

(60) Provisional application No. 62/622,303, filed on Jan. 26, 2018.

(51) Int. Cl.
*A61B 34/30* (2016.01)
*A61B 34/10* (2016.01)
(Continued)

(52) U.S. Cl.
CPC ............. *A61B 34/30* (2016.02); *A61B 34/10* (2016.02); *A61B 34/20* (2016.02); *A61B 34/74* (2016.02);
(Continued)

(58) Field of Classification Search
CPC .......... A61B 2017/00477; A61B 17/92; A61B 2017/922; A61B 34/20; A61B 34/30;
(Continued)

(56) References Cited

U.S. PATENT DOCUMENTS

| 5,441,042 A | * | 8/1995 | Putman | ..................... B25J 9/042 600/102 |
| 6,228,089 B1 | | 5/2001 | Wahrburg | |

(Continued)

FOREIGN PATENT DOCUMENTS

| DE | 20311610 U1 | 10/2003 |
| WO | 2015120108 A1 | 8/2015 |

(Continued)

OTHER PUBLICATIONS

International Search Report for Application No. PCT/US2019/015165 dated May 6, 2019, 4 pages.

(Continued)

*Primary Examiner* — Andrew Yang
(74) *Attorney, Agent, or Firm* — Howard & Howard Attorneys PLLC

(57) ABSTRACT

An end effector for impacting a prosthesis at a surgical site along a trajectory maintained by a surgical robot. The end effector comprises an impactor assembly and a guide. The impactor assembly has a head to receive impact force, an interface to releasably attach to the prosthesis, a shaft extending along an impactor axis between the head and the interface, and an impactor engagement surface disposed between the head and the interface. The guide is adapted to attach to the surgical robot and comprises a channel extending along a guide axis and defining an opening arranged to receive a portion of the shaft of the impactor assembly, a guide engagement surface shaped to abut the impactor engagement surface, and a limiter to maintain abutment of (Continued)

the impactor engagement surface with the guide engagement surface to facilitate coaxial alignment of the axes with the trajectory maintained by the surgical robot.

38 Claims, 66 Drawing Sheets

(51) Int. Cl.
    *A61B 34/20*     (2016.01)
    *A61B 34/00*     (2016.01)
    *A61F 2/46*     (2006.01)
    *A61B 90/00*     (2016.01)
    *A61B 17/00*     (2006.01)

(52) U.S. Cl.
    CPC .......... *A61F 2/4609* (2013.01); *A61F 2/4637* (2013.01); *A61B 2017/00477* (2013.01); *A61B 2034/107* (2016.02); *A61B 2034/2051* (2016.02); *A61B 2034/2055* (2016.02); *A61B 2034/305* (2016.02); *A61B 2034/743* (2016.02); *A61B 2034/744* (2016.02); *A61B 2090/034* (2016.02); *A61B 2090/062* (2016.02); *A61B 2090/0808* (2016.02); *A61B 2090/0811* (2016.02); *A61F 2/4603* (2013.01); *A61F 2002/4627* (2013.01); *A61F 2002/4632* (2013.01); *A61F 2002/4641* (2013.01); *A61F 2002/4681* (2013.01); *A61F 2002/4687* (2013.01)

(58) Field of Classification Search
    CPC .... A61B 2034/305; A61F 2/46; A61F 2/4603; A61F 2/4609; A61F 2002/4632; A61F 2/4637; A61F 2002/4681; A61F 2002/4687
See application file for complete search history.

(56) References Cited

U.S. PATENT DOCUMENTS

| | | | |
|---|---|---|---|
| 6,246,200 B1 | 6/2001 | Blumenkranz et al. |
| 6,866,671 B2 | 3/2005 | Tierney et al. |
| 7,001,393 B2 | 2/2006 | Schwenke et al. |
| 7,048,745 B2 | 5/2006 | Tierney et al. |
| 7,104,998 B2 | 9/2006 | Yoon et al. |
| 7,331,965 B2 | 2/2008 | Nielsen |
| 7,396,357 B2 | 7/2008 | Tornier et al. |
| 7,607,238 B2 | 10/2009 | Kim et al. |
| 7,670,343 B2 | 3/2010 | Meridew et al. |
| 7,725,162 B2 | 5/2010 | Malackowski et al. |
| 7,831,292 B2 | 11/2010 | Quaid et al. |
| 7,950,560 B2 | 5/2011 | Zemlok et al. |
| 8,010,180 B2 | 8/2011 | Quaid et al. |
| 8,133,234 B2 | 3/2012 | Meridew et al. |
| 8,167,823 B2 | 5/2012 | Nycz et al. |
| 8,182,469 B2 | 5/2012 | Anderson et al. |
| 8,182,470 B2 | 5/2012 | Devengenzo et al. |
| 8,206,405 B2 | 6/2012 | Beverland et al. |
| 8,219,177 B2 | 7/2012 | Smith et al. |
| 8,219,178 B2 | 7/2012 | Smith et al. |
| 8,241,296 B2 | 8/2012 | Wasielewski |
| 8,271,066 B2 | 9/2012 | Sarin et al. |
| 8,333,129 B2 | 12/2012 | Johnson et al. |
| 8,337,426 B2 | 12/2012 | Nycz |
| 8,419,717 B2 | 4/2013 | Diolaiti et al. |
| 8,454,619 B1 | 6/2013 | Head |
| 8,469,963 B2 | 6/2013 | Shoham |
| 8,491,603 B2 | 7/2013 | Yeung et al. |
| 8,572,860 B2 | 11/2013 | Fritzinger |
| 8,608,749 B2 | 12/2013 | Meridew et al. |
| 8,615,288 B2 | 12/2013 | Govari et al. |
| 8,620,473 B2 | 12/2013 | Diolaiti et al. |
| 8,657,829 B2 | 2/2014 | McCardel |
| 8,675,939 B2 | 3/2014 | Moctezuma de La Barrera |
| 8,709,016 B2 | 4/2014 | Park et al. |
| 8,740,885 B2 | 6/2014 | Larkin et al. |
| 8,753,346 B2 * | 6/2014 | Suarez .................. A61B 34/20 606/91 |
| 8,814,877 B2 | 8/2014 | Wasielewski |
| 8,864,752 B2 | 10/2014 | Diolaiti et al. |
| 8,876,837 B2 | 11/2014 | Smith et al. |
| 8,900,244 B2 | 12/2014 | Meridew et al. |
| 8,911,429 B2 | 12/2014 | Olds et al. |
| 8,951,256 B2 | 2/2015 | Burroughs |
| 8,961,526 B2 | 2/2015 | Burroughs |
| 8,979,859 B2 | 3/2015 | Leparmentier et al. |
| 8,998,909 B2 | 4/2015 | Gillman et al. |
| 9,008,757 B2 | 4/2015 | Wu |
| 9,011,456 B2 | 4/2015 | Ranawat et al. |
| 9,031,637 B2 * | 5/2015 | Ritchey .............. A61B 17/1707 600/424 |
| 9,078,685 B2 | 7/2015 | Smith et al. |
| 9,119,655 B2 | 9/2015 | Bowling et al. |
| 9,125,678 B2 | 9/2015 | Lye |
| 9,138,319 B2 | 9/2015 | Fanson et al. |
| 9,168,154 B2 | 10/2015 | Behzadi |
| 9,211,128 B2 | 12/2015 | Gillman et al. |
| 9,220,612 B2 | 12/2015 | Behzadi |
| 9,241,771 B2 | 1/2016 | Kostrzewski et al. |
| 9,243,881 B2 | 1/2016 | Bourque et al. |
| 9,283,048 B2 | 3/2016 | Kostrzewski et al. |
| 9,333,042 B2 | 5/2016 | Diolaiti et al. |
| 9,339,278 B2 | 5/2016 | Meridew et al. |
| 9,339,345 B2 | 5/2016 | Song et al. |
| 9,358,130 B2 | 6/2016 | Livorsi et al. |
| 9,439,675 B2 | 9/2016 | Penenberg |
| 9,452,019 B2 | 9/2016 | Schena et al. |
| 9,462,943 B2 | 10/2016 | Brownell |
| 9,468,538 B2 | 10/2016 | Nycz et al. |
| 9,492,239 B2 | 11/2016 | Greer et al. |
| 9,519,341 B2 | 12/2016 | Hasegawa et al. |
| 9,532,730 B2 | 1/2017 | Wasielewski |
| 9,532,849 B2 | 1/2017 | Anderson et al. |
| 9,539,112 B2 | 1/2017 | Thornberry |
| 9,549,781 B2 | 1/2017 | He et al. |
| 9,554,864 B2 | 1/2017 | Taylor et al. |
| 9,554,865 B2 | 1/2017 | Olds et al. |
| 9,585,768 B2 | 3/2017 | Sherman et al. |
| 9,622,757 B2 | 4/2017 | Bourque et al. |
| 9,649,160 B2 | 5/2017 | van der Walt et al. |
| 9,649,202 B2 | 5/2017 | Behzadi et al. |
| 9,662,174 B2 | 5/2017 | Taylor et al. |
| 9,693,878 B2 | 7/2017 | Kunz et al. |
| 9,724,167 B2 | 8/2017 | Ziaei et al. |
| 9,750,510 B2 | 9/2017 | Kostrzewski et al. |
| 9,750,545 B2 | 9/2017 | Cryder et al. |
| 9,782,229 B2 | 10/2017 | Crawford et al. |
| 9,795,319 B2 | 10/2017 | Lavallee et al. |
| 9,815,206 B2 | 11/2017 | Balicki et al. |
| 9,931,059 B2 | 4/2018 | Borja |
| 9,987,092 B2 | 6/2018 | Hladio et al. |
| 10,004,562 B2 | 6/2018 | Kostrzewski et al. |
| RE46,954 E | 7/2018 | Pedicini |
| 10,028,800 B2 | 7/2018 | Bourque et al. |
| 10,034,753 B2 | 7/2018 | Dressler et al. |
| 10,065,309 B2 | 9/2018 | Rose et al. |
| 10,076,385 B2 | 9/2018 | Shoham et al. |
| 10,080,509 B2 | 9/2018 | Wasielewski |
| 10,080,615 B2 | 9/2018 | Bartelme et al. |
| 2005/0149050 A1 | 7/2005 | Stifter et al. |
| 2007/0156157 A1 | 7/2007 | Nahum et al. |
| 2009/0182348 A1 | 7/2009 | Nahapetian et al. |
| 2010/0137871 A1 | 6/2010 | Borja |
| 2010/0145340 A1 | 6/2010 | Phan et al. |
| 2011/0066160 A1 | 3/2011 | Simaan et al. |
| 2011/0082462 A1 | 4/2011 | Suarez et al. |
| 2012/0071894 A1 | 3/2012 | Tanner et al. |
| 2012/0209117 A1 | 8/2012 | Mozes et al. |
| 2012/0283747 A1 | 11/2012 | Popovic |
| 2014/0031722 A1 | 1/2014 | Li et al. |
| 2014/0052150 A1 | 2/2014 | Taylor et al. |

(56) References Cited

U.S. PATENT DOCUMENTS

| | | |
|---|---|---|
| 2014/0135791 A1 | 5/2014 | Nikou et al. |
| 2014/0275955 A1 | 9/2014 | Crawford et al. |
| 2014/0360305 A1 | 12/2014 | Olds et al. |
| 2014/0378999 A1 | 12/2014 | Crawford et al. |
| 2015/0032164 A1 | 1/2015 | Crawford et al. |
| 2015/0039037 A1 | 2/2015 | Donner et al. |
| 2015/0066038 A1 | 3/2015 | McGinley et al. |
| 2015/0142372 A1 | 5/2015 | Singh |
| 2015/0196365 A1* | 7/2015 | Kostrzewski .......... A61B 17/17 606/130 |
| 2015/0209965 A1 | 7/2015 | Low et al. |
| 2015/0272696 A1 | 10/2015 | Fry et al. |
| 2015/0289992 A1 | 10/2015 | Anglin et al. |
| 2015/0313684 A1 | 11/2015 | Fanson et al. |
| 2015/0335386 A1 | 11/2015 | Smith et al. |
| 2015/0366624 A1 | 12/2015 | Kostrzewski et al. |
| 2015/0374445 A1* | 12/2015 | Gombert .............. B25J 15/0206 606/130 |
| 2016/0000512 A1 | 1/2016 | Gombert et al. |
| 2016/0038242 A1 | 2/2016 | Lo Iacono et al. |
| 2016/0081753 A1 | 3/2016 | Kostrzewski |
| 2016/0081754 A1 | 3/2016 | Kostrzewski et al. |
| 2016/0081819 A1 | 3/2016 | Kelman et al. |
| 2016/0095720 A1 | 4/2016 | Behzadi |
| 2016/0120612 A1 | 5/2016 | Yorimoto |
| 2016/0151120 A1 | 6/2016 | Kostrzewski et al. |
| 2016/0157941 A1 | 6/2016 | Anvari et al. |
| 2016/0175110 A1 | 6/2016 | Behzadi et al. |
| 2016/0220315 A1 | 8/2016 | Falardeau et al. |
| 2016/0220320 A1 | 8/2016 | Crawford et al. |
| 2016/0220385 A1 | 8/2016 | Falardeau et al. |
| 2016/0228133 A1 | 8/2016 | Meridew et al. |
| 2016/0235490 A1 | 8/2016 | Srivastava et al. |
| 2016/0242860 A1 | 8/2016 | Diolaiti et al. |
| 2016/0242934 A1 | 8/2016 | van der Walt et al. |
| 2016/0256225 A1 | 9/2016 | Crawford et al. |
| 2016/0278875 A1 | 9/2016 | Crawford et al. |
| 2016/0278941 A1 | 9/2016 | Livorsi et al. |
| 2016/0331479 A1 | 11/2016 | Crawford |
| 2016/0354162 A1 | 12/2016 | Yen et al. |
| 2016/0374769 A1 | 12/2016 | Schena et al. |
| 2017/0056116 A1 | 3/2017 | Kostrzewski |
| 2017/0065428 A1 | 3/2017 | Behzadi |
| 2017/0065432 A1 | 3/2017 | Singh |
| 2017/0071691 A1 | 3/2017 | Crawford et al. |
| 2017/0071759 A1 | 3/2017 | Behzadi et al. |
| 2017/0079727 A1 | 3/2017 | Crawford et al. |
| 2017/0086927 A1 | 3/2017 | Auld et al. |
| 2017/0086928 A1 | 3/2017 | Auld et al. |
| 2017/0086932 A1 | 3/2017 | Auld et al. |
| 2017/0105846 A1 | 4/2017 | Behzadi |
| 2017/0128136 A1 | 5/2017 | Post |
| 2017/0156805 A1 | 6/2017 | Taylor et al. |
| 2017/0172669 A1 | 6/2017 | Berkowitz et al. |
| 2017/0172762 A1 | 6/2017 | Sherman et al. |
| 2017/0182657 A1 | 6/2017 | Rose et al. |
| 2017/0196506 A1 | 7/2017 | Behzadi |
| 2017/0196599 A1 | 7/2017 | Kwon et al. |
| 2017/0196701 A1 | 7/2017 | Behzadi et al. |
| 2017/0196704 A1 | 7/2017 | Behzadi et al. |
| 2017/0196705 A1 | 7/2017 | Behzadi |
| 2017/0196706 A1 | 7/2017 | Behzadi |
| 2017/0196708 A1 | 7/2017 | Behzadi et al. |
| 2017/0196710 A1 | 7/2017 | Behzadi |
| 2017/0196711 A1 | 7/2017 | Behzadi |
| 2017/0202629 A1 | 7/2017 | Maillet et al. |
| 2017/0202683 A1 | 7/2017 | Behzadi |
| 2017/0239006 A1 | 8/2017 | Crawford et al. |
| 2017/0239007 A1 | 8/2017 | Crawford et al. |
| 2017/0258533 A1 | 9/2017 | Crawford et al. |
| 2017/0261348 A1 | 9/2017 | LeBoeuf, II et al. |
| 2017/0290666 A1 | 10/2017 | Behzadi |
| 2017/0296274 A1 | 10/2017 | van der Walt et al. |
| 2017/0312039 A1 | 11/2017 | Crawford et al. |
| 2017/0325892 A1 | 11/2017 | Aghazadeh |
| 2017/0333057 A1 | 11/2017 | Kostrzewski et al. |
| 2017/0333136 A1 | 11/2017 | Hladio et al. |
| 2017/0340448 A1 | 11/2017 | Behzadi |
| 2017/0340456 A1 | 11/2017 | Behzadi |
| 2017/0354368 A1 | 12/2017 | Behzadi |
| 2017/0354468 A1 | 12/2017 | Johnson et al. |
| 2017/0360575 A1 | 12/2017 | Behzadi et al. |
| 2017/0367847 A1 | 12/2017 | Piriou et al. |
| 2018/0000543 A1 | 1/2018 | Hibner |
| 2018/0008324 A1 | 1/2018 | Cryder et al. |
| 2018/0008358 A1 | 1/2018 | Kostrzewski et al. |
| 2018/0021096 A1 | 1/2018 | Kostrzewski et al. |
| 2018/0049792 A1 | 2/2018 | Eckert et al. |
| 2018/0049824 A1 | 2/2018 | Harris et al. |
| 2018/0049832 A1 | 2/2018 | Eckert et al. |
| 2018/0078201 A1 | 3/2018 | Behzadi |
| 2018/0078266 A1 | 3/2018 | Fry et al. |
| 2018/0092757 A1 | 4/2018 | Behzadi et al. |
| 2018/0147018 A1 | 5/2018 | Crawford et al. |
| 2018/0185107 A1 | 7/2018 | Nikou et al. |
| 2018/0193171 A1 | 7/2018 | van der Walt et al. |
| 2018/0199999 A1 | 7/2018 | Syverson et al. |
| 2018/0200002 A1 | 7/2018 | Kostrzewski et al. |
| 2018/0200016 A1 | 7/2018 | Chappuis et al. |
| 2018/0214223 A1 | 8/2018 | Turner |
| 2018/0250144 A1 | 9/2018 | Li et al. |
| 2018/0256259 A1 | 9/2018 | Crawford |
| 2018/0263714 A1 | 9/2018 | Kostrzewski et al. |
| 2018/0353248 A1* | 12/2018 | Bowling ................ A61B 17/92 |
| 2019/0290449 A1* | 9/2019 | Wu ........................ A61B 34/30 |

FOREIGN PATENT DOCUMENTS

| | | | |
|---|---|---|---|
| WO | 2017037127 | A1 | 3/2017 |
| WO | 2017123506 | A1 | 7/2017 |
| WO | 2017123506 | A9 | 9/2017 |
| WO | 2017151607 | A1 | 9/2017 |
| WO | 2017177046 | A1 | 10/2017 |
| WO | 2017218423 | A1 | 12/2017 |
| WO | 2018031752 | A1 | 2/2018 |
| WO | 2018072003 | A1 | 4/2018 |

OTHER PUBLICATIONS

Machine-assisted English translation for DE 203 11 610 extracted from espacenet.com database on May 15, 2019, 7 pages.

* cited by examiner

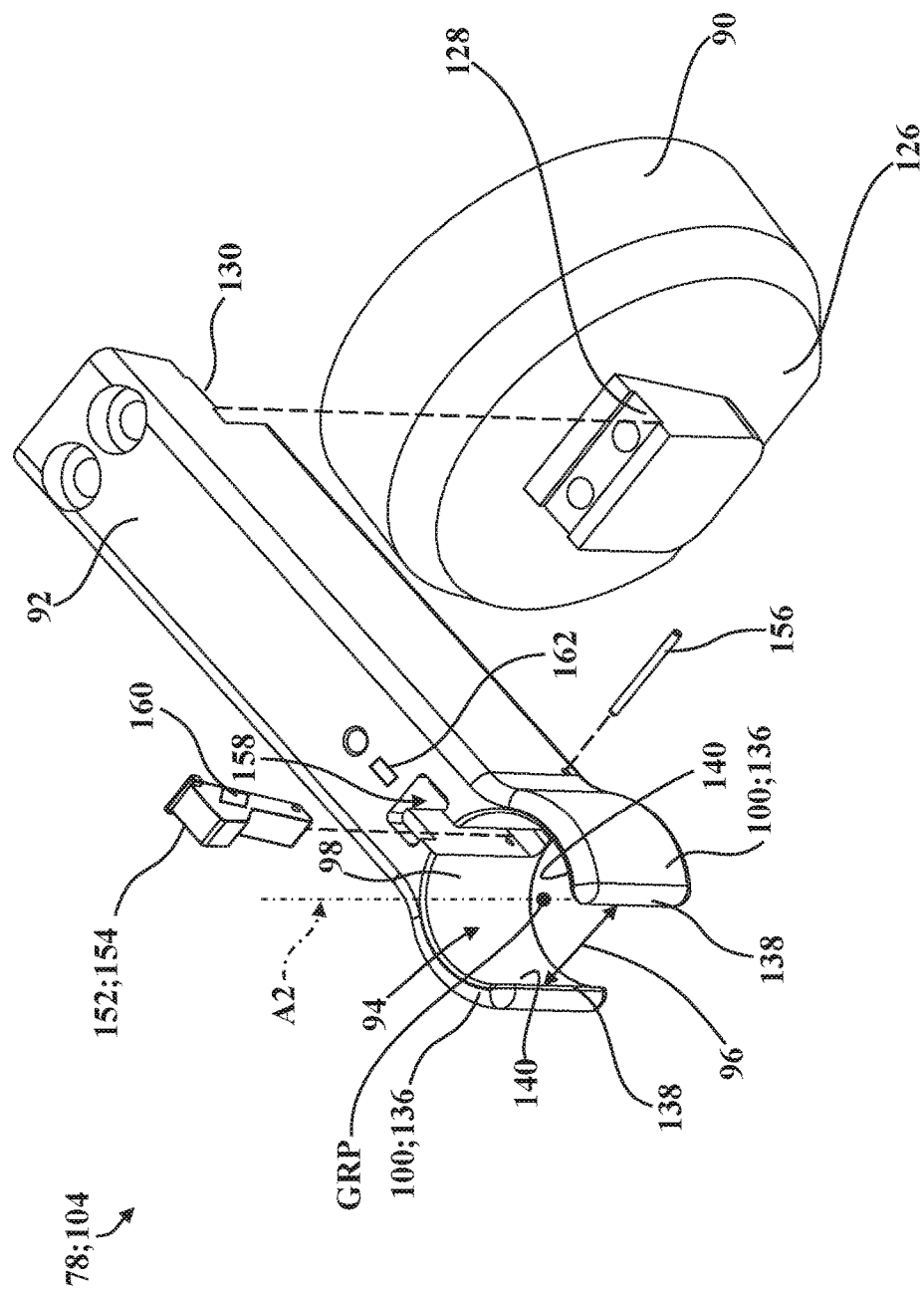

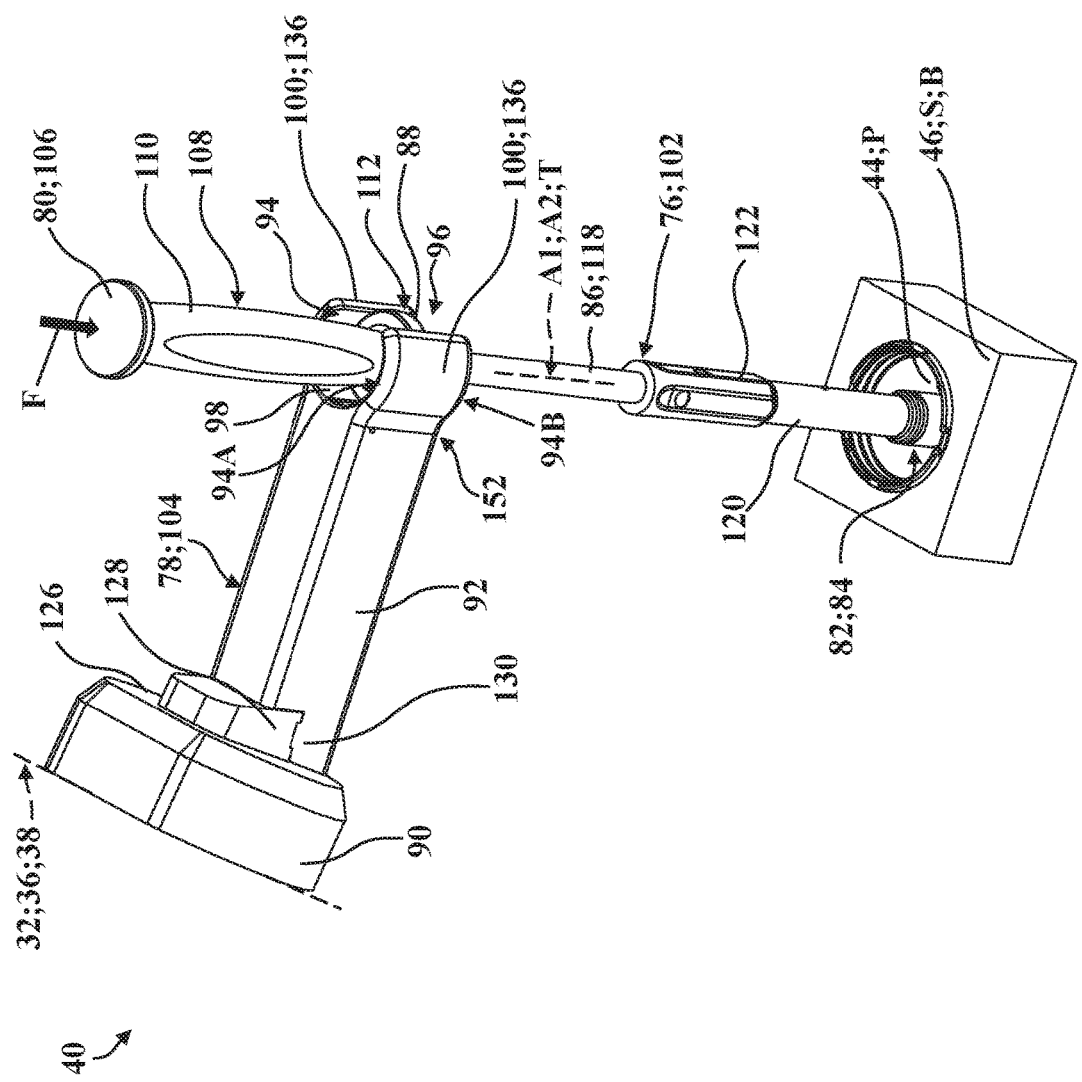

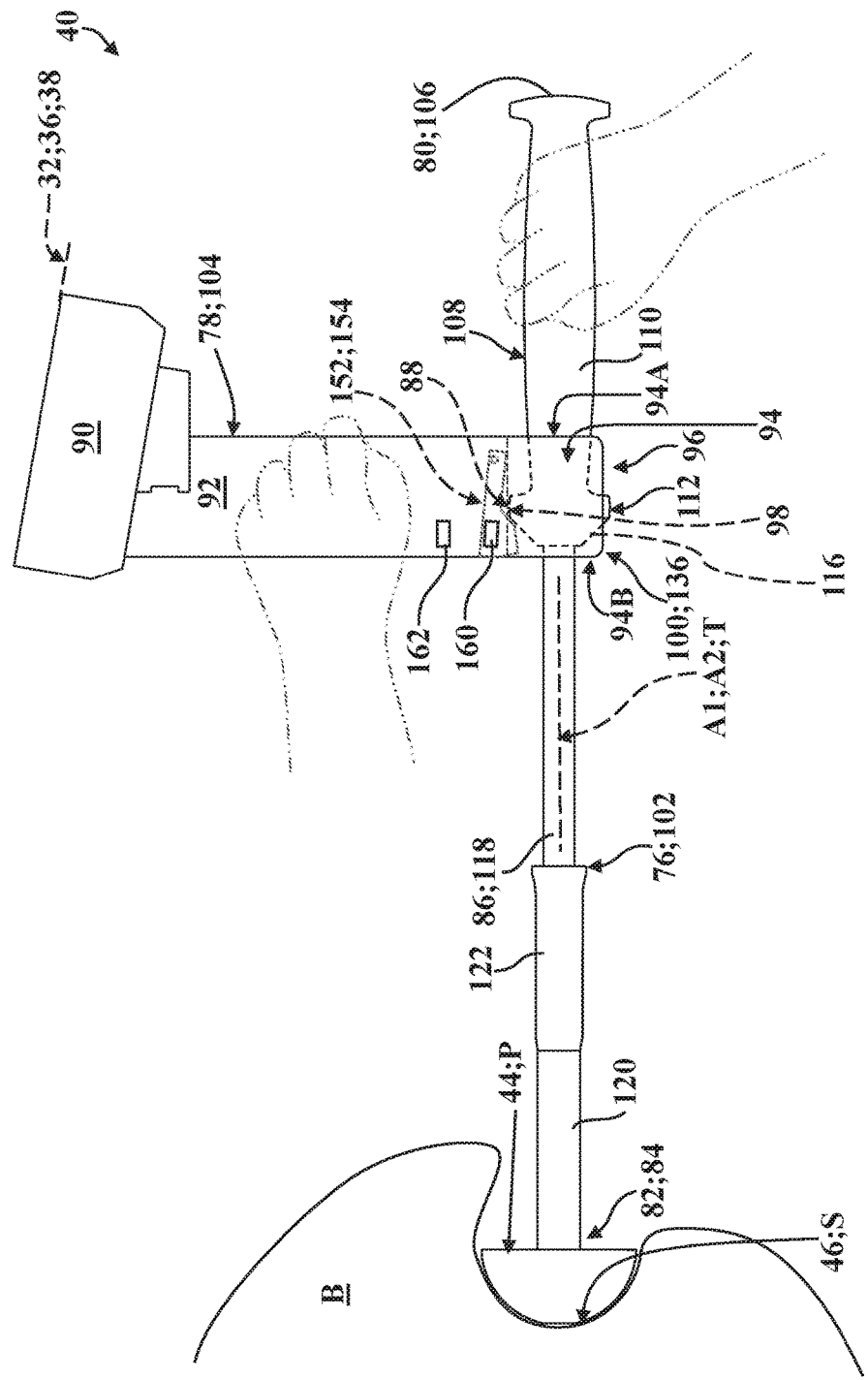

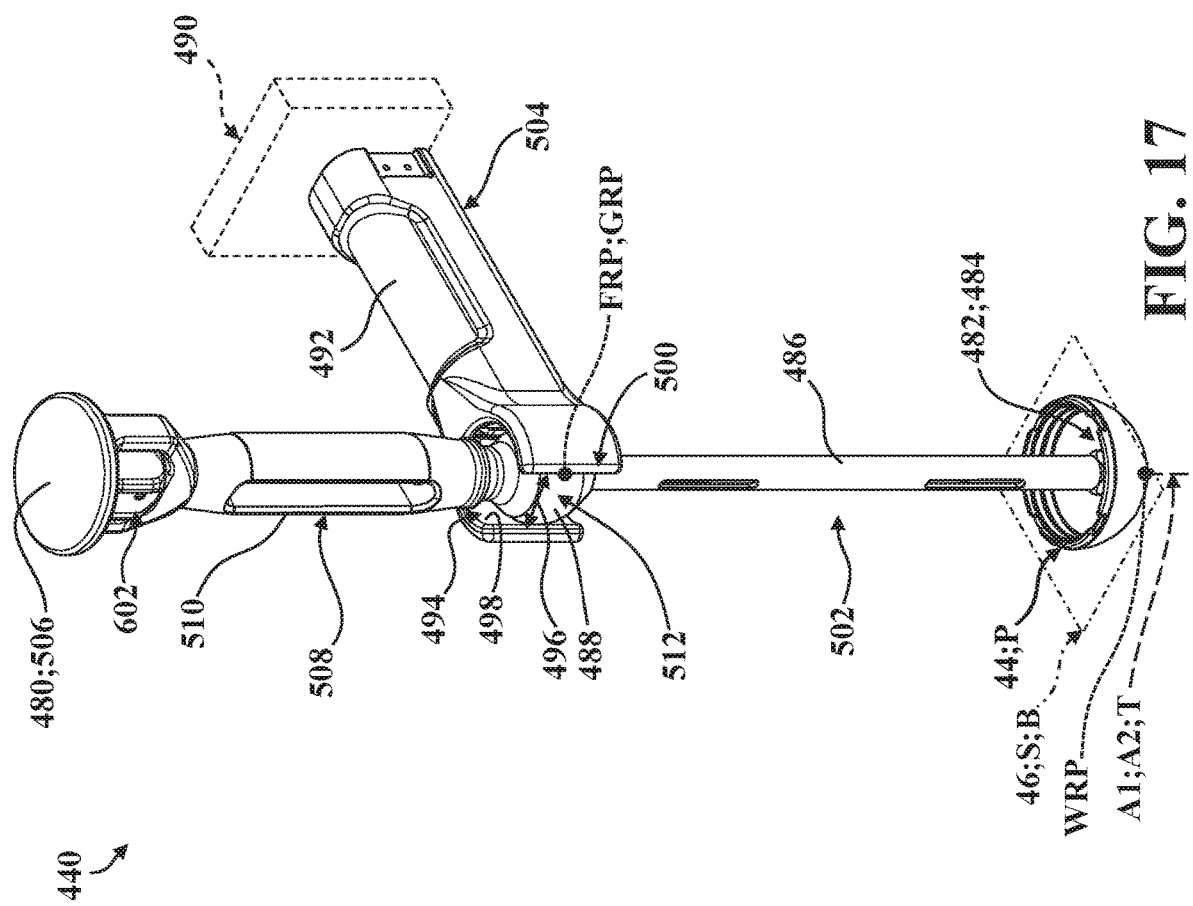

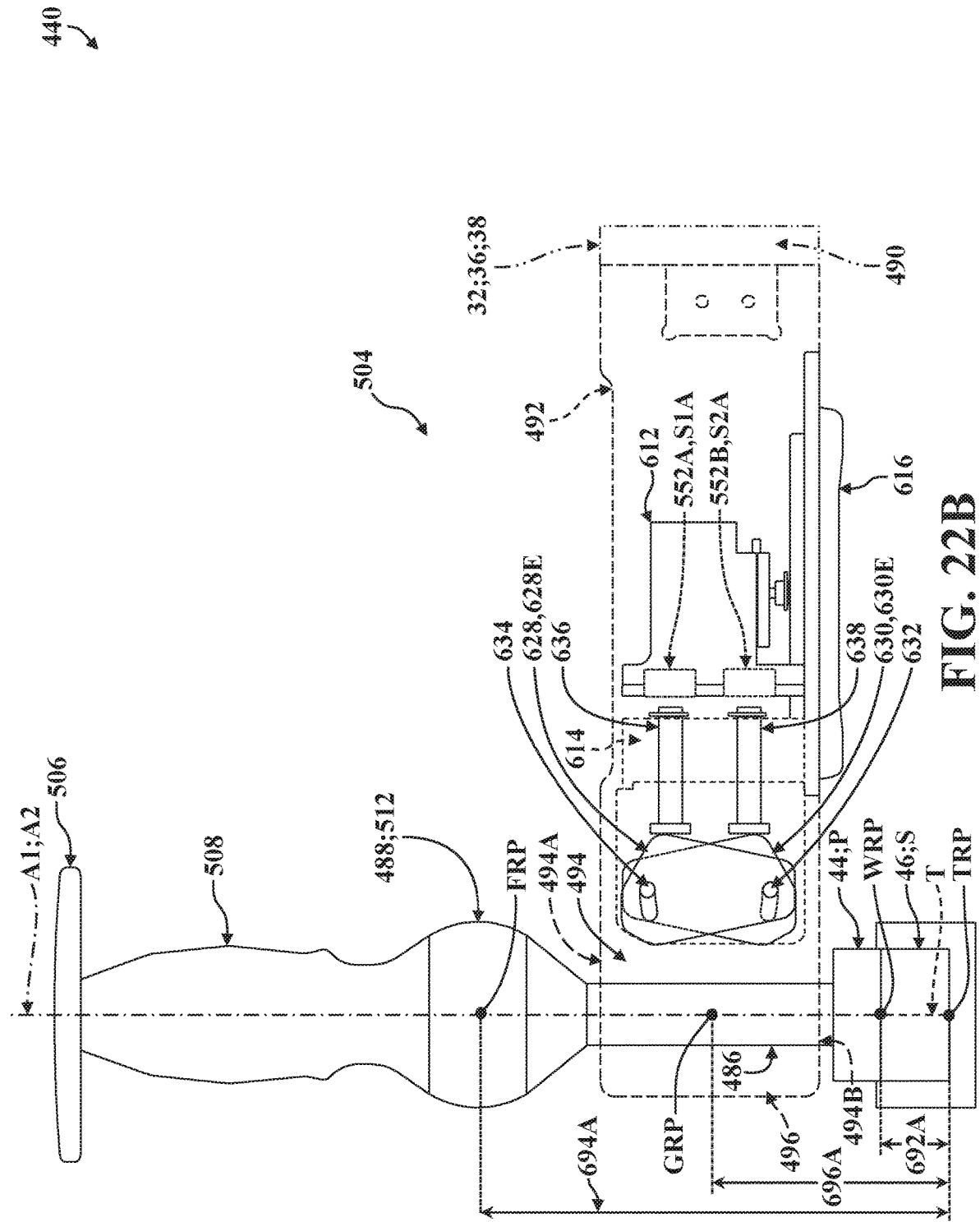

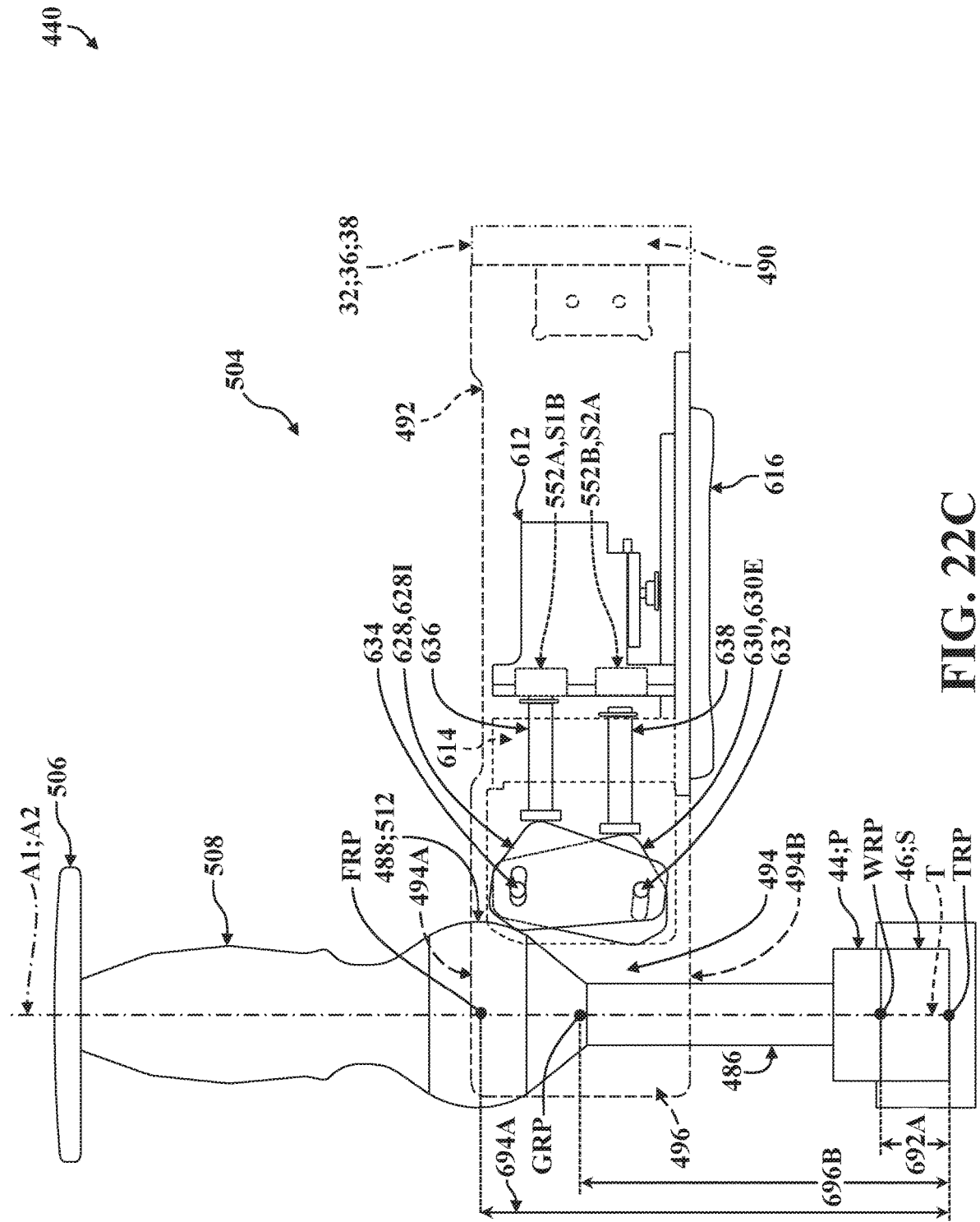

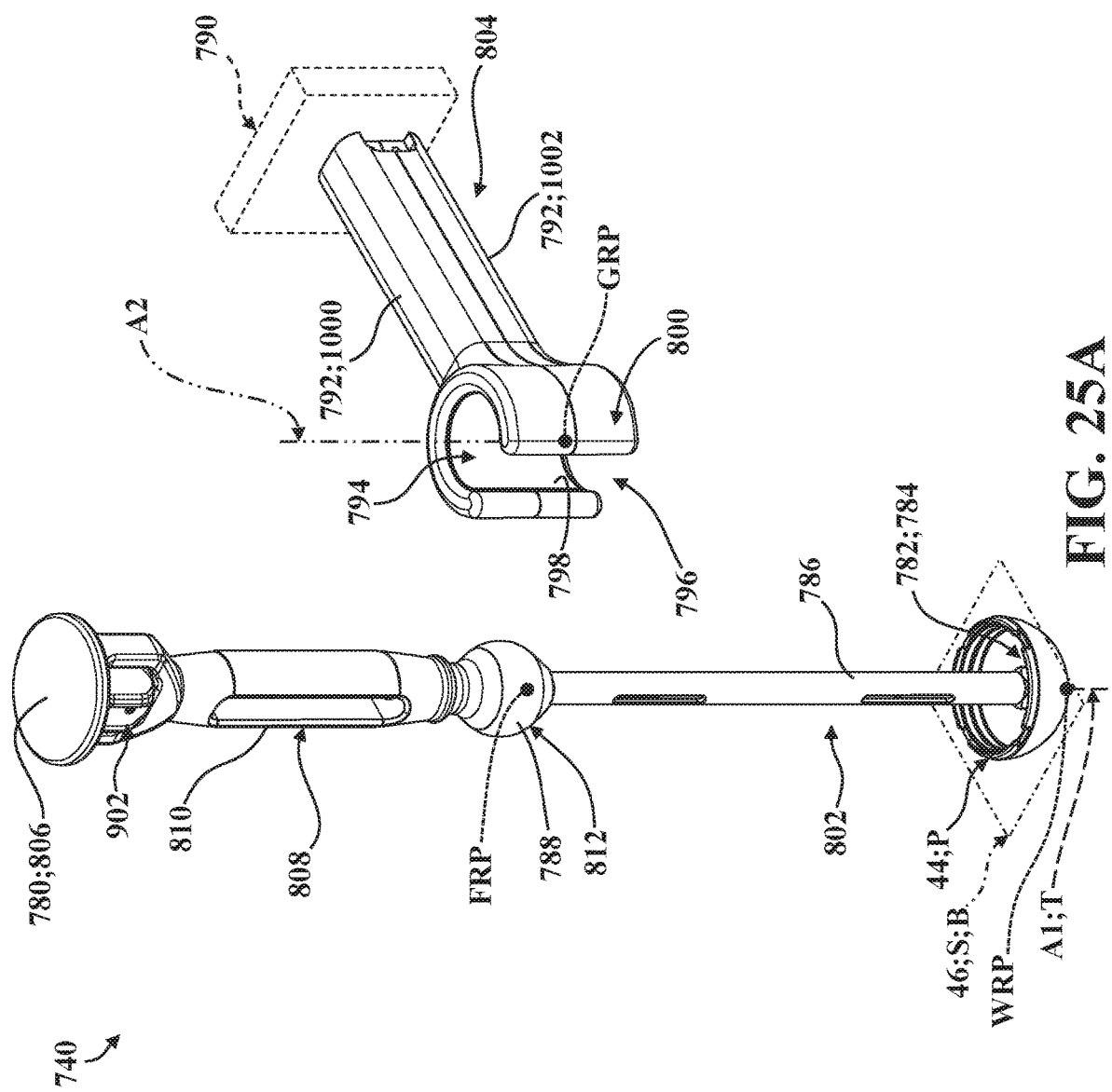

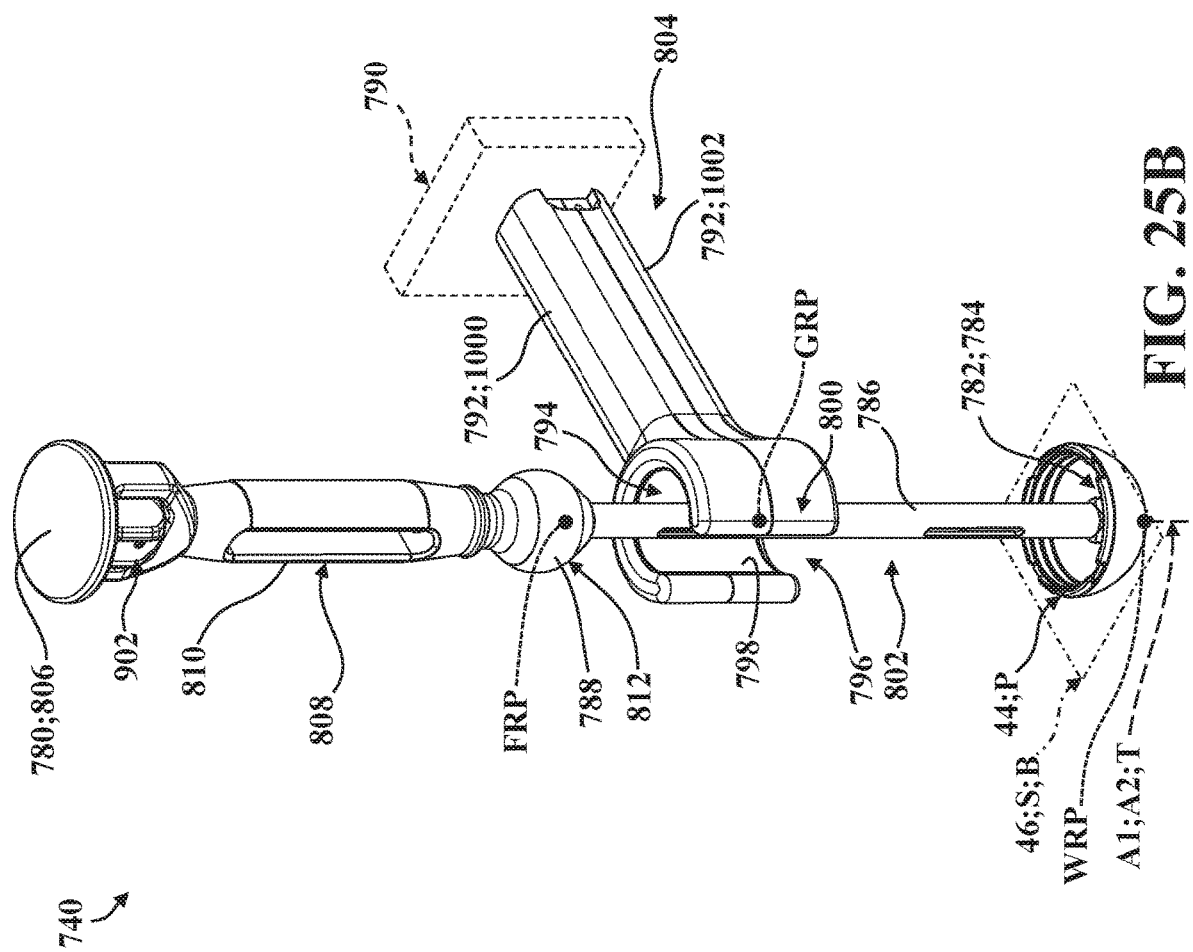

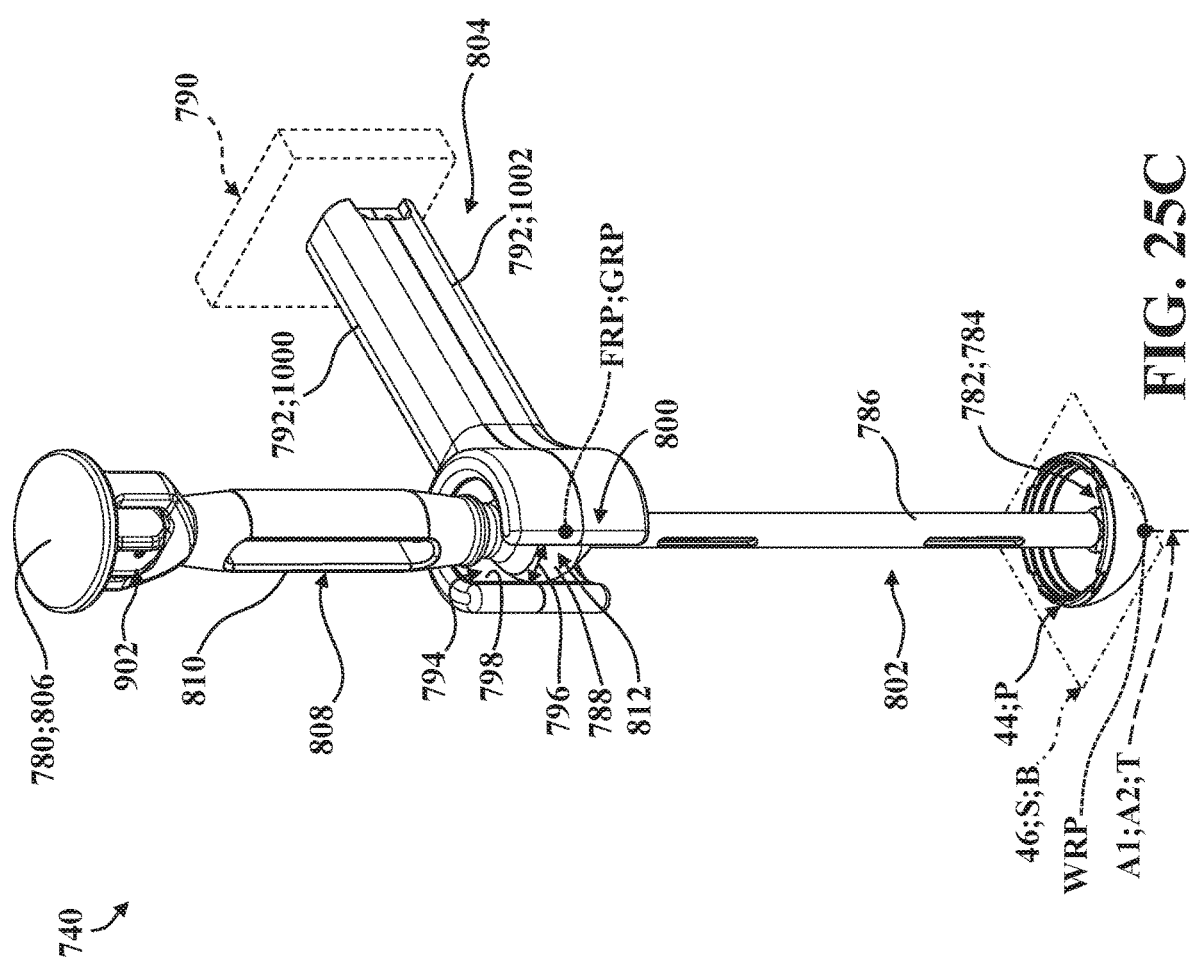

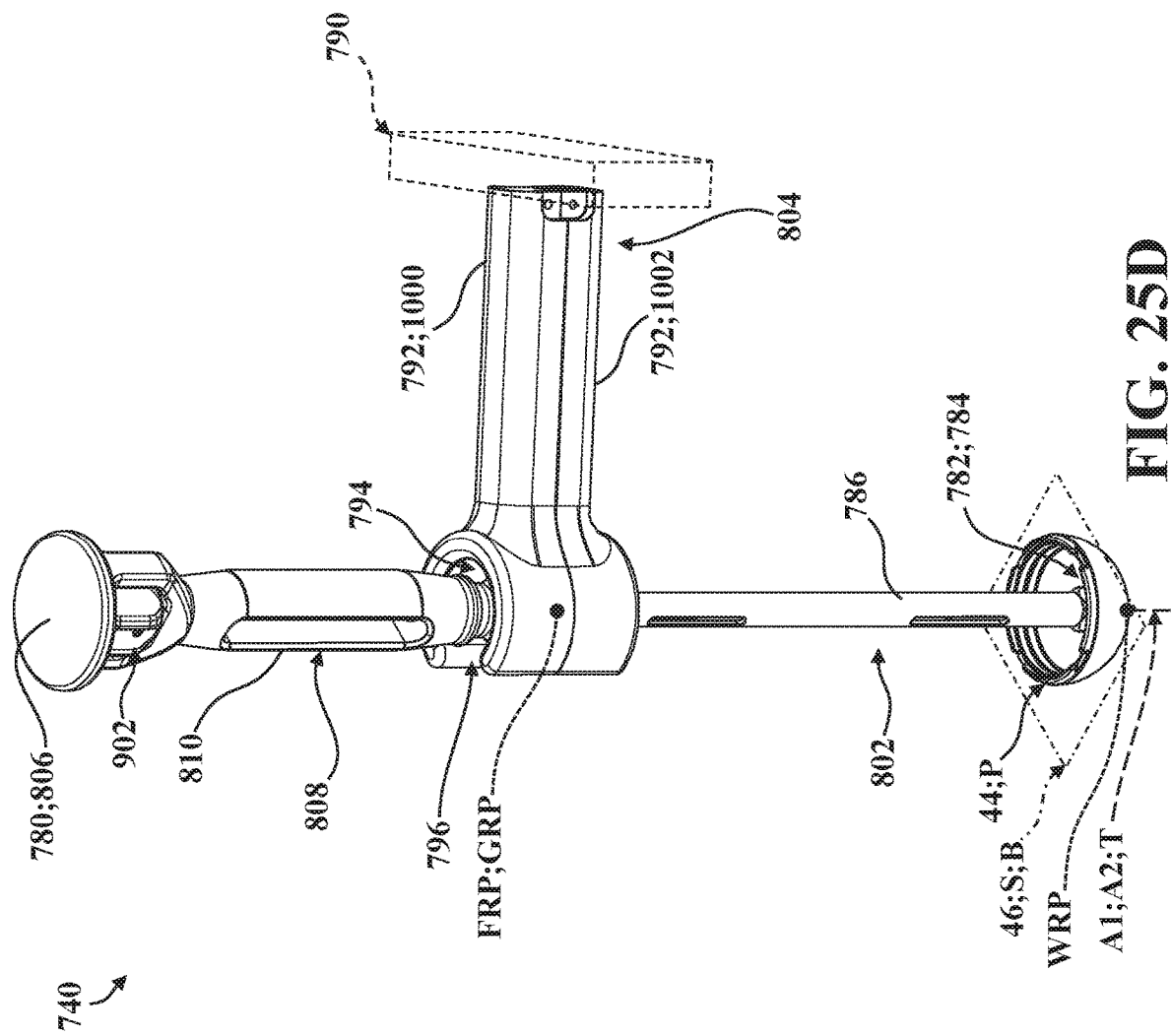

END EFFECTORS, SYSTEMS, AND METHODS FOR IMPACTING PROSTHETICS GUIDED BY SURGICAL ROBOTS

CROSS-REFERENCE TO RELATED APPLICATION

The subject patent application claims priority to and all the benefits of U.S. Provisional Patent Application No. 62/622,303 filed on Jan. 26, 2018, the disclosure of which is hereby incorporated by reference in its entirety.

BACKGROUND

Surgical robots are frequently used to assist medical professionals in carrying out various conventional surgical procedures. To this end, a surgeon may use a surgical robot to guide, position, move, actuate, or otherwise manipulate various tools, components, prostheses, and the like during surgery.

It will be appreciated that surgical robots can be used to assist surgeons in performing a number of different types of surgical procedures, and are commonly used in procedures involving the correction, resection, or replacement of degenerated joints to help improve patient mobility and reduce pain. By way of illustrative example, in hip replacement procedures, the surgeon replaces portions of the patient's hip joint with artificial prosthetic components. To this end, in total hip arthroplasty, the surgeon typically removes portions of the patient's femur to accommodate a prosthetic femoral component comprising a head, and resurfaces the acetabulum of the pelvis with a reamer to facilitate installing a prosthetic cup shaped to receive the head of the prosthetic femoral component.

Depending on the specific procedure being performed, the surgical robot may be used to help the surgeon approach the surgical site, remove portions of joints and/or bone, install prosthetic components, and the like. For example, in order to install the prosthetic cup into the acetabulum of the pelvis, the surgeon connects the cup to an impactor tool to implant the cup into the reamed acetabulum by striking the impactor tool to apply force (e.g., such as with a mallet). In order to facilitate installing the cup, the surgical robot helps keep the impactor tool aligned relative to the surgical site, and the surgeon closely monitors the trajectory and depth of the cup during impaction to ensure proper alignment of the cup into the reamed acetabulum. Here, reaming the acetabulum generally defines the intended position of the cup which, in turn, defines the trajectory of impaction.

Depending on the configuration of the prosthetic components, the impaction tools, and the surgical robot, ensuring that the cup is implanted properly can be complicated by a lack of visibility and limited access to the surgical site. Moreover, maintaining a set trajectory can be difficult with certain approaches and surgical techniques, whereby misalignment of the cup or other prosthetic components frequently results from improper alignment and/or application of impact force. Furthermore, because the surgical robot typically restricts movement of the impactor tool relative to the trajectory during impaction, approaching the reamed acetabulum with the cup coupled to the impactor tool can sometimes necessitate that the surgical robot and/or the patient's body be repeatedly re-positioned, require the surgeon to enlarge the exposed surgical site, and/or require the surgeon to disassemble the impactor tool and/or portions of the surgical robot to facilitate aligning the impactor tool to the trajectory.

Accordingly, there remains a need in the art for addressing one or more of these deficiencies.

SUMMARY

The present disclosure provides an end effector for impacting a prosthesis at a surgical site along a trajectory maintained by a surgical robot, the end effector having an impactor assembly and a guide. The impactor assembly has a head arranged to receive impact force, an interface adapted to releasably attach to the prosthesis, a shaft extending along an impactor axis between the head and the interface, and an impactor engagement surface disposed between the head and the interface. The guide is adapted to attach to the surgical robot and has a channel extending along a guide axis and defining an opening arranged to receive a portion of the shaft of the impactor assembly, a guide engagement surface shaped to abut the impactor engagement surface, and a limiter to maintain abutment of the impactor engagement surface with the guide engagement surface and to facilitate coaxial alignment of the axes with the trajectory maintained by the surgical robot.

The present disclosure also provides an end effector for positioning a workpiece at a target along a trajectory maintained by a surgical robot, the end effector having a first assembly and a second assembly. The first assembly has a proximal end, a distal end with an interface adapted to releasably attach to the workpiece, a shaft extending along a first axis between the proximal end and the distal end, and a first engagement surface disposed between the proximal end and the distal end. The second assembly has a mount adapted to attach to the surgical robot, and a guide operatively attached to the mount with a channel extending along a second axis. The channel defines an opening arranged to receive a portion of the shaft of the first assembly. The guide also has a second engagement surface and a limiter. The second engagement surface is shaped to abut the first engagement surface. The limiter maintains abutment of the first engagement surface with the second engagement surface and facilitates coaxial alignment of the axes with the trajectory maintained by the surgical robot.

The present disclosure also provides an impactor assembly for use in impacting a prosthesis along a trajectory maintained by a surgical robot having a guide with a C-shaped channel defining a guide engagement surface delineated by an opening extending in a direction of the trajectory. The impactor assembly has a head arranged to receive impact force, and an interface adapted to releasably attach to the prosthesis. A shaft extends along an impactor axis between the head and the interface, and is shaped to pass through the opening of the guide. A flange is coupled to the shaft between the head and the interface and defines an impactor engagement surface shaped to abut and rotatably engage the guide engagement surface to simultaneously permit rotation of the impactor assembly relative to the guide and to facilitate coaxial alignment of the impactor axis with the trajectory maintained by the surgical robot.

The present disclosure also provides a guide adapted for attachment to a surgical robot configured to support an impactor assembly along a trajectory maintained by the surgical robot, the impactor assembly being adapted to impact a prosthesis and having an impactor engagement surface and a shaft extending along an impactor axis. The guide has a mount adapted to attach to the surgical robot, and a body operatively attached to the mount with a channel extending along a guide axis. The channel defines an opening arranged to receive a portion of the shaft of the impactor assembly therethrough. The guide also has a guide engagement surface and a limiter. The guide engagement surface is shaped to abut the impactor engagement surface. The limiter maintains abutment of the guide engagement surface with the impactor engagement surface and to facilitate coaxial alignment of the guide axis with the impactor axis and with the trajectory maintained by the surgical robot.

The present disclosure also provides an end effector for positioning a workpiece at a target along a trajectory maintained by a surgical robot, the end effector having a first assembly and a second assembly. The first assembly has a proximal end, a distal end with an interface adapted to releasably attach to the workpiece, a shaft extending along a first axis between the proximal end and the distal end, and a flange arranged between the proximal end and the distal end and defining a first engagement surface. The second assembly has a mount adapted to attach to the surgical robot, and a guide operatively attached to the mount with a channel extending along a second axis between first and second axial channel ends and defining a second engagement surface that is shaped to abut the first engagement surface. The channel also defines an opening arranged to receive a portion of the shaft of the first assembly. The guide also has a limiter that maintains abutment of the first engagement surface with the second engagement surface and facilitates coaxial alignment of the axes with the trajectory maintained by the surgical robot. A sensor is coupled to the guide to determine a relative axial position of the flange between the first channel end and the second channel end. The sensor has a linear variable differential transformer (LVDT) coil assembly with at least one coil extending around the guide axis toward the opening.

The present disclosure also provides a method of impacting a prosthesis at a surgical site along a trajectory maintained by a surgical robot. The method comprises: providing an impactor assembly having a head, an interface, a shaft extending along an impactor axis between the head and the interface, and an impactor engagement surface; and providing a guide with a channel extending along a guide axis and defining an opening, a guide engagement surface, and a limiter. The method also comprises: positioning the impactor assembly to place the prosthesis at the surgical site; positioning the shaft of the impactor assembly through the opening of the guide and into the channel; and bringing the impactor engagement surface of the impactor assembly into abutment with the guide engagement surface of the guide; and moving the limiter of the guide relative to the impactor assembly to maintain abutment of the impactor engagement surface with the guide engagement surface. The method also comprises: coaxially-aligning the impactor axis and the guide axis with the trajectory maintained by the surgical robot; and applying impact force to the head of the impactor assembly to impact the prosthesis at the surgical site along the trajectory maintained by the surgical robot.

Other features and advantages of the embodiments of the present disclosure will be readily appreciated, as the same becomes better understood, after reading the subsequent description taken in conjunction with the accompanying drawings.

BRIEF DESCRIPTION OF THE DRAWINGS

FIG. 7 is another exploded perspective view of the guide of FIG. 6.

FIG. 8C is another perspective view of the end effector, the prosthesis, and the surgical site of FIGS. 8A-8B, shown with the guide moved into engagement with and supporting the impactor assembly along a trajectory.

FIG. 9G is another illustrative schematic view of the end effector, the prosthesis, and the surgical site of FIGS. 9A-9F, shown with the guide moved further away from the surgical site along the trajectory and engaging a flange of the impactor assembly.

FIG. 17 is a perspective view of yet another embodiment of an end effector according to the present disclosure, shown comprising a guide supporting the impactor assembly of FIGS. 16A-16B, and shown with the prosthesis attached to the impactor assembly.

FIG. 22B is another illustrative schematic view of the surgical site, the prosthesis, and the end effector of FIG. 22A, shown with the guide moved toward the impactor assembly to bring the shaft of the impactor assembly within the channel of the guide, and depicted with the guide axis in coaxial alignment with the trajectory.

FIG. 22C is another illustrative schematic view of the surgical site, the prosthesis, and the end effector of FIGS. 22A-22B, shown with the guide moved away from the surgical site along the trajectory with the channel engaging a flange of the impactor assembly adjacent to the shaft, the flange also shown engaging against the first trigger of the follower subassembly to translate the first pushrod toward a first pushrod sensor of the sensor subassembly.

FIG. 25A is a perspective view of yet another embodiment of an end effector according to the present disclosure, shown comprising a guide with a channel defining a guide axis spaced from the impactor assembly and prosthesis of FIG. 16A, the impactor assembly comprising a shaft adjacent to a flange aligned about an impactor axis spaced from the guide axis.

FIG. 25B is another perspective view of the prosthesis and the end effector of FIG. 25A, shown with the guide moved toward the impactor assembly to bring the shaft of the impactor assembly within the channel of the guide, and depicted with the guide axis in coaxial alignment with the impactor axis.

FIG. 25C is another perspective view of the prosthesis and the end effector of FIGS. 25A-25B, shown with the guide moved away from the prosthesis along the impactor axis with the channel of the guide engaging the flange of the impactor assembly at the vertical center of the channel.

FIG. 25D is another perspective view of the prosthesis and the end effector of FIGS. 25A-25C, still shown with the channel of the guide engaging the flange of the impactor assembly at the vertical center of the channel but with the guide rotationally repositioned relative to the impactor assembly while maintaining coaxial alignment between the guide axis and the impactor axis.

It will be appreciated that one or more of the embodiments depicted throughout the drawings may have certain components, structural features, and/or assemblies removed, depicted schematically, and/or shown in phantom for illustrative purposes.

DETAILED DESCRIPTION

Figure 1:
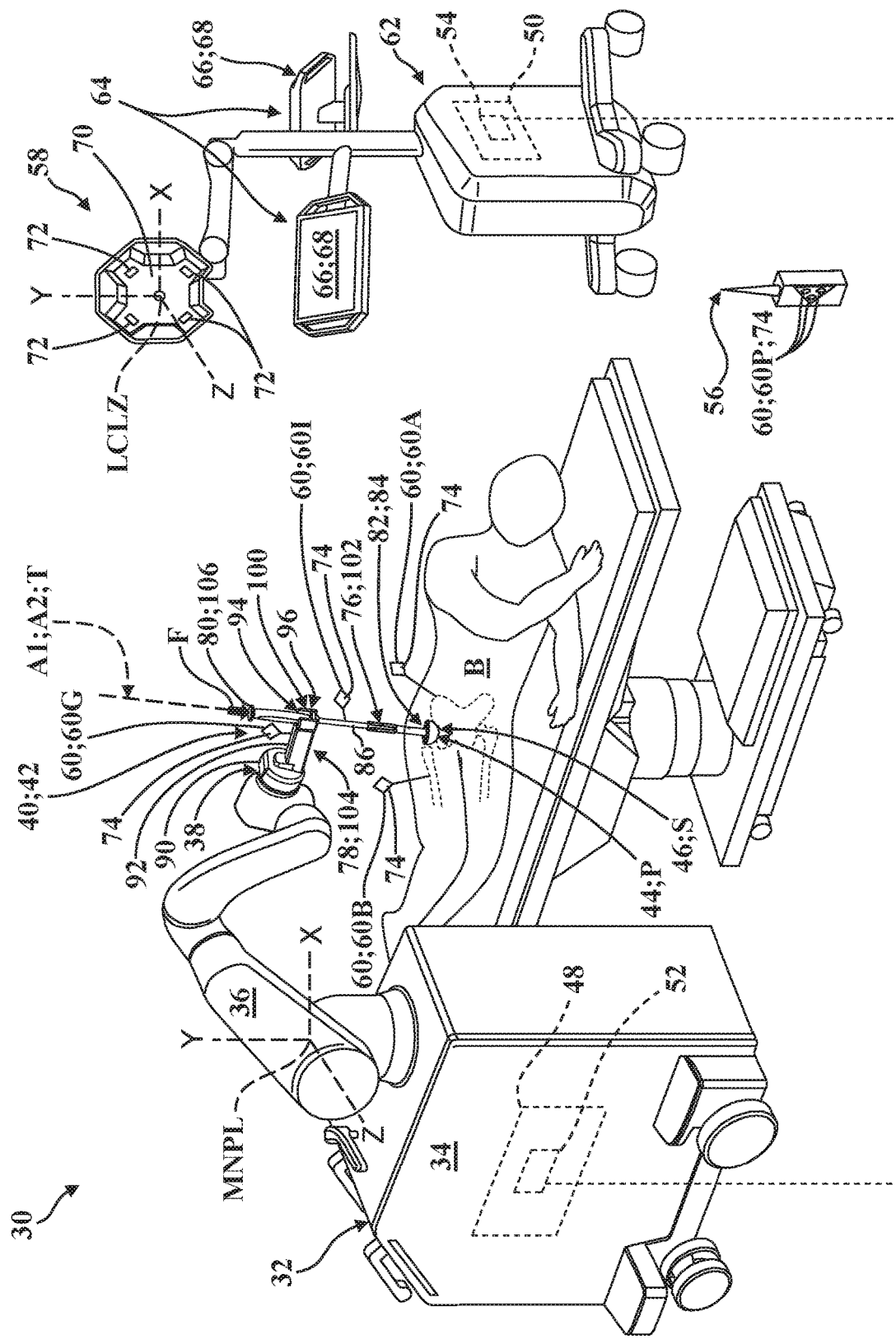
FIG. 1 is a perspective view of a surgical system comprising a surgical robot, a navigation system, and an end effector for impacting a prosthesis at a surgical site along a trajectory maintained by the surgical robot, the end effector shown having an impactor assembly coupled to the prosthesis and supported along a trajectory by a guide attached to the surgical robot.

Referring now to FIG. 1, a surgical system 30 comprising a surgical robot 32 is shown. The surgical robot 32 generally comprises a base 34, a robotic arm 36, and a coupling 38. The robotic arm 36 is supported by the base 34 and is configured to move, drive, maintain, or otherwise control the position and/or orientation of the coupling 38 relative to the base 34 during use. The coupling 38 is adapted to releasably secure an end effector 40 which, in turn, supports or otherwise includes a tool, generally indicated at 42. The tool 42 (e.g., an impactor) is configured to support, position, or otherwise facilitate driving a workpiece 44 (e.g., an acetabular cup) used in connection with various surgical procedures, as described in greater detail below. In some embodiments, the surgical system 30 is configured to guide the workpiece 44 relative to a target, generally indicated at 46, such as along or with respect to a trajectory T maintained by the surgical robot 32. In the representative embodiment illustrated herein, the target 46 is a surgical site S on a patient's body B, and the workpiece 44 is a prosthesis P supported by the end effector 40 (e.g., via the tool 42) and adapted for implantation at the surgical site S along a trajectory T (e.g., an impaction trajectory).

The surgical robot 32 moves the end effector 40 relative to the target 46 via the robotic arm 36 to, among other things, assist medical professionals in carrying out various types of surgical procedures with precise control over movement and positioning of end effector 40, the tool 42, and/or the workpiece 44. One exemplary arrangement of the robotic arm 36 is described in U.S. Pat. No. 9,119,655 entitled "Surgical Robotic arm Capable of Controlling a Surgical Instrument in Multiple Modes," the disclosure of which is hereby incorporated by reference in its entirety. It will be appreciated that the robotic arm 36 and other portions of the surgical robot 32 may be arranged in a number of different configurations.

The surgical system 30 is able to monitor, track, and/or determine changes in the relative position and/or orientation of one or more parts of the surgical robot 32, the robotic arm 36, the end effector 40, the tool 42, and/or the workpiece 44, as well as various parts of the patient's body B, within a common coordinate system by utilizing various types of trackers (e.g., multiple degree-of-freedom optical, inertial, and/or ultrasonic sensing devices), navigation systems (e.g., machine vision systems, charge coupled device cameras, tracker sensors, surface scanners, and/or range finders), anatomical computer models (e.g., magnetic resonance imaging scans of the patient's anatomy), data from previous surgical procedures and/or previously-performed surgical techniques (e.g., data recorded while reaming the acetabulum that are subsequently used to facilitate impacting the prosthesis), and the like. To these ends, and as is depicted schematically in FIG. 1, the surgical system 30 generally comprises a robotic control system 48 and a navigation system 50 which cooperate to allow the surgical robot 32 maintain alignment of the end effector 40 relative to the trajectory T, as well as to generally allow the surgical robot 32 to move the end effector 40 relative to the surgical site S and other parts of the surgical system 30.

As is depicted schematically in FIG. 1, the robotic control system 48 comprises a robot controller 52, and the navigation system 50 comprises a navigation controller 54. In the illustrated embodiment, the robot controller 52 and the navigation controller 54 are disposed in communication with each other, and/or with other components of the surgical system 30, such as via physical electrical connections (e.g., a tethered wire harness) and/or via one or more types of wireless communication (e.g., with a WiFi™ network, Bluetooth®, a radio network, and the like). The robot controller 52 and/or the navigation controller 54 may be realized as or with various arrangements of computers, processors, control units, and the like, and may comprise discrete components or may be integrated (e.g., sharing hardware, software, inputs, outputs, and the like). Other configurations are contemplated.

The surgical system 30 employs the robotic control system 48 to, among other things, articulate the robotic arm 36 to position the end effector 40 relative to the surgical site S, maintain the trajectory T, and the like. Here, the robot controller 52 of the robotic control system 48 is configured to articulate the robotic arm 36 by driving various actuators, motors, and the like (not shown) disposed at joints of the robotic arm 36. The robot controller 52 may also be configured to gather data from various sensors such as encoders (not shown) located along the robotic arm 36. Because the specific geometry of each of the components of the surgical robot 32 and the end effector 40 are known, these data can be used by the robot controller 52 to reliably adjust the position and/or orientation of the end effector 40 within a manipulator coordinate system MNPL. The manipulator coordinate system MNPL has an origin, and the origin is located relative to the robotic arm 36 in the illustrated embodiment. One example of this type of manipulator coordinate system MNPL is described in U.S. Pat. No. 9,119,655 entitled "Surgical Robotic Arm Capable of Controlling a Surgical Instrument in Multiple Modes," previously referenced. Other configurations are contemplated.

The navigation system 50 is configured to, among other things, track movement of various objects, such as the end effector 40, a pointer 56, and parts of the patient's body B (e.g. bones or other anatomy at or adjacent to the surgical site S). To this end, the navigation system 50 employs a localizer 58 configured to sense the position and/or orientation of trackers 60 within a localizer coordinate system LCLZ. The navigation controller 54 is disposed in communication with the localizer 58 and gathers position and/or orientation data for each tracker 60 sensed within a field of view of the localizer 58 in the localizer coordinate system LCLZ.

It will be appreciated that the localizer 58 can sense the position and/or orientation of a multiple number of trackers 60 to track a corresponding multiple number of objects within the localizer coordinate system LCLZ. By way of example, and as is depicted in FIG. 1, trackers 60 may comprise a pointer tracker 60P coupled to the pointer 56, one or more end effector trackers 60G, 60I, a first patient tracker 60A, and a second patient tracker 60B, as well as additional patient trackers, trackers for additional medical and/or surgical tools, and the like. I In some embodiments, and as is shown in FIG. 1, the one or more end effector trackers 60G, 60I may each be firmly affixed to different portions of the end effector 40, such as those that may be configured to move relative to each other. By way of non-limiting example, and as is described in greater detail below, an impactor tracker 60I could be attached to an impactor (or another type of tool 42) which is configured for movement relative to a guide to which a guide tracker 60G is attached. Here, the guide tracker 60G may move concurrently with the coupling 38 via the robotic arm 36, whereas the impactor tracker 60I may move relative to the coupling 38 in one or more degrees of freedom, as is described in greater detail below. While the guide tracker 60G and the impactor tracker 60I depicted in FIG. 1 can be used by the navigation system 50 to readily determine the relative positions and/or orientations of different parts of the end effector 40 via the localizer 58, certain embodiments of the present disclosure may be configured to facilitate this determination in other ways (e.g., such as with one or more sensors). However, other configurations are contemplated by the present disclosure, and it will be appreciated that various combinations of trackers 60, sensors, and predetermined geometric relationships, and the like can be utilized in order to track certain objects.

With continued reference to FIG. 1, the first patient tracker 60A is firmly affixed to one bone of the patient's body B at or adjacent to the surgical site S (e.g., to the pelvis near the acetabulum), and the second patient tracker 60B is firmly affixed to a different bone (e.g., to a portion of the femur). While not shown in detail, it will be appreciated that the patient trackers 60A, 60B can be coupled to a number of different bones in the patient's body B in various ways, such as by threaded engagement, clamping, or by other techniques. Similarly, the guide tracker 60G and/or the impactor tracer 60I could be fixed to portions of the end effector 40 and/or the tool 42 in various ways, such as by integration during manufacture or by releasable attachment ahead of or during a surgical procedure. It will be appreciated that various trackers 60 may be firmly affixed to different types of tracked objects (e.g., discrete bones, tools, pointers, and the like) in a number of different ways.

The position of the trackers 60 relative to the objects or anatomy to which they are attached can be determined by known registration techniques. For example, the position of the patient trackers 60A, 60B relative to the portions of the patient's body B to which they are attached can be accomplished with various forms of point-based registration, such as where a distal tip of the pointer 56 is used to engage against specific anatomical landmarks (e.g., touching specific portions of bone) or is used to engage several parts of a bone for surface-based registration as the localizer 58 monitors the position and orientation of the pointer tracker 60P. Conventional registration techniques can then be employed to correlate the pose of the patient trackers 60A, 60B to the patient's anatomy (e.g., to each of the femur and the acetabulum). Other types of registration are also possible, such as by using patient trackers 60A, 60B with mechanical clamps that attach to bone and have tactile sensors (not shown) to determine a shape of the bone to which the clamp is attached. The shape of the bone can then be matched to a 3D model of bone for registration. A known relationship between the tactile sensors and markers on the patient tracker 60A, 60B may be entered into or otherwise known by the navigation controller 54. Based on this known relationship, the positions of the markers relative to the patient's anatomy can be determined. Position and/or orientation data may be gathered, determined, or otherwise handled by the navigation controller 54 using a number of different registration/navigation techniques to determine coordinates of each tracker 60 within the localizer coordinate system LCLZ. These coordinates are communicated to the robotic control system 48 to facilitate articulation of the robotic arm 36 and/or to otherwise assist the surgeon in performing the surgical procedure, as described in greater detail below.

In the representative embodiment illustrated herein, the robot controller 52 is operatively attached to the surgical robot 32, and the navigation controller 54 and the localizer 58 are supported on a mobile cart 62 which is movable relative to the base 34 of the surgical robot 32. The mobile cart 62 also supports a user interface, generally indicated at 64, to facilitate operation of the surgical system 30 by displaying information to, and/or by receiving information from, the surgeon or another user. The user interface 64 is disposed in communication with the navigation system 50 and/or the robotic control system 48, and may comprise one or more output devices 66 (e.g., monitors, indicators, display screens, and the like) to present information to the surgeon or other users (e.g., images, video, data, a graphics, navigable menus, and the like), and one or more input devices 68 (e.g., buttons, touch screens, keyboards, mice, gesture or voice-based input devices, and the like). One type of mobile cart 62 and user interface 64 utilized in this type of navigation system 50 is described in U.S. Pat. No. 7,725,162 entitled "Surgery System," the disclosure of which is hereby incorporated by reference in its entirety.

Because the mobile cart 62 and the base 34 of the surgical robot 32 can be positioned relative to each other and also relative to the patient's body B, one or more portions of the surgical system 30 are generally configured to transform the coordinates of each tracker 60 sensed via the localizer 58 from the localizer coordinate system LCLZ into the manipulator coordinate system MNPL, or vice versa, so that articulation of the robotic arm 36 can be performed based at least partially on the relative positions and/or orientations of certain trackers 60 within a common coordinate system (e.g., the manipulator coordinate system MNPL, the localizer coordinate system LCLZ, or another common coordinate system). It will be appreciated that coordinates within the localizer coordinate system LCLZ can be transformed into coordinates within the manipulator coordinate system MNPL, and vice versa, using a number of different transformation techniques. One example of the translation or transformation of data between coordinate systems is described in U.S. Pat. No. 8,675,939 entitled "Registration of Anatomical Data Sets", the disclosure of which is hereby incorporated by reference in its entirety.

In the illustrated embodiment, the localizer 58 is an optical localizer and includes a camera unit 70 with one or more optical position sensors 72. The navigation system 50 employs the optical position sensors 72 of the camera unit 70 to sense the position and/or orientation of the trackers 60 within the localizer coordinate system LCLZ. In the representative embodiment illustrated herein, the trackers 60 each employ markers 74 which can be sensed by the optical position sensors 72 of the camera unit 70. One example of a navigation system 50 of this type is described in U.S. Pat. No. 9,008,757 entitled "Navigation System Including Optical and Non-Optical Sensors," the disclosure of which is hereby incorporated by reference in its entirety. In some embodiments, the markers 74 are active markers (e.g., light emitting diodes "LEDs") which emit light that is sensed by the optical position sensors 72. In other embodiments, the trackers 60 may employ passive markers (e.g., reflectors) which reflect light emitted from the camera unit 70 or another light source. Although one embodiment of the navigation system 50 is illustrated throughout the drawings, the navigation system 50 may have any other suitable configuration for monitoring trackers 60 which, as will be appreciated from the subsequent description below, may be of various types and configurations. For example, the navigation system 50 may comprise other types of localizers 58 and/or trackers 60.

In some embodiments, the navigation system 50 and/or the localizer 58 are radio frequency (RF) based. For example, the navigation system 50 may comprise an RF transceiver coupled to the navigation controller 54 and/or to another computing device, controller, and the like. Here, the trackers 60 may comprise RF emitters or transponders, which may be passive or may be actively energized. The RF transceiver transmits an RF tracking signal, and the RF emitters respond with RF signals such that tracked states are communicated to (or interpreted by) the navigation controller 54. The RF signals may be of any suitable frequency. The RF transceiver may be positioned at any suitable location to track the objects using RF signals effectively. Furthermore, it will be appreciated that embodiments of RF-based navigation systems may have structural configurations that are different than the active marker-based navigation system 50 illustrated herein.

In some embodiments, the navigation system 50 and/or localizer 58 are electromagnetically (EM) based. For example, the navigation system 50 may comprise an EM transceiver coupled to the navigation controller 54 and/or to another computing device, controller, and the like. Here, the trackers 60 may comprise EM components attached thereto (e.g., various types of magnetic trackers, electromagnetic trackers, inductive trackers, and the like), which may be passive or may be actively energized. The EM transceiver generates an EM field, and the EM components respond with EM signals such that tracked states are communicated to (or interpreted by) the navigation controller 54. The navigation controller 54 may analyze the received EM signals to associate relative states thereto. Here too, it will be appreciated that embodiments of EM-based navigation systems may have structural configurations that are different than the active marker-based navigation system 50 illustrated herein.

In some embodiments, the navigation system 50 and/or the localizer 58 could be based on one or more types of imaging systems that do not necessarily require trackers 60 to be fixed to objects in order to determine location data associated therewith. For example, an ultrasound-based imaging system could be provided to facilitate acquiring ultrasound images (e.g., of specific known structural features of tracked objects, of markers or stickers secured to tracked objects, and the like) such that tracked states (e.g., position, orientation, and the like) are communicated to (or interpreted by) the navigation controller 54 based on the ultrasound images. The ultrasound images may be 2D, 3D, or a combination thereof. The navigation controller 54 may process ultrasound images in near real-time to determine the tracked states. The ultrasound imaging device may have any suitable configuration and may be different than the camera unit 70 as shown in FIG. 1. By way of further example, a fluoroscopy-based imaging system could be provided to facilitate acquiring X-ray images of radio-opaque markers (e.g., stickers, tags, and the like with known structural features that are attached to tracked objects) such that tracked states are communicated to (or interpreted by) the navigation controller 54 based on the X-ray images. The navigation controller 54 may process X-ray images in near real-time to determine the tracked states. Similarly, other types of optical-based imaging systems could be provided to facilitate acquiring digital images, video, and the like of specific known objects (e.g., based on a comparison to a virtual representation of the tracked object or a structural component or feature thereof) and/or markers (e.g., stickers, tags, and the like that are attached to tracked objects) such that tracked states are communicated to (or interpreted by) the navigation controller 54 based on the digital images. The navigation controller 54 may process digital images in near real-time to determine the tracked states.

Accordingly, it will be appreciated that various types of imaging systems, including multiple imaging systems of the same or different type, may form a part of the navigation system 50 without departing from the scope of the present disclosure. Those having ordinary skill in the art will appreciate that the navigation system 50 and/or localizer 58 may have any other suitable components or structure not specifically recited herein. For example, the navigation system 50 may utilize solely inertial tracking or any combination of tracking techniques. Furthermore, any of the techniques, methods, and/or components associated with the navigation system 50 illustrated in FIG. 1 may be implemented in a number of different ways, and other configurations are contemplated by the present disclosure.

In some embodiments, the surgical system 30 is capable of displaying a virtual representation of the relative positions and orientations of tracked objects to the surgeon or other users of the surgical system 30, such as with images and/or graphical representations of the anatomy of the patient's body B, the end effector 40, the tool 42, the workpiece 44, and the like presented on one or more output devices 66. The robot controller 52 and/or the navigation controller 54 may also utilize the user interface 64 to display instructions or request information such that the surgeon or other users may interact with the robotic control system 48 to facilitate articulation of the robotic arm 36. Other configurations are contemplated.

It will be appreciated that the robotic control system 48 and the navigation system 50 can cooperate to facilitate control over the position and/or orientation of the end effector 40 and/or tool 42 in different ways. By way of example, the robotic control system 48, the surgical robot 32, and or other parts of the surgical system 30 could employ a number of different control methodologies, including without limitation impedance control and/or admittance control, in order to facilitate articulating the robotic arm 36, maintaining the trajectory T, and the like. Exemplary surgical robot 32 control methodologies are described in U.S. Patent Application Publication No. US20170128136A1 entitled "Robotic System and Method for Backdriving the Same," the disclosure of which is hereby incorporated by reference in its entirety. In some embodiments, the robot controller 52 is configured to control the robotic arm 36 (e.g., by driving joint motors) to provide haptic feedback to the surgeon via the robotic arm 36. Here, haptic feedback helps constrain or inhibit the surgeon from manually moving the end effector 40 and/or tool 42 beyond predefined virtual boundaries associated with the surgical procedure (e.g., to maintain alignment of the tool 42 and/or the workpiece 44 along or with respect to the trajectory T). Exemplary types of haptic feedback systems and associated haptic objects that define virtual boundaries are described, for example, in U.S. Pat. No. 8,010,180 entitled "Haptic Guidance System and Method;" and U.S. Pat. No. 7,831,292 entitled "Guidance System and Method for Surgical Procedures With Improved Feedback," the disclosures of which are each hereby incorporated by reference in their entirety. In some embodiments, the surgical system 30 may comprise the RIO™ Robotic Arm Interactive Orthopedic System manufactured by MAKO Surgical Corp. of Fort Lauderdale, Fla., USA.

As noted above, in the representative embodiment illustrated in FIG. 1, the tool 42 is provided for positioning the workpiece 44 with the surgical robot 32, where the workpiece 44 is realized as a prosthesis P adapted for implantation into the patient's body B. More specifically, the illustrated prosthesis P is a generally hemispherical-shaped cup which forms part of an artificial hip joint adapted for impaction into the patient's acetabulum, as is described in greater detail below. Prior to impaction, the patient's acetabulum is reamed or otherwise prepared so as to define the target 46 at the surgical site S. The Applicant has described the reaming, preparing, and impaction processes in greater detail in U.S. Pat. No. 8,979,859 entitled "Depth of Impaction;" and U.S. Pat. No. 8,753,346 entitled "Tool, Kit-of-Parts for Multi-Functional Tool, and Robotic System for Same," the disclosures of which are each hereby incorporated by reference in their entirety. While the present disclosure describes various orthopedic procedures involving hip joints, it will be appreciated that the subject matter described herein may be applicable to other joints in the patient's body B, such as for example, shoulders, elbows, wrists, spines, knees, ankles, and the like.

Referring now to FIGS. 1A-9N, the illustrated embodiment of the end effector 40 comprises a first assembly 76 (e.g., an impactor) which defines the tool 42 to releasably secure the workpiece 44 (e.g., an acetabular cup), and a second assembly 78 (e.g. an impactor guide) which is adapted to, among other things, attach to the coupling 38 of the robotic arm 36. This configurations allows the surgeon to releasably secure the workpiece 44 to the first assembly 76 and then manually handle the first assembly 76 to approach the target 46 (e.g., a reamed acetabulum) from advantageous positions and without unnecessarily impeding visibility. As is described in greater detail below, after the approach has been completed manually and the workpiece 44 has been disposed at the target 46, the surgeon can subsequently articulate the workpiece 44 and the first assembly 76 into engagement with the second assembly 78 in a quick, efficient, and reliable manner to facilitate aligning the workpiece 44 with the trajectory T maintained by the surgical robot 32.

The first assembly 76 which defines the tool 42 of the end effector 40 generally extends between a proximal end 80 and a distal end 82. An interface 84 provided at the distal end 82 is adapted to releasably attach to the prosthesis P which, as noted above, defines the workpiece 44 in the embodiments described herein. The first assembly 76 also comprises a shaft 86 which extends along a first axis A1 between the proximal end 80 and the distal end 82. A first engagement surface, generally indicated at 88 (see FIG. 2), is disposed between the proximal end 80 and the distal end 82.

The second assembly 78 of the end effector 40, in turn, generally comprises a mount 90 adapted to attach to the surgical robot 32, and a body 92 operatively attached to the mount 90 and having a channel 94 that extends along a second axis A2. The channel 94 defines an opening 96 arranged to receive a portion of the shaft 86 of the first assembly 76 therethrough. The second assembly 78 also comprises a second engagement surface, generally indicated at 98 (see FIG. 3), and a limiter 100. As will be appreciated from the subsequent description below, the second engagement surface 98 is shaped to abut the first engagement surface 88, and the limiter 100 is configured to maintain abutment between the engagement surfaces 88, 98 and to facilitate coaxial alignment of the axes A1, A2 with the trajectory T maintained by the surgical robot 32. Each of the components and structural features of the first and second assemblies 76, 78 introduced above will be described in greater detail below.

The various end effector 40 embodiments described herein generally comprise an impactor assembly 102 (which defines the first assembly 76 and serves as the tool 42) and a guide 104 (which defines the second assembly 78). The impactor assembly 102 and the guide 104 cooperate to facilitate impacting a prosthesis P (which defines the workpiece 44) at a surgical site S (which defines the target 46) on a patient's body B along the trajectory T maintained by the surgical robot 32. However, it should be appreciated that the embodiments of impactor assemblies 102 and guides 104 illustrated herein are exemplary, and the end effector 40 and/or tool 42 could be configured for use with a number of different medical and/or surgical procedures employed in connection with surgical robots 32 where manual positioning may be advantageous prior to attachment to the surgical robot 32. By way of non-limiting example, the end effector 40 and/or tool 42 could be used in connection with a rotary surgical instrument which employs a chuck assembly to releasably secure to and drive a drill bit or reamer head, and a holder or drill guide to receive the rotary surgical instrument. Here in this illustrative example, the rotary surgical instrument and the drill bit or reamer head could be manually positioned at the surgical site S, and then the rotary surgical instrument could be articulated into releasable engagement with the holder or drill guide coupled to the robotic arm 36 to bring the holder or drill guide, the rotary surgical instrument, and the drill bit or reamer head into alignment with the trajectory T maintained by the surgical robot 32. The surgical robot 32 could then drive, guide, position, and/or move a cutting end of the drill bit or reamer head relative to the surgical site S along a linear or nonlinear trajectory T (rotary surgical instrument, chuck assembly, holder/drill guide, and drill bit/reamer head not shown, but generally known in the related art).

As noted above, other configurations beyond the exemplary impactor assemblies 102 and guides 104 are contemplated, and it will be appreciated that the present disclosure is directed toward a number of different types of end effectors 40. However, for the purposes of clarity and consistency, subsequent description of the end effector 40 and the tool 42 will be made in connection with the illustrated embodiments, which are directed toward impacting the prosthesis P at the surgical site S as noted above.

Figure 2:
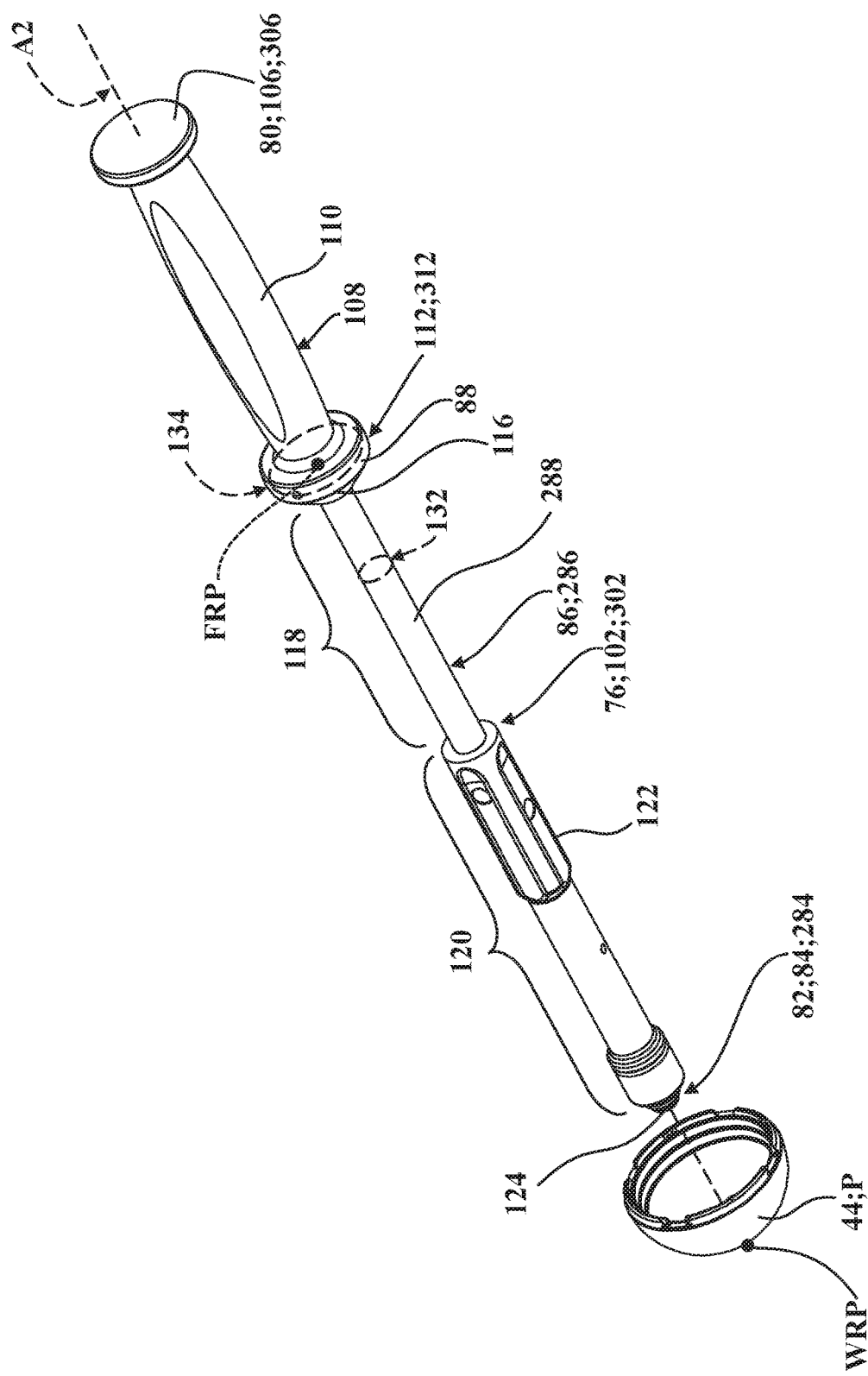
FIG. 2 is an exploded perspective view of the impactor assembly of FIG. 1 shown spaced from the prosthesis.

As is best shown in FIG. 2, the illustrated embodiment of the impactor assembly 102 comprises a head 106 arranged at the proximal end 80 which is configured to receive impact force F. The interface 84 is arranged at the distal end 82 and, in this representative embodiment, is adapted to releasably attach to the prosthesis P. The shaft 86 extends along an impactor axis A1 between the head 106 and the interface 84. The impactor axis A1 is synonymous with the first axis A1 in this embodiment (and in other embodiments described herein). The impactor assembly 102 also comprises an impactor engagement surface 88 disposed between the head 106 and the interface 84. The impactor engagement surface 88 is synonymous with the first engagement surface 88 in this embodiment (and in other embodiments described herein).

Figure 3:
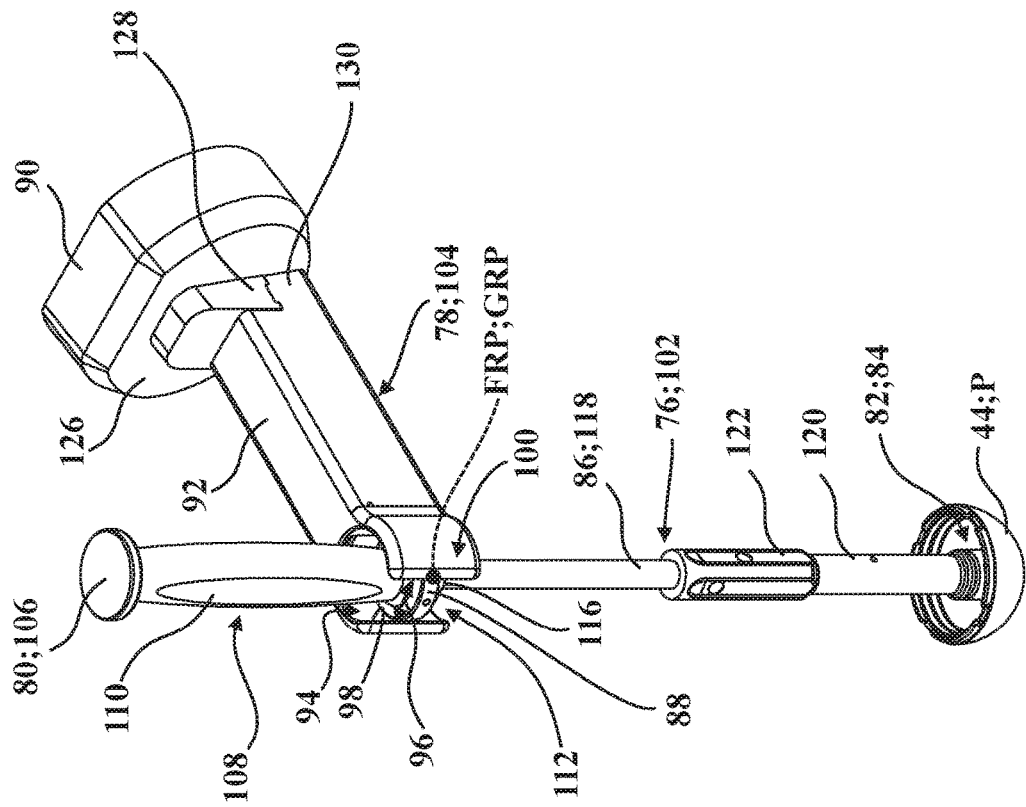
FIG. 3 is a perspective view of the end effector of FIG. 1, shown with the guide supporting the impactor assembly, and with the prosthesis attached to the impactor assembly.
Figure 4:
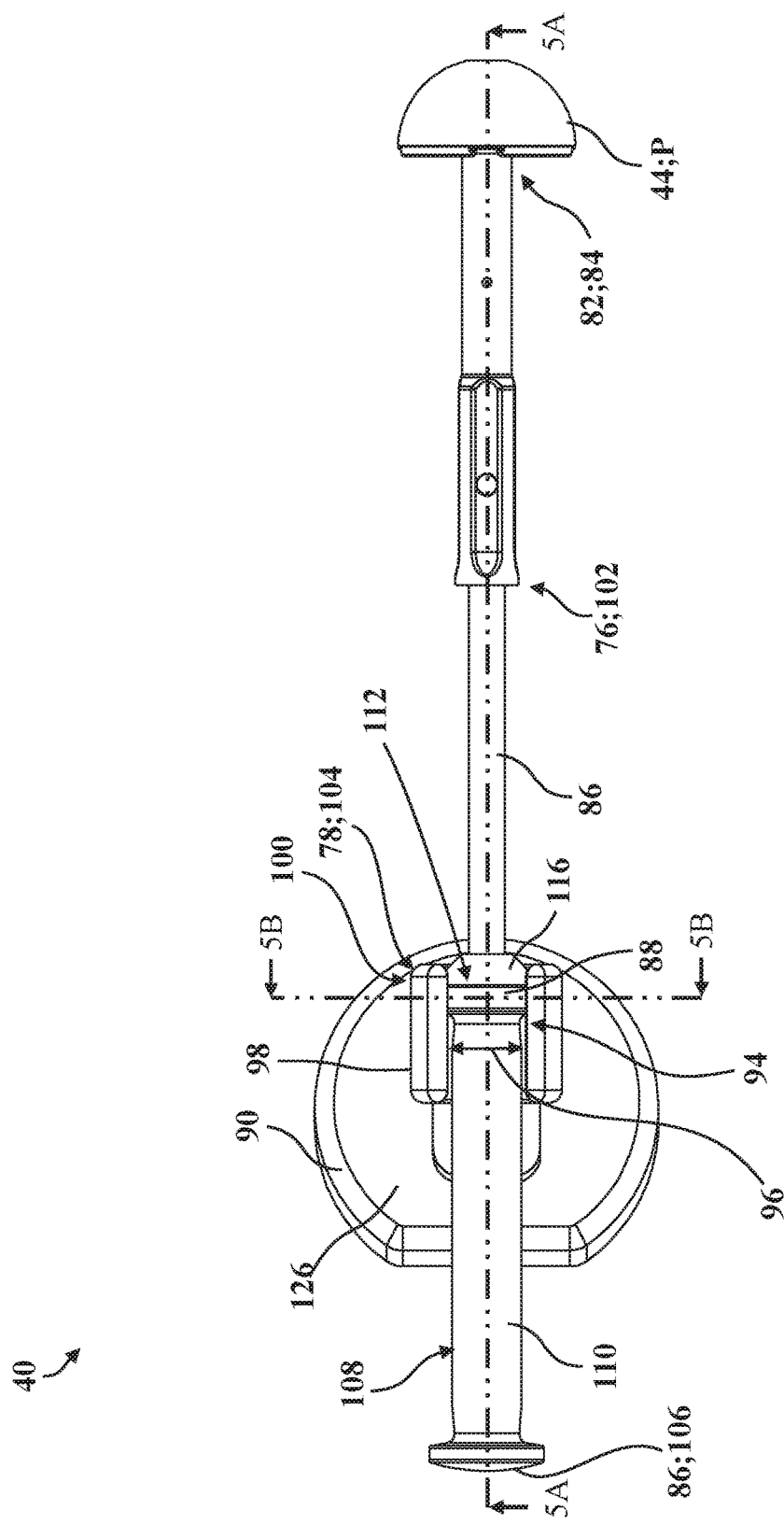
FIG. 4 is a side view of the end effector and the prosthesis of FIG. 3.

Referring to FIG. 3, the illustrated guide 104 generally comprises the mount 90 and the body 92. The mount 90 is adapted to attach to the surgical robot 32 and to couple to the body 92. The channel 94 extends through the body 92 along a guide axis A2 (see FIG. 6). The guide axis A2 is synonymous with the second axis A2 in this embodiment (and in other embodiments described herein). The channel 94 defines the opening 96, which is arranged to receive a portion of the shaft 86 of the impactor assembly 102 therethrough. The guide 104 also comprises a guide engagement surface 98 shaped to abut the impactor engagement surface 88. The guide engagement surface 98 is synonymous with the second engagement surface 98 in this embodiment (and in other embodiments described herein). The guide 104 further comprises the limiter 100, which is configured to maintain abutment of the impactor engagement surface 88 with the guide engagement surface 98. The limiter 100 is further configured to facilitate coaxial alignment of the axes A1, A2 with the trajectory T maintained by the surgical robot 32 during impaction of the prosthesis P at the surgical site S. Each of the components of the end effector 40 and tool 42 introduced above will be described in greater detail below.

Figure 5A:
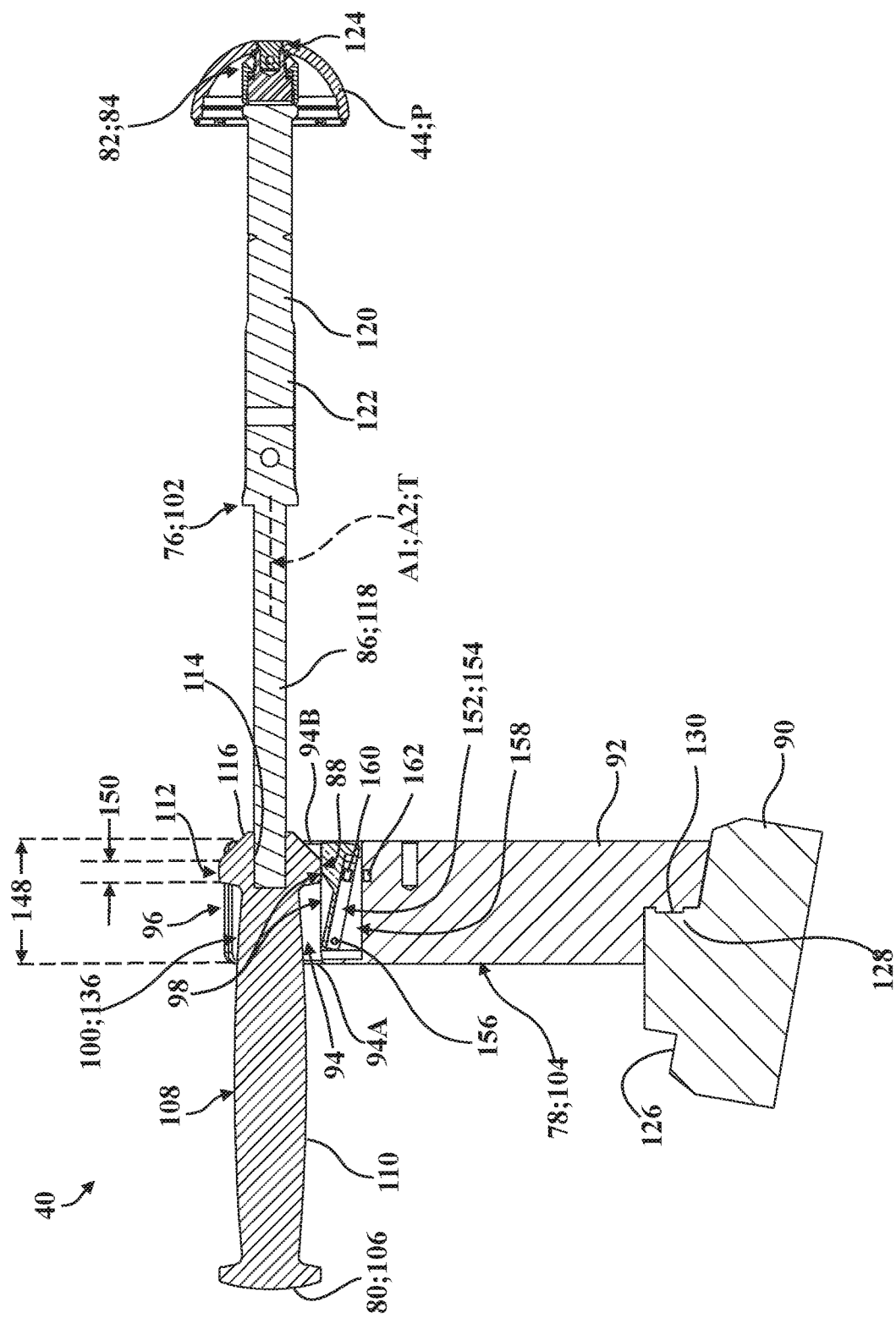
FIG. 5A is a section view taken along line 5A-5A in FIG. 4.
Figure 5B:
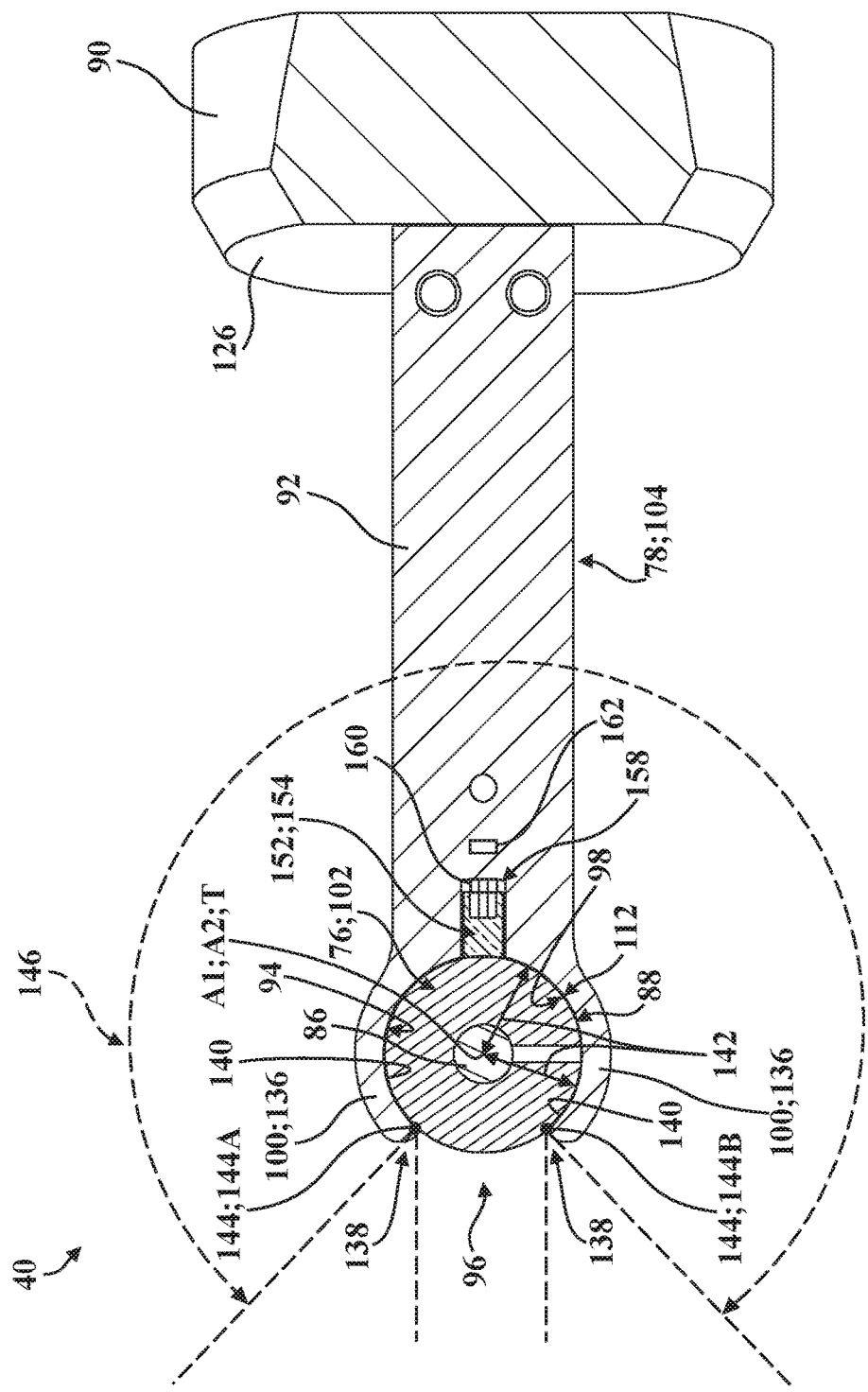
FIG. 5B is a section view taken along line 5B-5B in FIG. 4.

Referring to FIG. 2, the impactor assembly 102 is shown spaced from the prosthesis P along the impactor axis A1 adjacent to the interface 84. As noted above, the impactor assembly 102 generally extends along the impactor axis A1 and comprises the interface 84, the head 106, the shaft 86, and the impactor engagement surface 88. In the illustrated embodiment, the impactor assembly 102 is provided with a handle, generally indicated at 108, which comprises a grip 110 extending between a flange 112 and the head 106. As is best depicted in FIG. 5A, the handle 108 is generally formed as a unitary, one-piece component that defines the head 106, the grip 110, and the flange 112. However, as will be appreciated from the subsequent description below, the handle 108 may be formed as, or otherwise defined by, discrete components that are secured together for concurrent movement. By way of non-limiting example, the grip 110 could be defined by a portion of the shaft 86, and the head 106 and/or the flange 112 could be realized as discrete components that are fixed, attached or secured to, or otherwise formed integrally with the shaft 86. Other configurations are contemplated.

As is best depicted in FIG. 5A, the handle 108 is provided with a blind bore 114 which receives a portion of the shaft 86. Here, the handle 108 is rigidly secured to the shaft 86, such as by a press-fit engagement between the blind bore 114 and the shaft 86. However, it will be appreciated that the handle 108 and the shaft 86 may be operatively attached to each other in a number of different ways, including but not limited to "pinning" the handle 108 to the shaft 86 (e.g., transverse to the impactor axis A1), welding or otherwise bonding the handle 108 and the shaft 86, "shrink-fitting" the handle 108 to the shaft 86, and/or securing the handle 108 to the shaft 86 via corresponding structural features, such as a keyway/key arrangement or a threaded engagement. It is also conceivable that at least a portion of the shaft 86 could be formed integrally with the handle 108, as noted above. Other configurations are contemplated.

In the embodiment depicted in FIG. 5A, the grip 110 of the handle 108 has a generally tapered-cylindrical profile extending along the impactor axis A1 between the head 106 and the flange 112, and is shaped to help the surgeon handle and position the impactor assembly 102 manually. As is described in greater detail below, the head 106 of the impactor assembly 102 is adapted to receive external impact force F, applied such as via a mallet or hammer (not shown), to impact the prosthesis P at the surgical site S. The head 106 has a generally cylindrical profile which is radially-larger than the grip 110. It will be appreciated that this configuration allows the surgeon to safely grasp the grip 110 with one hand and strike the head 106 with a mallet or hammer held in the other hand. The impactor assembly 102 illustrated in FIG. 5A also comprises a taper, generally indicated at 116, which is arranged axially between the flange 112 and the interface 84. The taper 116 has a generally frustoconical profile transitioning between the flange 112 and the shaft 86 to help direct the flange 112 into the channel 94 of the guide 104 in response to contact occurring between the taper 116 and portions of the channel 94 of the guide 104. As is described in greater detail below in connection with FIGS. 9A-9I, contact of the type described above may occur as the guide 104 is moved in a direction away from the surgical site S.

With continued reference to FIG. 5A, the shaft 86 of the impactor assembly 102 extends between the handle 108 and the interface 84 as noted above, and has a generally cylindrical proximal shaft region 118, a distal shaft region 120, and a shaft grip region 122. The proximal shaft region 118 is coupled to the handle 108 and extends into the blind bore 114 adjacent to the flange 112. The distal shaft region 120 is coupled to the interface 84 which, as noted above, is configured to releasably attach to the prosthesis P such that the impactor assembly 102 and the prosthesis P move together when attached. To this end, the interface 84 and the prosthesis P are each provided with a respective threaded engagement, generally indicated at 124 (e.g., internal and external threads), which allows the prosthesis P to be releasably attached to the impactor assembly 102. The distal shaft region 120 also defines the shaft grip region 122 in the illustrated embodiment. As will be appreciated from the subsequent description below, the shaft grip region 122 and the handle 108 help promote ease of handling the impactor assembly 102 manually.

While the interface 84 is formed separately from the shaft 86 and is operatively attached to the distal shaft region 120 in the embodiment illustrated in FIG. 5A, it will be appreciated that the interface 84 and/or the shaft 86 could be configured in a number of different ways without departing from the scope of the present disclosure. By way of non-limiting illustration, while the interface 84 depicted herein is configured to facilitate impacting the prosthesis P at the surgical site S, it is conceivable that a portion of the shaft 86 may define the interface 84 in some embodiments. Other configurations are contemplated.

The shaft grip region 122 of the shaft 86 of the impactor assembly 102 is arranged between the proximal and distal shaft regions 118, 120 of the shaft 86, and has a profile which is shaped to help the surgeon handle and position the impactor assembly 102 manually, such as to approach the surgical site S with the prosthesis P attached to the interface 84. While the proximal shaft region 118, the distal shaft region 120, and the shaft grip region 122 are provided with respectively different shapes and sizes in the illustrated embodiments, it is conceivable that the shaft 86 could comprise a generally cylindrical profile, with a generally constant radius, extending along the impactor axis A1 between the handle 108 and the interface 84. Thus, it will be appreciated that the shaft 86 may be configured without a discrete shaft grip region 122 in some embodiments.

As noted above, the impactor engagement surface 88 of the impactor assembly 102 is shaped and arranged to engage the guide engagement surface 98 of the guide 104. As will be appreciated from subsequent description of the embodiments of the end effector 40 below, the impactor engagement surface 88 can be defined by different parts of the impactor assembly 102 to correspond with different embodiments and/or configurations of the guide 104 and/or the guide engagement surface 98. Specifically, the impactor engagement surface 88 is defined by the flange 112 of the impactor assembly 102 when used in connection with the first embodiment of the guide 104 illustrated in FIGS. 3-9N, whereas the impactor engagement surface 88 is defined by a portion of the proximal shaft region 118 of the shaft 86 when used in connection with the second embodiment of the guide and illustrated in FIGS. 10-15C. While embodiments of impactor assemblies 102 illustrated herein can generally be used interchangeably with embodiments of guides 104 illustrated herein, it will be appreciated that certain impactor assemblies 102 could be configured to engage only certain guides 104 in some embodiments. Other configurations are contemplated.

Figure 6:
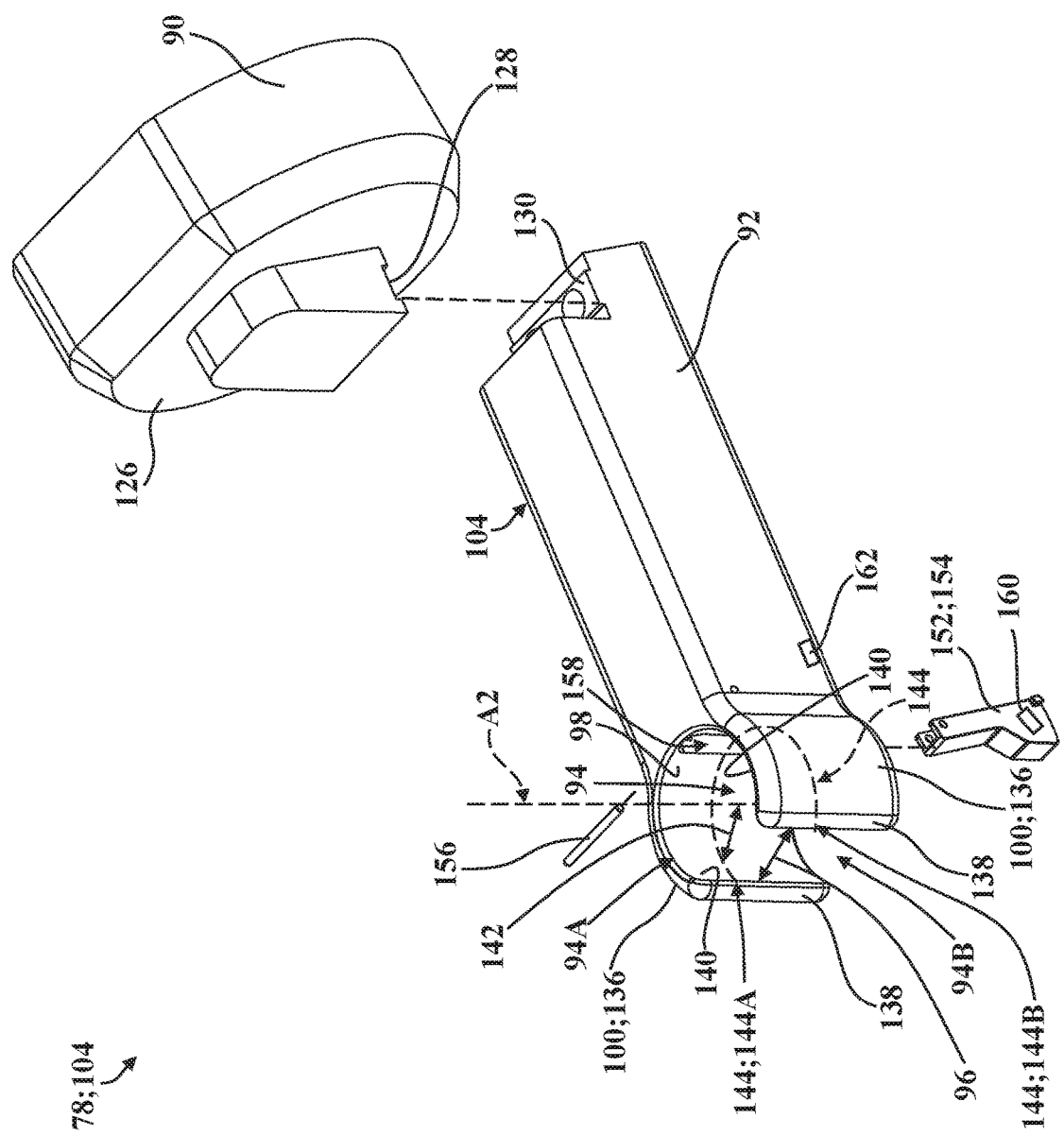
FIG. 6 is an exploded perspective view of the guide of FIGS. 3-5B.

Referring now to FIGS. 1-15C, as noted above, the guide 104 of the end effector 40 is provided with the mount 90 to facilitate releasable attachment to the coupling 38 of the robotic arm 36 of the surgical robot 32 such that the robotic arm 36 can move, drive, maintain, and/or otherwise control the position and/or orientation of the end effector 40 and, thus, the tool 42. In the representative embodiments illustrated herein, and as is best depicted in FIGS. 5A, 6, and 7, the mount 90 comprises a mount plate 126 which is adapted to releasably attach to the coupling 38 either directly or indirectly (see FIG. 1; attachment not shown in detail). The mount 90 is also provided with a receiver 128 operatively attached to the mount plate 126. The receiver 128 is adapted to receive and secure to a brace 130 formed in the body 92 (see FIGS. 6-7). The channel 94 and the brace 130 are formed at opposing ends of the body 92 of the guide 104. In some embodiments, the receiver 128 of the mount 90 and the brace 130 of the body 92 are shaped so as to interlock or otherwise align to each other such that the mount 90 and the body 92 of the guide 104 can be secured together in alignment, such as with fasteners (not shown). However, it will be appreciated that the guide 104 can be configured in a number of different ways sufficient to attach to the coupling 38 of the surgical robot 32. By way of non-limiting example, rather than securing the receiver 128 of the body 92 to the brace 130 of the mount 90 with fasteners, the body 92 and the mount 90 could be formed as a unitary component or could be fixed together in other ways, such as via welding. Other configurations are contemplated.

As noted above, in certain embodiments of the guide 104, the channel 94 is formed in or otherwise defined by the body 92 of the guide 104 and extends along the guide axis A2 to define the opening 96 which, in turn, is arranged to receive a portion of the shaft 86 of the impactor assembly 102 therethrough. Moreover, when used in connection with the first embodiment of the guide 104 depicted in FIGS. 3-9N, the impactor engagement surface 88 is defined by the flange 112 of the impactor assembly 102 as noted above. Thus, in the embodiment illustrated in FIGS. 3-9N, the guide engagement surface 98 of the guide 104 is shaped and arranged to abut the flange 112 and cooperates with the limiter 100 to maintain alignment of the impactor axis A1 and the guide axis A2 along the trajectory T maintained by the surgical robot 32.

Referring specifically now to the embodiment illustrated in FIGS. 3-8C, the opening 96 of the guide 104 is arranged to permit the shaft 86 of the impactor assembly 102 to pass therethrough when the guide 104 is disposed between the flange 112 and the interface 84 of the impactor assembly 102 (see FIGS. 8A-8C) so as to facilitate bringing the impactor axis A1 into alignment with the guide axis A2. As is depicted with phantom lines in FIG. 2, the shaft 86 of the impactor assembly 102 has a first perimeter 132, and the flange 112 of the impactor assembly 102 has a second perimeter 134 which is larger than the first perimeter 132. Put differently, the flange 112 is larger than the shaft 86 and cannot pass through the opening 96 of the guide 104, but the shaft 86 is sized so as to be able to pass through the opening 96 when the guide 104 as the impactor assembly 102 is pivoted about the surgical site S to move the shaft 86 through the opening 96, as is described in greater detail below in connection with FIGS. 9A-9I.

As noted above, the limiter 100 of the guide 104 is configured to maintain abutment between the impactor engagement surface 88 and the guide engagement surface 98 during impaction, and helps facilitate achieving coaxial alignment of the axes A1, A2 with the trajectory T maintained by the surgical robot 32. To this end, the limiter 100 of the embodiment depicted in FIGS. 3-8C comprises a pair of fingers, generally indicated at 136, disposed adjacent to the channel 94. The fingers 136 extend from the body 92 of the guide 104 to respective finger ends 138 spaced from each other so as to define the opening 96 therebetween (see FIG. 5B). The fingers 136 also each define a respective arc-shaped surface, generally indicated at 140. The arc-shaped surfaces 140 are arranged to contact the flange 112 of the impactor assembly 102 when the guide engagement surface 98 abuts the impactor engagement surface 88, which maintains abutment of the impactor engagement surface 88 with the guide engagement surface 98 and limits movement of the impactor assembly 102 relative to the guide 104 as described below.

The arc-shaped surfaces 140 of the limiter 100 are substantially continuous with the guide engagement surface 98 of the guide 104, and both the guide engagement surface 98 and the arc-shaped surfaces 140 are defined by the channel 94 in this embodiment. More specifically, and as is best depicted in FIG. 5A, the arc-shaped surface 140 of the limiter 100 and the guide engagement surface 98 of the guide 104 are each spaced from the guide axis A2 at a common radius 142 such that the channel 94 has a continuous and generally cylindrical, C-shaped profile, and defines both the guide engagement surface 98 and the arc-shaped surfaces 140. Furthermore, the portions of the guide 104 which define the guide engagement surface 98 and the arc-shaped surfaces 140 of the limiter 100 cooperate to define a common arc 144 having first and second arc ends 114A, 114B. The first and second arc ends 114A, 114B are radially spaced from each other about the guide axis A2 at an arc reference angle 146 greater than 180-degrees (see FIG. 5B). As will be appreciated from the subsequent description below in connection with FIGS. 9A-9I, this configuration allows the flange 112 of the impactor assembly 102 to rotatably engage the channel 94 of the guide 104 such that the impactor assembly 102 can be rotated about the axes A1, A2 while, at the same time, helping to facilitate achieving coaxial alignment of the axes A1, A2 with the trajectory T maintained by the surgical robot 32. Similarly, this arrangement also allows the guide 104 to rotate relative to the impactor assembly 102 about the axes A1, A2.

As noted above, the surgical robot 32 is configured to position the end effector 40 with respect to the surgical site S and to maintain the trajectory T which, in the illustrated embodiments, is generally linear and is aligned with the axes A1, A2, to allow the tool 42 (e.g., the impactor assembly 102) to be correspondingly positioned along the trajectory T. Here, external impact force F applied to the head 106 of the impactor assembly 102 translates through the impactor assembly 102 and to the prosthesis P which, in turn, causes the prosthesis P to advance along the trajectory T toward the surgical site S. While the process of impacting the prosthesis P is described in greater detail below in connection with FIGS. 9A-9I, it will be appreciated that maintaining the trajectory T may involve the surgical robot 32 restricting all or certain types of movement of the guide 104 relative to the surgical site S in certain conditions, and/or may involve limiting or directing movement of the guide 104 into translation along the trajectory T relative to the surgical site S in some embodiments. The surgical robot 32 may permit the surgeon to translate the guide 104 along the trajectory T to, among other things, facilitate passing the shaft 86 of the impactor assembly 102 through the opening 96 of the guide 104 (see FIGS. 8A-8C), as noted above. It will be appreciated that certain steps of surgical procedures may involve controlling the surgical robot 32 in different ways.

Depending on the type of surgical procedure being performed and the specific configuration of the surgical robot 32, movement of the end effector 40 via the robotic arm 36 may be effected via admittance control in order to, among other things, allow the surgeon to touch or otherwise engage against different parts of the robotic arm 36 to move them in certain directions during certain operational conditions. Put differently, when utilizing admittance control, the surgical robot 32 may be configured to interpret external force (e.g., determined via a force-torque sensor) an input that is used to control the robotic arm 36. Thus, it will be appreciated that proper application of impact force F to the head 106 of the impactor assembly 102 results in axial movement of the impactor assembly 102 relative to the guide 104 without translating significant amounts of force into the guide 104 which might otherwise cause the surgical robot 32 to move the guide 104 off of the trajectory T or in a way that brings the engagement surface 98 out of abutment with the impactor engagement surface 88.

In order to prevent inadvertent movement of the guide 104 along the trajectory T during the process of applying external impact force F to the head 106 of the impactor assembly 102, the illustrated embodiments of the end effector 40 are generally configured to permit rotation of the impactor assembly 102 relative to the guide 104, and/or vice-versa. This relative rotation is achieved by bearing-type contact (e.g., sliding contact) occurring between the impactor engagement surface 88 and the guide engagement surface 98.

In the first embodiment illustrated in FIGS. 3-8C, the flange 112 has a generally spherical profile which defines the impactor engagement surface 88, and the channel 94 has a generally cylindrical profile which defines the guide engagement surface 98 as noted above. This arrangement allows the flange 112 rotate within the channel 94 during impaction, which helps prevent translating impact forces to the surgical robot 32. This arrangement also allows the flange 112 to translate along the channel 94 in order to facilitate impaction of the prosthesis P at the surgical site S without compromising the coaxial alignment of the axes A1, A2 with respect to the trajectory T maintained by the surgical robot 32. Put differently, this configuration allows impact force F applied to the head 106 of the impactor assembly 102 to translate into axial movement of the flange 112 along the channel 94 without restricting rotation of the impactor assembly 102 that might otherwise cause lateral force to translate to and cause movement of the guide 104 along the trajectory T while, at the same time, maintaining coaxial alignment of the impactor axis A1 with the guide axis A2 and with the trajectory T maintained by the surgical robot 32. Moreover, and as will be appreciated from the subsequent description of FIGS. 9J-9N below, this configuration also allows pivoting to occur between the flange 112 and the channel 94 when the surgical robot 32 brings the axes A1, A2 into coaxial alignment with each other and with the trajectory T defined by the intended location of the impacted prosthesis P, which may be advantageous in situations where it could otherwise be impractical to initially align the guide axis A2 coaxially with the trajectory T, and/or where the robotic arm 36 needs to be articulated prior to impaction in certain directions or positioned in certain ways which require that the guide axis A2 be moved off of the trajectory T.

As noted above, the guide engagement surface 98 of the guide 104 and the impactor engagement surface 88 of the impactor assembly 102 are shaped so as to allow relative rotation therebetween by bearing against each other such that the impactor assembly 102 can rotate relative to the guide 104. However, it is conceivable that rotation of the impactor assembly 102 described above could be achieved where the guide engagement surface 98 and the impactor engagement surface 88 do not necessarily bear against each other to facilitate rotation. By way of non-limiting example, it is conceivable that abutment between the impactor engagement surface 88 and the guide engagement surface 98 could be static in some embodiments, achieved such as with a splined, keyed, or other arrangement which prevents rotation, and the impactor assembly 102 could comprise a bearing or spherical joint (not shown) disposed between the shaft 86 and the impactor engagement surface 88 to facilitate rotation of the shaft 86 relative to the impactor engagement surface 88 about the impactor axis A1. Other configurations are contemplated.

As noted above, the prosthesis P and the impactor assembly 102 necessarily translate along the trajectory T as impact force F is applied to the head 106 of the impactor assembly 102. Thus, it will be appreciated that the guide 104 and the impactor assembly 102 are configured so as to ensure that abutment between the impactor engagement surface 88 and the guide engagement surface 98 is maintained as the flange 112 moves within the channel 94 (e.g., as the surgeon successively strikes the head 106 with a mallet). To this end, and in the embodiment of the guide 104 depicted in FIGS. 3-8C, the channel 94 of the guide 104 extends between first and second axial channel ends 94A, 94B which are spaced from each other along the guide axis A2 at a channel depth 148. The channel depth 148 is greater than a flange thickness 150 of the flange 112, which is defined axially between the taper 116 and the grip 110 of the handle 108 in this embodiment (see FIG. 5A). Because the flange 112 has a generally spherical profile as noted above, only a portion of the flange 112 which defines the impactor engagement surface 88 actually engages the cylindrical channel 94 when the guide engagement surface 98 abuts the impactor engagement surface 88. Thus, it will be appreciated that the channel depth 148 is advantageously large enough to ensure that the flange 112 can be readily positioned within the channel 94 and can remain in abutment with the channel 94 during impaction. However, and as is described in greater detail below, maintaining abutment between the guide engagement surface 98 and the impactor engagement surface 88 can be achieved in other ways, such as by advancing the guide 104 along the trajectory T and toward the surgical site S with the surgical robot 32 during impaction. Other configurations are contemplated.

In some embodiments, the end effector 40 further comprises a sensor (or, "sensor subassembly"), generally indicated at 152, which is coupled to the guide 104 and is configured to determine engagement of the impactor assembly 102 relative to the channel 94. Here, the sensor 152 may be used to determine a relative axial position of the flange 112 of the impactor assembly 102 between the first axial channel end 94A and the second axial channel end 94B, such as to facilitate "tracking" movement of the prosthesis P along the trajectory T during impaction at the surgical site S based on corresponding to changes in the axial position of the flange 112 along the channel 94 as determined by the sensor 152.

As will be appreciated from the subsequent description below, the sensor 152 can also be employed to determine the presence (or lack thereof) of the impactor assembly 102 within the channel 94 which, under certain conditions, can be used to change how the surgical robot 32 is controlled. By way of non-limiting example, the surgical robot 32 could be controlled in certain ways when the sensor 152 determines that no portion of the impactor assembly 102 is disposed within the channel 94 of the guide 104, but could be controlled differently when the sensor 152 determines that the shaft 86 has been brought through the opening 96 and into the channel 94 in order to, among other things, help promote proper articulation of the robotic arm 36 as the axes A1, A2 are brought into coaxial alignment with each other and with the trajectory T. Furthermore, for example, by knowing the relative position of the flange 112 between the axial channel ends 94A, 94B, the surgical robot 32 can ensure that there is consistent engagement between the impactor engagement surface 88 and the guide engagement surface 98 during movement of the guide 104 which pivots the impactor assembly 102 about the surgical site S and results in lateral translation of the flange 112 relative to the trajectory T as the axes A1, A2 are moved toward and/or away from the trajectory T. Furthermore, and as is described in greater detail below in connection with the embodiments illustrated in FIGS. 16A-28B, the sensor 152 can also be utilized to facilitate advancing the guide 104 along the trajectory T during impaction (e.g., by sensing movement of the flange 112 following the application of impact force F to the head 106). Other configurations are contemplated.

In the embodiment illustrated in FIG. 7, the sensor 152 is disposed in communication with a trigger 154 which, in turn, is rotatably supported by a pin 156 that is coupled to the body 92 of the guide 104 adjacent to the channel 94. More specifically, the trigger 154 is disposed within a trigger aperture 158 arranged adjacent to the channel 94, and the trigger 154 has a tapered profile that is shaped so as to come into abutment with the flange 112. The trigger 154 may be biased at least partially into the channel 94 by a spring or other biasing element (not shown here), and may contact different portions of the impactor assembly 102 to determine relative movement and/or positioning of the impactor assembly 102, as described in greater detail below.

Figure 8A:
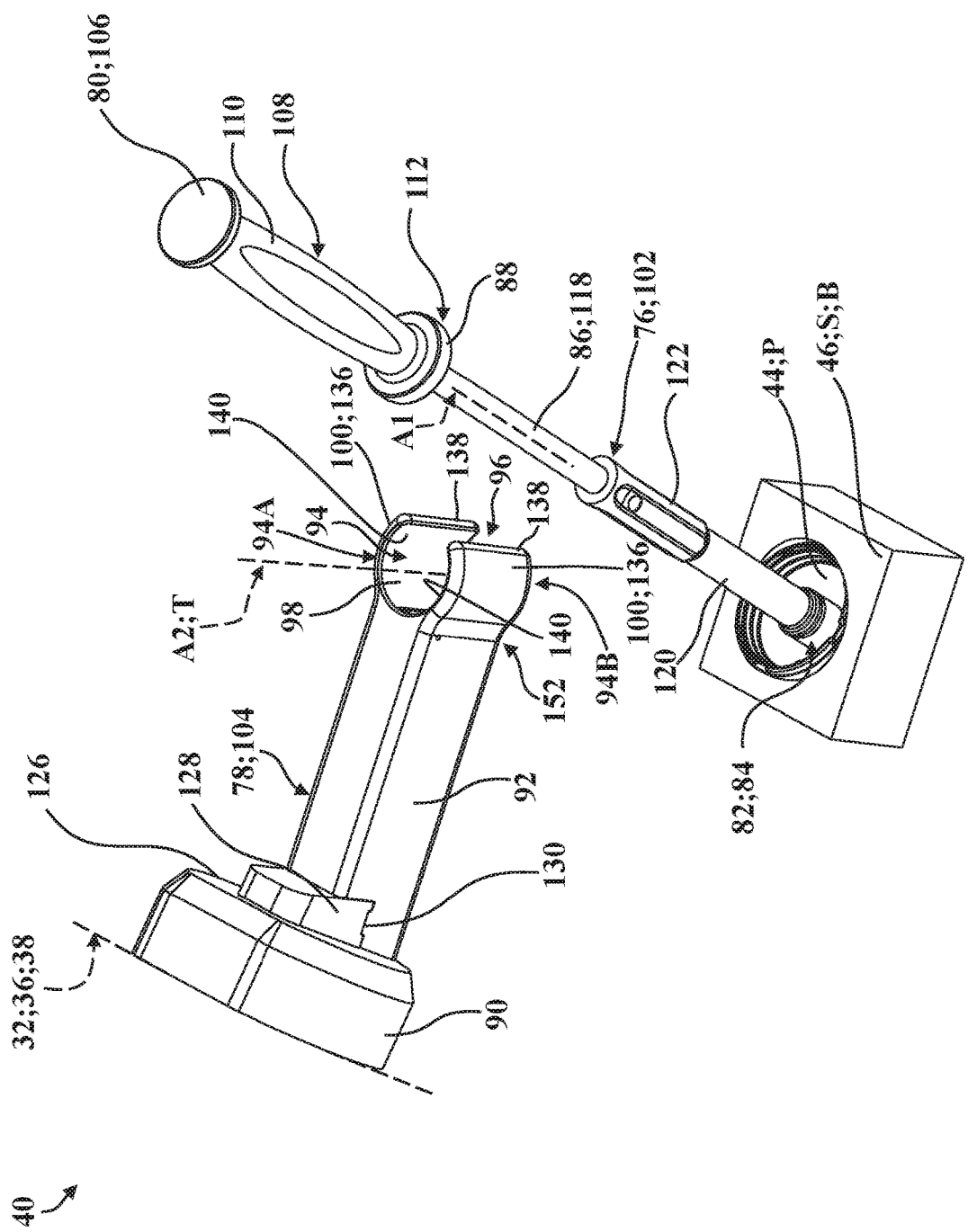
FIG. 8A is a perspective view of the end effector and the prosthesis of FIGS. 3-5B, shown with the prosthesis arranged at a generically-illustrated surgical site, and with the impactor assembly attached to the prosthesis and articulated away from the guide.
Figure 8B:
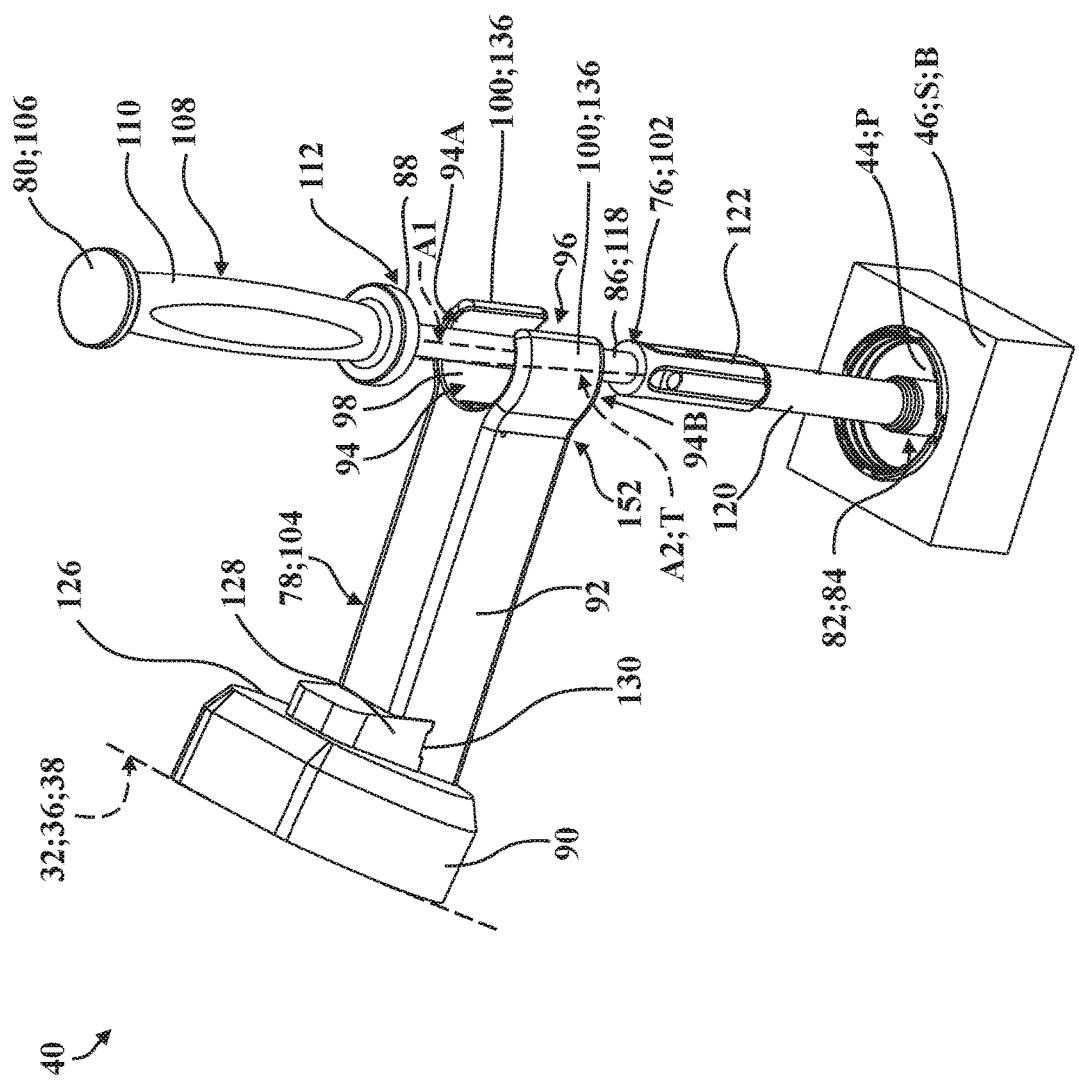
FIG. 8B is another perspective view of the end effector, the prosthesis, and the surgical site of FIG. 8A, shown with the impactor assembly articulated into the guide.

In some embodiments, when the shaft 86 passes through the opening 96 of the guide 104 as depicted in FIGS. 8A-8B, the trigger 154 may contact the shaft 86 such that the sensor 152 acts like a "switch" indicating that the shaft 86 is positioned within the channel 94. Determining the presence of the shaft 86 within the channel 94 could then be used to facilitate controlling the surgical robot 32 in particular ways or in particular modes, such as to allow the surgeon to subsequently move the guide 104 along the trajectory T in order to advance the flange 112 into the channel 94. In addition or alternatively, the sensor 152 may be configured to determine a relative position of the trigger 154 with respect to the body 92 of the guide 104, such that the trigger 154 moves in response to contact with the flange 112 of the impactor assembly 102 as the flange 112 travels between the first and second axial channel ends 94A, 94B. Put differently, the trigger 154 and/or sensor 152 could be configured to act as a "contact switch" and/or as a "displacement sensor" in certain embodiments.

Thus, it will be appreciated that the sensor 152 and/or the trigger 154 can be of a number of different configurations, types, arrangements, and the like, without departing from the scope of the present disclosure. By way of non-limiting example, and as is depicted schematically in FIG. 5A, the sensor 152 could comprise an emitter 160 coupled to the trigger 154 for concurrent movement, and a detector 162 coupled to the body 92 of the guide 104 and configured to respond to changes in the position of the emitter 160. Alternatively, the sensor 152 could comprise a rotary potentiometer interposed between the trigger 154 and the pin 156 (not shown). Furthermore, rather than relying on movement of the trigger 154 in response to physical contact with the impactor assembly 102, the sensor 152 could instead be configured as a hall-effect sensor, a proximity sensor, an optical sensor, and the like, so as to sense the proximity and/or relative position of any suitable portion of the impactor assembly 102 relative to the guide 104 without necessitating physical contact. Other configurations are contemplated, and additional sensor arrangements are described in greater detail below in connection with FIGS. 16A-28B.

Figure 9A:
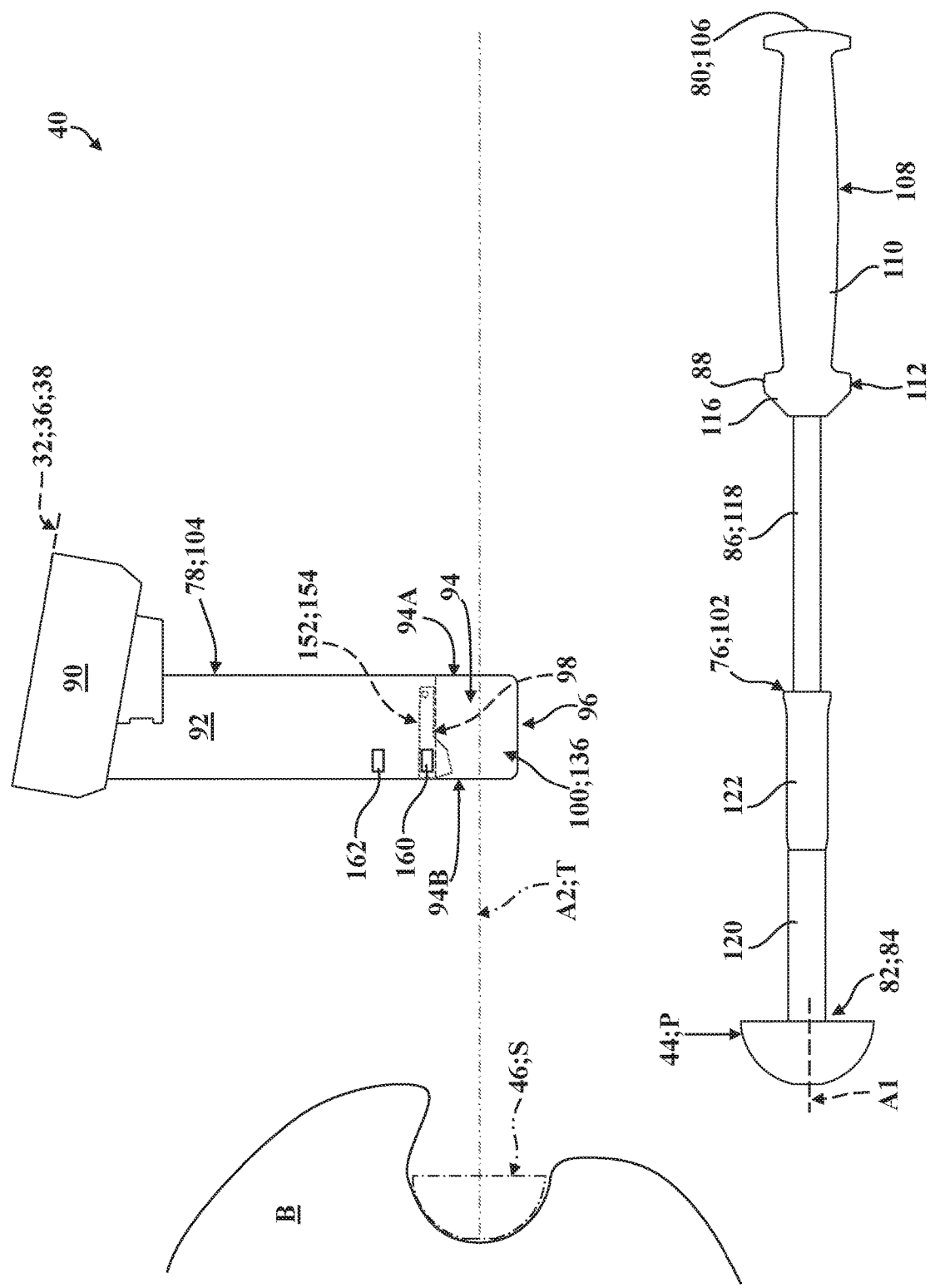
FIG. 9A is an illustrative schematic view of the prosthesis and the end effector of FIGS. 8A-8C, shown with the guide defining a guide axis aligned with a surgical site and arranged for movement along a trajectory, and shown with the impactor assembly attached to the prosthesis and spaced from both the surgical site and the guide.

Referring now to FIGS. 9A-9I, certain steps for utilizing the illustrated end effector 40 to impact the prosthesis P into the surgical site S are shown sequentially. In FIG. 9A, the mount 90 and the guide 104 of the end effector 40 are positioned adjacent to the surgical site S, with the guide axis A2 aligned to the trajectory T. In the illustrated embodiments, the trajectory T is defined by the surgical site S based on the intended position of the prosthesis P after being implanted into the acetabulum (intended position shown in phantom in FIG. 9A), as noted above. Moreover, both the trajectory T and the intended position of the prosthesis P are monitored, known, or otherwise determined by the surficial robot 32, such as with various combinations of trackers, sensors, cameras, and the like. For the purpose of clarity, the guide 104 is initially positioned in FIG. 9A such that the guide axis A2 is coaxially aligned with the trajectory T which, in turn, is defined by the intended position of the prosthesis P. However, it will be appreciated that the forgoing scenario is illustrative, and the trajectory T can be defined, determined, or otherwise set in a number of different ways. Specifically, and as will be appreciated from the subsequent description of FIGS. 9J-9N below, the guide 104 could be initially positioned such that the guide axis A2 is not necessarily coaxial with the trajectory T.

Figure 9B:
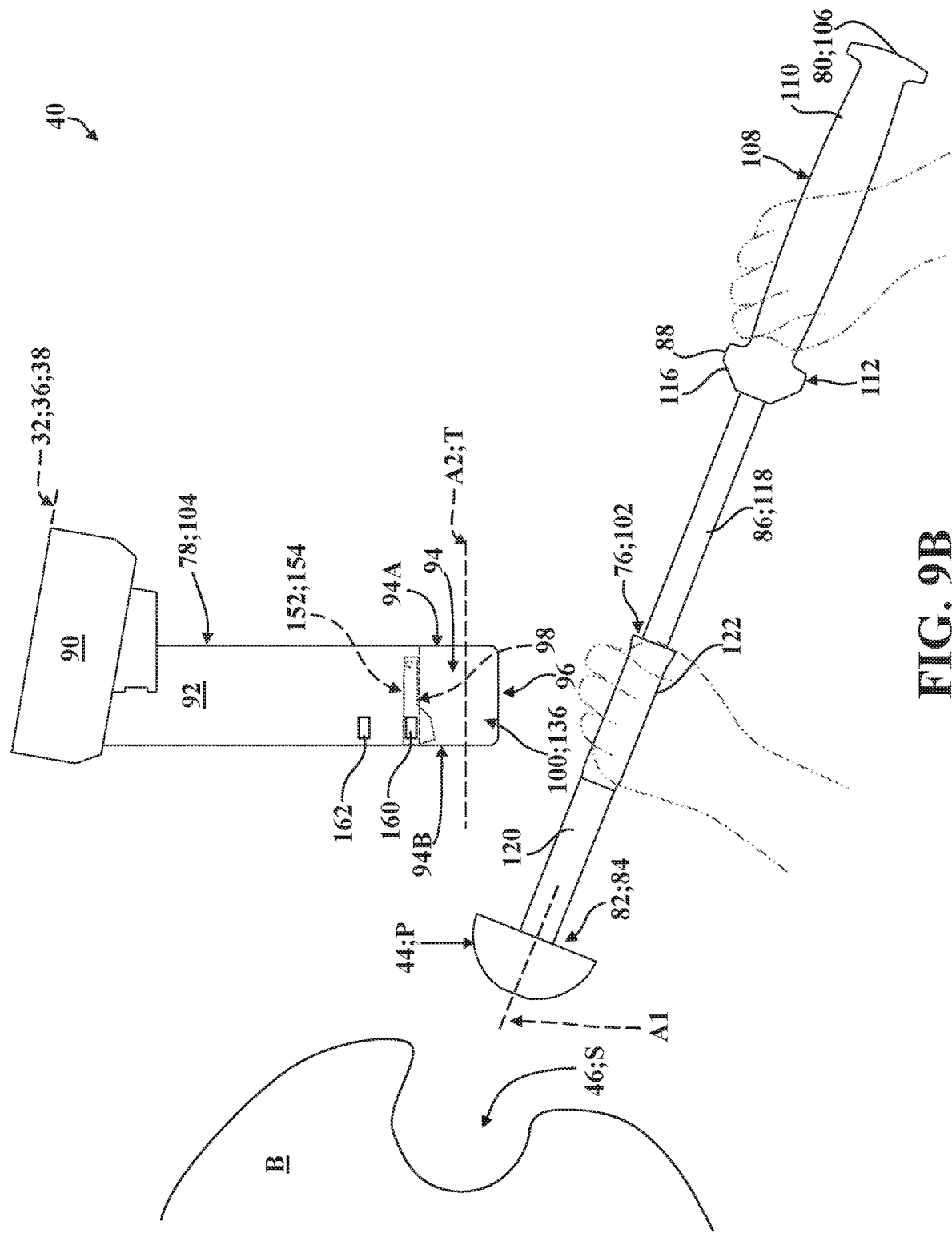
FIG. 9B is another illustrative schematic view of the end effector, the prosthesis, and the surgical site of FIG. 9A, shown with the prosthesis and the impactor assembly positioned adjacent to the surgical site.
Figure 9C:
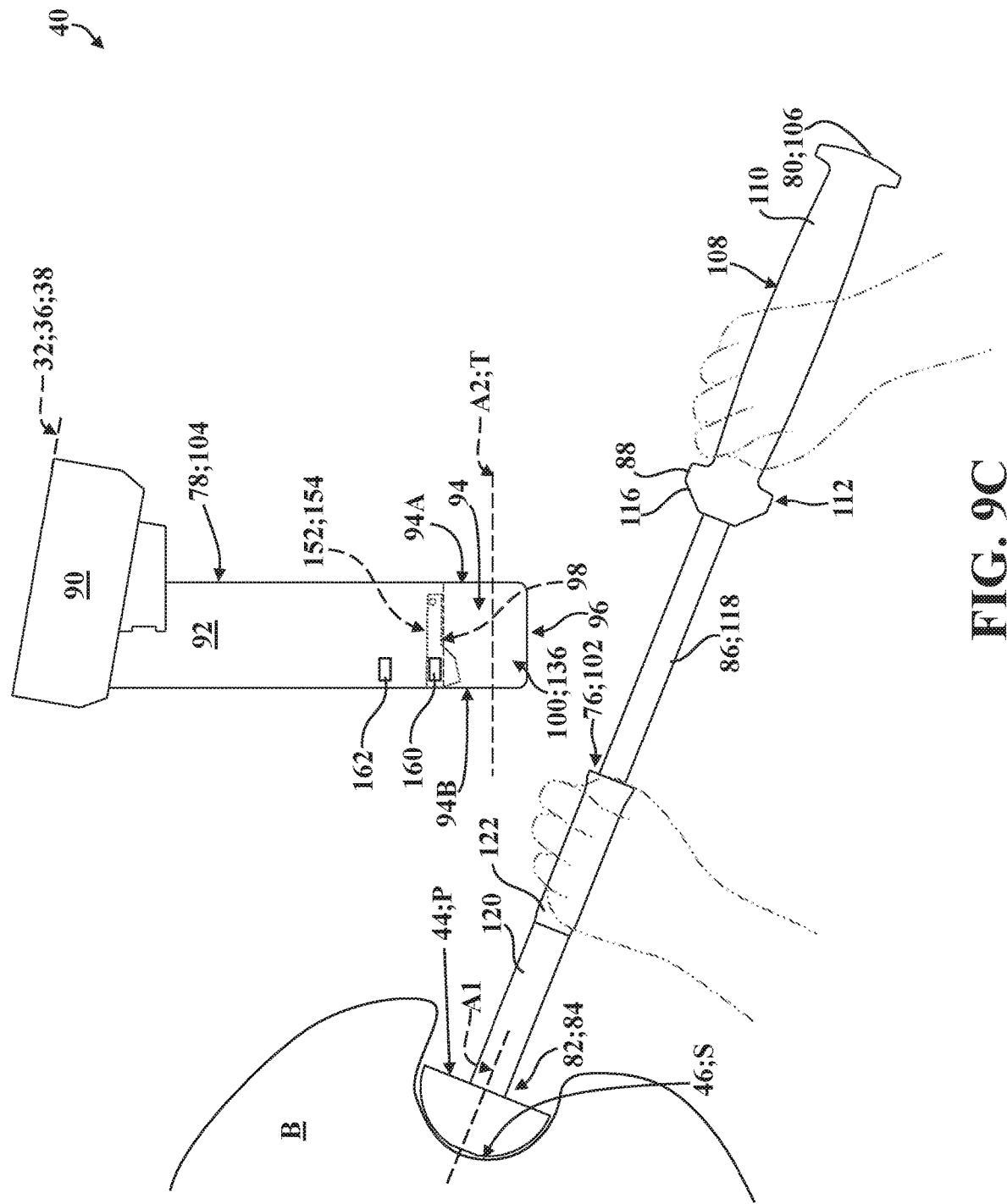
FIG. 9C is another illustrative schematic view of the end effector, the prosthesis, and the surgical site of FIGS. 9A-9B, shown with the prosthesis positioned at the surgical site.
Figure 9D:
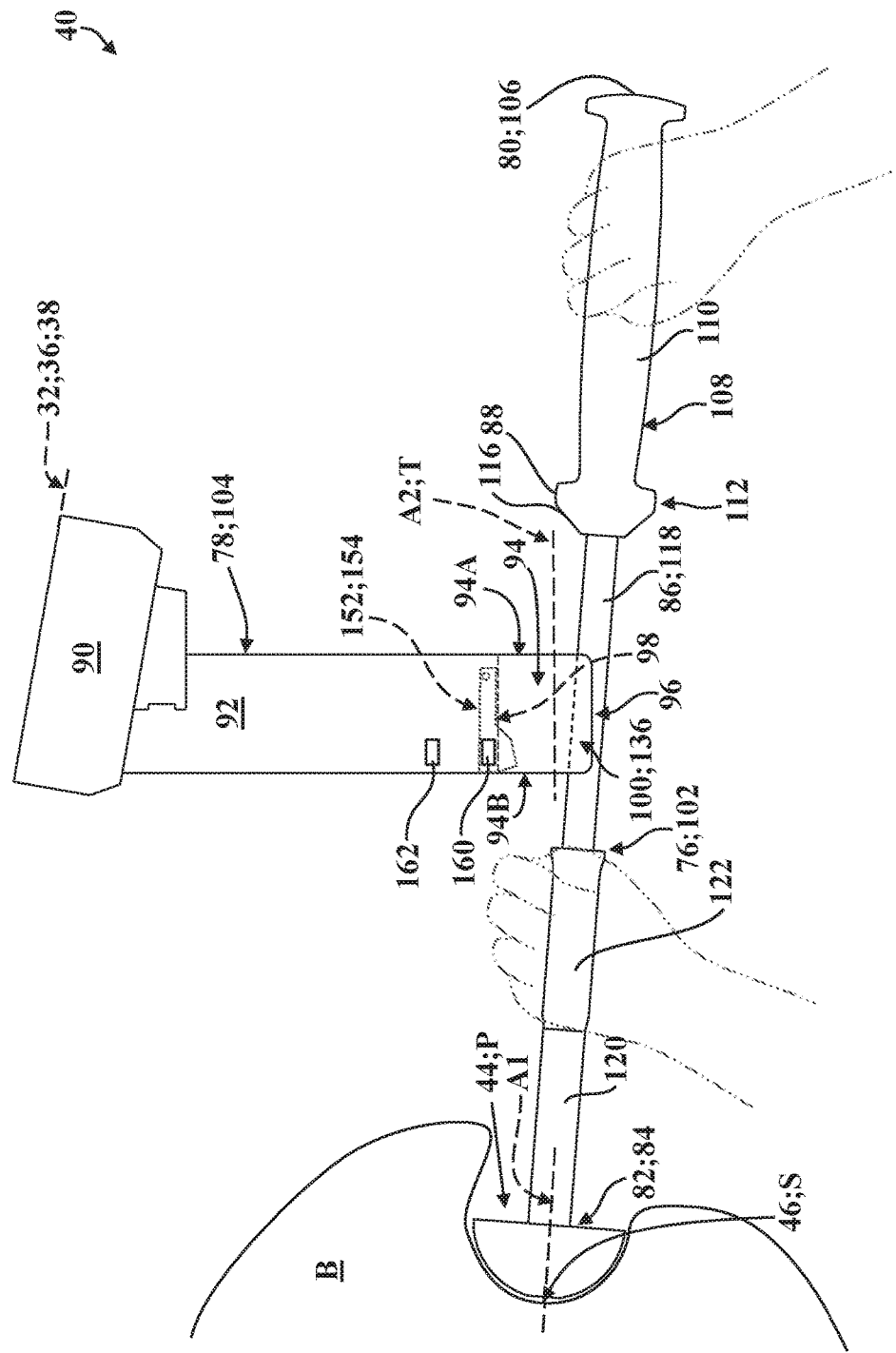
FIG. 9D is another illustrative schematic view of the end effector, the prosthesis, and the surgical site of FIGS. 9A-9C, shown with the prosthesis and the impactor assembly articulated partially into the guide.
Figure 9E:
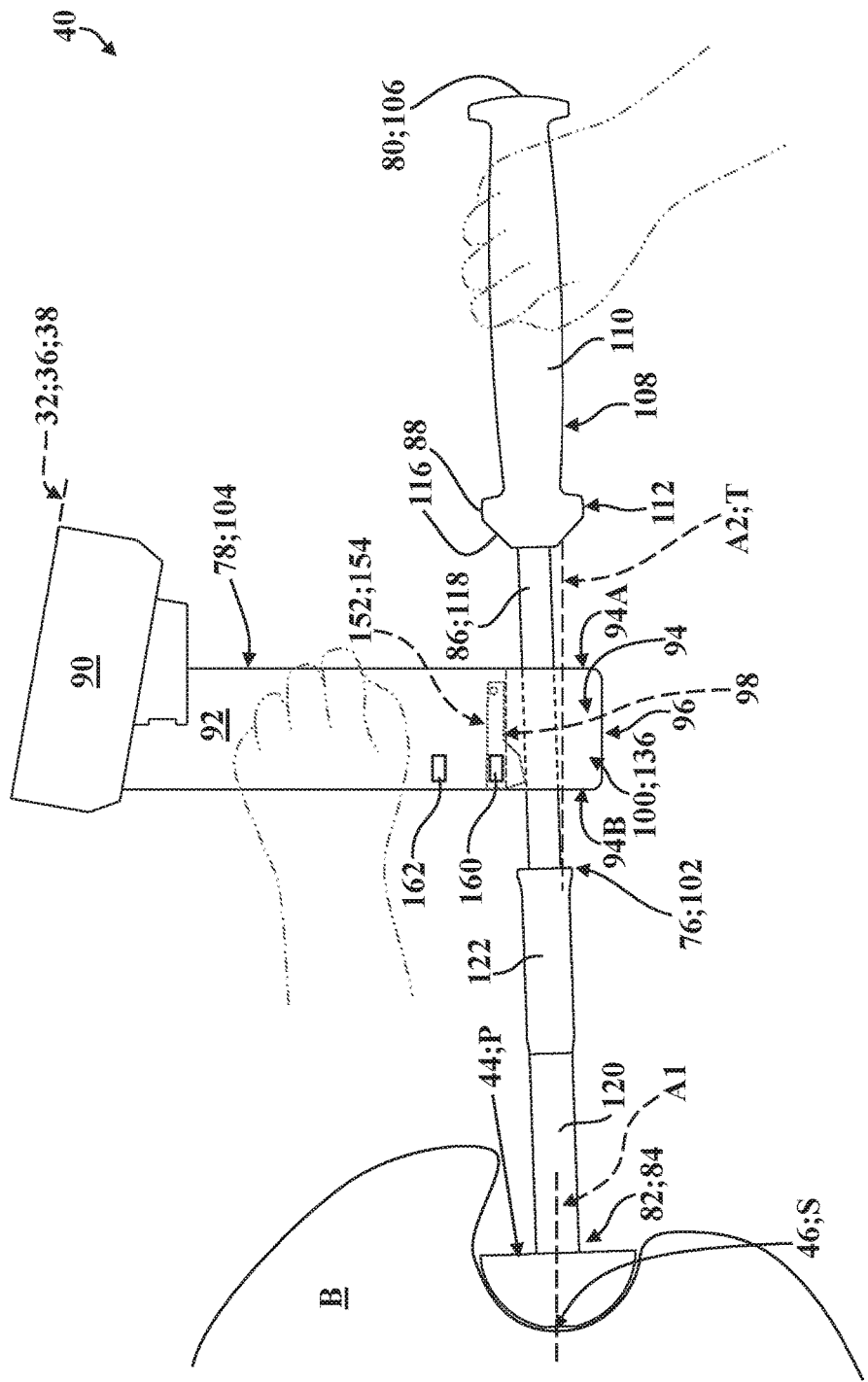
FIG. 9E is another illustrative schematic view of the end effector, the prosthesis, and the surgical site of FIGS. 9A-9D, shown with the prosthesis and the impactor assembly articulated further into the guide.
Figure 9F:
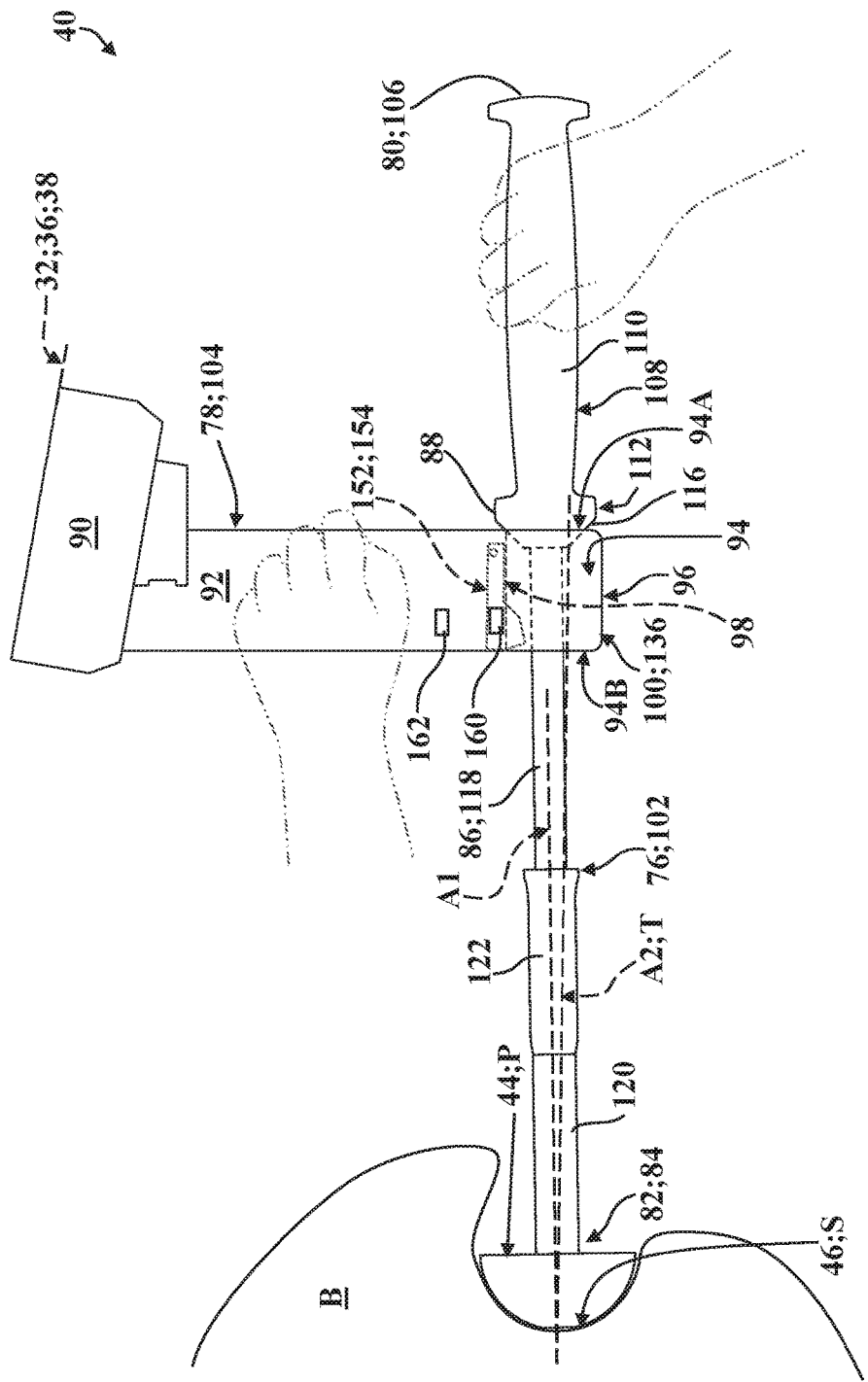
FIG. 9F is another illustrative schematic view of the end effector, the prosthesis, and the surgical site of FIGS. 9A-9E, shown with the guide moved away from the surgical site along the trajectory and engaging a taper of the impactor assembly.
Figure 9H:
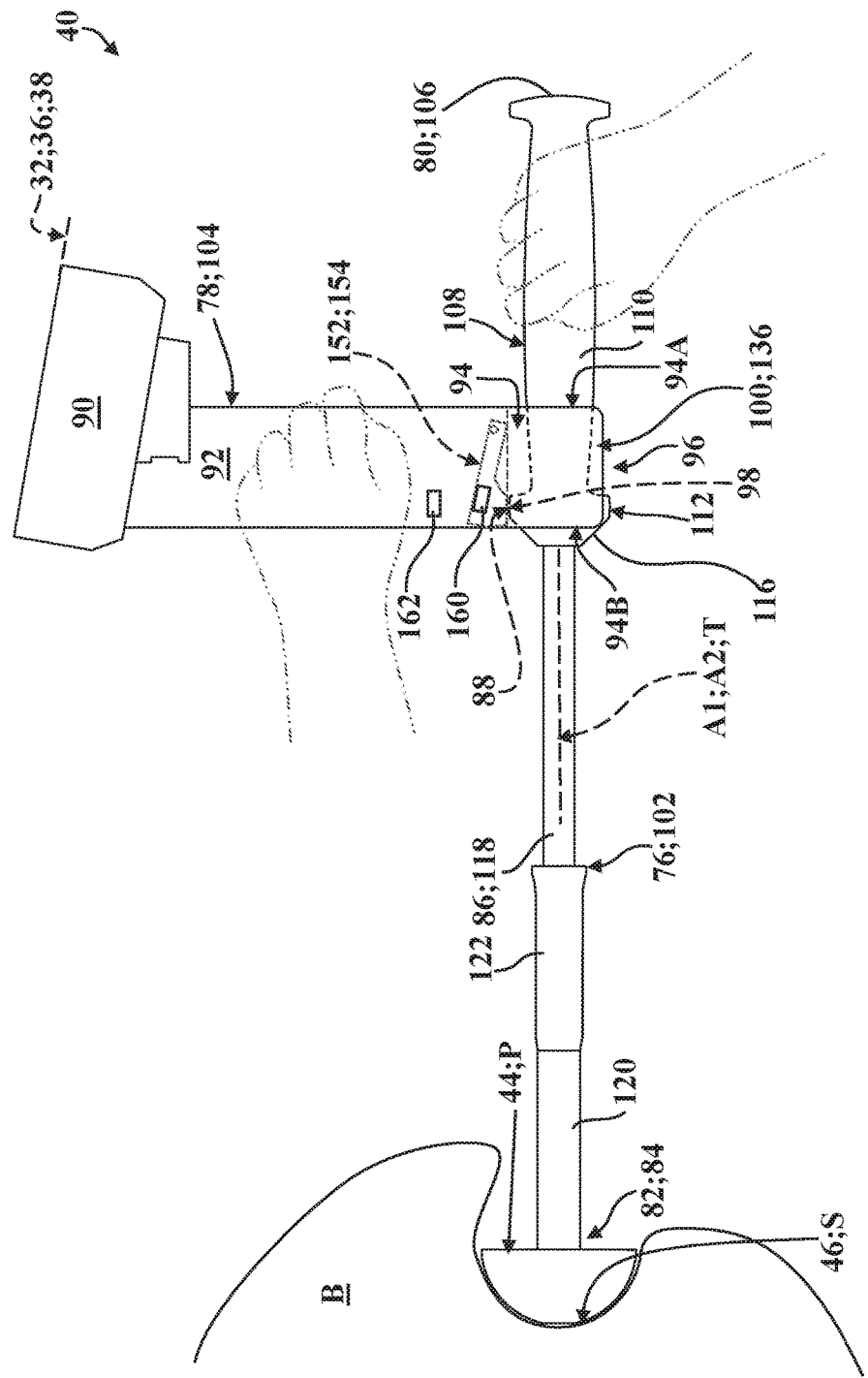
FIG. 9H is another illustrative schematic view of the end effector, the prosthesis, and the surgical site of FIGS. 9A-9G, shown with the guide moved further away from the surgical site along the trajectory, with the flange of the impactor assembly shown adjacent to a sensor coupled to the guide.
Figure 9I:
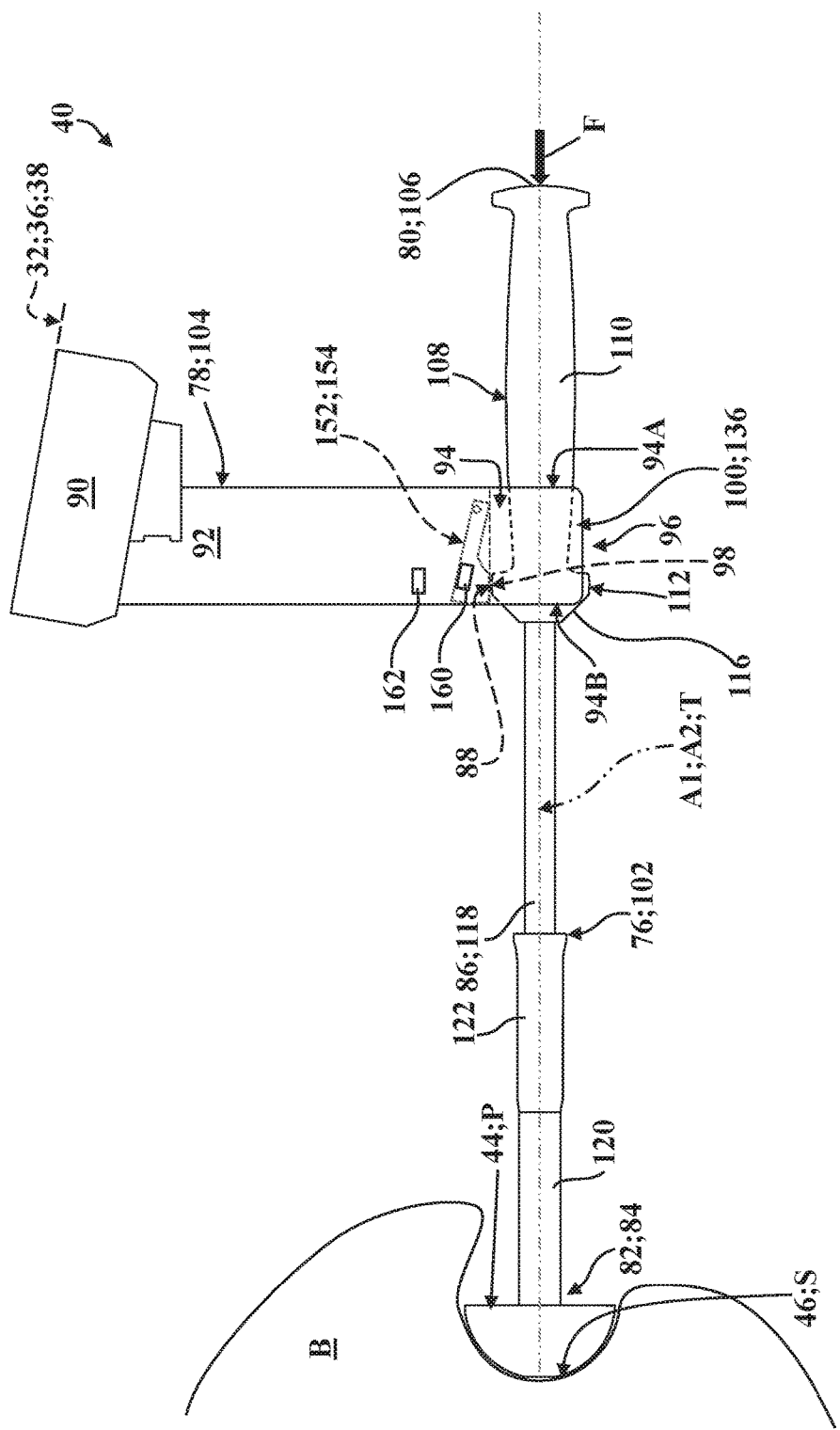
FIG. 9I is an alternate illustrative schematic view of the end effector, the prosthesis, and the surgical site of FIG. 9H.
Figure 9J:
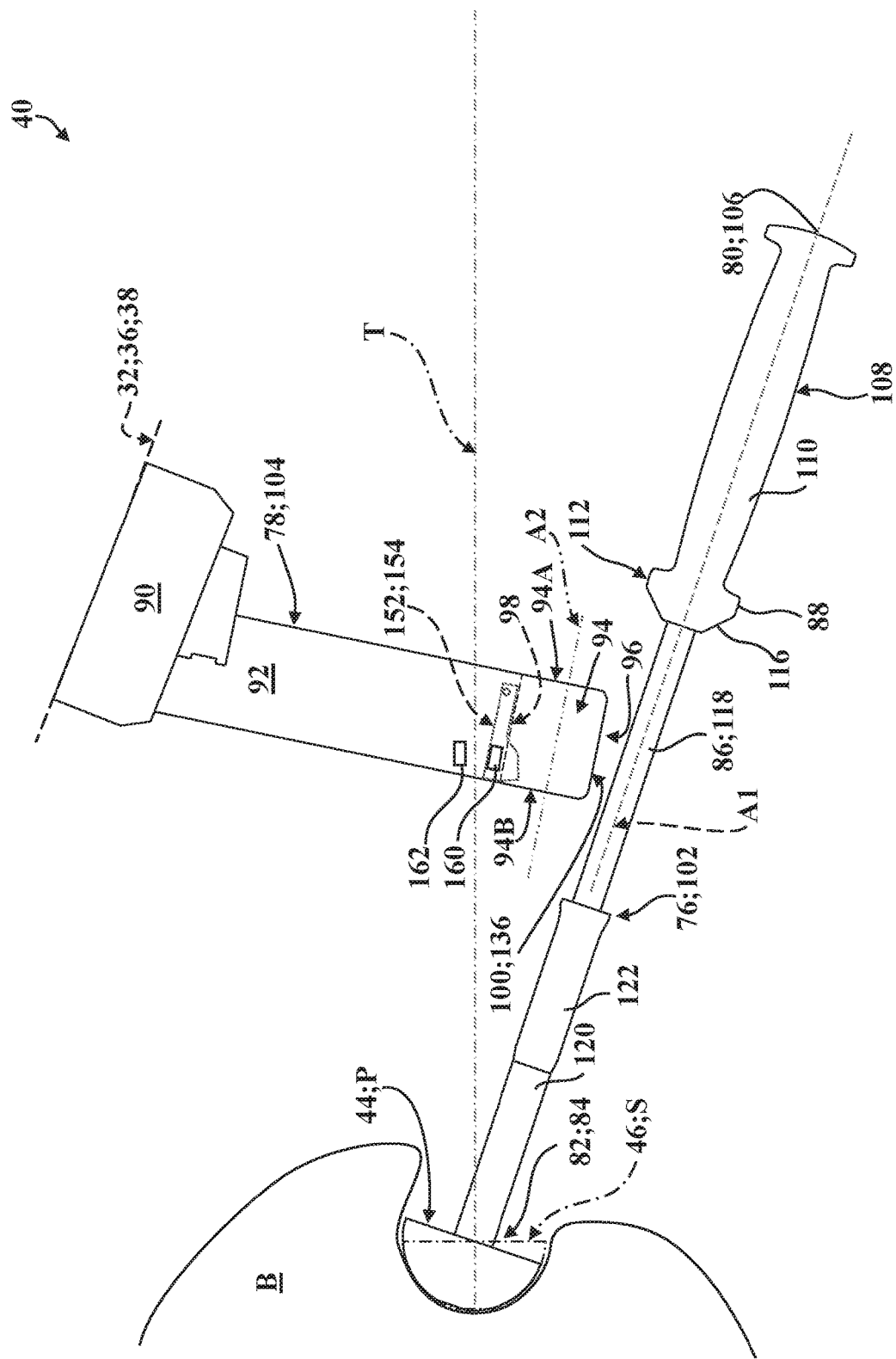
FIG. 9J is an illustrative schematic view of the prosthesis and the end effector of FIGS. 8A-8C, shown with the guide defining a guide axis spaced from and out of coaxial alignment with a surgical site defining a trajectory, and shown with the impactor assembly attached to the prosthesis and defining an impactor axis spaced out of coaxial alignment with both the guide axis and the trajectory.
Figure 9K:
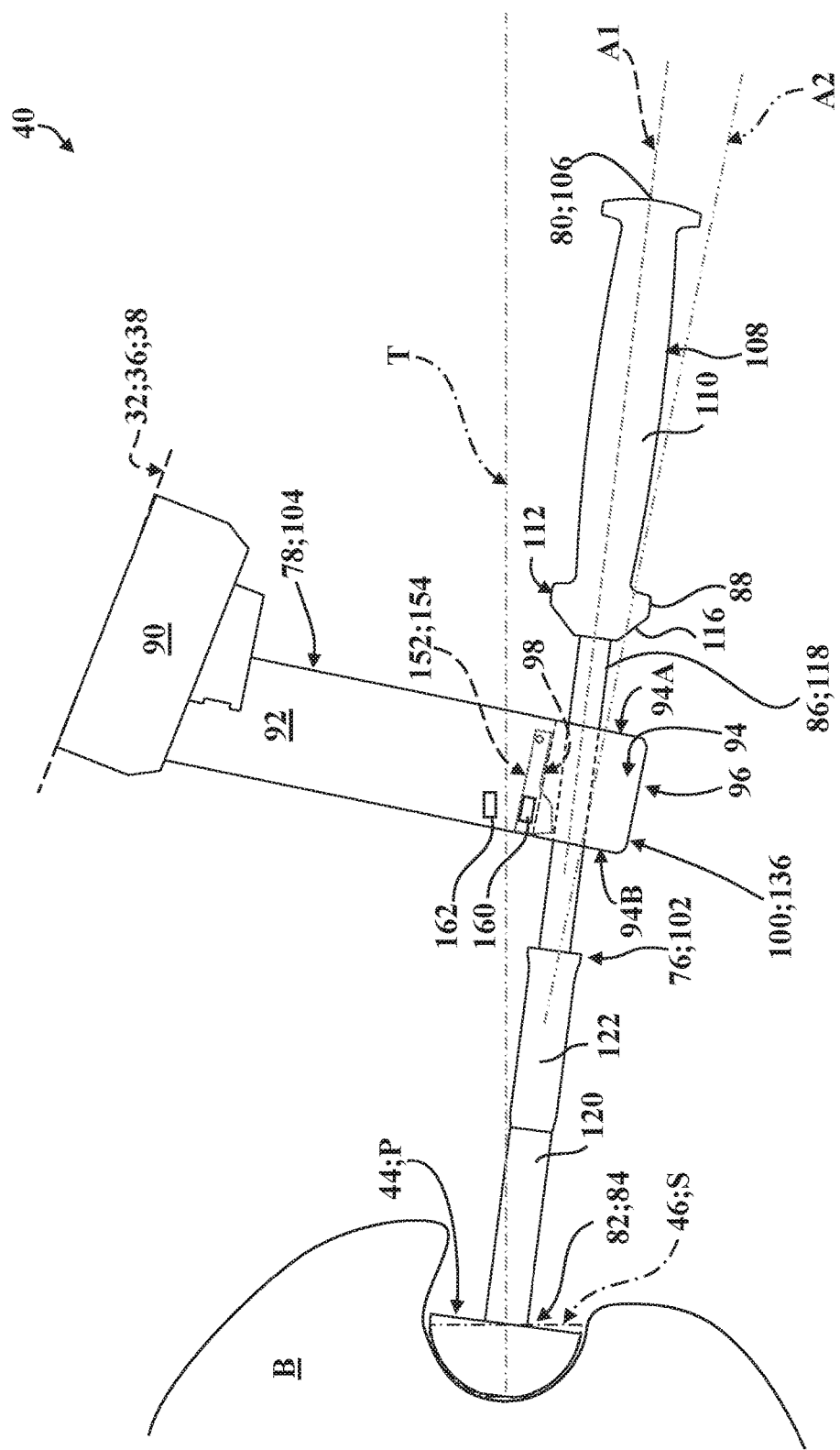
FIG. 9K is another illustrative schematic view of the end effector, the prosthesis, and the surgical site of FIG. 9J, shown with impactor assembly articulated partially into the guide.
Figure 9L:
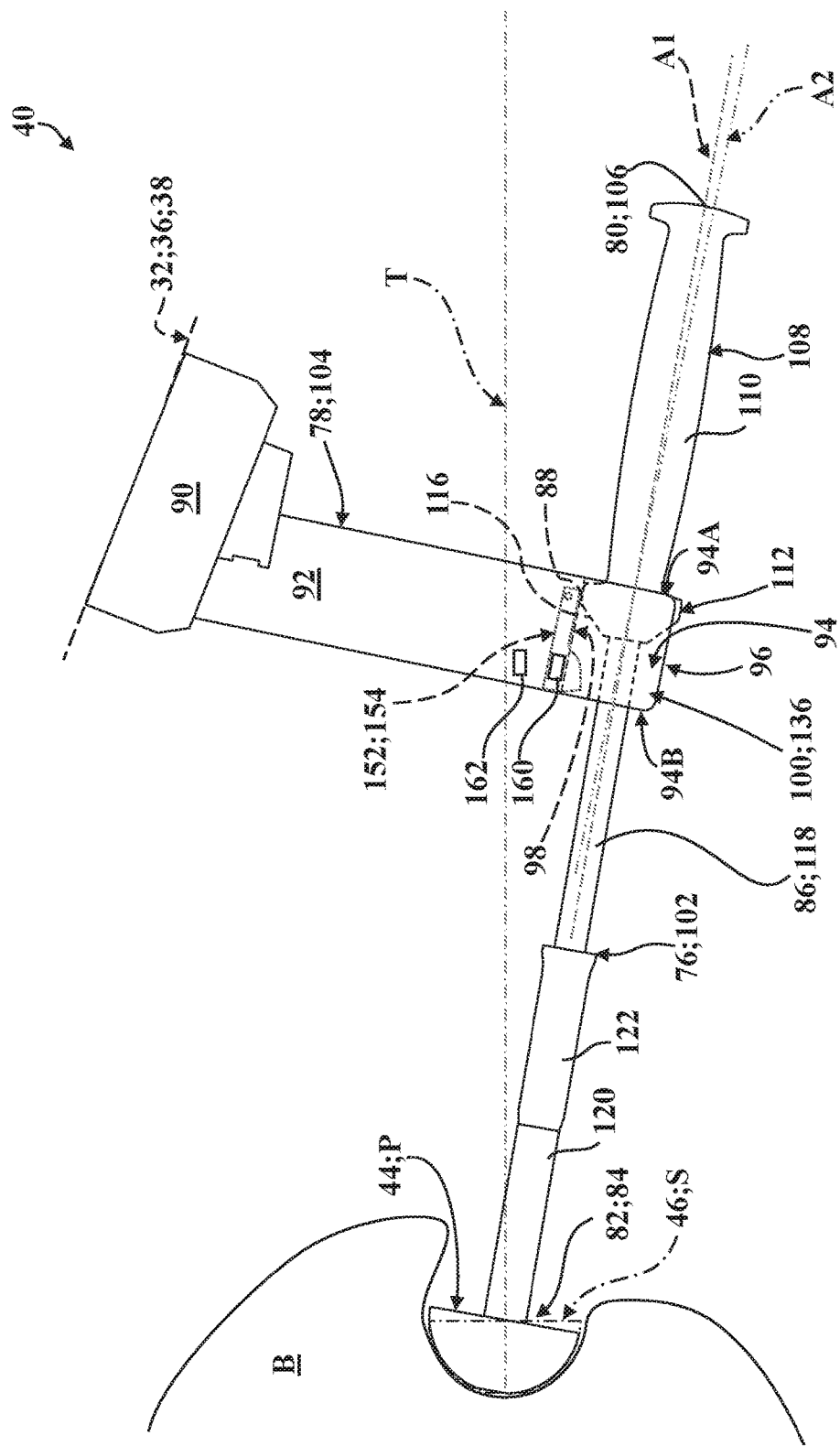
FIG. 9L is another illustrative schematic view of the end effector, the prosthesis, and the surgical site of FIGS. 9J-9K, shown with the guide moved away from the surgical site and engaging a flange of the impactor assembly, and shown with the guide axis out of coaxial alignment with the trajectory T.
Figure 9M:
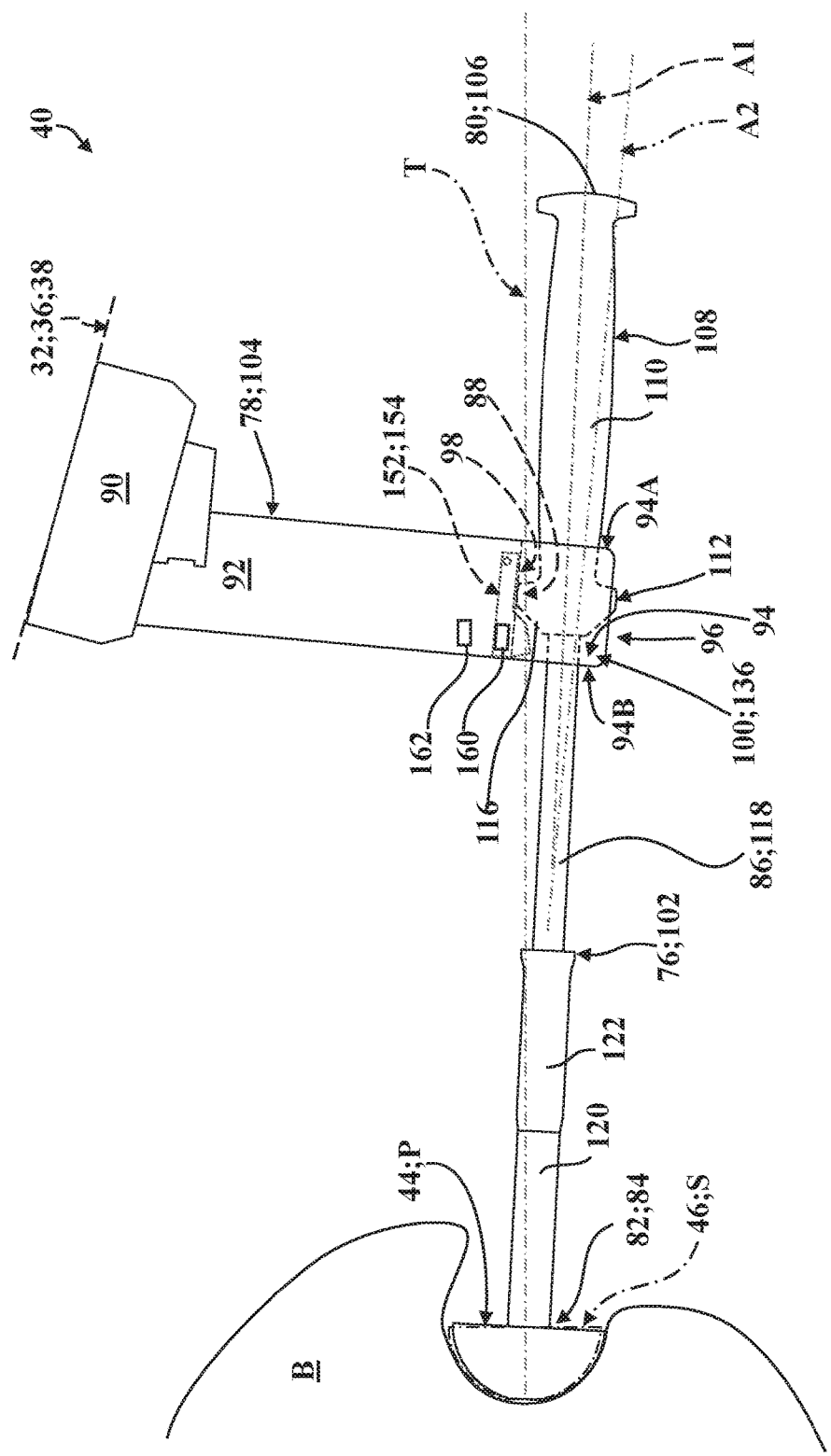
FIG. 9M is another illustrative schematic view of the end effector, the prosthesis, and the surgical site of FIGS. 9J-9L, shown with the guide moved further and articulated relative to the trajectory to bring the impactor axis and the guide axis toward coaxial alignment with the trajectory.
Figure 9N:
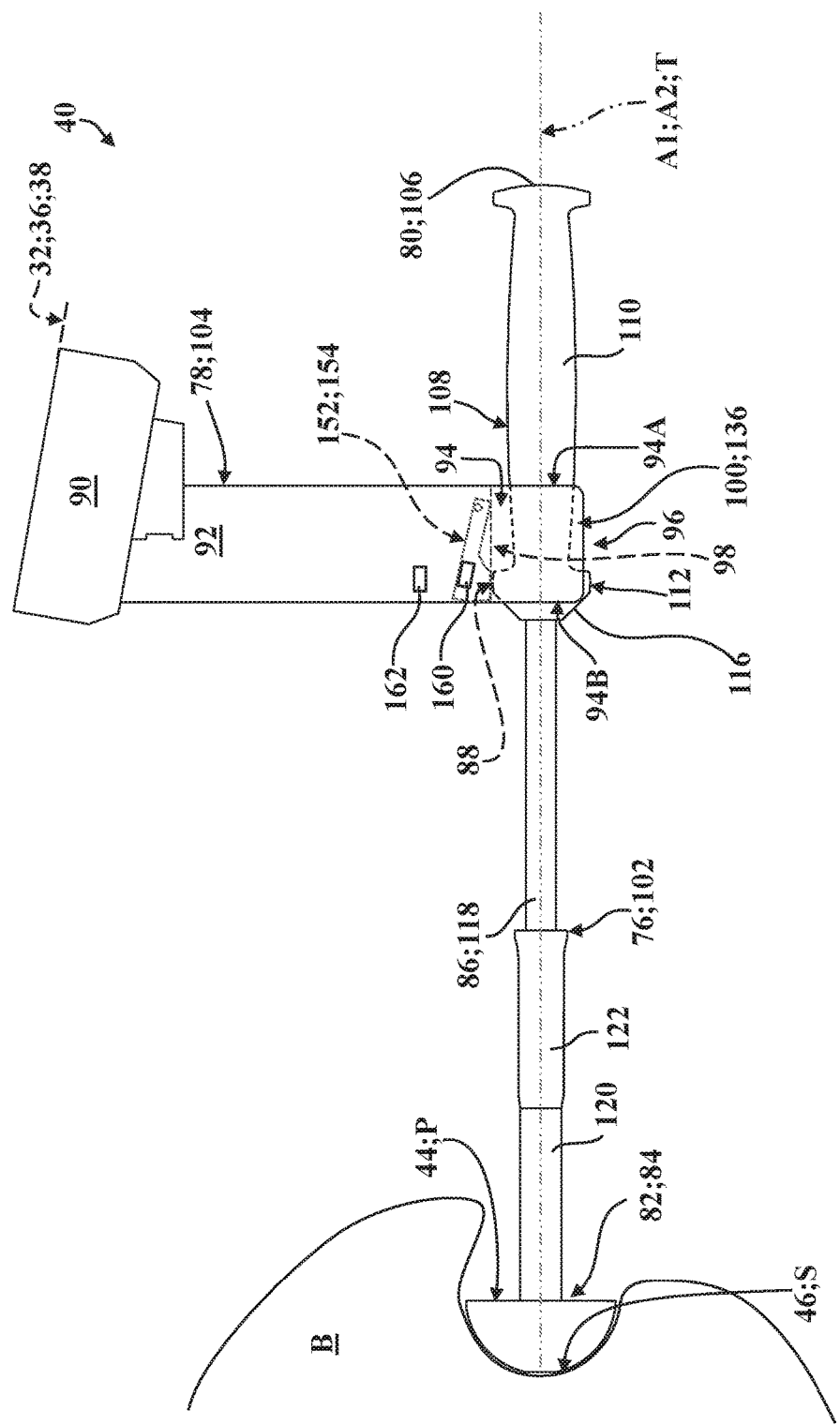
FIG. 9N is another illustrative schematic view of the end effector, the prosthesis, and the surgical site of FIGS. 9J-9M, shown with the guide moved and articulated to position the impactor axis in coaxial alignment with the guide axis and the trajectory.
Figure 10:
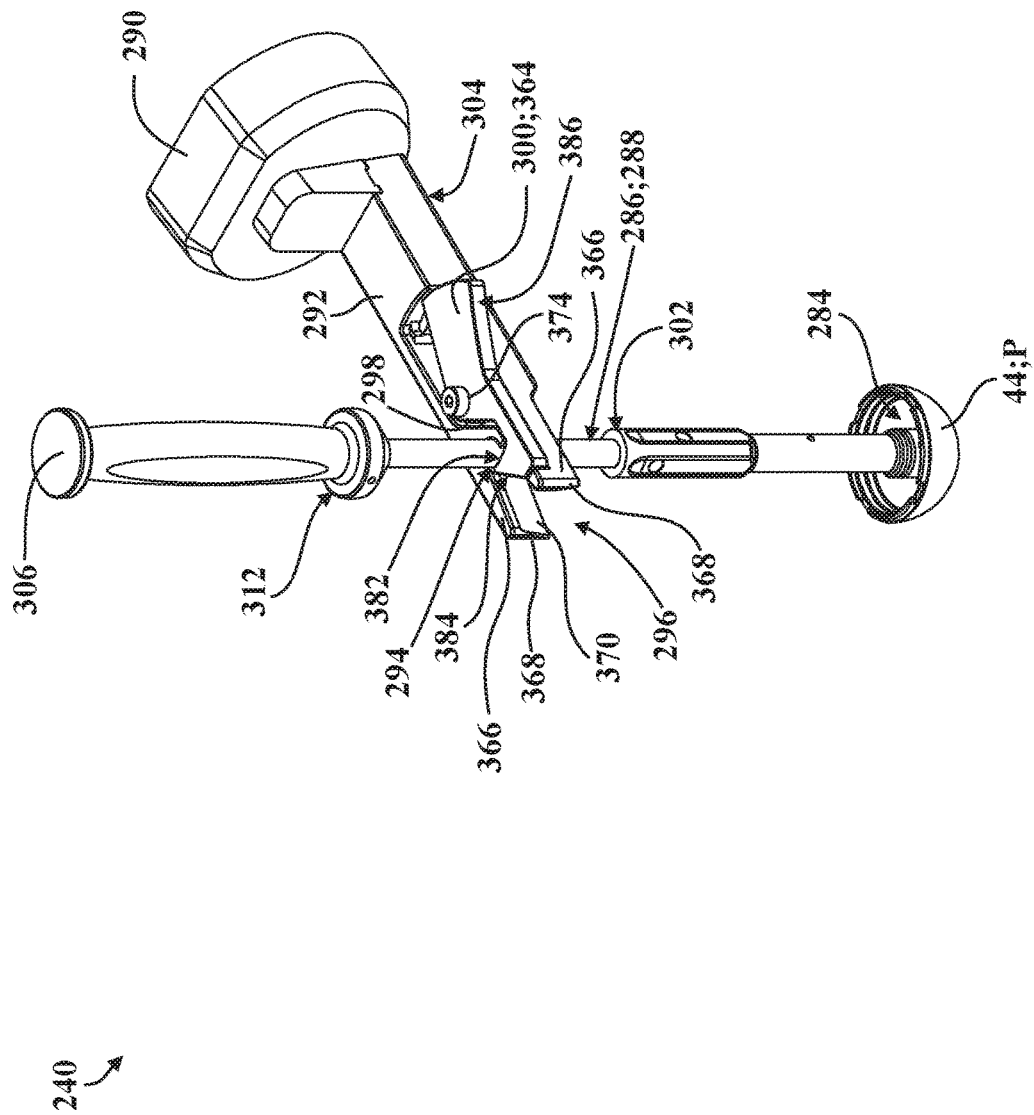
FIG. 10 is a perspective view of another embodiment of an end effector according to the present disclosure, shown having a guide supporting an impactor assembly to which a prosthesis is attached.
Figure 11:
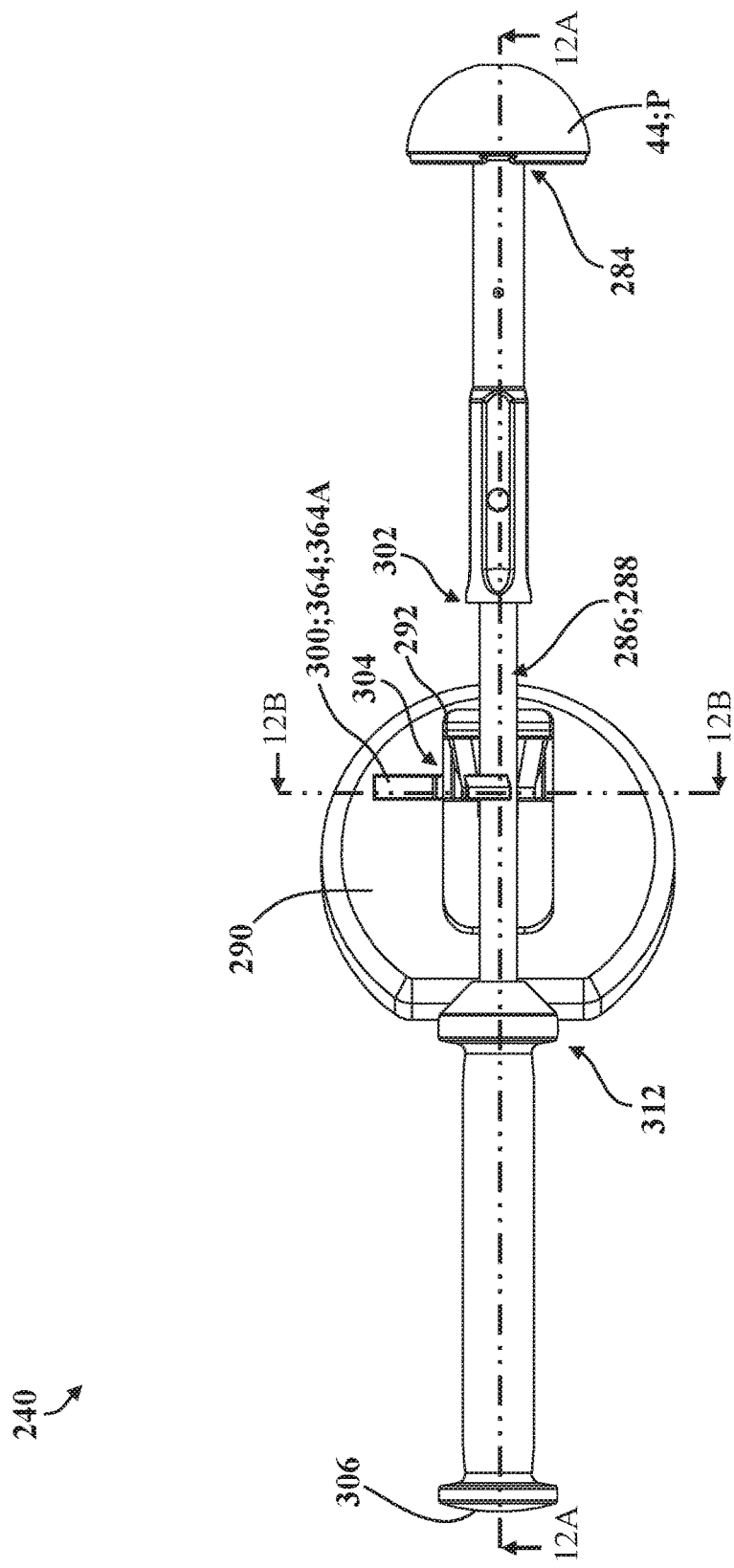
FIG. 11 is a side view of the end effector and the prosthesis of FIG. 10.

As is depicted generically in FIGS. 9A-9N, portions of the patient's body B adjacent the surgical site S, such as muscle, cartilage, portions of the pelvic bone, and the like, may limit the surgeon's ability to approach the surgical site S directly along the trajectory T to position the prosthesis P at the surgical site S prior to impaction. Here, the surgical system 30 and end effectors 40 of the present disclosure allow the surgeon to approach and initially position the prosthesis P at the surgical site S without necessitating large incisions or excessive bone/tissue removal at the surgical site S which might otherwise be required to facilitate approaching the surgical site S. Moreover, the surgical system 30 and end effectors 40 of the present disclosure also allow the surgeon to set the trajectory T and approach the surgical site S with the prosthesis P without necessarily requiring subsequent manipulation of the guide 104 and/or the robotic arm 36 off of the trajectory T. This also allows the surgeon to minimize manipulation of the patient's body B to facilitate approaching of the surgical site S with the prosthesis P. Furthermore, and as will be appreciated from the subsequent description below, the surgical system 30 and end effectors 40 afford significant advantages related to positioning the prosthesis P and approaching the surgical site S in certain scenarios in that the impactor assembly 102 can be used to manually position the prosthesis P and approach the surgical site S without being coupled to the guide 104. Once the prosthesis P has been initially positioned at the surgical site S, the impactor assembly 102 can then be pivoted about or otherwise orientated relative to the surgical site S in order to move the shaft 86 into the opening 96 of the guide 104. This allows alignment of the axes A1, A2 with respect to the trajectory T to be achieved quickly, efficiently, and without necessitating that portions of the impactor assembly 102 and/or guide 104 be disassembled and then re-assembled prior to impaction.

With continued reference to FIG. 9A, as noted above, in this illustrative example, the guide 104 of the end effector 40 is initially positioned along the trajectory T such that the guide axis A2 is coaxial with the trajectory T defined by the intended position of the impacted prosthesis P, determined such as by reaming the acetabulum. Here, the impactor assembly 102 and the prosthesis P are positioned adjacent to, but not yet at, the surgical site S. Because the trajectory T is known, in some embodiments, the surgical robot 32 can maintain the position and orientation of the guide 104 along the trajectory T relative to the surgical site S as the surgeon manually approaches the surgical site with the prosthesis P attached to the impactor assembly 102 (see FIG. 9B; compare with FIG. 9A).

As shown in FIG. 9C, the prosthesis P and the impactor assembly 102 can be manually brought toward the surgical site S without necessitating movement of the guide 104 off of the trajectory T (compare FIG. 9C with FIG. 9B). However, as noted above and as is described in greater detail below in connection with FIGS. 9J-9N, the surgical robot 32 may be configured to permit movement of the guide 104 off of the trajectory T during certain steps of the surgical procedure. Similarly, in some embodiments, the surgical robot 32 may be configured to permit certain articulation of the robotic arm 36 (e.g., within "null space") that results in "rotational" movement of the guide 104 about the trajectory T (e.g., see FIGS. 25A-25D). Once the surgeon has manually approached the surgical site S with the prosthesis P as shown in FIG. 9C, the impactor assembly 102 can then be "pivoted" about the surgical site S to bring the shaft 86 of the impactor assembly 102 through the opening 96 of the guide 104 (see FIG. 9D; compare to FIG. 9C; see also FIGS. 8A-8B).

Once the surgeon has moved the shaft 86 of the impactor assembly 102 through the opening 96 of the guide 104 such that the shaft 86 is generally disposed within the channel 94 (see FIG. 9E), the surgeon can then move the guide 104 away from the surgical site S and toward the flange 112 of the impactor assembly 102. As noted above, the surgical robot 32 may be configured to permit restricted movement of the guide 104 in response to the surgeon touching or otherwise applying directional force to facilitate force control in some conditions. As illustrated in FIG. 9E, the surgeon can grasp or otherwise push against the body 92 of the guide 104 to move the guide 104 relative to the surgical site S along the trajectory T (e.g., away from the surgical site S). Here, depending on the configuration of the surgical robot 32, the surgical procedure being performed, and/or the preferences of the surgeon, the surgical robot 32 may not allow the guide 104 to translate along the trajectory T until certain conditions are met, such as, for example, until the sensor 152 determines that the shaft 86 of the impactor assembly 102 has passed through the opening 96 and/or is properly disposed within the channel 94. The sensor 152 can make this determination in a number of different ways, as noted above and as described in greater detail below, but in the embodiment illustrated in FIG. 9E, the shaft 86 of the impactor assembly 102 is shown physically contacting the trigger 154 to represent determination via the sensor 152 that the shaft 86 has been moved within the channel 94.

It is also conceivable that the surgical robot 32 could be configured to prevent all or certain types of movement of the guide 104 relative to the surgical site S in the positions illustrated in and described in connection with FIGS. 9A-9D, and can be further configured to subsequently permit translation of the guide 104 along the trajectory T away from the surgical site S (or, in some embodiments, away from and/or toward the surgical site S) when the sensor 152 determines that the shaft 86 of the impactor assembly 102 has passed through the opening 96 of the guide 104. However, it will be appreciated that the surgical robot 32 could also be permitted to translate along the trajectory T in one or both directions relative to the surgical site S in each of the positions illustrated in and described in connection with FIGS. 9A-9D, such as where the sensor 152 is employed to track the position of the flange 112 along the channel 94 and is not necessarily used to determine the presence and/or proximity of the shaft 86. Nevertheless, where the sensor 152 is used to determine the presence and/or proximity of the shaft 86 relative to the channel 94, the surgical robot 32 could be configured to permit and/or restrict movement of the guide 104 in a number of different ways. For example, if the sensor 152 determines that the shaft 86 has passed through the opening 96 and into the channel 94, the surgical robot 32 could subsequently permit movement of the guide 104 in directions other than along the trajectory T, such as in other directions which facilitate movement away from the surgical site S. Other configurations are contemplated.

As noted above, FIG. 9E depicts the surgeon grasping or otherwise applying force to the body 92 of the guide 104 to move the guide 104 away from the surgical site S along the trajectory T. In FIG. 9F, the guide 104 is shown moved away from the surgical site S along the trajectory T to bring the first axial channel end 94A of the channel 94 of the guide 104 into contact with the taper 116 of the impactor assembly 102. As noted above, the taper 116 has a generally frustoconical profile extending along the impactor axis A1 between the shaft 86 and the flange 112, and this shape and arrangement helps direct the flange 112 into the channel 94 in response to contact occurring between the taper 116 and the first axial channel end 94A of the channel 94. Thus, because the guide axis A2 is aligned coaxially with the trajectory T in the illustrative scenario depicted in FIGS. 9A-9I, as the surgeon brings the guide 104 toward the taper 116, contact occurring between the taper 116 and the channel 94 also helps bring the impactor axis A1 into coaxial alignment with the guide axis A2 and the trajectory T.

Because the surgeon can control movement of the guide 104 along the trajectory T away from the surgical site S in certain conditions, the impactor axis A1 can be brought into coaxial alignment with the guide axis A2 in an efficient, controlled manner to bring the impactor engagement surface 88 into abutment with the guide engagement surface 98 and also with the arc-shaped surfaces 140 to maintain the coaxial alignment of the axes A1, A2. After alignment of the axes A1, A2 is achieved, the surgeon can move the guide 104 along the trajectory T further away from the surgical site S to bring the flange 112 of the impactor assembly 102 into contact with the trigger 154, as depicted in FIG. 9G. Here, depending on the specific configuration of the end effector 40, the surgical robot 32, the surgical procedure being performed, and/or the preferences of the surgeon, a certain amount of contact occurring between the flange 112 and the trigger 154 could be interpreted by the sensor 152 in a way that is used to slow, limit, or otherwise restrict subsequent movement of the guide 104 along the trajectory T to ensure that the flange 112 is properly positioned axially along the channel 94 ahead of impaction.

In FIG. 9H, the flange 112 is shown contacting the trigger 154 in a way that fully displaces the trigger 154 out of the channel 94 and into the trigger aperture 158. In this position, the sensor 152 could be used to limit subsequent movement of the guide 104 along the trajectory T, to change how the surgical robot 32 operates by responding differently to applied force in admittance control to initiate tracking and/or increase the sensitivity of tracking the depth of the flange 112 along the channel 94, to provide feedback to the surgeon about the position of the flange 112 indicating that impaction can proceed safely, and the like. Next, as is depicted schematically in FIG. 9I, external impact force F can be applied to the head 106 of the impactor assembly 102 to advance the prosthesis P along the impactor axis A1 at the surgical site S. As will be appreciated from the subsequent description of the embodiment illustrated in FIGS. 22A-24D, the relative position of the flange 112 between the first and second axial channel ends 94A, 94B may be arranged differently than as is illustrated in FIGS. 9H-9I, such as to "center" the flange 112 within the channel 94 to ensure that engagement between the impactor engagement surface 88 and the guide engagement surface 98 is maintained as the prosthesis P is advanced along the trajectory T and toward the surgical site S. Put differently, the position of the flange 112 along the channel 94 as depicted in FIGS. 9H-9I (and also in FIG. 9N) is illustrative and does not necessarily correspond to an ideal relative position of the flange 112 between the first and second axial channel ends 94A, 94B just prior to the application of impact force F.

While the illustrative example depicted in FIGS. 9A-9I represents restricted movement of the guide 104 along the trajectory T where the guide axis A2 is initially aligned coaxially with the trajectory T, it will be appreciated that the surgical robot 32 could also be configured to accommodate positioning and moving the guide 104 in other ways, including in orientations and directions other than where the guide axis A2 is initially aligned coaxially with the trajectory T. As will be appreciated from the subsequent description of FIGS. 9J-9N below, this may help facilitate positioning and moving the shaft 86 of the impactor assembly 102 through the opening 96 in certain circumstances.

In FIG. 9J, the prosthesis P is attached to the impactor assembly 102 and has been manually positioned at the surgical site S. Here too, the surgical site S defines the trajectory T for impaction, which is known by the surgical robot 32 as noted above. In this illustrative embodiment, the robotic arm 36 has moved the guide 104 toward the shaft 86 of the impactor assembly 102, but the guide axis A2 is not aligned coaxially with the trajectory T (compare the relative positions of the guide 104 in FIGS. 9J and 9C).

In FIG. 9K, the impactor assembly 102 has been "pivoted" about the surgical site S to move the shaft 86 through the opening 96 and into the channel 94 (compare FIG. 9K with FIG. 9J). Here, the impactor axis A1 is shown passing through the channel 94, and both the impactor axis A1 and the guide axis A2 remain out of coaxial alignment with the trajectory T.

As noted above, the surgical robot 32 can use information from the sensor 152 concerning the position of the impactor assembly 102 relative to the guide 104 to permit the guide 104 to be moved away from the surgical site S once the shaft 86 has passed through the opening 96 and is disposed within the channel 94. In FIG. 9L, the guide 104 has been moved away from the surgical site S and the flange 112 of the impactor assembly 102 is disposed within the channel 94 of the guide 104 such that the impactor engagement surface 88 is disposed in abutment with the guide engagement surface 98. Here, because of the spherical profile of the flange 112 and the cylindrical profile of the channel 94, pivoting can occur between the impactor assembly 102 and the guide 104 as the flange 112 translates along or otherwise rotates relative to the channel 94, as noted above.

Because the surgical robot 32 knows the orientations of the guide axis A2 and the trajectory T, as well as the structural configurations of the impactor assembly 102 and the prosthesis P, and because the surgical robot 32 can use the sensor 152 to determine the presence and/or position of the flange 112 within the channel 94, the surgical robot 32 can thus be configured to derive the orientation of the impactor axis A1 relative to the trajectory T and/or the guide axis A2 based on the relative positions and orientations of the surgical site S and the guide 104 and the relative position of the flange 112 along the channel 94. Alternatively or in addition, it is conceivable that the impactor assembly 102 and/or the guide 104 could be equipped with one or more sensors, as well as the guide tracker 60G and/or the impactor tracker 60I (depicted schematically in FIG. 1), in order to help facilitate determining the orientation of the impactor axis A1. Here, because the surgical robot 32 knows or can determine the relative orientations of the impactor axis A1, the guide axis A2, and the trajectory T, the surgical robot 32 may be configured to drive the robotic arm 36, or permit the surgeon to articulate the robotic arm 36, in order to guide the impactor axis A1 and the guide axis A2 into coaxial alignment with the trajectory T prior to impaction. This type of articulation is depicted sequentially in FIGS. 9L-9N.

A second embodiment of the end effector is depicted in FIGS. 10-15C. As will be appreciated from the subsequent description below, this embodiment shares similar structure and components, as well as similar features, advantages, and operational use, to the first embodiment of the end effector 40 described above. Thus, the structure and components of the second embodiment that are the same as or that otherwise correspond to the structure and components of the first embodiment are provided with the same reference numerals increased by 200 in the drawings and in the description below.

The second embodiment of the end effector 240 is depicted in FIGS. 10-15C, and is similar to the first embodiment of the end effector 40 depicted in FIGS. 3-8C as noted above. While the specific differences between the second embodiment of the end effector 240 and the first embodiment of the end effector 40 are described in detail below, for the purposes of clarity, consistency, and brevity, the majority of the structure and components common between the embodiments are not reintroduced or re-described below.

As such, and unless otherwise indicated below, it will be appreciated that the description of the first embodiment of the end effector 40 above may be incorporated by reference with respect to the second embodiment of the end effector 240 without limitation. Moreover, because the drawings views of the second embodiment of the end effector 240 depicted in FIGS. 10-15C generally correspond to the drawing views of the first embodiment of the end effector 40 depicted in FIGS. 3-8C, only the structure and components which are discussed herein with respect to the second embodiment of the end effector 240 are identified with reference numerals in FIGS. 10-15C. Nevertheless, reference numerals appearing in FIGS. 3-8C which correspond to the description of the first embodiment of the end effector 40 can be used to readily identify and understand corresponding or otherwise common structure and components depicted (but not necessarily identified with reference numerals) in FIGS. 10-15C for the second embodiment of the end effector 240.

Referring now to FIGS. 10-15C, the second embodiment of the end effector 240 is shown in various views. As noted above, in this second embodiment, the impactor assembly 302 is structurally-equivalent to the first embodiment of the impactor assembly 102 described above. However, in this second embodiment, the impactor engagement surface 288 is defined by a portion of the shaft 286 as opposed to a portion of the flange 312, as described above in connection with the first embodiment. Here too, the shaft 286 has a generally cylindrical profile aligned about the impactor axis A1. Thus, in this embodiment, the impactor engagement surface 288 is correspondingly-realized as a portion of a generally cylindrical surface of the shaft 286.

Figure 12A:
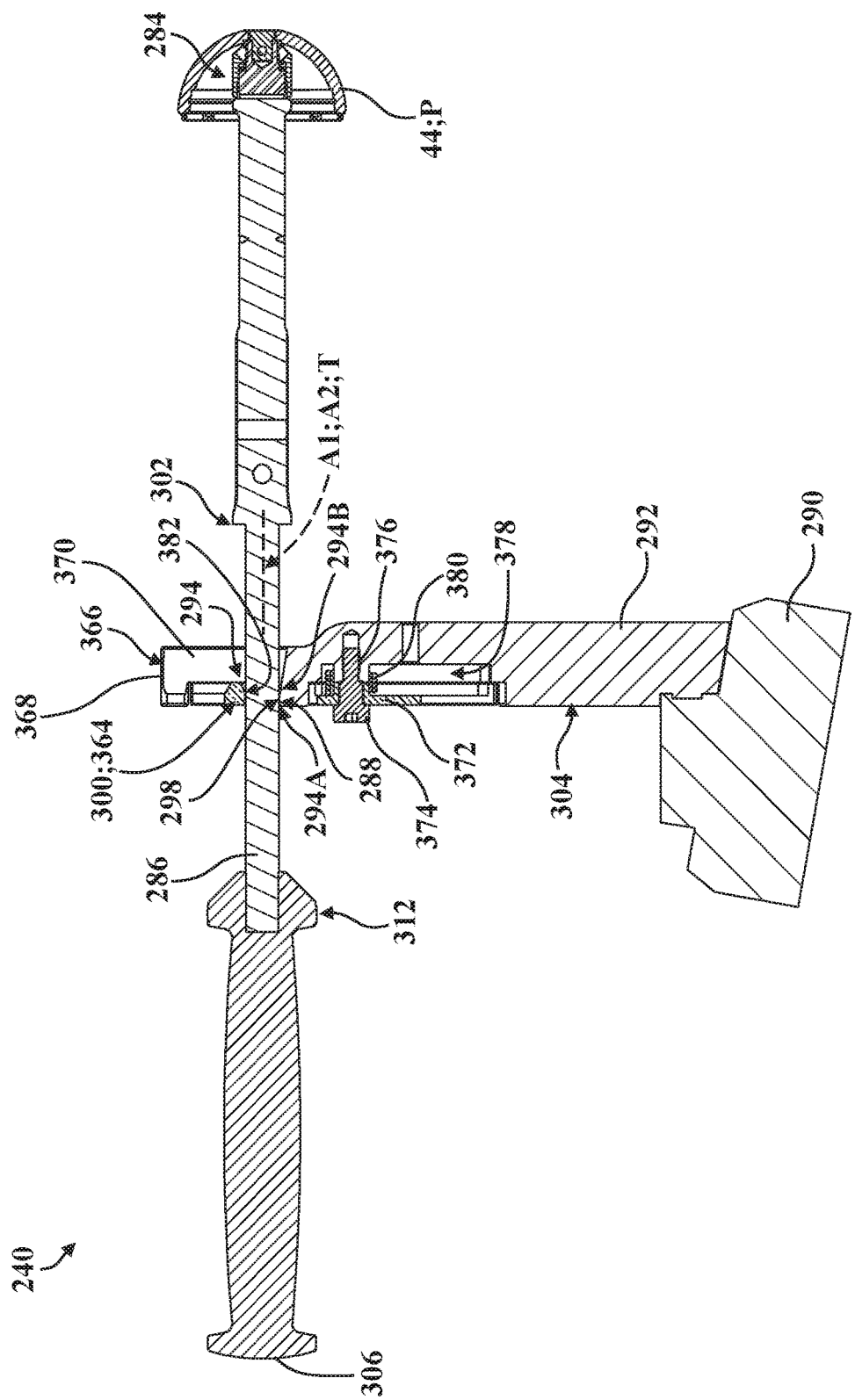
FIG. 12A is a section view taken along line 12A-12A in FIG. 11.
Figure 12B:
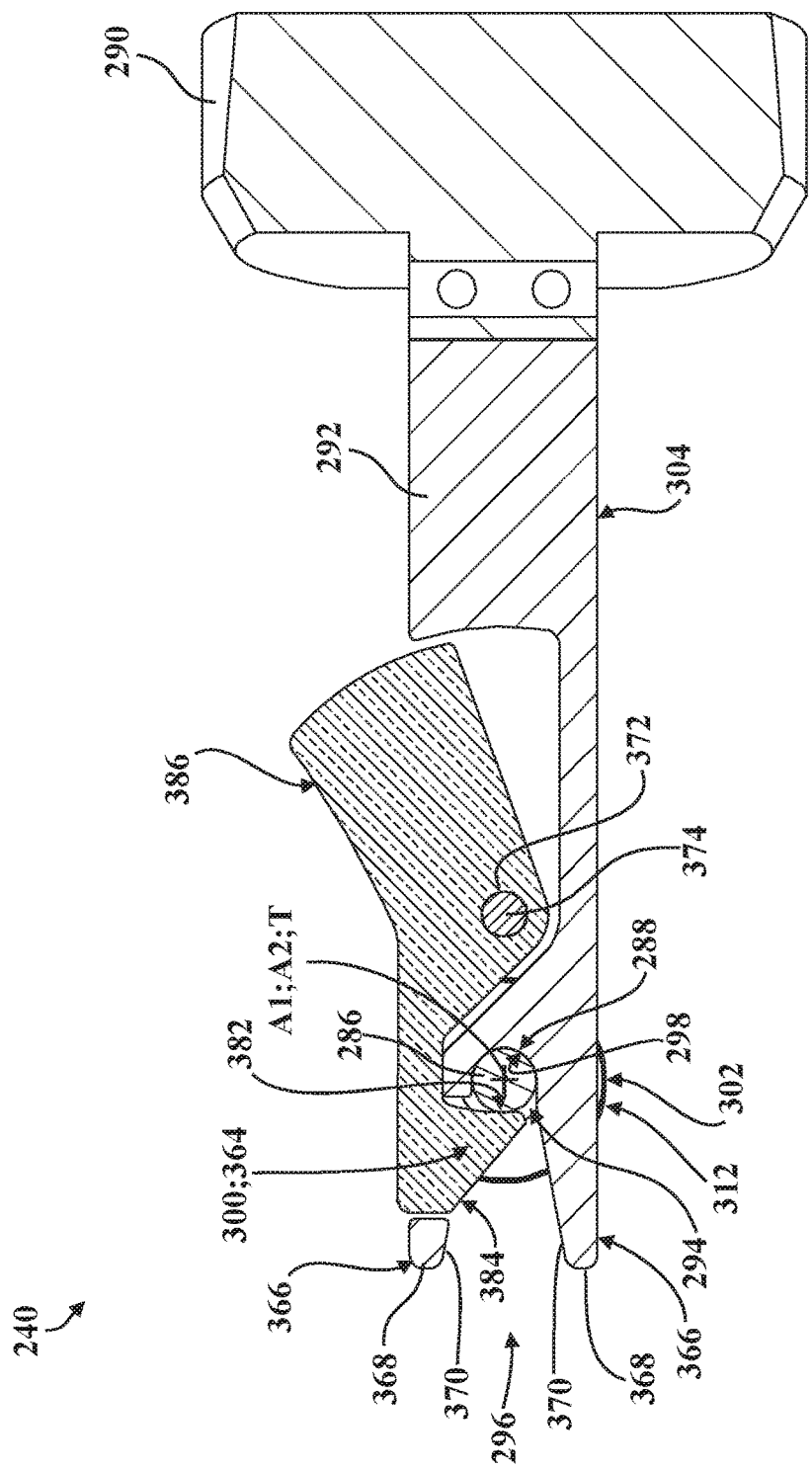
FIG. 12B is a section view taken along line 12B-12B in FIG. 11.

In the second embodiment of the end effector 240, the limiter 300 of the guide 304 is likewise employed to maintain abutment between the guide engagement surface 298 and the impactor engagement surface 288 and help promote coaxial alignment of the axes A1, A2 with each other and with the trajectory T maintained by the surgical robot 32 (see, for example, FIG. 12B). However, because the impactor engagement surface 288 is defined as a portion of the shaft 286 in this embodiment, the limiter 300 here is realized as a discrete component which is formed separately from the body 292 of the guide 304. Specifically, in this embodiment, the limiter 300 comprises a latch, generally indicated at 364, which is movable relative to the body 292 of the guide 304 between a first latch position 364A and a second latch position 364B. In the first latch position 364A, the limiter 300 inhibits movement of the impactor assembly 302 out of the opening 296 of the body 292 to maintain coaxial alignment of the axes A1, A2 with the guide engagement surface 298 abutting the impactor engagement surface 288 (see FIG. 15C). In the second latch position 364B, the limiter 300 permits movement of the impactor assembly 302 across the opening 296 (see FIG. 15B).

Figure 15A:
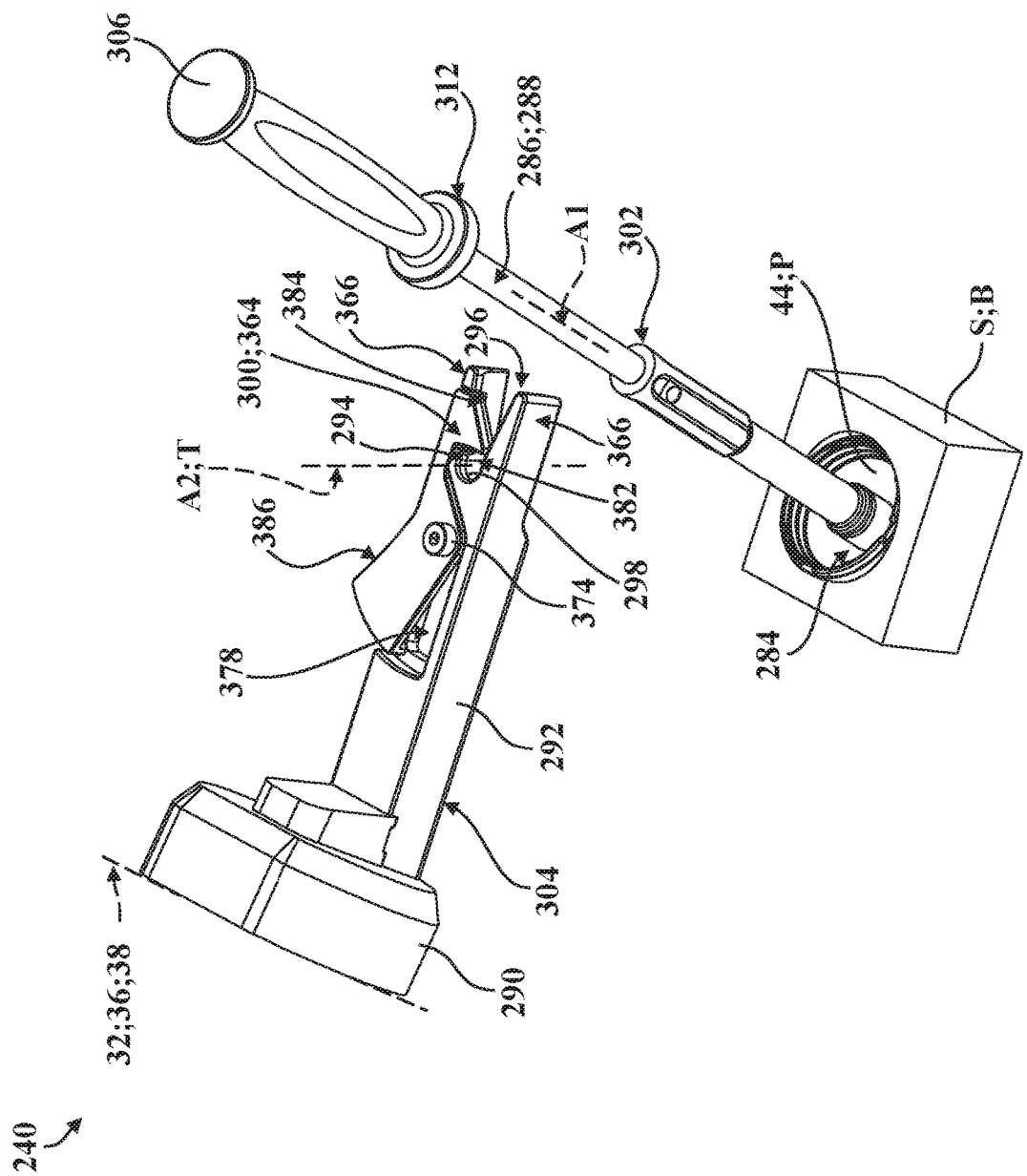
FIG. 15A is a perspective view of the end effector and the prosthesis of FIGS. 10-12B, shown with the prosthesis arranged at a generically-illustrated surgical site, and with the impactor assembly attached to the prosthesis and articulated away from the guide.
Figure 15B:
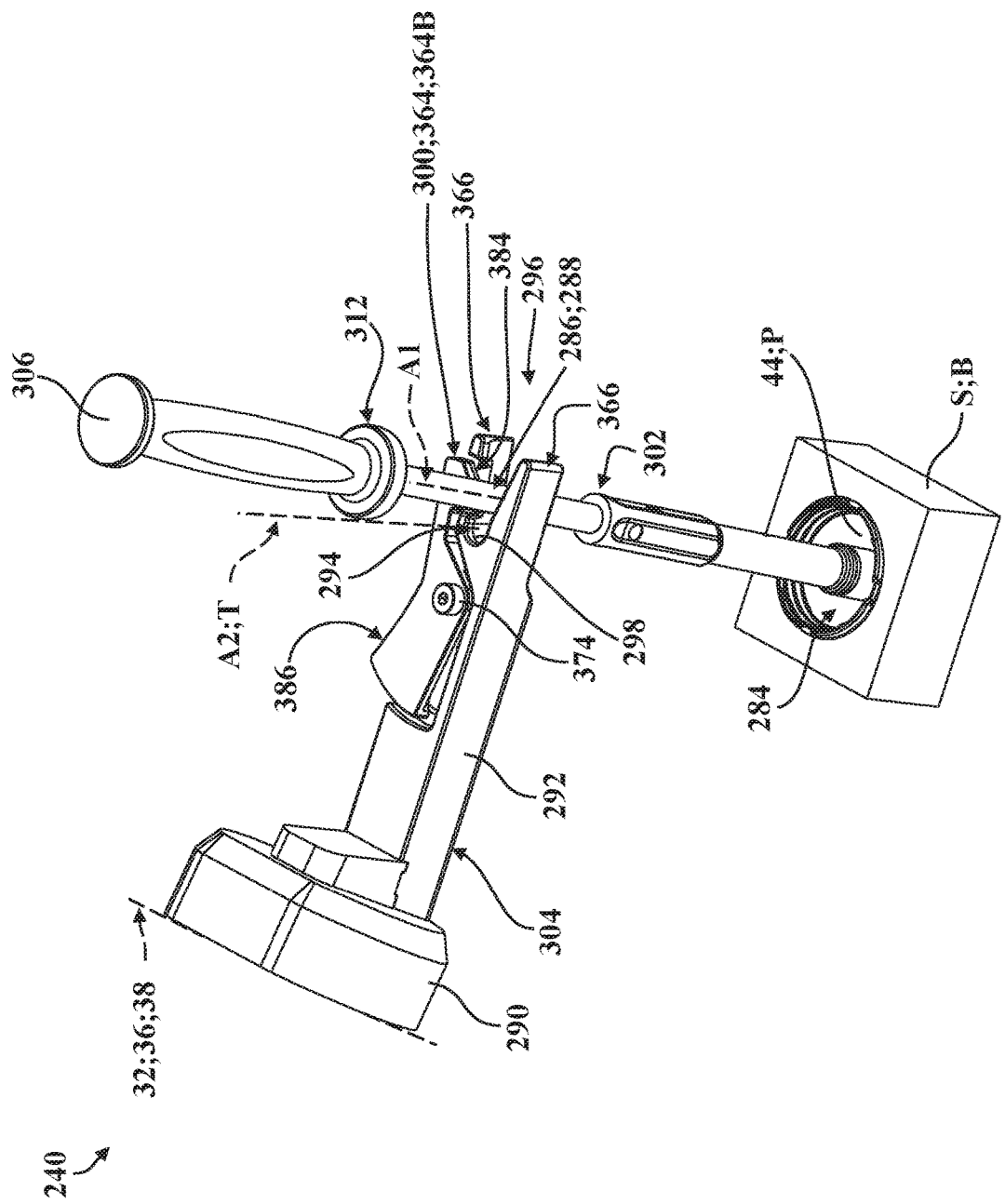
FIG. 15B is another perspective view of the end effector, the prosthesis, and the surgical site of FIG. 15A, shown with the impactor assembly articulated into the guide.
Figure 15C:
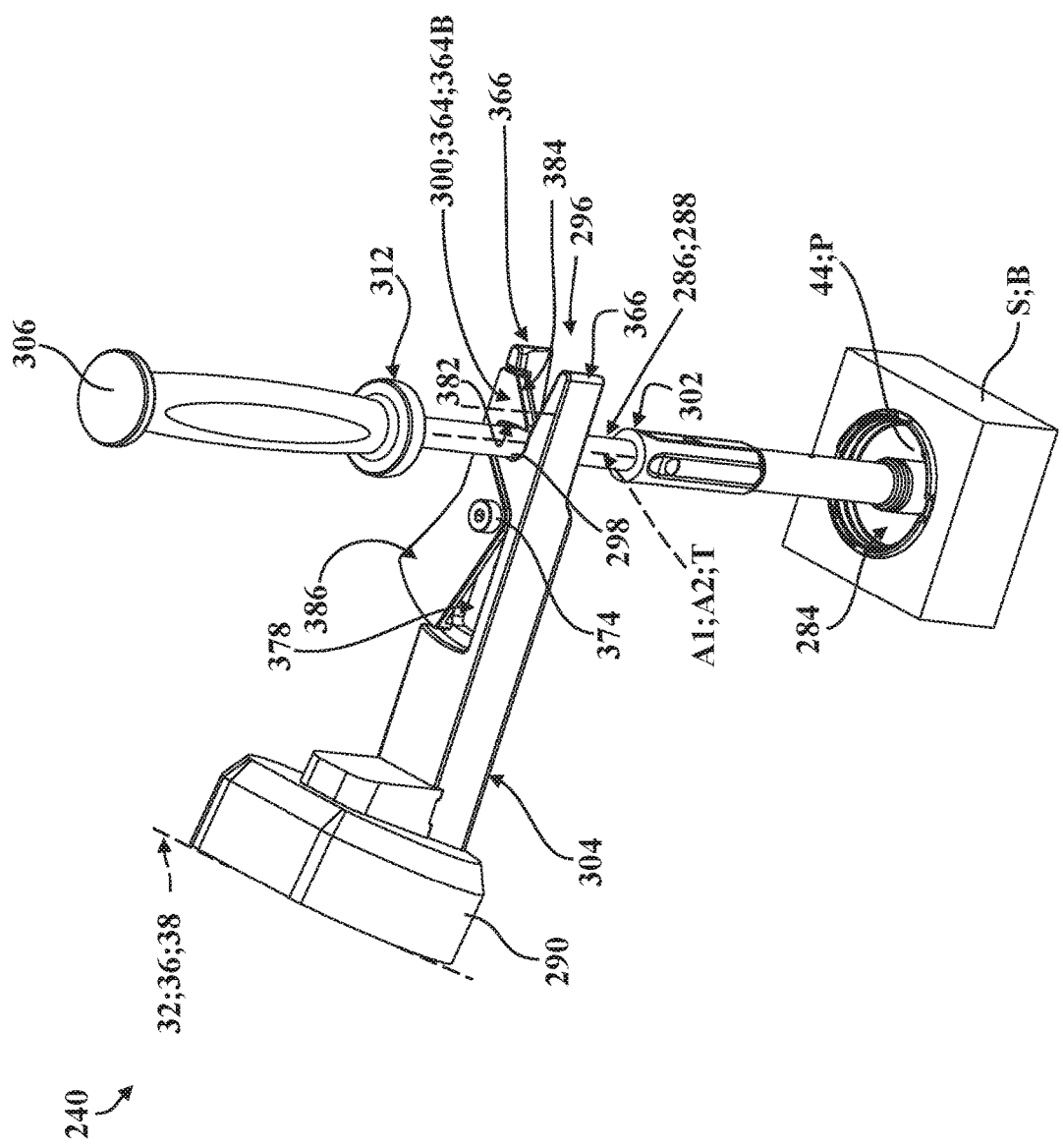
FIG. 15C is another perspective view of the end effector, the prosthesis, and the surgical site of FIGS. 15A-15B, shown with the impactor assembly articulated into engagement with and supporting the impactor assembly along a trajectory.

When viewed sequentially, FIGS. 15A-15C illustrate how the impactor assembly 302 can pivot about the surgical site S to bring the shaft 286 toward and through the opening 296 to approach and come into contact with the guide engagement surface 298 of the body 292. Here, movement of the latch 364 between the first and second latch positions 364A, 364B results from contact with the shaft 286 against the latch 364, as described in greater detail below. However, it will be appreciated that the first latch position 364A can be defined in any suitable way sufficient for the limiter 300 to inhibit movement of the impactor assembly 302 out of the opening 296 to maintain coaxial alignment of the axes A1, A2 with the guide engagement surface 298 abutting the impactor engagement surface 288. Similarly, the second latch position 364B can be defined in any suitable way sufficient for the limiter 300 to permit movement of the impactor assembly 302 across the opening 296, including movement into the channel 294 to move toward abutment with the guide engagement surface 298, as well as movement out of the channel 294 to move out of abutment with the guide engagement surface 298.

As is best depicted in FIGS. 12A-14, in the illustrated embodiment, the body 292 of the guide 304 is likewise adapted for attachment to the mount 290 and defines the opening 296 and the guide engagement surface 298. In this embodiment, however, the guide engagement surface 298 has a generally U-shaped profile (see FIG. 12B), and the body 292 comprises a pair of arms 366 which extend away from the guide engagement surface 298 to respective arm ends 368 which, in turn, are spaced from each other so as to define the opening 296 therebetween. The arms 366 each define an arm surface 370 extending between the respective arm end 368 and the guide engagement surface 298. Here, the arm surfaces 370 are arranged in a generally V-shaped configuration, tapering between the opening 296 and the guide engagement surface 298 to help bring axes A1, A2 into coaxial alignment. This configuration also helps promote guiding the impactor engagement surface 288 of the shaft 286 into abutment with the guide engagement surface 298 in scenarios where the guide axis A2 is not initially aligned coaxially with the trajectory T maintained by the surgical robot 32. Thus, here too in this second embodiment of the end effector 240, the surgeon can articulate the shaft 286 and/or the guide 304 so as to bring the impactor engagement surface 288 into abutment with the guide engagement surface 298, with abutment maintained by the limiter 300, and the surgical robot 32 can subsequently articulate the guide 304 to bring the axes A1, A2 into coaxial alignment with the trajectory T.

Figure 13:
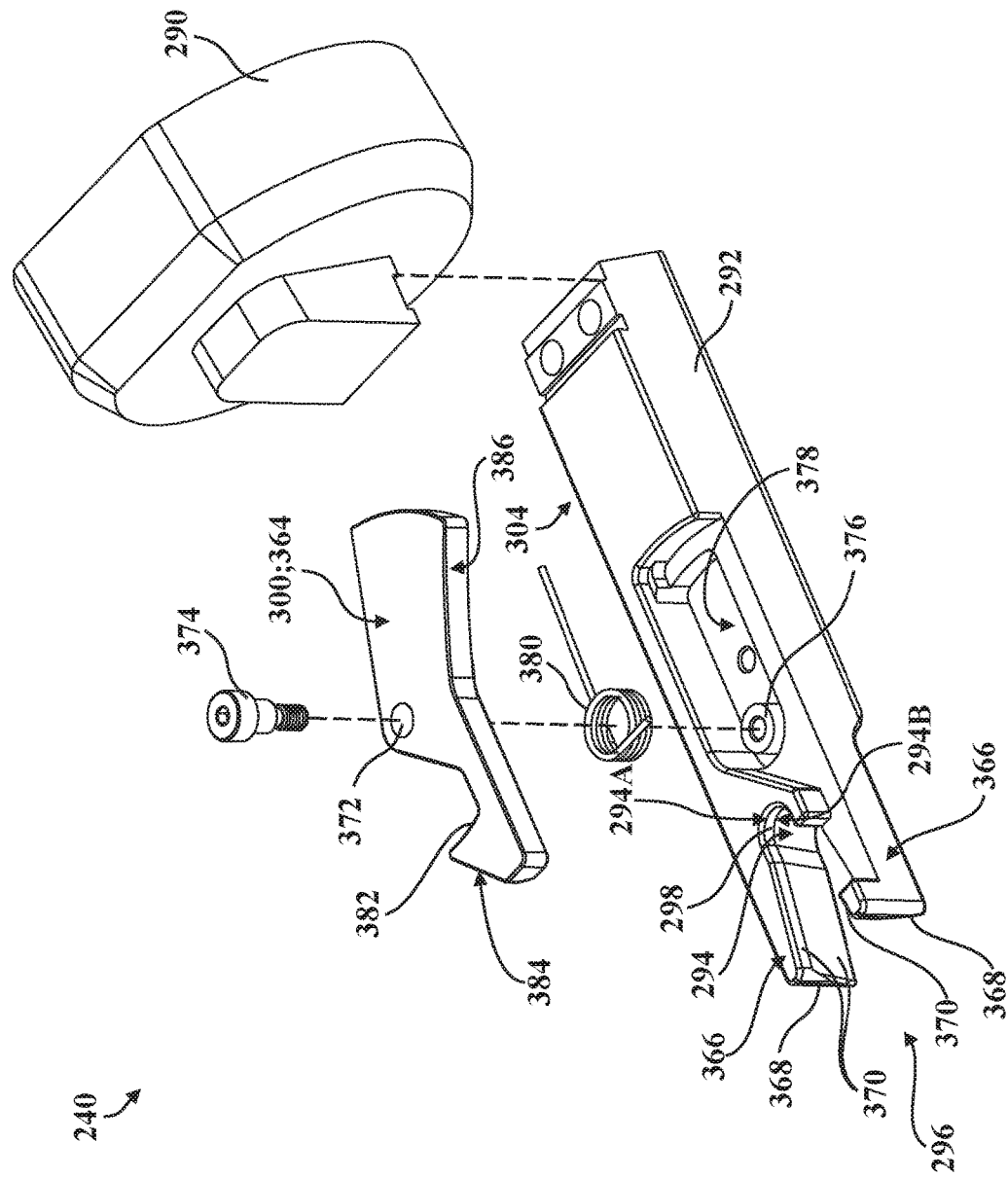
FIG. 13 is an exploded perspective view of the guide of FIGS. 10-12B.
Figure 14:
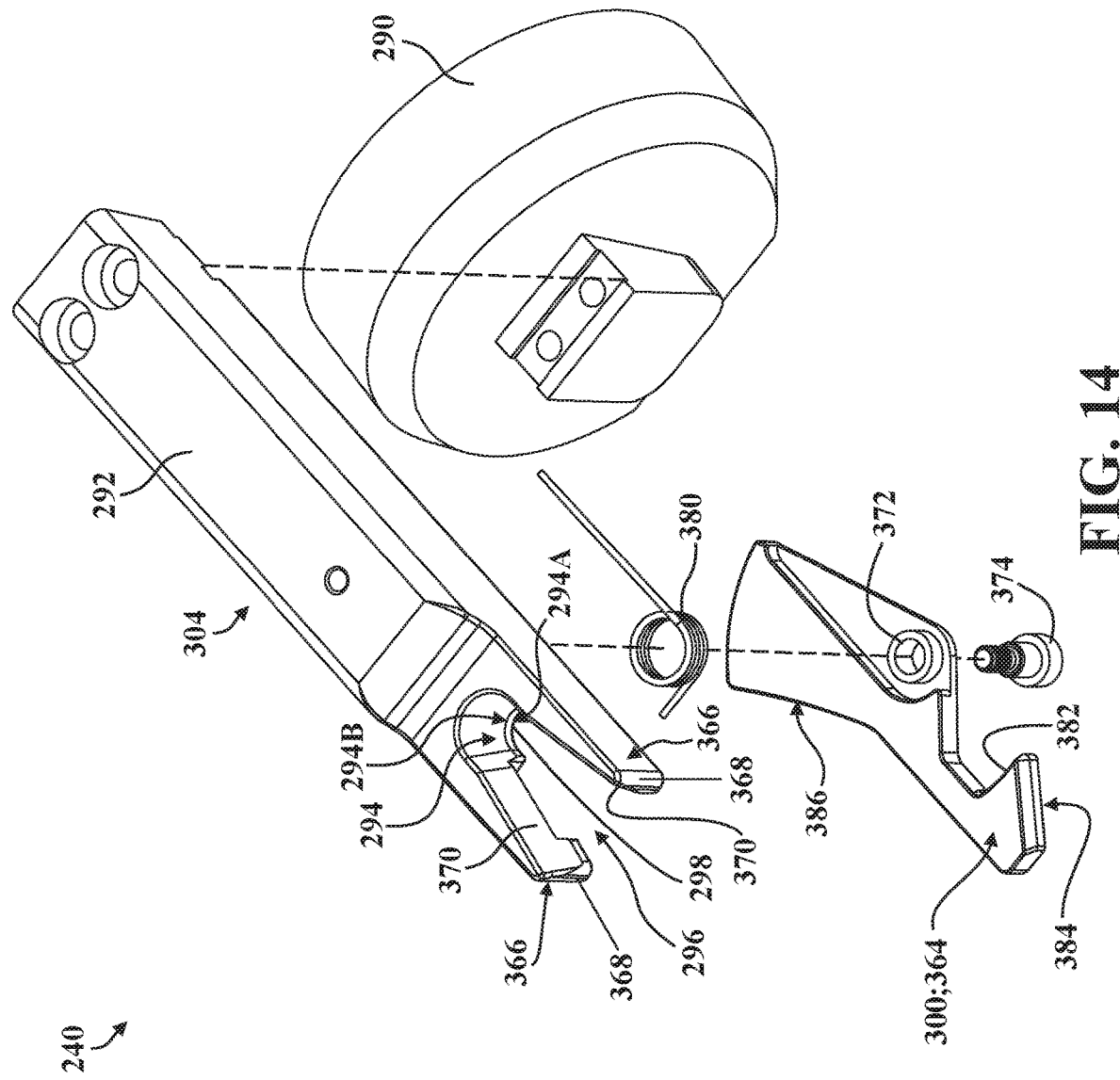
FIG. 14 is another exploded perspective view of the guide of FIG. 13.

As is best depicted in FIG. 13, the channel 294 of the second embodiment of the end effector 240 similarly extends between the first and second axial channel ends 294A, 294B. However, in this embodiment, the channel 294 also tapers away from the guide axis A2 between the second axial channel end 294 and the adjacent portions of the body 292 (see also FIG. 14). This arrangement also helps bring the axes A1, A2 into coaxial alignment and allows for a broad range of movement and orientations to be utilized when moving the shaft 286 and/or the guide 304 to facilitate abutment between the impactor engagement surface 288 and the guide engagement surface 298. However, it will be appreciated that other configurations are contemplated.

With continued reference to FIG. 13, in order to facilitate movement of the latch 364 between the first and second latch positions 364A, 364B, in the illustrated embodiment, an aperture 372 is formed extending through the latch 364 to rotatably support the latch 364 for movement relative to the body 292 via a fastener 374. The fastener 374 is secured to a boss 376 formed in the body 292. Thus, the latch 364 is able to pivot about the fastener 374 between the first and second latch positions 364A, 364B. In the illustrated embodiment, the boss 376 is disposed within a pocket 378 formed in the body 292. The pocket 378 also accommodates a biasing element 380, realized herein as a torsional spring, which is supported about the boss 376 and is interposed between the latch 364 and the body 292 of the guide 304 to urge the latch 364 toward the first latch position 364A. However, it will be appreciated that the latch 364 may arranged for movement relative to the body 292 between the first and second latch positions 364A, 364B in a number of different ways without departing from the scope of the present disclosure.

Referring now to FIGS. 12A-15C, the latch 364 is shaped and arranged so as to at least partially traverse the channel 294 of the body 292 of the guide 304 when in the first latch position 364A so as to inhibit movement of the impactor assembly 302 out of the opening 296 (see, for example, FIG. 12B). It will be appreciated that this arrangement helps ensure that the coaxial alignment of the axes A1, A2 is maintained by the limiter 300 with the impactor engagement surface 288 abutting the guide engagement surface 298.

In the illustrated embodiment, and as is best depicted in FIG. 12B, the latch 364 comprises a retention face, generally indicated at 382, which is shaped and arranged to engage against the shaft 286 of the impactor assembly 302 when in the first latch position 364A. Thus, the retention face 382 of the latch 364 abuts the shaft 286 to form part of the limiter 300 to maintain coaxial alignment of the axes A1, A2 with the impactor engagement surface 288 abutting the guide engagement surface 298. Here, it will be appreciated that the biasing element 380 is advantageously configured to maintain abutment between the retention face 382 and the shaft 286 with sufficient force to also maintain abutment of the impactor engagement surface 288 against the guide engagement surface 298. It is also conceivable that a lock mechanism (not shown) could be provided to restrict movement of the latch 364 out of the first latch position 364A in some embodiments. Other configurations are contemplated.

The latch 364 is also provided with a cam portion, generally indicated at 384, which faces away from the guide engagement surface 298. The cam portion 384 is arranged to abut a portion of the impactor assembly 302 (see FIG. 15B) so as to facilitate movement of the latch 364 toward the second latch position 364B from the first latch position 364A. This permits the shaft 286 of the impactor assembly 302 to pass through the opening 296 of the guide 304 and toward the guide engagement surface 298 so as to bring the impactor engagement surface 288 into abutment with the guide engagement surface 298. In addition, the latch 364 further comprises a release portion, generally indicated at 386, which is arranged for actuation by the surgeon or a user to move the latch 364 from the first latch position 364A to the second latch position 364B in order to permit the impactor assembly to pass out of the opening 296 of the body 292 of the guide 304. However, those having ordinary skill in the art will appreciate that the latch 364 could be formed in a number of different ways and, thus, could have a number of different shapes, profiles, and/or configurations sufficient to move between the first and second latch position 364A, 364B.

A third embodiment of the end effector is generally depicted in FIGS. 16A-24D. As will be appreciated from the subsequent description below, this embodiment shares similar structure and components, as well as similar features, advantages, and operational use, to the first embodiment of the end effector 40 described above. Thus, the structure and components of the third embodiment that are the same as or that otherwise correspond to the structure and components of the first embodiment are provided with the same reference numerals increased by 400 in the drawings and in the description below. Furthermore, the third embodiment also shares certain similar structure and components, as well as similar features, advantages, and operational use, to the second embodiment of the end effector 240 described above. Thus, the structure and components of the third embodiment that are the same as or that otherwise correspond to the structure and components of the second embodiment are provided with the same reference numerals increased by 200 in the drawings and in the description below.

The third embodiment of the end effector 440 is depicted in FIGS. 16A-24D, and is similar to other embodiments described and illustrated herein. While the specific differences between the third embodiment of the end effector 440 and the other embodiments are described in detail below, for the purposes of clarity, consistency, and brevity, the majority of the structure and components common between the embodiments are not reintroduced or re-described below. As such, and unless otherwise indicated below, it will be appreciated that the description of the other embodiments above may be incorporated by reference with respect to the third embodiment of the end effector 440 without limitation. Furthermore, it will be appreciated that various aspects of the third embodiment of the end effector 440 could also apply to other embodiments of the present disclosure.

Figure 16A:
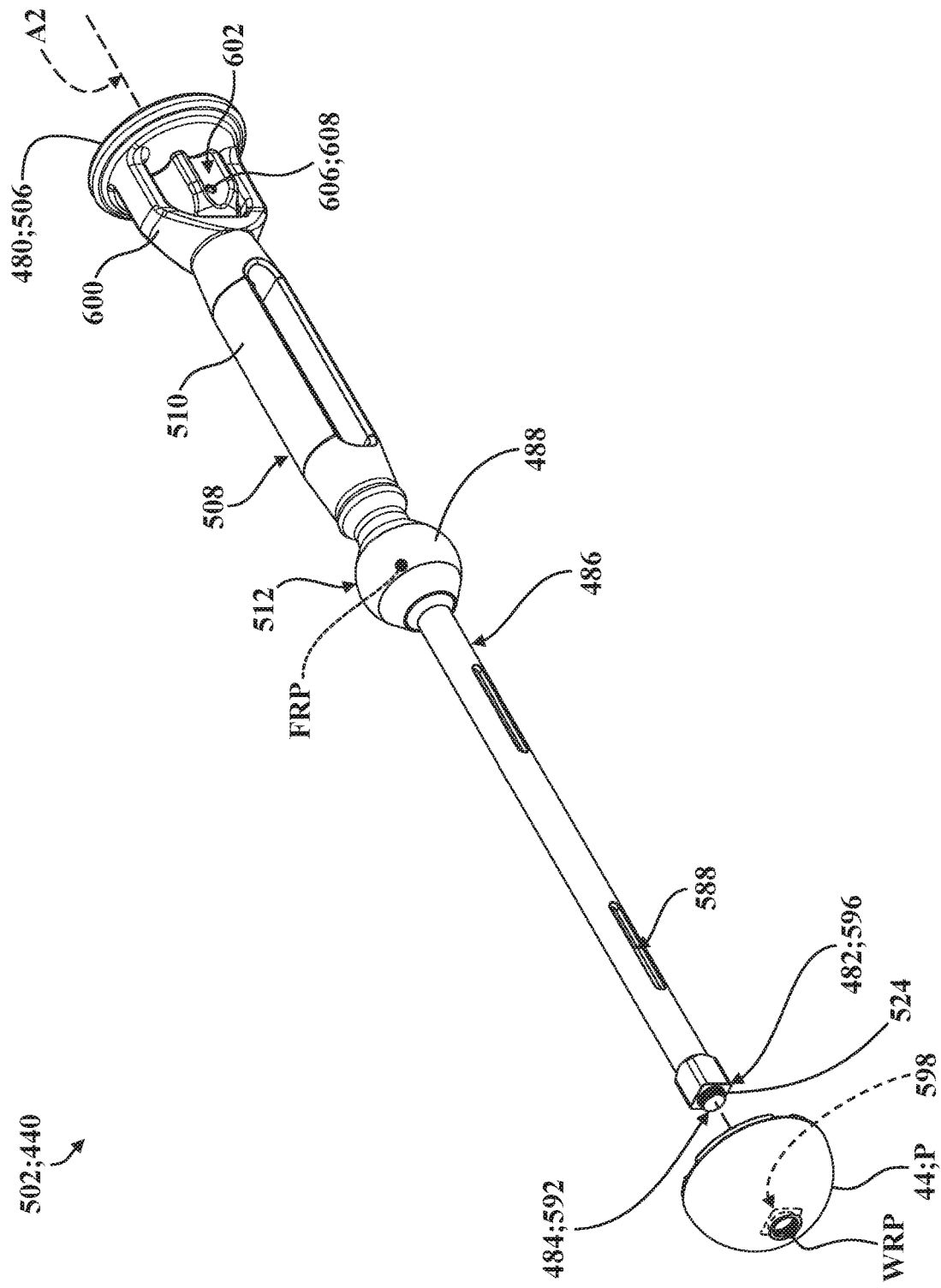
FIG. 16A is a perspective view of another embodiment of an impactor assembly according to the present disclosure, with the impactor assembly shown spaced from a prosthesis.
Figure 16B:
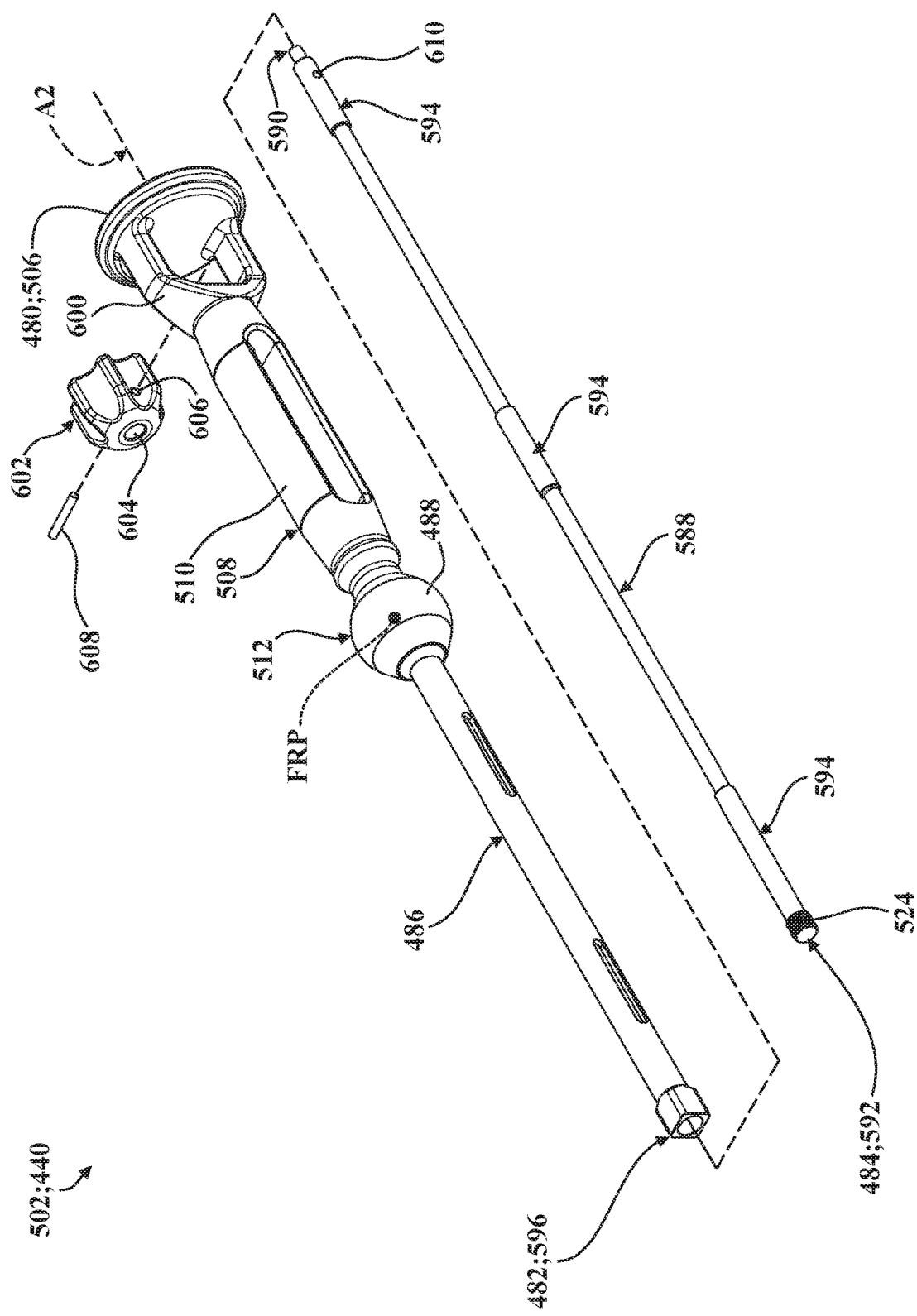
FIG. 16B is an exploded perspective view of the impactor assembly of FIG. 16A.

Referring now to FIGS. 16A-16B, the impactor assembly 502 of the third embodiment of the end effector 440 is shown. Here too, the impactor assembly 502 employs the head 506 at the proximal end 480 of the handle 508 to receive impact force F along the impactor axis A1, and comprises the flange 512 arranged between the shaft 486 and the grip 510 of the handle 508 and provided with a generally spherical configuration which defines the impactor engagement surface 488. However, in this third embodiment, the interface 484 that releasably attaches to the prosthesis P adjacent to the distal end 482 of the shaft 486 is defined by a carrier shaft, generally indicated at 588 (see FIG. 16B). The carrier shaft 588 is supported for rotation about the impactor axis A1 relative to the shaft 486 and the handle 508, and is also supported for a limited amount of translation along the impactor axis A1, as described in greater detail below. To this end, the third embodiment of the shaft 486 and the handle 508 are generally hollow and may comprise one or more cylindrical regions (not shown in detail) to accommodate the carrier shaft 588 therein, facilitate rotation and/or translation, and the like. The carrier shaft 588 generally extends along the impactor axis A1 between a proximal shaft end 590 and a distal shaft end 592, with one or more bearing regions 594 provided therebetween to facilitate rotation and force distribution.

The interface 484 in this third embodiment is realized by the threaded engagement 524 arranged at the distal shaft end 592 of the carrier shaft 588, as opposed to the distal end 482 of the shaft 486 itself. Rather, in this embodiment, the distal end 482 of the shaft 486 is provided with a key portion 596 having a generally rectangular profile shaped to engage a correspondingly-shaped notch portion 598 formed in the prosthesis P (see FIG. 16A; depicted in phantom). This configuration permits the prosthesis P to be indexed relative to the shaft 486 (and, thus, the handle 508), which may be advantageous for applications where the prosthesis P has certain features that need to be aligned relative to the surgical site S. Furthermore, this configuration also helps facilitate releasable attachment between the prosthesis P and the impactor assembly 502 in that rotation and translation of the carrier shaft 588 relative to the shaft 486 can be used to disengage the threaded engagement 524 without also rotating the shaft 486 about the impactor axis A1. To this end, the handle 508 is also provided with a cage 600 disposed between the head 506 and the grip 510 shaped to accommodate and facilitate access to a knob 602 which, in turn, is operatively attached to the proximal shaft end 590 of the carrier shaft 588. In the illustrated embodiment, the knob 602 comprises an axial knob aperture 604 formed along the impactor axis A1, and a transverse knob aperture 606 formed transverse to the impactor axis A1 and disposed in communication with the axial knob aperture 604. The axial knob aperture 604 is shaped to receive the proximal shaft end 590 of the carrier shaft 588, and the transverse knob aperture 606 is shaped to receive a transverse pin 608 which is also received within a transverse shaft aperture 610 formed in the carrier shaft 588 (see FIG. 16B). In addition to ensuring retention of the carrier shaft 588, this configuration also permits the knob 602 and the carrier shaft 588 rotate and translate concurrently about the impactor axis A1. Here, the cage 600 of the handle 508 has a generally U-shaped profile and is configured to permit limited translation of the knob 602 along the impactor axis A1 while also providing the surgeon with access to the knob 602.

Referring now to FIGS. 17-21, the guide 504 of the third embodiment of the end effector 440 is generally shown, and likewise comprises the body 492 which is operatively attached to the mount 490 (not shown in detail) to facilitate releasable attachment to the coupling 38 of the surgical robot 32 (see FIG. 1). Here too, the body 492 generally comprises the channel 494, the opening 496, the guide engagement surface 498, and the limiter 500. As is best depicted in FIG. 18B, the body 492 of the guide 504 employs the pocket 578 in this embodiment to, among other things, accommodate a sensor subassembly 612, a follower subassembly 614, and an input module 616, each of which are described in greater detail below.

Figure 18A:
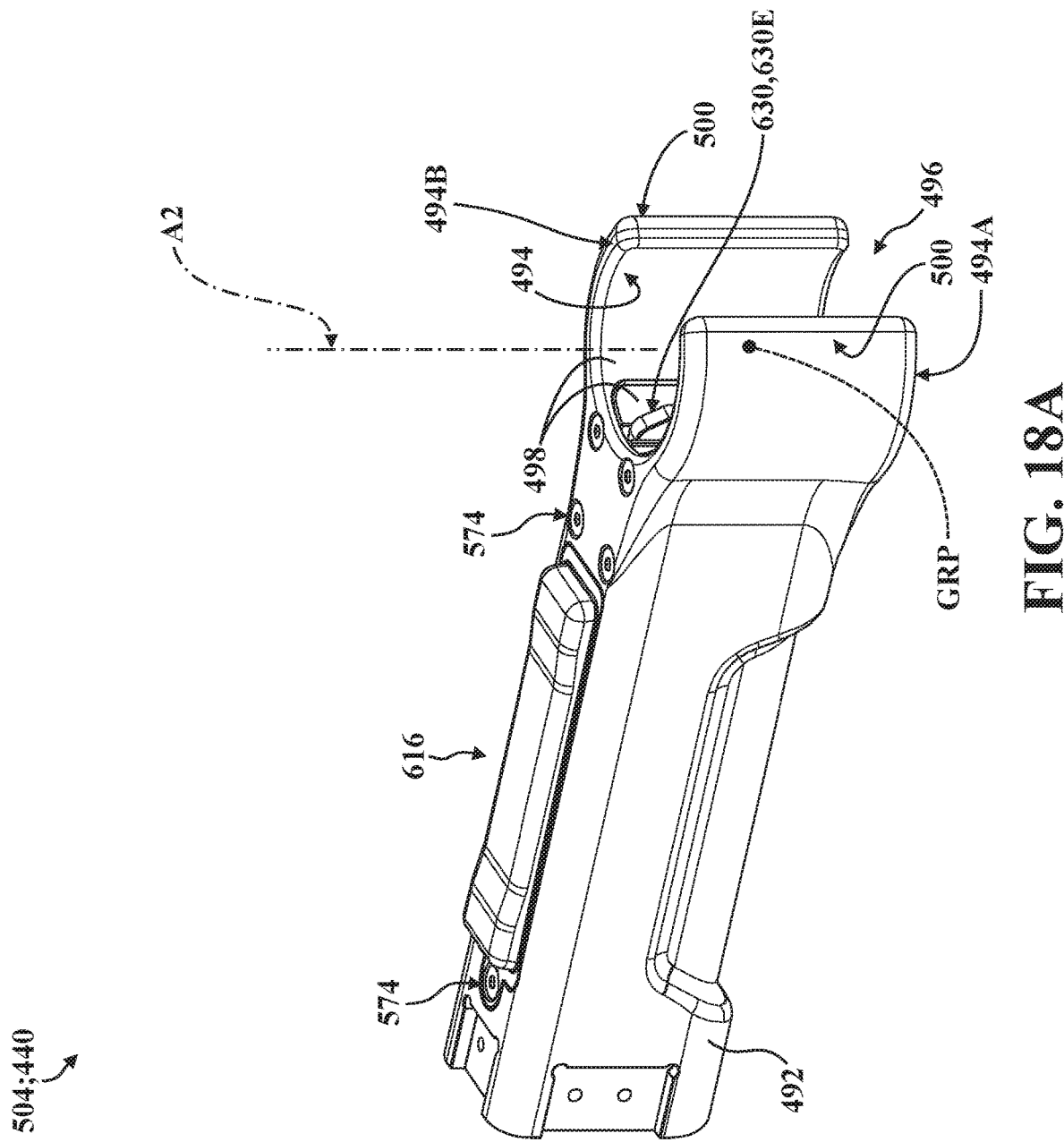
FIG. 18A is a perspective view of the guide of FIG. 17.
Figure 18B:
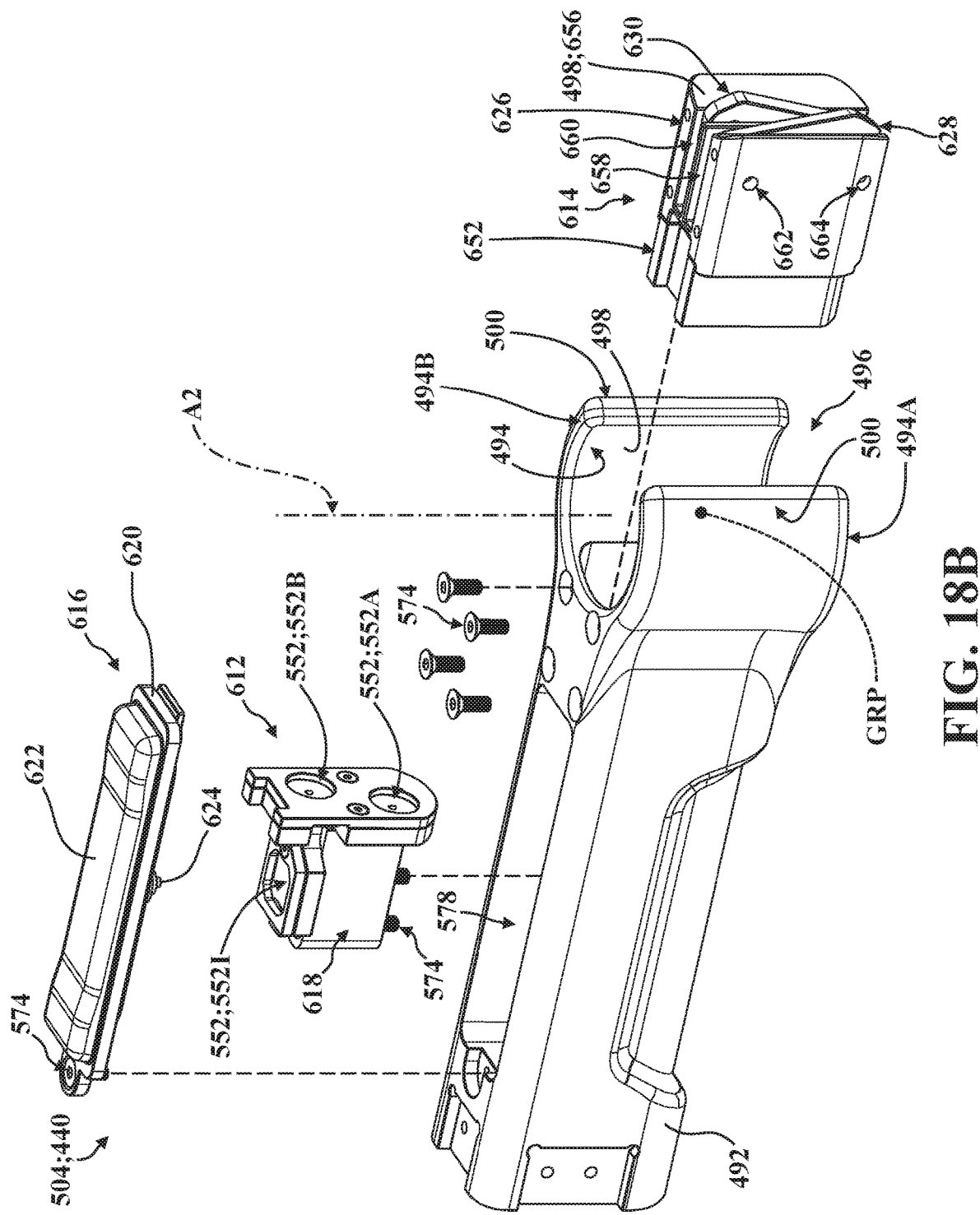
FIG. 18B is an exploded perspective view of the guide of FIGS. 17-18A, shown comprising a body defining a channel, and shown with the body spaced from a follower subassembly, a sensor subassembly, and an input module.
Figure 19A:
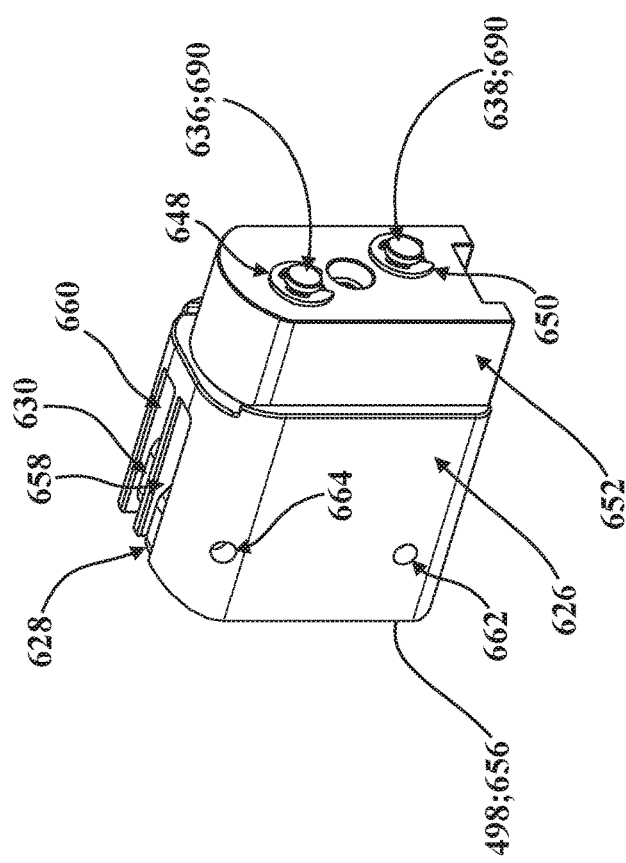
FIG. 19A is a perspective view of the follower subassembly of FIG. 18B.
Figure 19B:
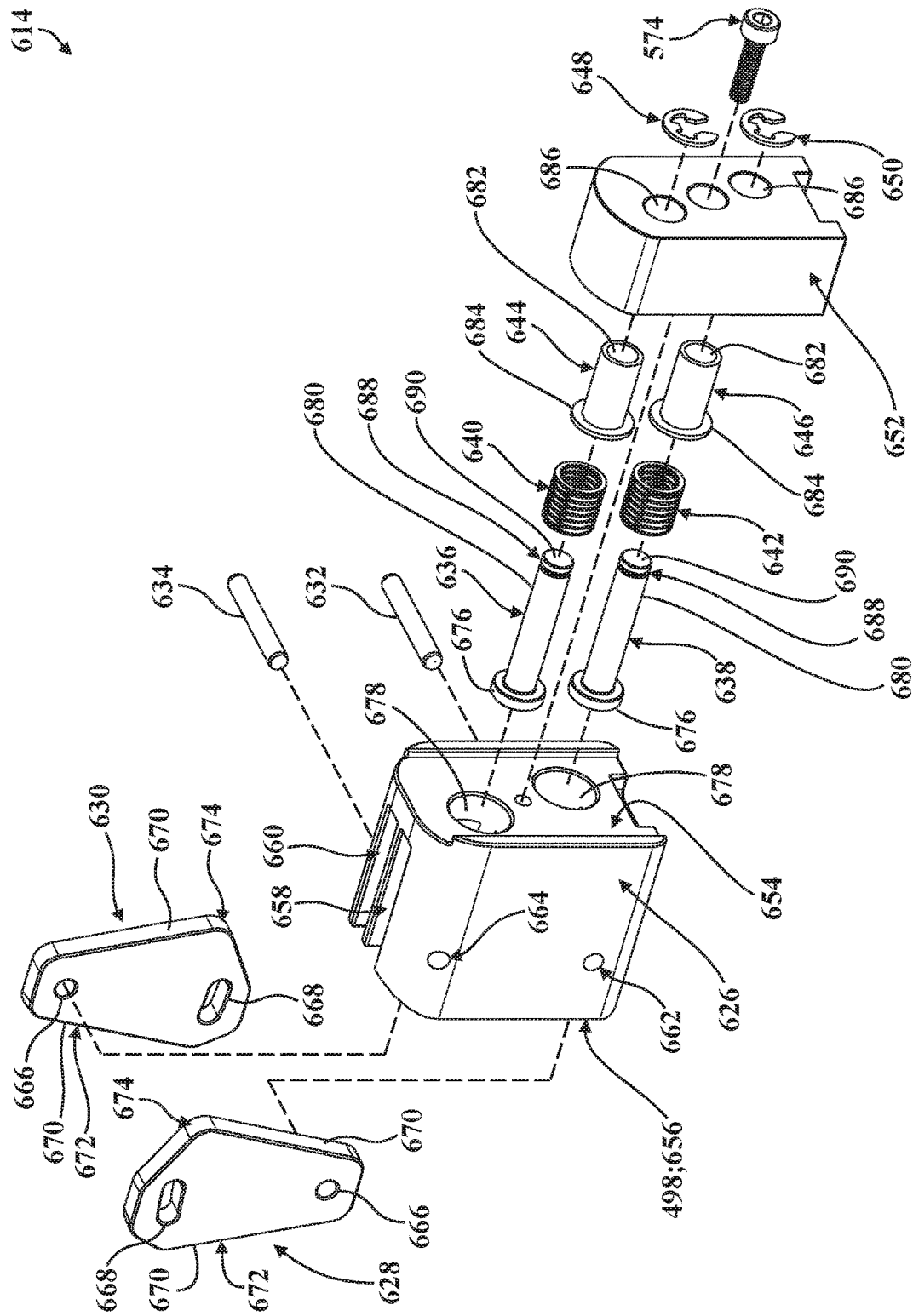
FIG. 19B is an exploded perspective view of the follower subassembly of FIG. 19A, shown comprising first and second triggers arranged to move first and second pushrods.
Figure 20:
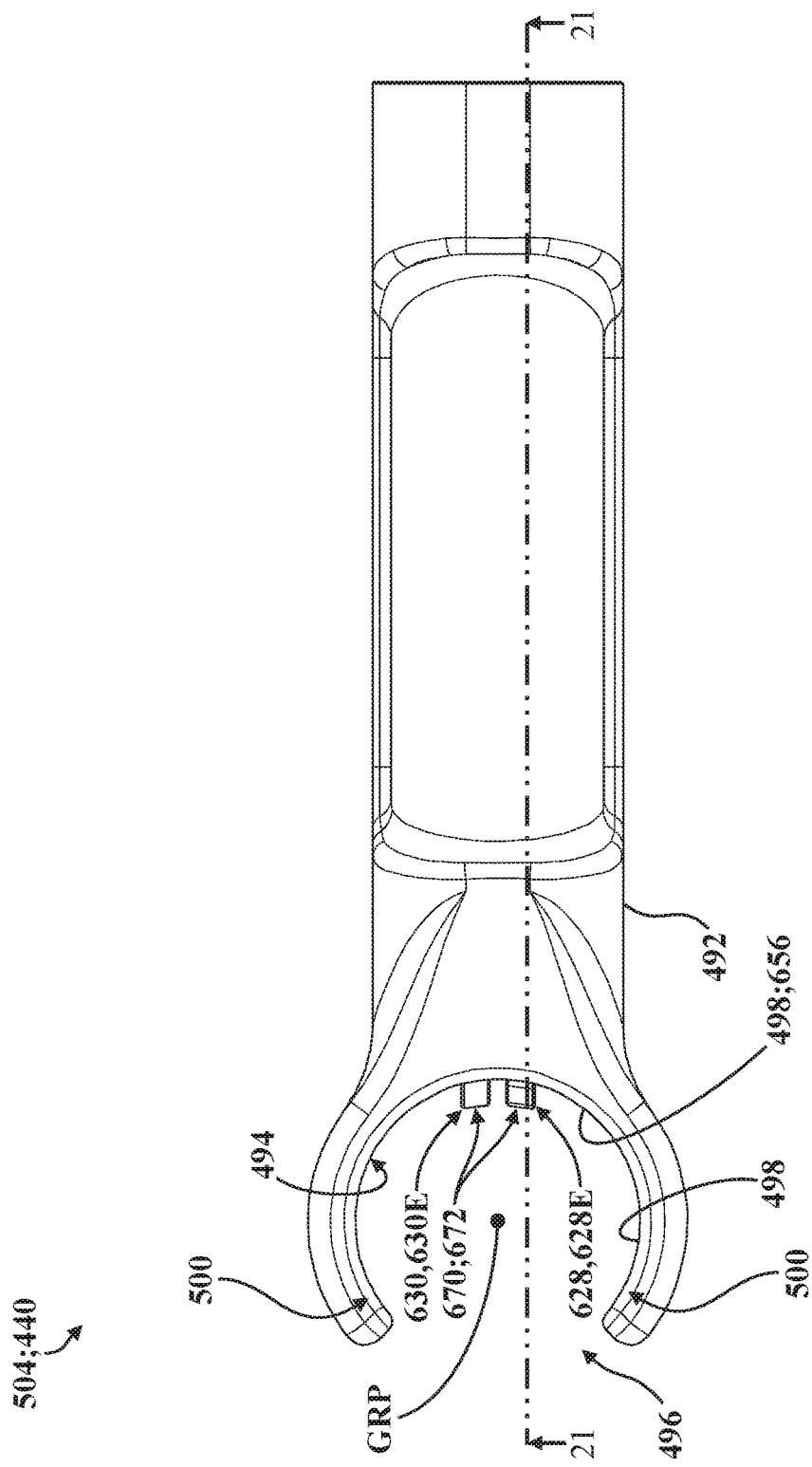
FIG. 20 is a top-side view of the guide of the end effector of FIGS. 17-18B.
Figure 21:
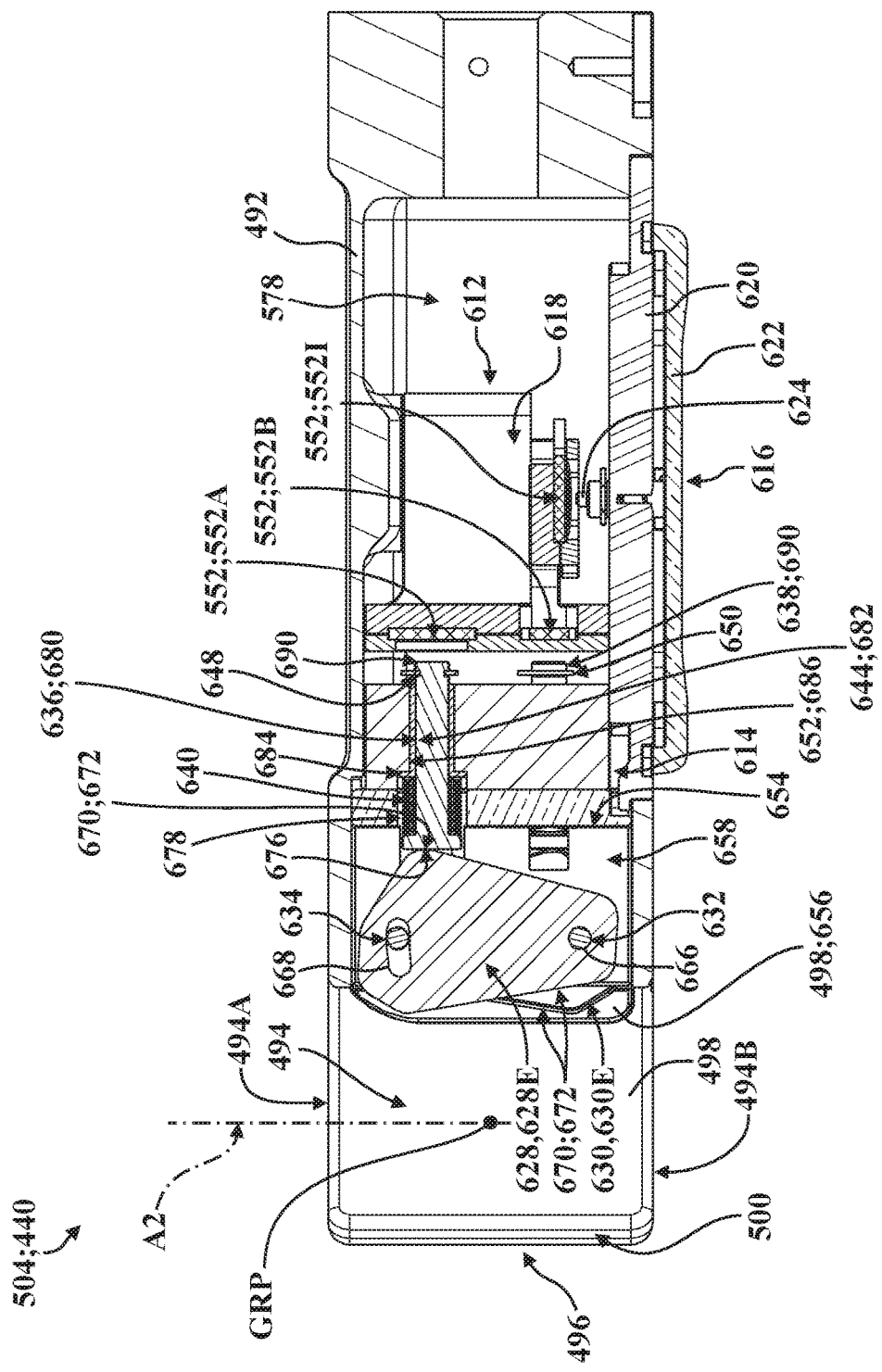
FIG. 21 is a section view taken along line 21-21 in FIG. 20.

In this third embodiment, the sensor subassembly 612 generally comprises a sensor housing 618 which supports a plurality of sensors 552 and is secured to the body 492 of the guide 504 via fasteners 574. More specifically, and as is best depicted in FIG. 18B, the sensor subassembly 612 comprises a first pushrod sensor 552A, a second pushrod sensor 552B, and an input sensor 552I, each of which may be disposed in communication (e.g., wired or wireless electrical communication) with the robotic control system 48 (e.g., the robot controller 52) or other components of the surgical system 30. The input sensor 552I is arranged so as to be engaged by or otherwise disposed in communication with the input module 616, and the first and second pushrod sensors 552A, 552B are arranged so as to be engaged by or otherwise disposed in communication with the follower subassembly 614. As will be appreciated from the subsequent description below, each of the sensors 552 of the sensor subassembly 612 could be of a number of different types, styles, configurations, and the like, and other configurations besides those specifically illustrated herein are contemplated by the present disclosure.

As shown in FIG. 18B, the input module 616 is configured for selective actuation by the surgeon and generally comprises an input frame 620 and an input button 622. The input frame 620 is secured to the body 492 of the guide 504 via one or more fasteners 574, and supports the input button 622 for movement relative thereto. The input button 622 comprises a protrusion 624 arranged to engage the input sensor 5521 in response to actuation by the surgeon (e.g., by pressing on the input button 622). In some embodiments, the input button 622 could be resiliently biased away from the input frame, such as by a spring (not shown). However, other configurations are contemplated. As is described in greater detail below, the input module 616 may be configured to facilitate operating the surgical robot 32 in different ways during a surgical procedure.

The follower subassembly 614, like the sensor subassembly 612, is configured so as to be accommodated within the pocket 578 formed in the body 492 of the guide 504, and is secured to the body 492 with fasteners 574. In this third embodiment, the pocket 578 extends into communication with the channel 494 to facilitate attachment of the follower subassembly 614 which, as is described in greater detail below, comprises a follower housing 626 that sits in the pocket 578 adjacent to the channel 494 and is sized and shaped so as to be able to pass through the opening 496. This configuration helps facilitate assembly of the guide 504 and ensures that the sensor subassembly 612 is positioned properly relative to the channel 494 (see FIG. 18A). Because the pocket 578 extends into the channel 494 in this third embodiment, the guide engagement surface 498 is defined by both the body 492 and a by a portion of the follower housing 626. Put differently, the impactor engagement surface 488 defined by the flange 512 of the impactor assembly 502 abuts both the body 492 and the follower housing 626 in this embodiment.

Referring now to FIGS. 18A-19B and 21, in addition to the follower housing 626, the follower subassembly 614 also generally comprises first and second triggers 628, 630, first and second trigger pins 632, 634, first and second pushrods 636, 638, first and second springs 640, 642, first and second seats 644, 646, first and second keepers 648, 650, and a manifold body 652. Each of these components will be described in greater detail below.

As is described in connection with FIGS. 22A-24D, the follower housing 626 generally supports the first and second triggers 628, 630 for pivoting movement about the first and second trigger pins 632, 634, respectively. To this end, the follower housing 626 defines a flange face 654 which has a generally flat profile to abut the manifold body 652, and an opposing engagement face 656 which has a curved profile that is complimentary to the channel 494 and forms parts of the guide engagement surface 498 in this embodiment (see FIGS. 18A-18B and 20). A fastener 574 operatively attaches the manifold body 652 to the follower housing 626 (attachment not shown in detail). First and second trigger slots 658, 660 each having a generally rectangular profile (not shown in detail) are defined in the engagement face 656 extending longitudinally toward the flange face 654, and are shaped and arranged to accommodate the first and second triggers 628, 630, respectively, therein. To this end, first and second pin bores 662, 664 are also defined in the follower housing 626 extending laterally through each of the first and second trigger slots 658, 660 and through the lateral sides of the follower housing 626. The first and second pin bores 662, 664 are shaped and arranged to accommodate the first and second trigger pins 632, 634, respectively, which each extend through the first and second triggers 628, 630.

The triggers 628, 630 are similar to the trigger 154 described above in connection with the first embodiment of the end effector 40 in that they are configured so as to extend into the channel 494 and to deflect towards sensors in response to engagement with the flange 512, but are nevertheless described separately herein because of certain difference in their configurations. More specifically, the first and second triggers 628, 630 each define a respective trigger bore 666 and a trigger slot 668 that are shaped to receive the first and second trigger pins 632, 634, with the trigger bore 666 of the first trigger 628 being rotatably supported about the first trigger pin 632, and with the trigger bore 666 of the second trigger 630 being rotatably supported about the second trigger pin 634. Furthermore, the second trigger pin 634 extends through the trigger slot 668 of the first trigger 628, and the first trigger pin 632 extends through the trigger slot 668 of the second trigger 630.

The trigger slots 668 are shaped and arranged to permit limited movement of each of the triggers 628, 630 about the respective trigger pins 632, 634 in response to engagement with the flange 512 of the impactor assembly 502. More specifically, the first trigger 628 is arranged for movement between an extended first position 628E defined by an absence of engagement with the impactor assembly 502 (see FIGS. 22A-22B and 22G-22H), a retracted first position 628R (see FIGS. 22D-22E), and one or more intermediate first positions 628I (see FIGS. 22C and 22F) between the extended first position 628E and the retracted first position 628R. Similarly, the second trigger 630 is arranged for movement between an extended second position 630E (see FIGS. 22A-22C and 22H), a retracted second position 630R (see FIGS. 22E-22F), and one or more intermediate second positions 630I (see FIGS. 22D and 22G) between the extended second position 630E and the retracted second position 630R.

The first and second triggers 628, 630 also each comprise an edge surface 670 which defines a flange region 672 and pushrod region 674. The flange regions 672 are generally disposed within the channel 494 when the triggers 628, 630 are in their extended positions 628E, 630E, and are shaped and arranged to abut, engage, or otherwise contact the flange 512 of the impactor assembly 502 and to promote pivoting movement about the respective trigger pins 632, 634 in response. The flange regions 672 may also have curved and/or angled profiles (see FIG. 20) to compliment the curved profile of the channel 494 when fully pivoted via engagement with the flange 512. The pushrod regions 674 of the first and second triggers 628, 630 are shaped to abut respective stems 676 of the first and second pushrods 636, 638 in order to translate pivoting movement of the first and second triggers 628, 630 into axial movement of the first and second pushrods 636, 638. Here, and as is described in greater detail below, the first and second pushrods 636, 638 are interposed in force-translating relation between the first and second triggers 628, 630 and the first and second pushrod sensors 552A, 552B, respectively, to engage the sensors 552A, 552B in response to movement of the respective triggers 628, 630 away from their extended positions 628E, 630E, which allows the relative axial position of the flange 512 between the first and second axial channel ends 494A, 494B of the channel 494 to be determined.

The stems 676 of the first and second pushrods 636, 638 are disposed within respective stem bores 678 defined in the flange face 654 of the follower housing 626 extending into communication with the first and second trigger slots 658, 660, respectively, to facilitate abutment with the pushrod regions 674 of the first and second triggers 628, 630. The first and second pushrods 636, 638 each also comprise a respective shank 680 extending axially from the stem 676. The shanks 680 of the first and second pushrods 636, 638 extend through respective shank bores 682 formed in the first and second seats 644, 646, and respectively support (or at least restrict movement of) the first and second springs 640, 642 between the stems 676 of the first and second pushrods 636, 638 and brims 684 of the first and second seats 644, 646 (see FIG. 19B). Portions of the first and second seats 644, 646, as well as portions of the shanks 680 of the first and second pushrods 636, 638, extend through seat bores 686 defined longitudinally though the manifold body 652. Here, the first and second keepers 648, 650 are seated in notches 688 formed in the respective first and second pushrods 636, 638 adjacent to pushrod ends 690 of the first and second pushrods 636, 638 which, in turn, engage or otherwise interact with the first and second pushrod sensors 552A, 552B, respectively. This configuration retains the first and second pushrods 636, 638 and, in some embodiments, preloads the first and second springs 640, 642 between the stems 676 and the brims 684 such that the first and second pushrods 636, 638 are each respectively and independently biased into engagement with the first and second triggers 628, 630. Thus, pivoting movement of the first and second triggers 628, 630 between their respective extended and retracted positions 628E, 630E; 628R; 630R is translated into axial movement of the pushrod ends 690 of the first and second pushrods 636, 638 that can be sensed or otherwise determined via the pushrod sensors 552A, 552B.

Referring now to FIGS. 22A-22H and 24A-24D, portions of the third embodiment of the end effector 440, the prosthesis P, and the surgical site S are depicted with schematic outlines, with some of the schematic outlines shown in phantom and/or with exaggerated geometry for illustrative purposes. FIGS. 22A-22H represent various positions of the guide 504 relative to the impactor assembly 502 to, among other things, demonstrate operation of the sensor subassembly 612, as described in greater detail below. Here, the prosthesis P and the surgical site S are represented generically for clarity and to reiterate that aspects of the present disclosure can be used in connection with a number of different types of surgical procedures that involve various types of workpieces 44 and/or targets 46.

Figure 22A:
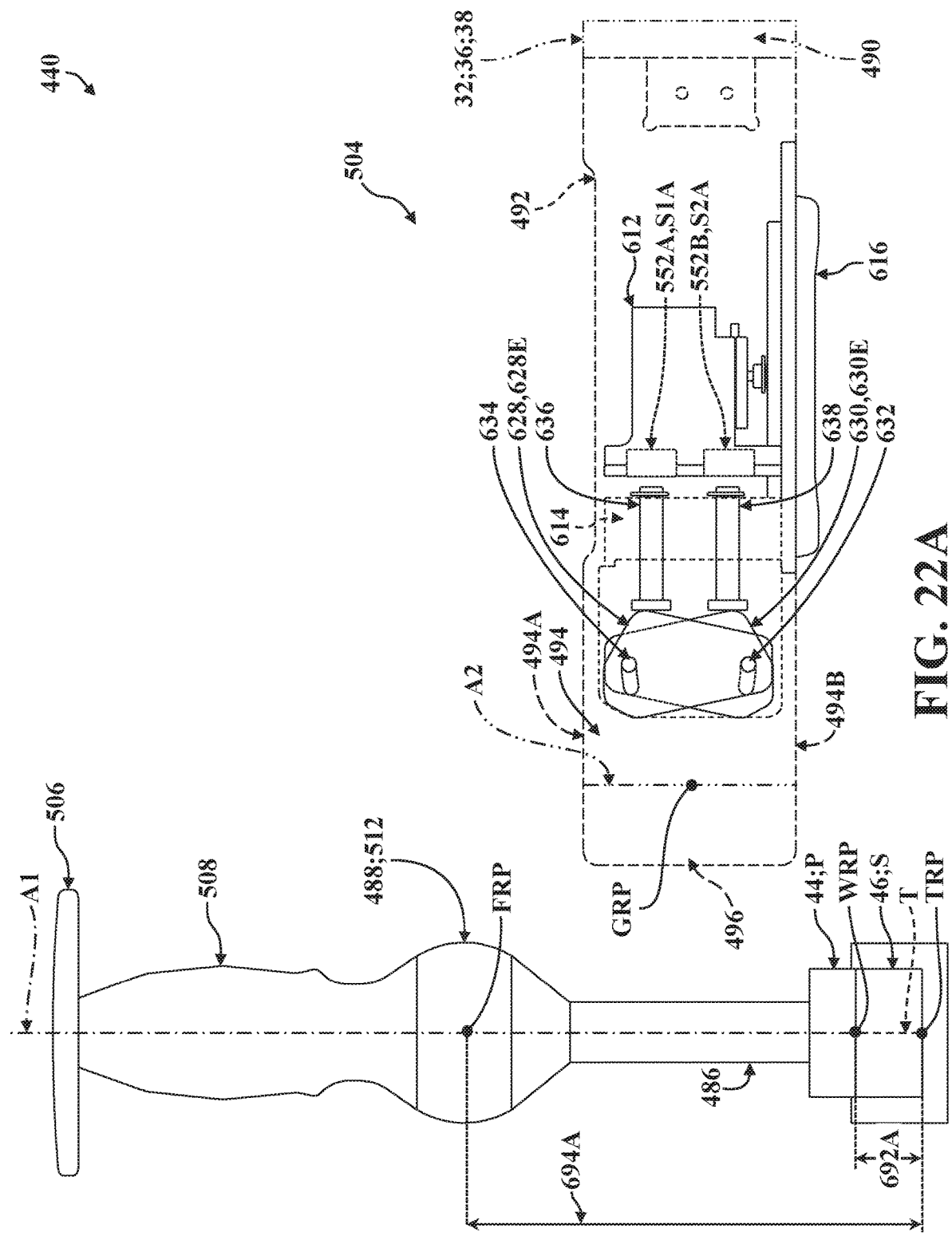
FIG. 22A is an illustrative schematic view of the prosthesis and the end effector of FIG. 17, shown with the impactor assembly comprising a shaft and an interface attached to the prosthesis arranged at a surgical site for impaction along a trajectory, and shown with a channel of the guide defining guide axis and spaced from the impactor assembly with the guide axis arranged parallel to the trajectory.

As best shown in FIG. 22A, the surgical site S defines a target reference point TRP along the trajectory T, and the prosthesis P defines a workpiece reference point WRP along the impactor axis A1 of the impactor assembly 502 to which the prosthesis P is releasably attached. Here too, the impactor assembly 502 defines a flange reference point FRP along the impactor axis A1 that is arranged in the center of the flange 512 (e.g., at the geometric center of the spherical profile which defines the impactor engagement surface 488). Similarly, the guide 504 defines a guide reference point GRP along the guide axis A2 that is arranged in the center of the channel 494 (e.g., spaced equidistantly between the first and second axial channel ends 494A, 494B).

In the illustrative example shown in FIG. 22A, the prosthesis P is positioned for impaction at the surgical site S with the impactor axis A1 aligned along the trajectory T such that the workpiece reference point WRP is spaced from the target reference point TRP, with the intended position of the prosthesis P after impaction defined by the workpiece reference point WRP being coincident with the target reference point TRP. FIGS. 22A-22B depict the workpiece reference point WRP being spaced from the target reference point TRP at a first workpiece-to-target distance 692A, represented here as the distance between the coordinate points of the workpiece reference point WRP and the target reference point TRP within a common coordinate system (e.g., the localizer coordinate system LCLZ). Moreover, FIGS. 22A-22B also depict the flange reference point FRP being spaced from the target reference point TRP at a first flange-to-target distance 694A, represented here as the distance between the coordinate points of the flange reference point FRP and the target reference point TRP within a common coordinate system (e.g., the localizer coordinate system LCLZ). Furthermore, FIG. 22B depicts the guide reference point GRP being spaced from the target reference point TRP at a first guide-to-target distance 696A, represented here as the distance between the coordinate points of the guide reference point GRP and the target reference point TRP within a common coordinate system (e.g., the localizer coordinate system LCLZ). While described herein as "points," it is conceivable that one or more of the guide, flange, target, and/or workpiece reference points GRP, FRP, TRP, WRP could be defined in other ways, such as with coordinate systems (e.g., to represent both position and orientation).

While not illustrated in FIGS. 22A-22B, it will be appreciated that the guide tracker 60G, the impactor tracker 60I, and the first patient tracker 60A shown in FIG. 1 demonstrate one way in which the guide reference point GRP, the flange reference point FRP, and the target reference point TRP can be monitored within the localizer coordinate system LCLZ (and/or one or more other common coordinate systems). Here, because the prosthesis P is releasably secured to the interface 484 of the impactor assembly 502, it will be appreciated that the workpiece reference point WRP can be determined by transforming the flange reference point FRP based on known geometrical relationships of and between the impactor assembly 502 and the prosthesis P. Thus, in some embodiments, the navigation system 50 can be used to monitor the guide, flange, target, and workpiece reference points GRP, FRP, TRP, WRP within the localizer coordinate system LCLZ by using trackers 60. However, it will also be appreciated that various tracking techniques can be utilized and, in certain applications, it may be unnecessary or otherwise impractical to utilize certain trackers 60 with certain components of the surgical system 30.

By way of non-limiting example, the guide reference point GRP could be determined without using the guide tracker 60G, such as based on the specific configuration and arrangement of the robotic arm 36 (e.g., determined by sensors at the joints) considered alongside the known geometrical relationships of and between the guide 504 and the coupling 38. By way of further non-limiting example, while utilizing the impactor tracker 60I advantageously allows the navigation system 50 to monitor the workpiece reference point WRP relative to the target reference point TRP, certain embodiments of the impactor assembly 502 (e.g., as depicted in connection with FIGS. 22A-22H) may omit the impactor tracker 60I. In such cases, and as is described in greater detail below, one or more sensors 552 can be utilized in order to determine the flange reference point FRP (and, thus, the workpiece reference point WRP) by transforming the guide reference point GRP based on known geometric relationships between the impactor assembly 502 and the guide 504 that result in predetermined interaction with one or more sensors 552 that causes the one or more sensors 552 to generate signal(s) which indicate that the impactor assembly 502 is positioned, arranged, or otherwise orientated in a known way relative to the guide 504.

FIGS. 22A-24D illustrate various aspects of the third embodiment (as well as other embodiments of the present disclosure) of the end effector 440, including how one or more sensors 552 coupled to the guide 504 can be used to determine (or otherwise respond to changes in) the position of the impactor assembly 502. In the representative embodiment described herein in connection with FIGS. 22A-24D, the first and second pushrod sensors 552A, 552B are realized as momentary switches, but may be of other types and configurations, as described in greater detail below. Nevertheless, for the purposes of clarity and consistency, the forgoing description of FIGS. 22A-24D is based on the first pushrod sensor 552A being operable between a disengaged first sensor state S1A and an engaged first sensor state S1B, as well as based on the second pushrod sensor 552B being operable between a disengaged second sensor state S2A and an engaged second sensor state S2B.

While the engagement/disengagement of the first and second pushrod sensors 552A, 552B will be described in detail below relative to FIGS. 22A-22H, FIG. 23 also presents a graphical representation of signals SN1, SN2 respectively generated by the first and second pushrod sensors 552A, 552B that may be communicated to other parts of the surgical system 30. In FIG. 23, vertical lines A, B, C, D, E, F, G, and H correspond, respectively, to what is illustrated in FIGS. 22A, 22B, 22C, 22D, 22E, 22F, 22G, and 22H. Furthermore, in FIG. 23, dash-dot-dash lines represent the first signal SN1 between the disengaged and engaged first sensor states S1A, S1B (represented here by horizontal lines), and dash-dot-dot-dash lines represent the second signal SN2 between the disengaged and engaged second sensor states S2A, S2B (also represented here by horizontal lines).

In FIG. 22A, the guide 504 is shown spaced horizontally from the impactor assembly 502, and FIG. 22B shows the guide 504 having been moved horizontally to the left in order to position the shaft 486 of the impactor assembly 502 within the channel 494 of the guide 504. More specifically, in FIG. 22B, the surgical robot 32 has moved the guide 504 relative to the surgical site S in order to align the guide axis A2 with the trajectory T. While not illustrated herein, it will be appreciated that the surgical robot 32 can compensate for movement of the surgical site S by controlling or otherwise driving the robotic arm 36 in order to maintain alignment of the guide axis A2 with the trajectory T.

FIG. 22B shows the shaft 486 of the impactor assembly 502 arranged within the channel 494 of the guide 504 which, in turn, is disposed vertically between the prosthesis P and the flange 512 of the impactor assembly 502. As noted above, this arrangement advantageously allows the surgeon to articulate, manipulate, or otherwise handle the impactor assembly 502 independent of the guide 504, and once positioned within the channel 494, the surgeon can then move the guide 504 along the trajectory T away from the surgical site S and toward the flange 512 (e.g., vertically). FIG. 22B (as well as FIG. 22A) also shows the first trigger 628 and the second trigger 630 each arranged in their respective extended positions 628E, 630E. For the purposes of clarity and consistency, and unless otherwise indicated, the first pushrod sensor 552A is considered to be out of engagement with the first trigger 628 in the first extended position 628E, and is considered to be in engagement with the first trigger 628 in the first retracted position 628R or in one of the intermediate first positions 628I. Similarly, unless otherwise indicated, the second pushrod sensor 552B is considered to be out of engagement with the second trigger 630 in the extended second position 630E, and is considered to be in engagement with the second trigger 630 in the retracted second position 630R or in one of the intermediate second positions 630I. Put differently, the extended positions 628E, 630E are defined by an absence of engagement with the impactor assembly 502, and the retracted positions 628R, 630R (as well as the intermediate positions 628I, 630I) are defined by engagement with the flange 512 of the impactor assembly 502. However, other configurations are contemplated.

FIG. 22C shows the guide 504 having been moved such that the guide reference point GRP is arranged at a second guide-to-target distance 696B, with the flange 512 of the impactor assembly 502 disposed within the channel 494 of the guide 504. Put differently, in this arrangement, the impactor engagement surface 488 is abutting the guide engagement surface 498 (abutment not shown here), and the guide reference point GRP is arranged vertically below the flange reference point FRP. FIG. 22C also shows the flange 512 of the impactor assembly 502 abutting against the flange region 672 of the first trigger 628, which has pivoted about the first trigger pin 632 away from the extended first position 628E and to one of the intermediate first positions 628I in response. This, in turn, has advanced the first pushrod 636 toward and into engagement with the first pushrod sensor 552A (compare FIG. 22C to FIG. 22B). However, when arranged in this way at the second guide-to-target distance 696B, the flange region 672 of the second trigger 630 remains out of abutment with the flange 512 and remains disposed in the extended second position 630E. Thus, the second pushrod 638 remains out of engagement with the second pushrod sensor 552B. Accordingly, FIG. 23 depicts the first signal SN1 (at vertical line C) as having moved from the disengaged first sensor state S1A to the engaged first sensor state S1B, and depicts the second signal SN2 (at vertical line C) as having remained at the disengaged second sensor state S2A.

Figure 22D:
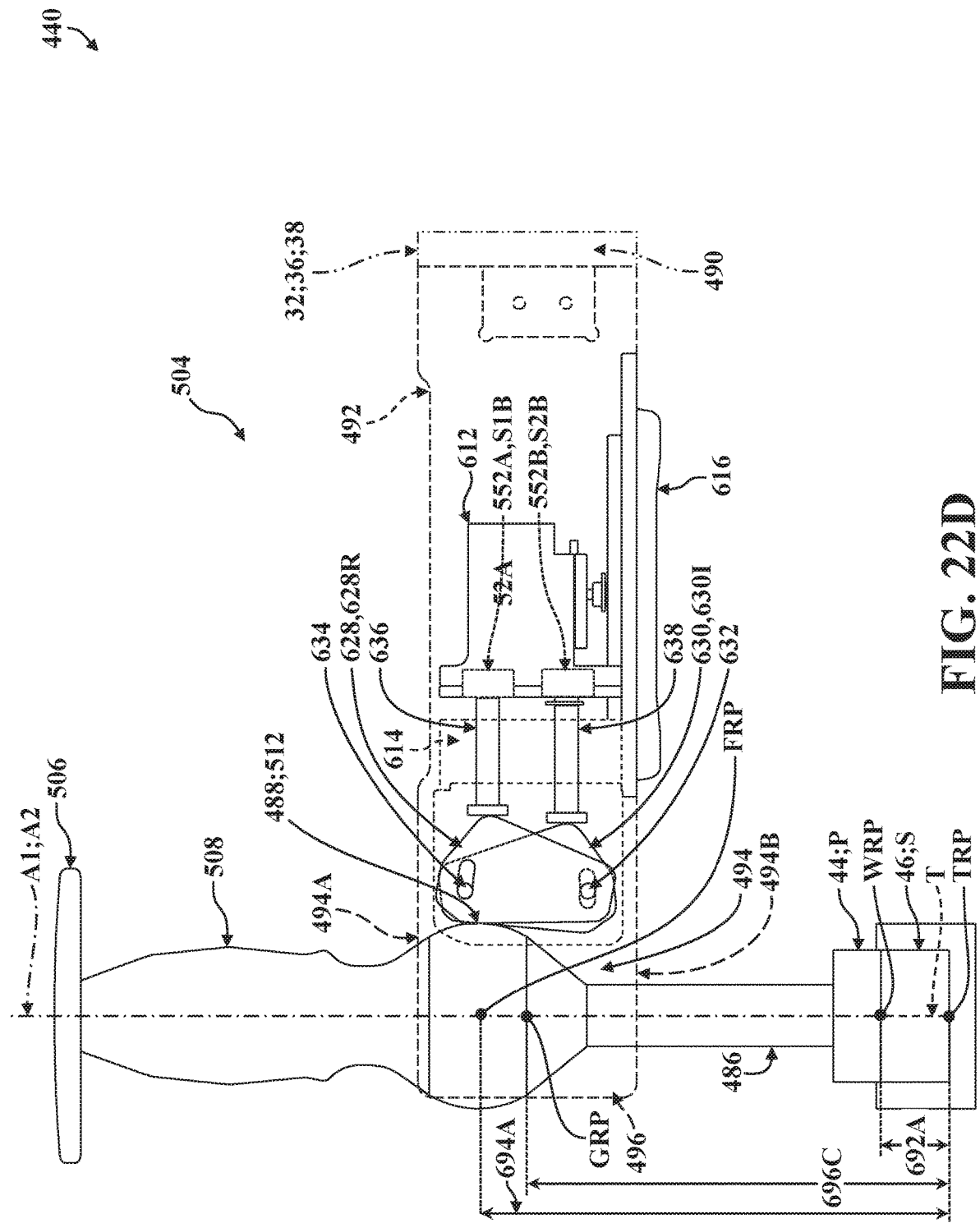
FIG. 22D is another illustrative schematic view of the surgical site, the prosthesis, and the end effector of FIGS. 22A-22C, shown with the guide moved further away from the surgical site along the trajectory with the flange still engaging the channel and the first trigger, and also shown with the flange engaging against the second trigger of the follower subassembly to translate the second pushrod toward a second pushrod sensor of the sensor subassembly.
Figure 23:
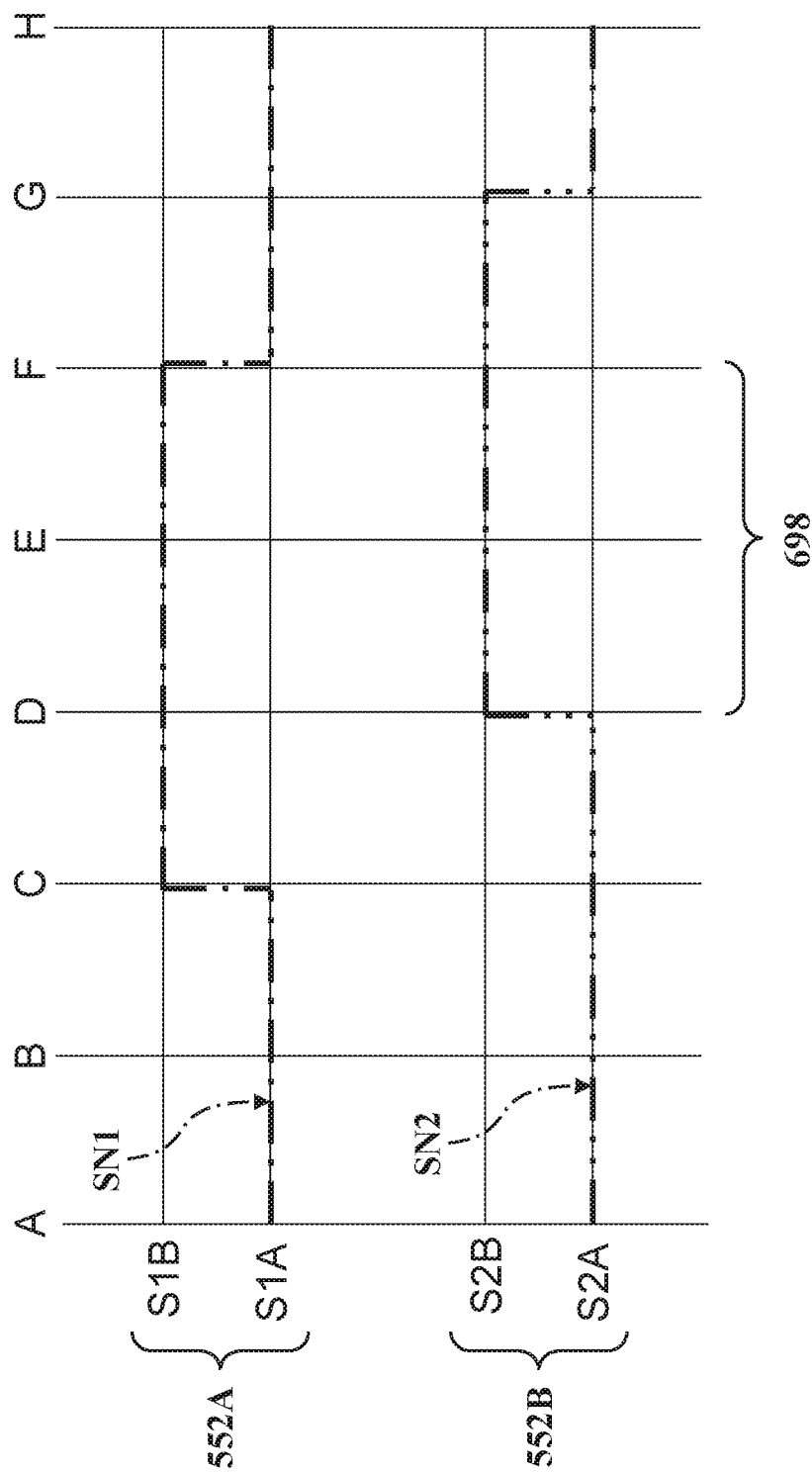
FIG. 23 is a graphical representation of signals generated by the first and second pushrod sensors corresponding to the relative states of the first and second triggers illustrated in FIGS. 22A-22H.

FIG. 22D shows the guide 504 having been moved such that the guide reference point GRP is arranged at a third guide-to-target distance 696C, with the flange 512 of the impactor assembly 502 disposed further into the channel 494 of the guide 504. Here too in FIG. 22D, the guide reference point GRP is arranged vertically below the flange reference point FRP. FIG. 22D also shows the flange 512 of the impactor assembly 502 abutting against the flange region 672 of the first trigger 628, which has pivoted further about the first trigger pin 632 to the retracted first position 628R in response. This, in turn, has advanced the first pushrod 636 further toward and into engagement with the first pushrod sensor 552A (compare FIG. 22D to FIG. 22C). Here, it will be appreciated that other types of sensors 552 besides switches could be utilized to generate analog signals that represent relative positions of the pushrods 636, 638 as opposed to digital signals that represent engagement/disengagement with the pushrods 636, 638. Other configurations are contemplated. Nevertheless, FIG. 22D also shows the flange 512 of the impactor assembly 502 abutting against the flange region 672 of the second trigger 630, which has pivoted about the second trigger pin 634 away from the extended second position 630E and to one of the intermediate second positions 630I in response. This, in turn, has advanced the second pushrod 638 toward and into engagement with second first pushrod sensor 552B (compare FIG. 22D to FIG. 22C). Accordingly, FIG. 23 depicts the first signal SN1 (at vertical line D) as having remained at the engaged first sensor state S1B, and depicts the second signal SN2 (at vertical line D) as having moved from the disengaged second sensor state S2A to the engaged second sensor state S2B.

Figure 22E:
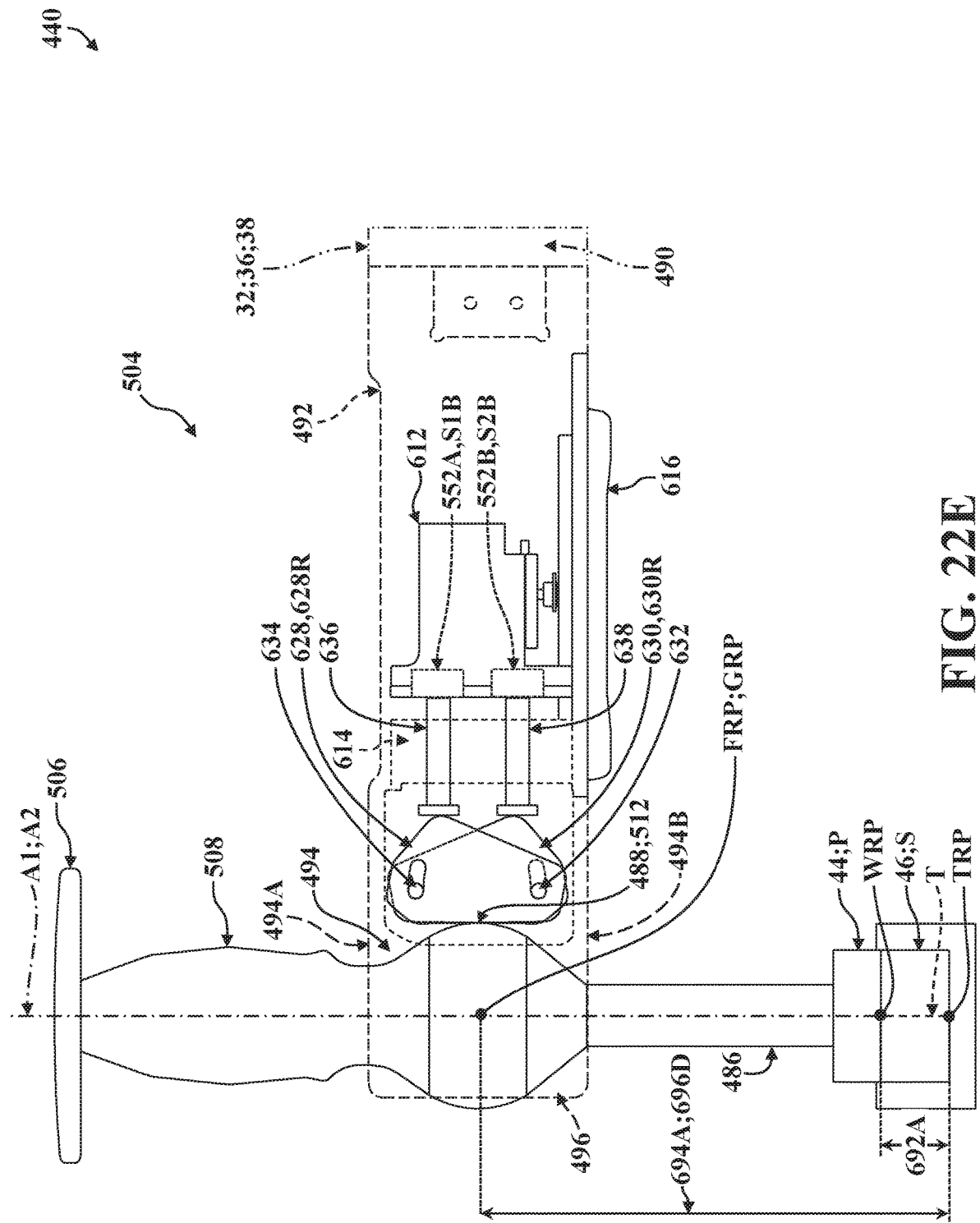
FIG. 22E is another illustrative schematic view of the surgical site, the prosthesis, and the end effector of FIGS. 22A-22D, shown with the guide moved further away from the surgical site along the trajectory with the flange still engaging the channel, the first trigger, and the second trigger, and shown with the flange of the impactor assembly disposed in the vertical center of the channel of the guide.

FIG. 22E shows the guide 504 having been moved such that the guide reference point GRP is arranged at a fourth guide-to-target distance 696D, with the flange 512 of the impactor assembly 502 disposed further into the channel 494 of the guide 504. More specifically, in FIG. 22E, the guide reference point GRP is arranged coincident with the flange reference point FRP. FIG. 22E also shows the flange 512 of the impactor assembly 502 abutting against the flange region 672 of the first trigger 628, which has remained generally in the same arrangement as depicted in FIG. 22D based, among other things, on the geometry of the first trigger 628 and the flange 512. As such, the first pushrod 636 remains similarly disposed in engagement with the first pushrod sensor 552A (compare FIG. 22E to FIG. 22D). FIG. 22E also shows the flange 512 of the impactor assembly 502 abutting against the flange region 672 of the second trigger 630, which has pivoted further about the second trigger pin 634 to the retracted second position 630R in response. This, in turn, has advanced the second pushrod 638 further toward and into engagement with second first pushrod sensor 552B (compare FIG. 22E to FIG. 22D). Accordingly, FIG. 23 depicts the first signal SN1 (at vertical line E) as having remained at the engaged first sensor state S1B, and depicts the second signal SN2 (at vertical line E) as having remained at the engaged second sensor state S2B.

Figure 22F:
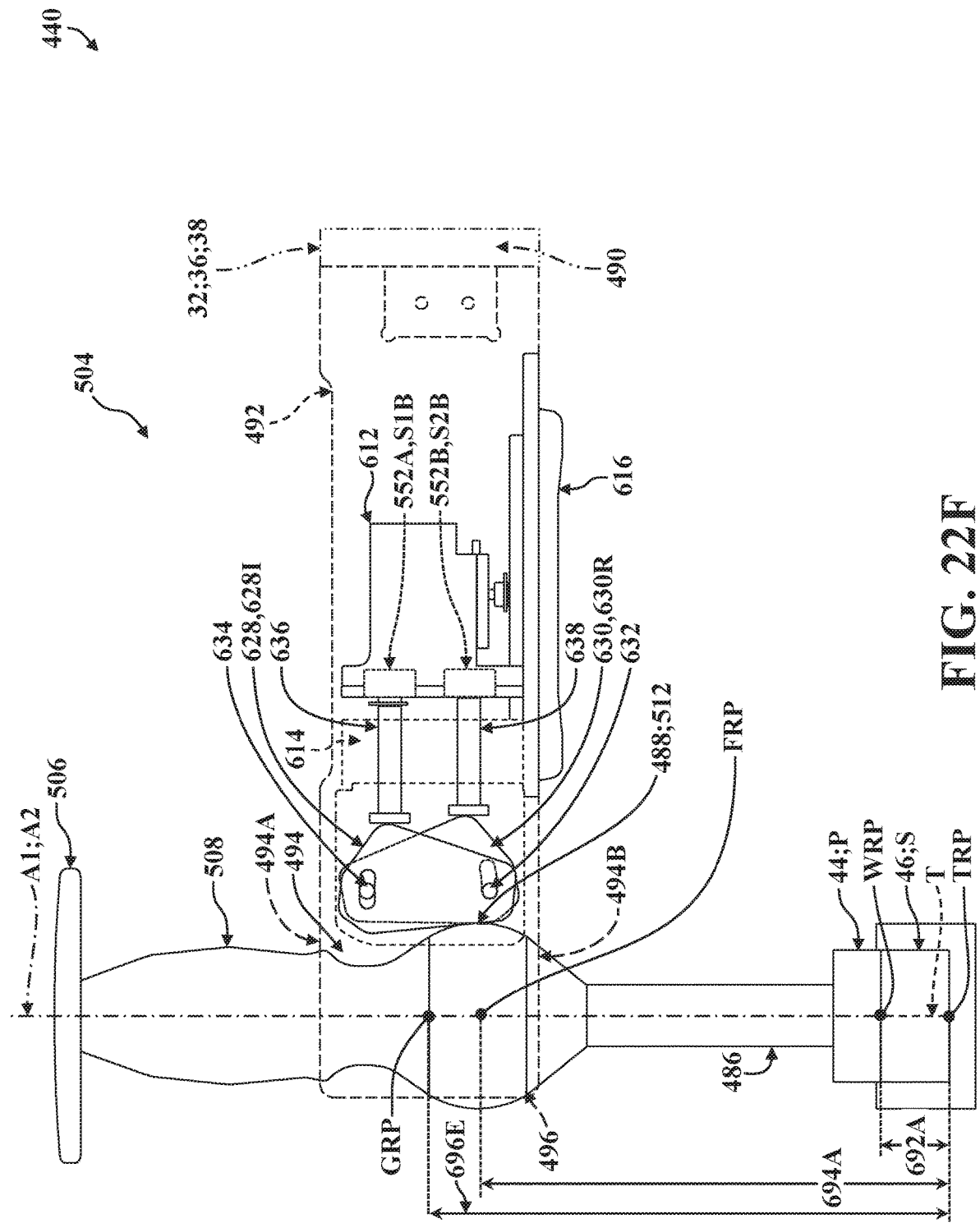
FIG. 22F is another illustrative schematic view of the surgical site, the prosthesis, and the end effector of FIGS. 22A-22E, shown with the guide moved further away from the surgical site along the trajectory with the flange still engaging the channel, the first trigger, and the second trigger.

FIG. 22F shows the guide 504 having been moved such that the guide reference point GRP is arranged at a fifth guide-to-target distance 696E, with the flange 512 of the impactor assembly 502 disposed further into the channel 494 of the guide 504. More specifically, in FIG. 22F, the guide reference point GRP is arranged vertically above the flange reference point FRP. FIG. 22F also shows the flange 512 of the impactor assembly 502 abutting against the flange region 672 of the first trigger 628, which has begun to pivot back about the first trigger pin 632 away from the retracted first position 628R to one of the intermediate first positions 628I. As such, the first pushrod 636 is slightly retracted but still remains disposed in engagement with the first pushrod sensor 552A (compare FIG. 22F to FIG. 22E). FIG. 22F also shows the flange 512 of the impactor assembly 502 abutting against the flange region 672 of the second trigger 630, which has remained generally in the same arrangement as depicted in FIG. 22E based, among other things, on the geometry of the second trigger 630 and the flange 512. As such, the second pushrod 638 remains similarly disposed in engagement with the second pushrod sensor 552B (compare FIG. 22F to FIG. 22E). Accordingly, FIG. 23 depicts the first signal SN1 (at vertical line F) as having remained at the engaged first sensor state S1B, and depicts the second signal SN2 (at vertical line F) as having remained at the engaged second sensor state S2B.

Figure 22G:
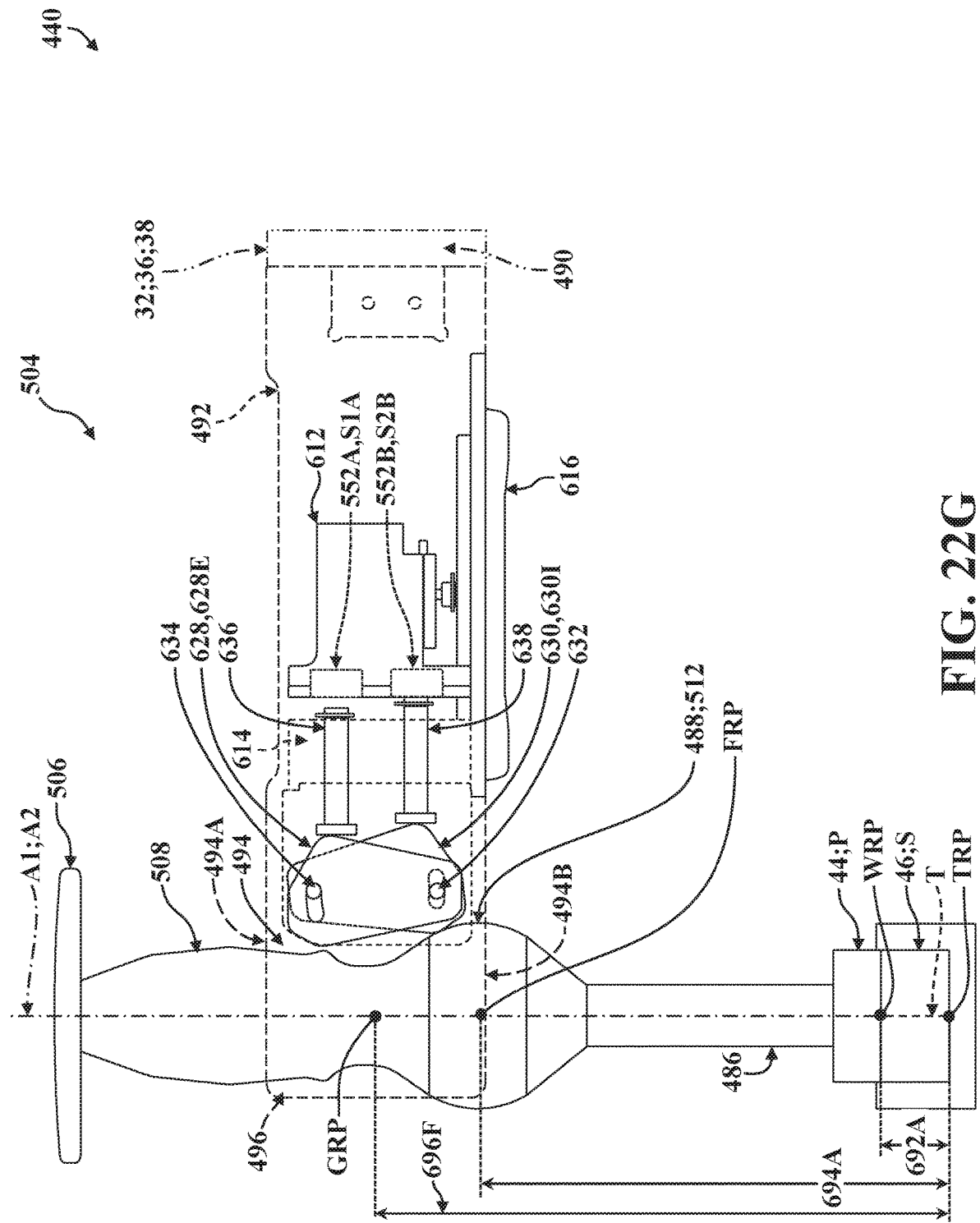
FIG. 22G is another illustrative schematic view of the surgical site, the prosthesis, and the end effector of FIGS. 22A-22F, shown with the guide moved further away from the surgical site along the trajectory with the flange still engaging the channel and the second trigger, and with the flange disposed out of engagement with the second trigger.

FIG. 22G shows the guide 504 having been moved such that the guide reference point GRP is arranged at a sixth guide-to-target distance 696F, with the flange 512 of the impactor assembly 502 disposed further into the channel 494 of the guide 504. More specifically, in FIG. 22G, the guide reference point GRP is arranged vertically above the flange reference point FRP. FIG. 22G also shows that the flange 512 of the impactor assembly 502 has come out of abutment with the first trigger 628, which has fully pivoted back about the first trigger pin 632 to the first extended position 628E. As such, the first pushrod 636 has also retracted back and is now disposed out of engagement with the first pushrod sensor 552A (compare FIG. 22G to FIG. 22F). FIG. 22G also shows the flange 512 of the impactor assembly 502 abutting against the flange region 672 of the second trigger 630, which has begun to pivot back about the second trigger pin 634 away from the retracted second position 630R to one of the intermediate second positions 630I. As such, the second pushrod 638 is slightly retracted but still remains disposed in engagement with the second pushrod sensor 552B (compare FIG. 22G to FIG. 22F). Accordingly, FIG. 23 depicts the first signal SN1 (at vertical line G) as having moved from the engaged first sensor state S1B to the disengaged first sensor state S1A, and depicts the second signal SN2 (at vertical line G) as having remained at the engaged second sensor state S2B.

Figure 22H:
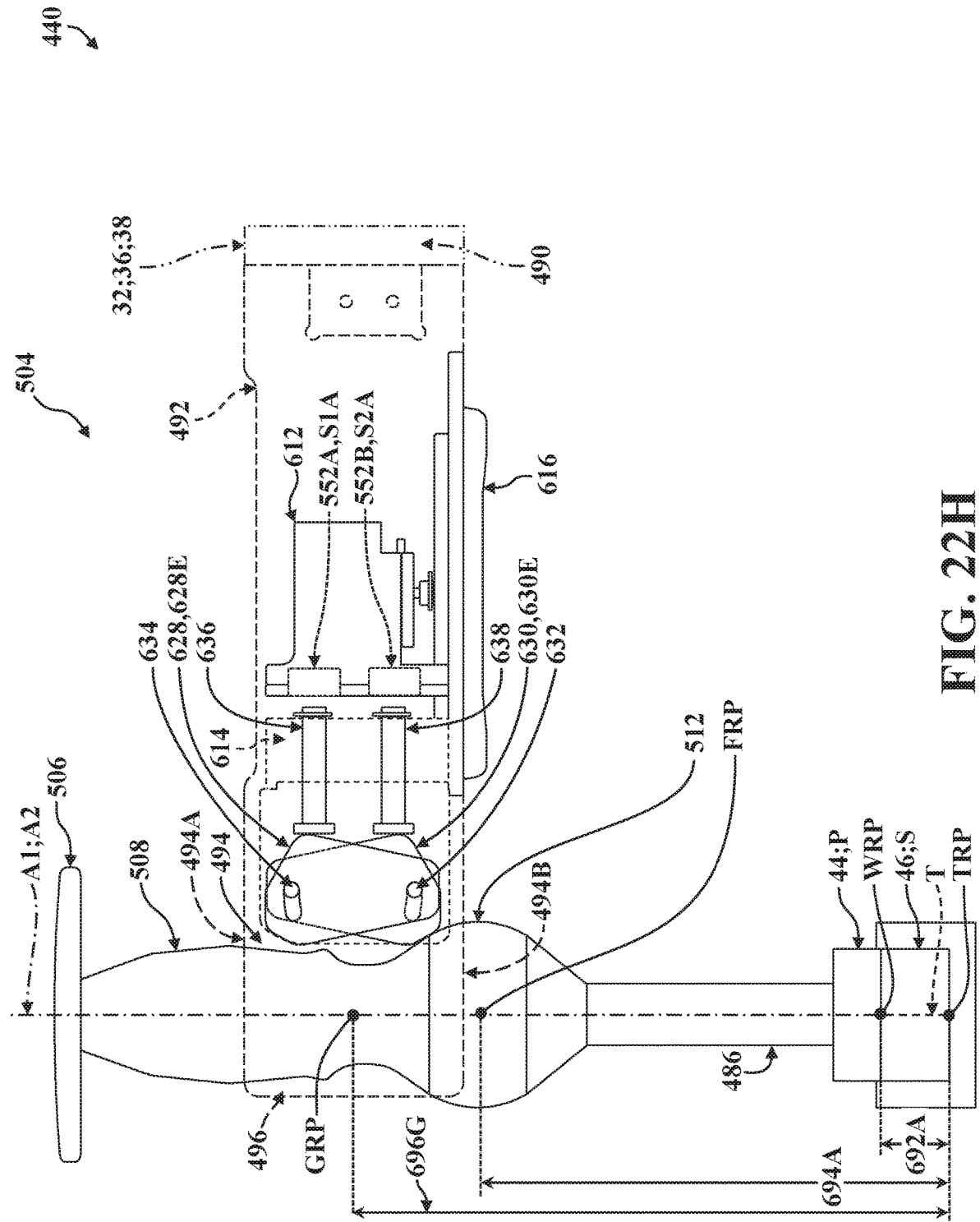
FIG. 22H is another illustrative schematic view of the surgical site, the prosthesis, and the end effector of FIGS. 22A-22G, shown with the guide moved further away from the surgical site along the trajectory with the flange partially disposed within the channel, and shown with the flange disposed out of engagement with the first and second triggers.

FIG. 22H shows the guide 504 having been moved such that the guide reference point GRP is arranged at a seventh guide-to-target distance 696G, with the flange 512 of the impactor assembly 502 disposed slightly within the channel 494 of the guide 504 without abutment. Here too in FIG. 22H, the guide reference point GRP is arranged vertically above the flange reference point FRP. FIG. 22H also shows that the flange 512 of the impactor assembly 502 has remained out of abutment with the first trigger 628 in the first extended position 628E. As such, the first pushrod 636 has also remained disposed out of engagement with the first pushrod sensor 552A (compare FIG. 22H to FIG. 22G). FIG. 22H also shows that the flange 512 of the impactor assembly 502 has come out of abutment with the second trigger 630, which has fully pivoted back about the second trigger pin 634 to the extended second position 630E. As such, the second pushrod 638 has also retracted back and is now disposed out of engagement with the second pushrod sensor 552B (compare FIG. 22H to FIG. 22G). Accordingly, FIG. 23 depicts the first signal SN1 (at vertical line H) as having remained at the disengaged first sensor state S1A, and depicts the second signal SN2 (at vertical line H) as having moved from the engaged second sensor state S2B to the disengaged second sensor state S2A.

As noted above, FIG. 23 depicts a graphical representation of the first and second signals SN1, SN2 generated, respectively, by the first and second pushrod sensors 552A, 552B for each of the positions shown in FIGS. 22A-22H. The signals SN1, SN2 are depicted here as comprising respective "square waves" which represent movement between the disengaged states S1A, S2A and the engaged states S1B, S2B as described above. However, it will be appreciated that the signals SN1, SN2 could be realized in other ways based, among other things, on the specific configuration of the sensors 552 and/or various other components of the sensor subassembly 612, the guide 504, and/or the impactor assembly 502. By way of non-limiting example, and as noted previously, it is contemplated that the first and/or second pushrod sensors 552A, 552B could be configured so as to generate analog signals which represent the relative positions of the pushrods 636, 638. Other configurations are contemplated.

With continued reference to FIG. 23, it will be appreciated that the horizontal spacing between vertical lines A, B, C, D, E, F, G, and H is arbitrary. Nevertheless, the intersection of each vertical line A, B, C, D, E, F, and G with the first signal SN1 and the second signal SN2 corresponds to the respective states of the first and second pushrod sensors 552A, 552B consistent with the above description of FIGS. 22A-22H. In this representative embodiment of the end effector 440, the head 506 of the impactor assembly 502 is too large to fit into the channel 494 of the guide 504, thereby necessitating that the surgeon move the guide 504 away from the surgical site S in order to bring the guide engagement surface 498 into abutment with the impactor engagement surface 488. While other arrangements are contemplated by the present disclosure (e.g., with a head 506 that could fit within the channel 494), it will be appreciated that the illustrated configuration depicted in connection with the third embodiment of the end effector 440 is such that abutment between the first trigger 628 and the flange 512 of the impactor assembly 502 occurs before abutment with the second trigger 630 and the flange 512 as the guide 504 is moved progressively further away from the surgical site S (sequentially compare FIGS. 22B-22H). Because the surgical system 30 is able to determine the arrangement of the guide 504 relative to the surgical site S in order to, among other things, maintain alignment of the guide axis A2 with the trajectory T, the position of the impactor assembly 502 relative to the guide 504 can be determined by comparing the known location the guide 504 with the states of the first and second signals SN1, SN2, as described in greater detail below.

While the illustrated embodiment of the impactor assembly 502 is configured such that the head 506 cannot enter into the channel 494 of the guide 504, as noted above, it is nevertheless contemplated that the impactor assembly 502 could be configured in other ways, such as where the flange 512 is spaced from the handle 508 by a narrower region (e.g., sized similar to the shaft 486) that could pass into the channel 494 through the opening 496. Put differently, the flange 512 could enter the channel 494 in ways other than those illustrated in FIGS. 22A-22H. Here, and as will be appreciated from the subsequent description below, utilizing two sensors 552 (e.g., the first and second pushrod sensors 552A, 552B) that are arranged in a predetermined way relative to each other to define the impaction range 698 depicted in FIG. 23 can also be used to facilitate determining how the flange 512 enters into the channel 494 based on which of the signals SN1, SN2 changes state first.

Because the illustrated embodiment of the third embodiment of the end effector 440 is configured such that the guide 504 has to move away from the surgical site S in order to initially bring the flange 512 into the channel 494, both signals SN1, SN2 being in their respective disengaged states S1A, S2A generally indicates that the flange 512 is positioned above the guide 504 or is otherwise not fully positioned within the channel 494 in a way that affords sufficient abutment between the impactor engagement surface 488 and the guide engagement surface 498 (e.g., see FIG. 22C).

Furthermore, the first signal SN1 being in the engaged first sensor state S1B and the second signal SN2 being in the disengaged second sensor state S2A generally indicates that the flange 512 is positioned within the channel 494 of the guide 504 with sufficient abutment between the impactor engagement surface 488 and the guide engagement surface 498, and also generally indicates that the flange reference point FRP is arranged vertically above the guide reference point GRP (see FIG. 22D). Similarly, the first signal SN1 being in the disengaged first sensor state S1A and the second signal SN2 being in the engaged second sensor state S2B generally indicates that the flange 512 is positioned within the channel 494 of the guide 504 with sufficient abutment between the impactor engagement surface 488 and the guide engagement surface 498, and also generally indicates that the flange reference point FRP is arranged vertically below the guide reference point GRP (see FIG. 22F). However, depending on the specific configuration of the prosthesis P, the guide 504, and/or the impactor assembly 502, it may be advantageous to ensure that the flange 512 is disposed further into the channel 494 before initiating impaction. To this end, the first signal SN1 and the second signal SN1 each being in their respective engaged states S1B, S2B generally indicates that the flange 512 is positioned far enough into the channel 494 to initiate impaction (e.g., see FIG. 22E). In some embodiments, both of the signals SN1, SN2 being in their respective engaged states S1B, S2B may define an impaction range 698 based, among other things, on abutment occurring between the impactor engagement surface 488 and the guide engagement surface 498 and only a predetermined amount of distance separating the flange reference point FRP from the guide reference point GRP.

Because the position of the guide 504 relative to the surgical site S is known and can be monitored or otherwise recorded over time, one or more controllers (e.g., the robot controller 52, the navigation controller 54, and the like) or other components of the surgical system 30 could be configured to monitor the signals SN1, SN2 for changes between the disengaged and engaged states S1A, S2A; S1B, S2B and could record the position of the guide 504 any time there is a change in either signal SN1, SN2. Here, based on known geometrical parameters of various components of the guide 504 and the impactor assembly 502, the state changes illustrated in FIG. 23 as "steps" occurring adjacent to vertical lines C, D, F, and G could each represent a specific position of the guide reference point GRP relative to the flange reference point FRP. Moreover, the state changes illustrated in FIG. 23 as "steps" occurring adjacent to vertical lines D and F could each represent outer limits of the impaction range 698 such that the difference between them corresponds to coincident alignment of the guide reference point GRP with the flange reference point FRP (e.g., as depicted in FIG. 22E).

Figure 24A:
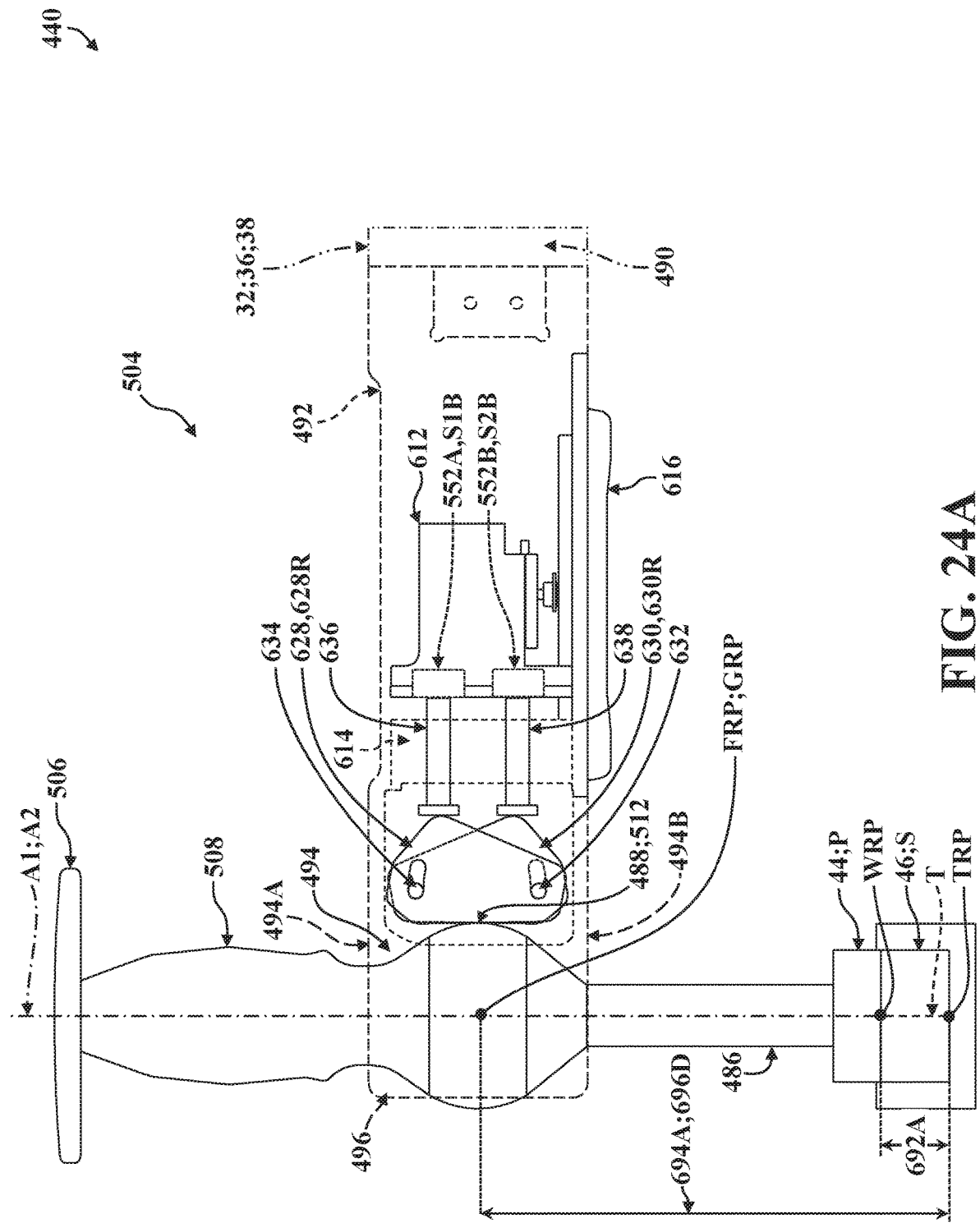
FIG. 24A is an illustrative schematic view of the surgical site, the prosthesis, and the end effector arranged as depicted in FIG. 22E with the flange of the impactor assembly disposed in the vertical center of the channel of the guide and engaging the first and second triggers, shown here with a guide reference point of the channel of the guide arranged at an initial guide-to-target distance relative to the surgical site, and with an impactor reference point of the flange of the impactor assembly arranged at an initial flange-to-target distance equal to the initial guide-to-target distance.

Referring now to FIG. 24A, the guide 504 is shown positioned in the same way as in FIG. 22E described above, with the guide reference point GRP arranged coincident with the flange reference point FRP, and with the impactor and guide axes A1, A2 each aligned to the trajectory T maintained by the surgical robot 32. Here too, the prosthesis P is secured to the impactor assembly 502 and is positioned at the surgical site S prior to impaction. More specifically, FIG. 24A depicts the workpiece reference point WRP being spaced from the target reference point TRP at the first workpiece-to-target distance 692A, depicts the flange reference point FRP being spaced from the target reference point TRP at the first flange-to-target distance 694A, and depicts the guide reference point GRP being spaced from the target reference point TRP at the fourth guide-to-target distance 696D. Here, the first flange-to-target distance 694A is equal to the fourth guide-to-target distance 696D because the flange 512 of the impactor assembly 502 is centered within the channel 494 of the guide 504 (put differently, the guide reference point GRP and the flange reference point FRP are coincident). While not described in detail, it will be appreciated that FIG. 24A also depicts both of the pushrod sensors 552A, 552B as being engaged by their respective pushrods 636, 638.

Figure 24B:
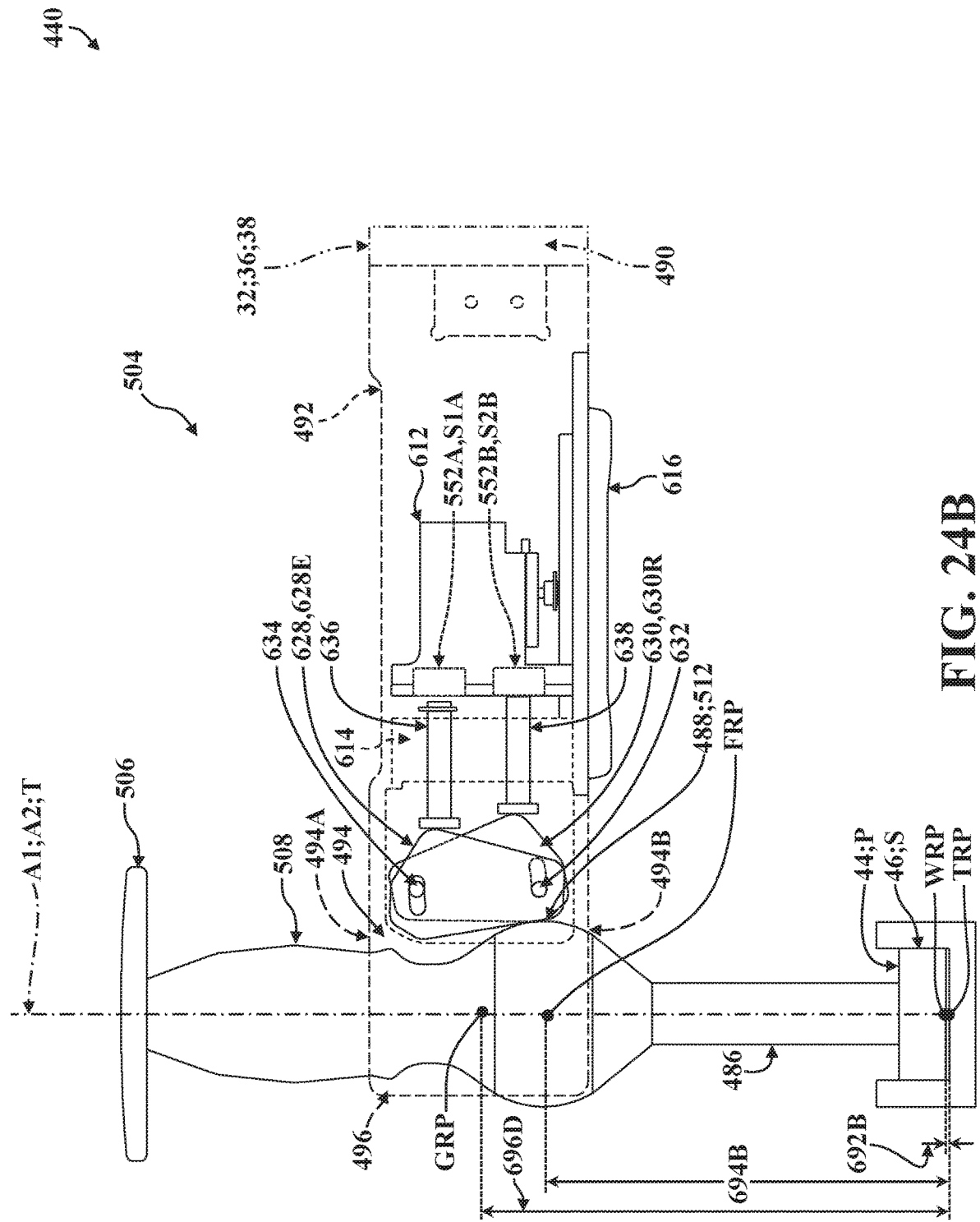
FIG. 24B is another illustrative schematic view of the surgical site, the prosthesis, and the end effector of FIG. 24A, shown with the guide still arranged at the initial guide-to-target distance relative to the surgical site, and depicting the impactor assembly and the prosthesis advanced along the trajectory toward the surgical site in response to the application of impact force to the impactor assembly resulting in the impactor reference point being arranged at a secondary flange-to-target distance relative to the surgical site that is smaller than the initial flange-to-target distance.

Continuing from FIG. 24A to FIG. 24B, the guide 504 has not moved, but the impactor assembly 502 and the prosthesis P have been advanced along the trajectory T toward the surgical site S in response to impaction force F applied to the head 506. Here too, the workpiece reference point WRP and the flange reference point FRP have each moved closer to the target reference point TRP such that the workpiece reference point WRP is spaced from the target reference point TRP at a second workpiece-to-target distance 692B, and such that the flange reference point FRP is spaced from the target reference point TRP at a second flange-to-target distance 694B. The movement of the impactor assembly 502 has also resulted in a change in the abutment between the flange region 672 of the first trigger 628, causing the first trigger 628 to pivot about the first trigger pin 632 and correspondingly bringing the first pushrod 636 out of engagement with the first pushrod sensor 552A which, consistent with the discussion of FIG. 23 above, has also resulted in the first signal SN1 being in the disengaged first signal state S1A. Here, because the second signal SN2 remains in the engaged second signal state S2B, the guide reference point GRP is positioned somewhere above the flange reference point FRP, and the flange 512 remains in abutment with the channel 494 but is outside of the impaction range 698.

Figure 24C:
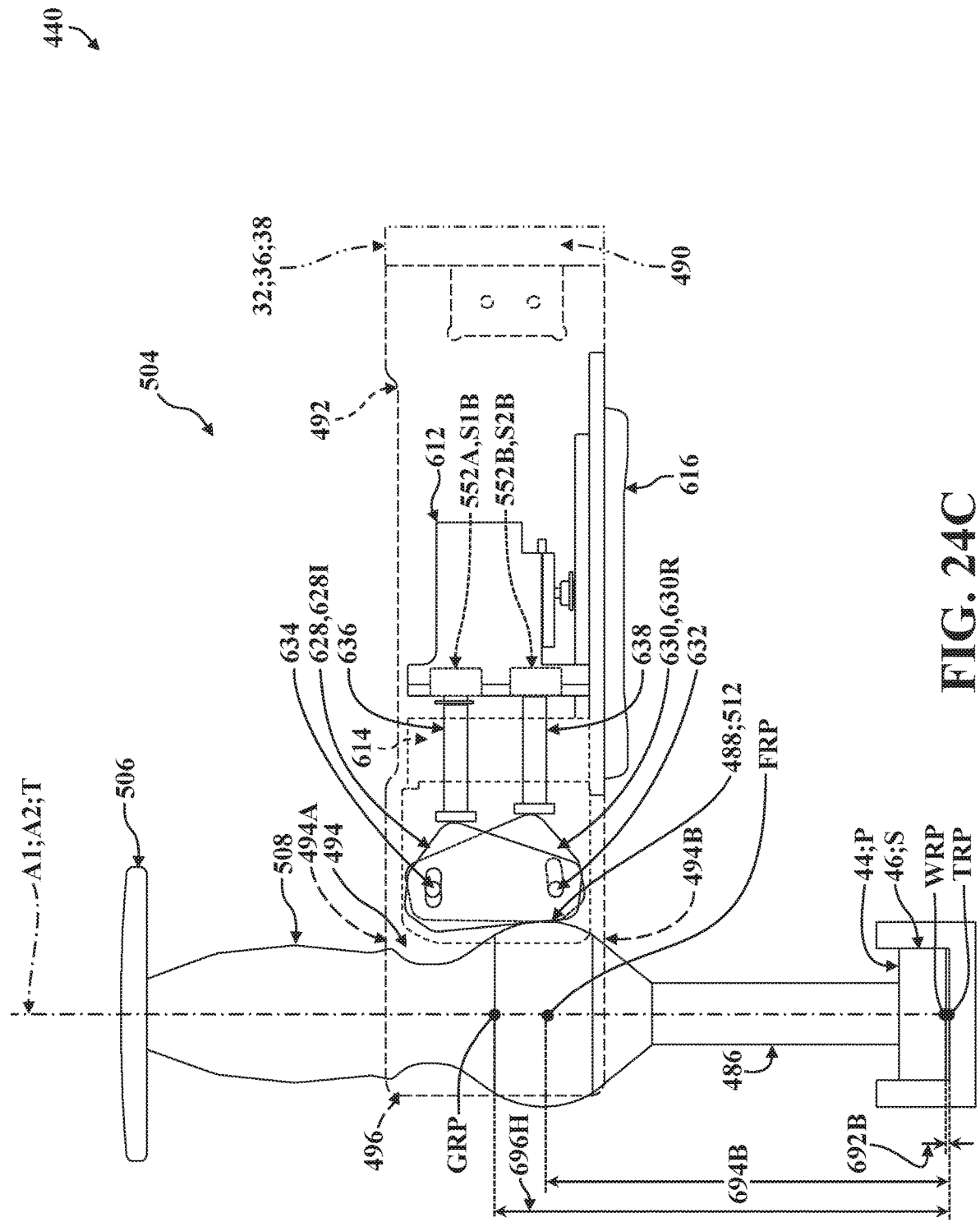
FIG. 24C is another illustrative schematic view of the surgical site, the prosthesis, and the end effector of FIGS. 24A-24B, shown with the impactor assembly still arranged at the secondary flange-to-target distance relative to the surgical site, and depicting the guide advanced along the trajectory toward the surgical site resulting in the guide reference point being arranged closer to the surgical site.

Referring now to FIG. 24C, the guide 504 has been advanced along the trajectory T toward the surgical site S to the point at which the first signal SN1 has just changed back to the engaged first signal state S1B. More specifically, in FIG. 24C the guide reference point GRP is now spaced from the target reference point TRP at an eighth guide-to-target distance 696H that is smaller than the fourth guide-to-target distance 696D. Because both of the signals SN1, SN2 are in their respective engaged signal states S1B, S2B, the flange 512 remains in abutment with the channel 494 and is also within the impaction range 698. Furthermore, because the guide reference point GRP and the target reference point TRP are both monitored by the surgical system (e.g., via the robotic control system 48 and/or the navigation system 50), and because the impactor assembly 502 and the guide 504 are configured such that the outer limits of the impaction range 698 are known based on changes in the signals SN1, SN2 as described above, the location of the flange reference point FRP can be determined relative to the guide reference point GRP.

It will be appreciated that the configuration described above also allows the second flange-to-target distance 694B, as well as the second workpiece-to-target distance 692B, to be readily determined. Put differently, after the impactor assembly 502 and the prosthesis P have been advanced along the trajectory T toward the surgical site S in response to the application of impact force F (compare FIGS. 24A-24B), the guide 504 can subsequently be moved along the trajectory T toward the surgical site S (compare FIGS. 24B-24C) until one of the signals SN1, SN2 changes so as to indicate that the flange 512 has traversed one of the known outer limits of the impaction range 698 corresponding to a known positional relationship between the guide reference point GRP and the flange reference point FRP. Accordingly, this configuration allows changes in the position of the prosthesis P to be determined based, for example, on the difference between the first workpiece-to-target distance 692A (see FIG. 24A) and the second workpiece-to-target distance 692B (see FIGS. 24B-24D).

Figure 24D:
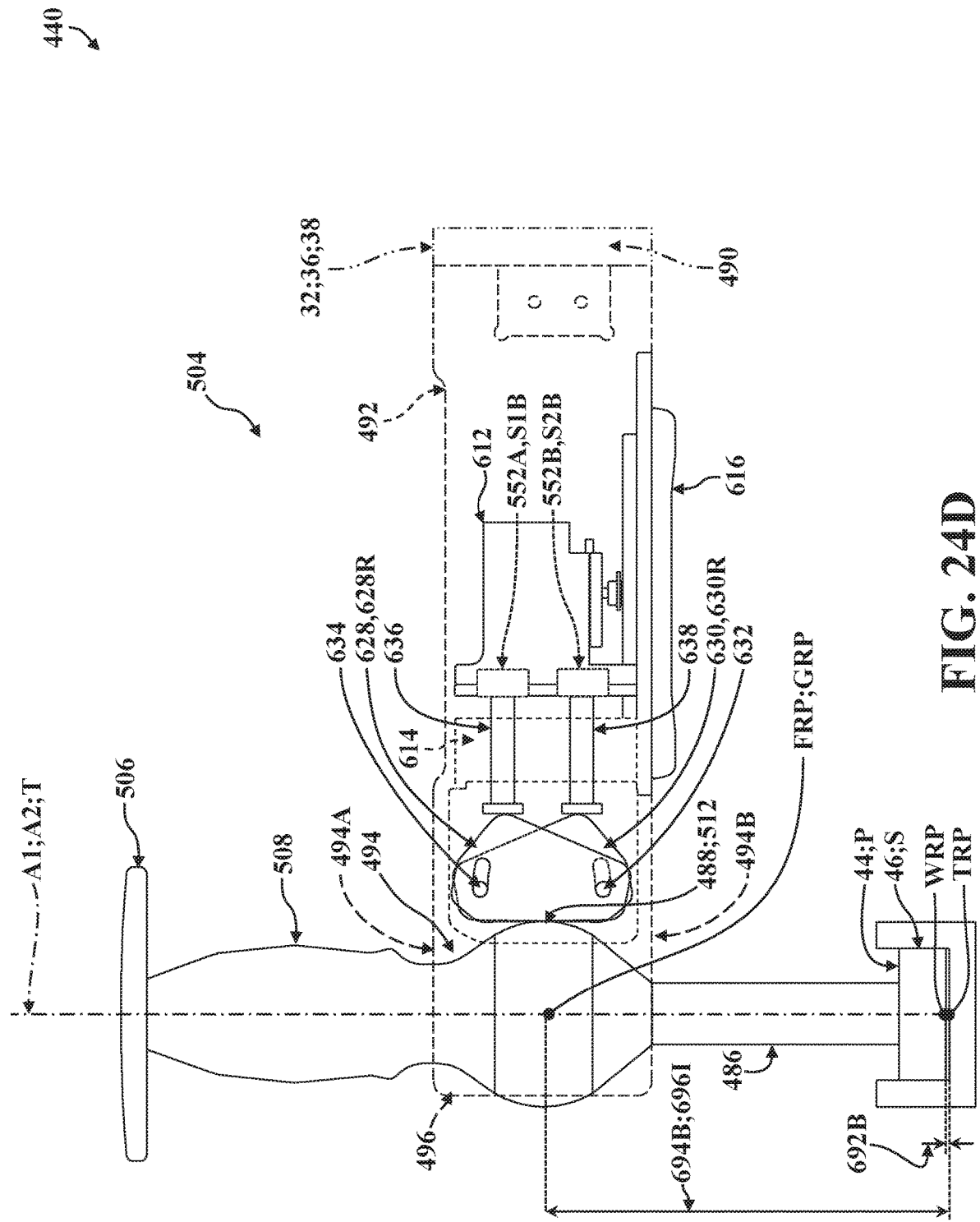
FIG. 24D is another illustrative schematic view of the surgical site, the prosthesis, and the end effector of FIGS. 24A-24C, shown with the impactor assembly still arranged at the secondary flange-to-target distance relative to the surgical site, and depicting the guide advanced even further along the trajectory toward the surgical site resulting in the guide reference point being arranged at a different guide-to-target distance relative to the surgical site that is equal to the secondary flange-to-target distance.

Referring now to FIG. 24D, the guide 504 has been advanced even further along the trajectory T toward the surgical site S so as to re-align the guide reference point GRP with the flange reference point FRP. More specifically, in FIG. 24C the guide reference point GRP is now spaced from the target reference point TRP at a ninth guide-to-target distance 696I that is smaller than the eighth guide-to-target distance 696H and is equal to the second flange-to-target distance 694B. Here, it will be appreciated that the flange 512 is again centered within the channel 494 in the middle of the impaction range 698, and the surgeon can again apply impaction force F to further advance the prosthesis P along the trajectory T toward the surgical site S until the workpiece reference point WRP is coincident with the target reference point TRP (not shown in detail). In some embodiments, the surgical system 30 may be configured so as to sense the application of impact force F based, among other things, on a change in the signals SN1, SN2 and/or based on data from other types of sensors (e.g., a force-torque sensor). Here, it will be appreciated that the surgical robot 32 could advance the guide 504 along the trajectory T after detecting the application of impact force F in order to re-align the guide reference point GRP with the flange reference point FRP and/or determine changes in the position of the workpiece reference point WRP.

By way of illustrative example, if a given surgical procedure results in the surgeon having to apply impaction force F by successively striking the head 506 of the impactor assembly 502 with a mallet (not shown) multiple times until the prosthesis P is fully implanted at the surgical site S, the surgical system 30 could be configured to control the surgical robot 32 to advance the guide 504 along the trajectory T and present the surgeon with an updated "depth to target" distance after each successive strike (e.g., a value displayed on the output device 66 in FIG. 1) based on the difference between the target reference point TRP and the workpiece reference point WRP. This, among other things, can allow the surgeon to adjust their application of force F as needed (e.g., apply more or less impaction force F during the next strike).

As noted above, the third embodiment of the end effector 440 is configured such that the flange 512 can enter the channel 494 by moving the guide 504 away from the surgical site S along the trajectory T (and along the axes A1, A2 aligned therewith). However, the head 506 is too large to enter into the channel 494, the grip 510 is too large to pass through the opening 496, and the handle 508 is generally arranged too close to the flange 512 to permit the flange 512 to enter the channel 494 from the opposite direction (e.g., by moving the guide 504 along the trajectory T toward both the flange 512 and the surgical site S). While other configurations of the impactor assembly 502 are contemplated as noted above, it will be appreciated that configuring the impactor assembly 502 to enter the channel 494 from only one direction may also allow certain concepts described in connection with the embodiments illustrated in FIGS. 22A-24D to be implemented in other ways or otherwise configured differently. By way of non-limiting example, it is contemplated that a single trigger and sensor arrangement could be utilized (e.g., similar to the sensor 152 and the trigger 154 described in connection with the first embodiment of the end effector 40) where the end effector is configured to ensure that the flange can only enter the channel from one direction. Other configurations are contemplated.

Referring again to FIGS. 22A-22H, it will be appreciated that the surgical robot 32 can be configured to facilitate moving the guide 504 toward the impactor assembly 502 so as to achieve initial alignment of the guide axis A2 with the trajectory T in a number of different ways. For example, the surgical robot 32 could be configured to operate the robotic arm 36 to facilitate initially orientating the guide 504 such that the guide axis A1 is parallel to the trajectory T before approaching too close to the surgical site S, or such that the guide axis A1 is brought into alignment with the trajectory T as the guide 504 moves toward the surgical site S. The surgical robot 32 could also be configured to operate the robotic arm 36 so as to facilitate moving the guide 504 toward an expected position of the shaft 486 of the impactor assembly 502 (e.g., toward the position depicted in FIG. 22A). In some embodiments, the surgical robot 32 could be configured such that the surgeon can move the guide 504 by pushing on it and could utilize haptic feedback (e.g., attractive/repulsive haptic forces) to, among other things, help control movement based on virtual objects, boundaries, and the like to guide the guide axis A2 into alignment with the trajectory T.

Furthermore, it will be appreciated that the surgical robot 32 can also be configured in various ways to facilitate moving the guide 504 along the trajectory T while maintaining alignment of the guide axis A2 with the trajectory T. For example, the surgical robot 32 could be configured to operate the robotic arm 36 to facilitate moving the guide 504 away from the surgical site S and along the trajectory T while utilizing haptic feedback (e.g., attractive/repulsive forces) to, among other things, help bring the guide reference point GRP into initial alignment with the flange reference point FRP (e.g., see FIG. 22E) and/or help maintain alignment during impaction. In certain embodiments where the surgical robot 32 is configured to maintain alignment of the guide reference point GRP with the flange reference point FRP during impaction by advancing the guide 504 along the trajectory between mallet strikes, the surgical robot 32 could be configured to prevent manual movement of the guide 504 in one or both directions along the trajectory T until certain conditions are met, such as until the surgeon engages the input button 622 of the input module 616, at which point the surgical robot 32 could then permit movement of the guide 504 along the trajectory T. Here, the movement along the trajectory T could be limited only to translation of the guide 504 (and may also permit rotating the guide 504 about the trajectory T) until reaching a position where the guide 504 can be properly removed from the impactor assembly 502 (e.g., the position depicted in FIG. 22B), at which point the surgical robot 32 could then allow movement of the guide 504 away from the trajectory T (e.g., to the position depicted in FIG. 22A). Other configurations are contemplated.

A fourth embodiment of the end effector is generally depicted in FIGS. 25A-28B. As will be appreciated from the subsequent description below, this embodiment shares similar structure and components, as well as similar features, advantages, and operational use, to the first embodiment of the end effector 40 described above. Thus, the structure and components of the fourth embodiment that are the same as or that otherwise correspond to the structure and components of the first embodiment are provided with the same reference numerals increased by 700 in the drawings and in the description below. Moreover, the fourth embodiment also shares certain similar structure and components, as well as similar features, advantages, and operational use, to the second embodiment of the end effector 240 described above. Thus, the structure and components of the fourth embodiment that are the same as or that otherwise correspond to the structure and components of the second embodiment are provided with the same reference numerals increased by 500 in the drawings and in the description below. Furthermore, the fourth embodiment also shares certain similar structure and components, as well as similar features, advantages, and operational use, to the third embodiment of the end effector 440 described above. Thus, the structure and components of the fourth embodiment that are the same as or that otherwise correspond to the structure and components of the third embodiment are provided with the same reference numerals increased by 300 in the drawings and in the description below.

The fourth embodiment of the end effector 740 is generally depicted in FIGS. 25A-28B, and is similar to other embodiments described and illustrated herein. While the specific differences between the fourth embodiment of the end effector 740 and the other embodiments are described in detail below, for the purposes of clarity, consistency, and brevity, the majority of the structure and components common between the embodiments are not reintroduced or re-described below. As such, and unless otherwise indicated below, it will be appreciated that the description of the other embodiments above may be incorporated by reference with respect to the fourth embodiment of the end effector 740 without limitation. Furthermore, it will be appreciated that various aspects of the fourth embodiment of the end effector 740 could also apply to other embodiments of the present disclosure.

Referring now to FIG. 25A, the impactor assembly 802 and the guide 804 of the fourth embodiment of the end effector 740 are shown spaced from each other. Here, the impactor assembly 802 is identical to the impactor assembly 502 described above in connection with the third embodiment depicted, for example, in FIGS. 16A-16B. While the guide 804 is configured differently in this embodiment as described in greater detail below, the general process of bringing the guide 804 into engagement with the impactor assembly 802 is similar. Here too, the guide 804 is likewise configured such that the shaft 786 of the impactor assembly 802 can pass through the opening 796 and into the channel 794 (see FIG. 25B), and the guide 804 can then be moved toward the flange 812 (e.g., away from the surgical site S along the trajectory T) so as to bring the impactor engagement surface 788 into abutment with the guide engagement surface 798 (see FIG. 25C), where alignment of the axes A1, A2 with the trajectory T maintained by the surgical robot 32 is effected via the limiter 800. Here too, depending on how the surgical robot 32 is configured to control movement of the guide 804, relative rotation between the guide 804 and the impactor assembly 802 can generally be performed such as by controlling one or more joints of the robotic arm 36 while still maintaining alignment of the guide axis A2 with the trajectory T (see FIG. 25D, compare with FIG. 25C).

Figure 26A:
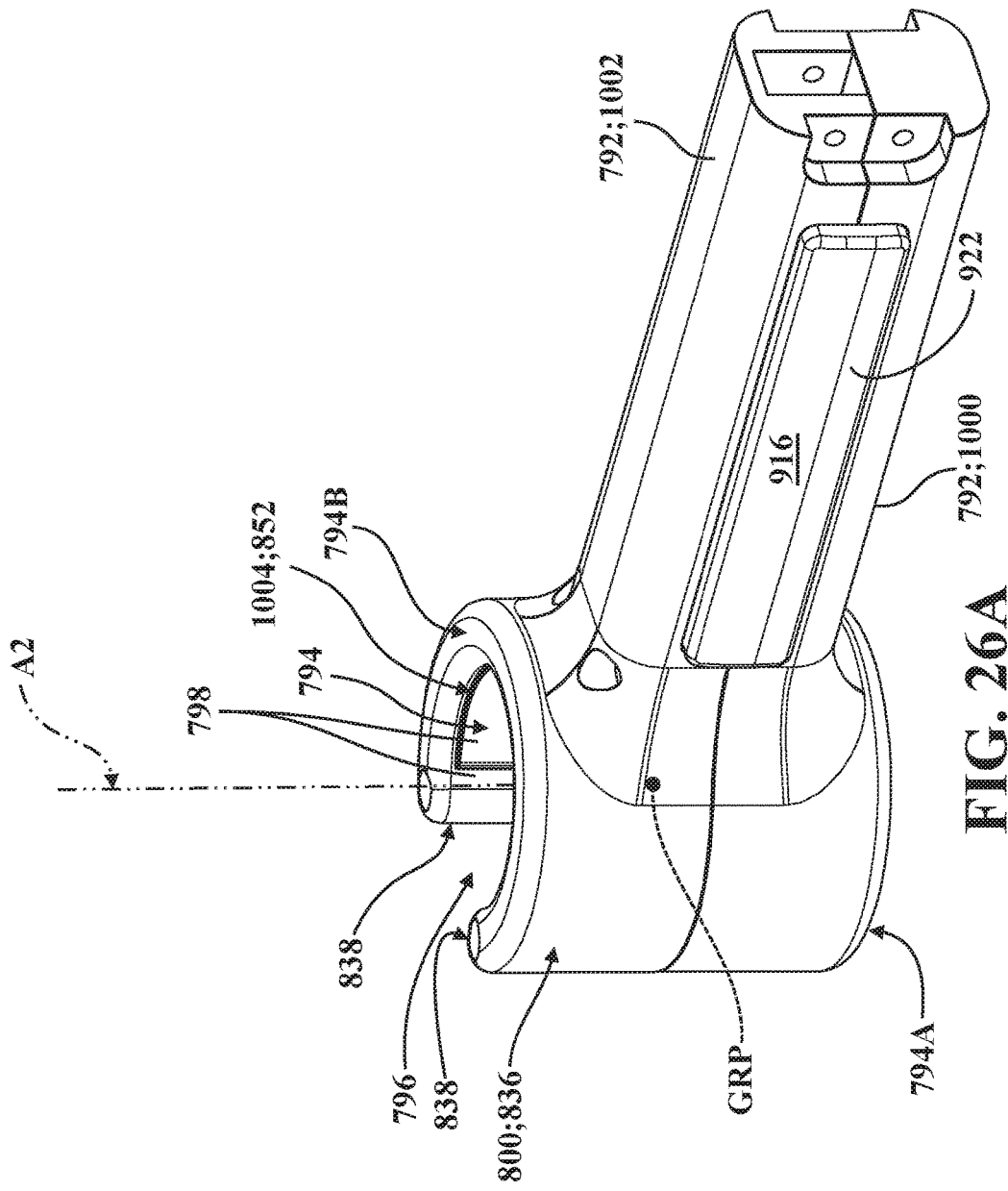
FIG. 26A is a perspective view of the guide of FIGS. 25A-25D.
Figure 26B:
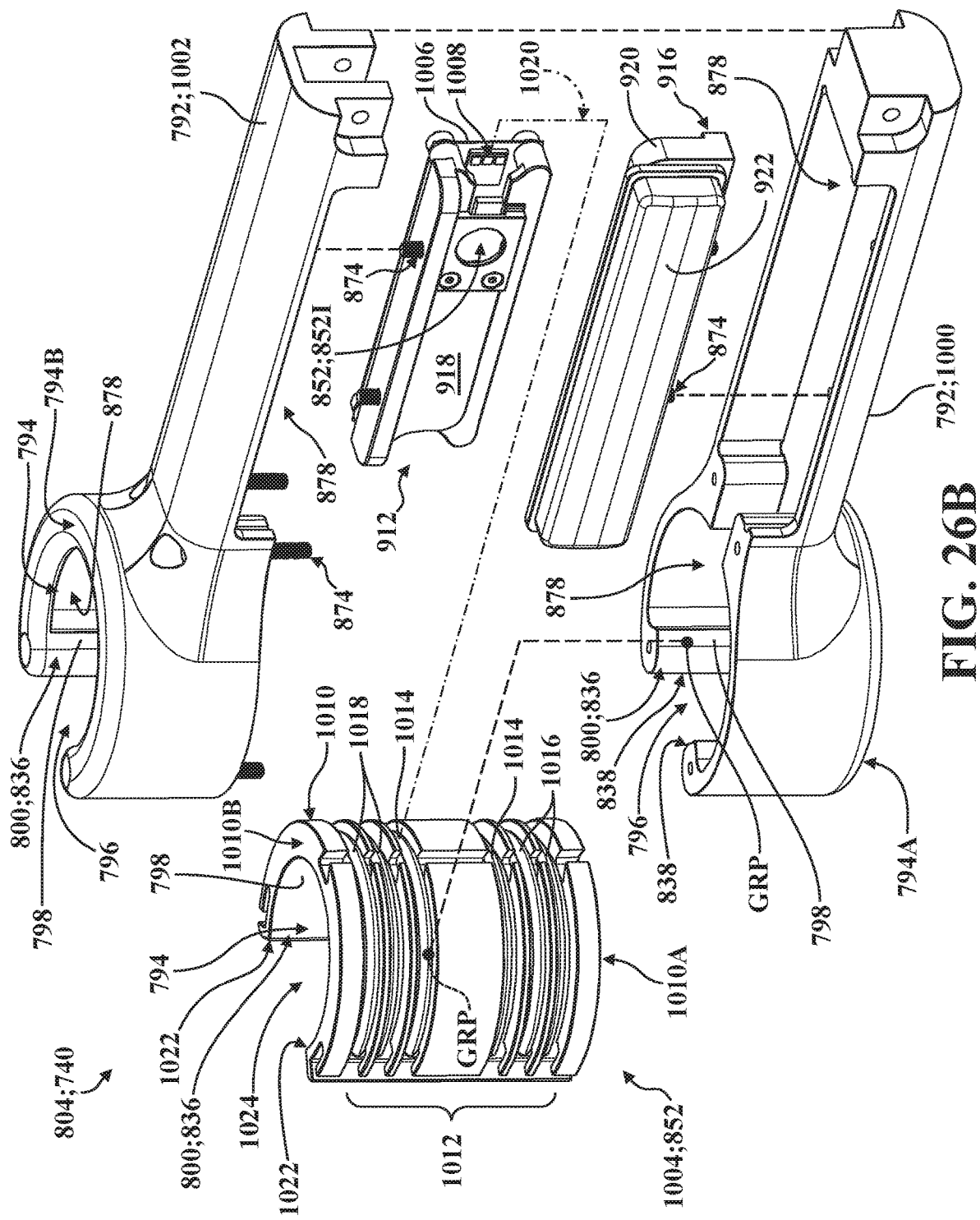
FIG. 26B is an exploded perspective view of the guide of FIGS. 25A-26A, shown comprising a body with first and second body components spaced from a sensor subassembly, and input module, and a coil assembly.

Referring now to FIGS. 26A-26B, the guide 804 illustrated in connection with the fourth embodiment of the end effector 740 comprises a differently-configured body 792 defined by first and second body components 1000, 1002 which are secured together via fasteners 874. Nevertheless, the body 792 is operatively attached to the mount 790 (not shown in detail) to facilitate releasable attachment to the coupling 38 of the surgical robot 32 (see FIG. 1). While the first and second body components 1000, 1002 cooperate to define the opening 796 in this embodiment, a coil assembly 1004 generally comprises (or otherwise defines significant portions of) the channel 794, the guide engagement surface 798, and the limiter 800, as described in greater detail below.

As shown in FIG. 26B, the body components 1000, 1002 each define portions of the pocket 878 which, in this embodiment, likewise accommodates the sensor subassembly 912 and the input module 916, and also accommodates the coil assembly 1004. While not depicted in detail, the input module 916 similarly comprises the input frame 920 which supports the input button 922, is secured to the first body component 1000 of the guide 804 via fasteners 874, and is arranged so as to engage the input sensor 8521 in response to actuation by the surgeon. The input sensor 8521 is similarly coupled to the sensor housing 918, which is secured to the second body component 1002 of the guide 804 via fasteners 874. In this embodiment, a circuit board 1006 is also coupled to the sensor housing 918, and supports a sensor controller 1008 thereon which is wired to the coil assembly 1004 as described in greater detail below, and may also be disposed in communication (e.g., wired or wireless electrical communication) with various components of the surgical system 30 (e.g., the robot controller 52, the navigation controller 54, and the like). In some embodiments, the sensor controller 1008 may be disposed in other locations, and may be realized with other parts of the surgical system 30.

In this embodiment, the coil assembly 1004 defines the sensor 852 that is configured to determine the relative position of the flange 812 between the first and second axial channel ends 794A, 794B. To this end, the coil assembly 1004 is realized as a linear variable differential transformer (LVDT) coil assembly 1004 that is coupled to the guide 804 adjacent to the channel 794, as described in greater detail below. As will be appreciated from the subsequent description below, various configurations of LVDT coil assemblies 1004 are contemplated by the present disclosure. More specifically, one style of LVDT coil assembly 1004 is illustrated in FIGS. 26A-27B, and another style of LVDT coil assembly 1004 is illustrated in FIGS. 28A-28B. Because the LVDT coil assemblies 1004 illustrated in FIGS. 26A-28B are similar, the same reference numerals are used in the drawings and in the description below to refer to structure and components that are common to each style, and specific differences will be described in detail and will be identified with additional reference numerals. Here, the LVDT coil assemblies 1004 illustrated in FIGS. 26A-29B each generally comprises a coil frame 1010 which supports a coil arrangement 1012 with a transmit coil 1014, a proximal receive coil 1016, and a distal receive coil 1018, each of which are described in greater detail below.

With continued reference to FIG. 26B, in this fourth embodiment, the pocket 878 is shaped and arranged so as to accommodate the LVDT coil assembly 1004 securely therein when the first and second body components 1000, 1002 are secured together. The pocket 878 is also configured to accommodate a wire harness 1020 (depicted generically) which extends between the coil arrangement 1012 and the circuit board 1006 (e.g., with multiple wires in communication with the sensor controller 1008).

The coil frame 1010 of the LVDT coil assembly 1004 has a profile that is complimentary to the portions of the channel 794 that are defined by the first and second body components 1000, 1002 adjacent to the finger ends 838 of the fingers 836. Put differently, the coil frame 1010 has a generally C-shaped profile extending vertically along the guide axis A2 between opposing first and second frame ends 1010A, 1010B which are respectively arranged adjacent to the first and second axial channel ends 794A, 794B defined by the first and second body components 1000, 1002.

As noted above, the coil frame 1010 defines at least a portion of the channel 794 (e.g., the portion extending between the first and second frame ends 1010A, 1010B), which similarly has a continuous and generally cylindrical, C-shaped profile. Accordingly, the coil frame 1010 also defines portions of the guide engagement surface 798 spaced from the guide axis A2 at the common radius 842. Furthermore, the illustrated coil frame 1010 also defines portions of the limiter 800 (e.g., portions of the fingers 836), including at least a portion of the arc-shaped surfaces 840 which, here too, are spaced from the guide axis A2 at the common radius 842 (see FIG. 27A; not shown in detail). However, in this embodiment, the portions of the fingers 836 of the limiter 800 that are defined by the coil frame 1010 do not define the finger ends 838 and, as explained in greater detail below, do not define the opening 796. Rather, the finger ends 838 of the first and second body components 1000, 1002 define the opening 796 of the guide 804. On the other hand, the portions of the fingers 836 of the limiter 800 that are defined by the coil frame 1010 each comprise respective frame finger ends 1022 that are spaced from each other to define a frame opening 1024 that is wider than the opening 796 defined by the first and second body components 1000, 1002 in the illustrated embodiment. However, it will be appreciated that other configurations are contemplated.

In the illustrated embodiments, the coil frame 1010 defines various slots which, among other things, support the coil arrangement 1012 and generally define the shape and arrangement of the coils 1014, 1016, 1018. While other configurations of slots are contemplated by the present disclosure, the coil frames 1010 illustrated in FIGS. 27A-28B each generally define a first proximal receive winding slot 1026, a second proximal receive winding slot 1028, a first distal receive winding slot 1030, a second distal receive winding slot 1032, a first transmit winding slot 1034, a second transmit winding slot 1036, an access routing slot 1038, a first linking slot 1040, and a second linking slot 1042. The coil frame 1010 illustrated in FIGS. 28A-28B also defines a third linking slot 1044 and a fourth linking slot 1046.

The winding slots 1026, 1028, 1030, 1032, 1034, 1038 are each formed in the coil frame 1010 as arc-shaped recesses that are vertically spaced from each other between the first and second frame ends 1010A, 1010B (e.g., along the guide axis A2) so as to isolate that the coils 1014, 1016, 1018 from each other. The access routing slot 1038 is formed in the coil frame 1010 between the first and second frame ends 1010A, 1010B extending through (e.g., in communication with) each of the winding slots 1026, 1028, 1030, 1032, 1034, 1038. While not shown in detail, the access routing slot 1038 may be provided to, among other things, facilitate routing ends of the coils 1014, 1016, 1018 (e.g., via the wire harness 1020) to the circuit board 1006. The first and second linking slots 1040, 1042 extending through (e.g., in communication with) each of the winding slots 1026, 1028, 1030, 1032, 1034, 1038. As shown in FIG. 28, the third and fourth linking slots 1044, 1046 are also formed in the coil frame 1010 between the first and second frame ends 1010A, 1010B, but only extend through (e.g., in communication with) the first and second transmit winding slots 1034, 1036 (compare FIGS. 27A and 28A). This is based, among other things, on the proximity of the linking slots 1040, 1042, 1044, 1046 relative to each other and to the frame finger ends 1022, as described in greater detail below. In the illustrated embodiments, the linking slots 1040, 1042, 1044, 1046 also define hooks 1048 adjacent to (or otherwise formed as a part of) the winding slots 1026, 1028, 1030, 1032, 1034, 1038. As will be appreciated from the subsequent description of the coils 1014, 1016, 1018 below, the hooks 1048 may be provided to facilitate routing, winding, or otherwise forming wires within various slots to ensure proper construction of (and spacing between) the coils 1014, 1016, 1018.

While the coils 1014, 1016, 1018 are depicted generically throughout the drawings for illustrative purposes, it will be appreciated that each coil 1014, 1016, 1018 generally comprises a respective wire that has been wound in loops in predetermined ways throughout specific winding slots 1026, 1028, 1030, 1032, 1034, 1038 and linking slots 1040, 1042, 1044, 1046, as described in greater detail below. Those having ordinary skill in the art will appreciate that the coils 1014, 1016, 1018 could comprise wires of various sizes, wound in in various loop quantities, and the like. As is best depicted in FIGS. 27B and 28B, each of the coils 1014, 1016, 1018 generally comprises a respective proximal coil portion 1050, a distal coil portion 1052, a first link portion 1054, and a second link portion 1056, each of which represents a "segment" of a continuous wire loop or winding.

Figure 27A:
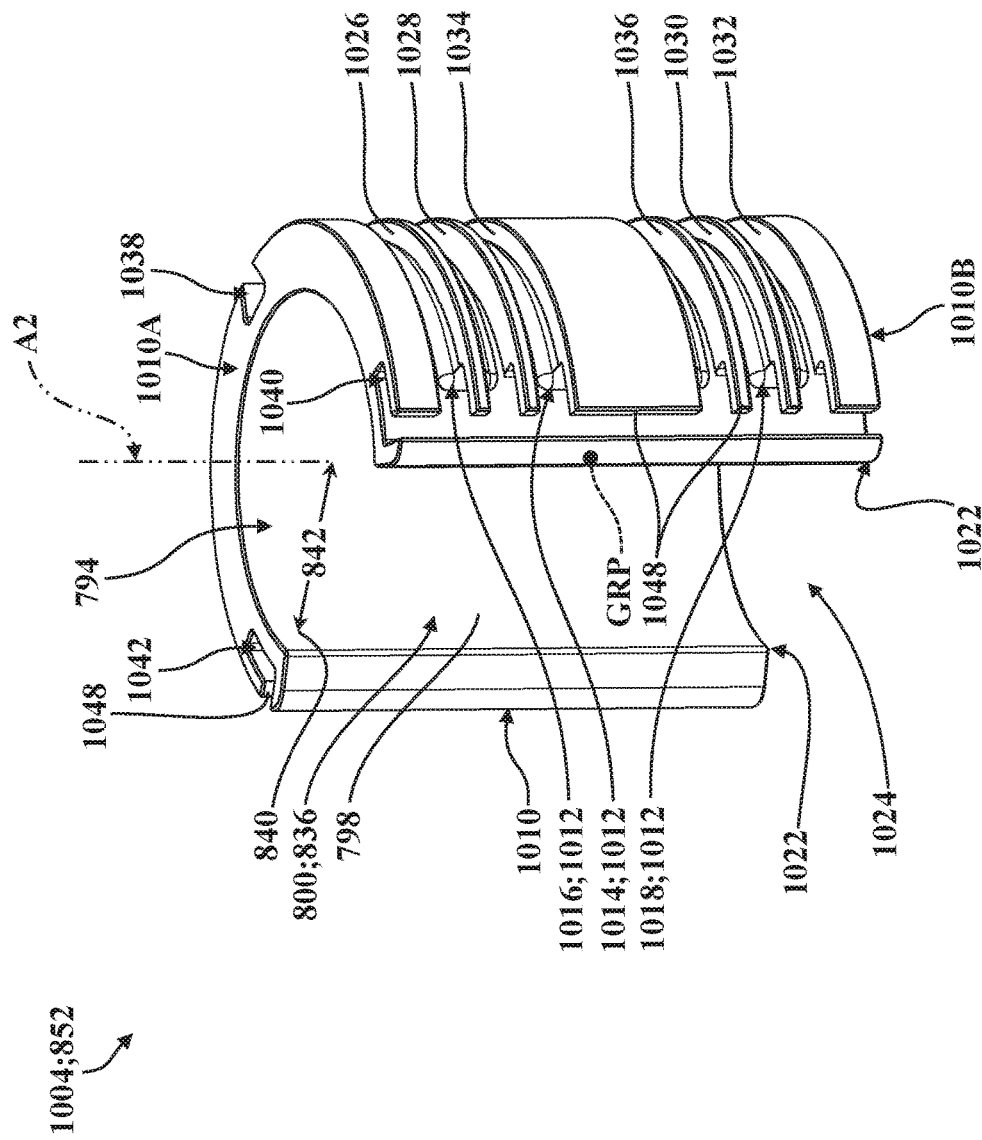
FIG. 27A is a perspective view of the coil assembly of FIG. 26B, shown having a coil frame supporting a generically-depicted coil arrangement comprising a transmit coil arranged generally between a proximal receive coil and a distal receive coil.
Figure 27B:
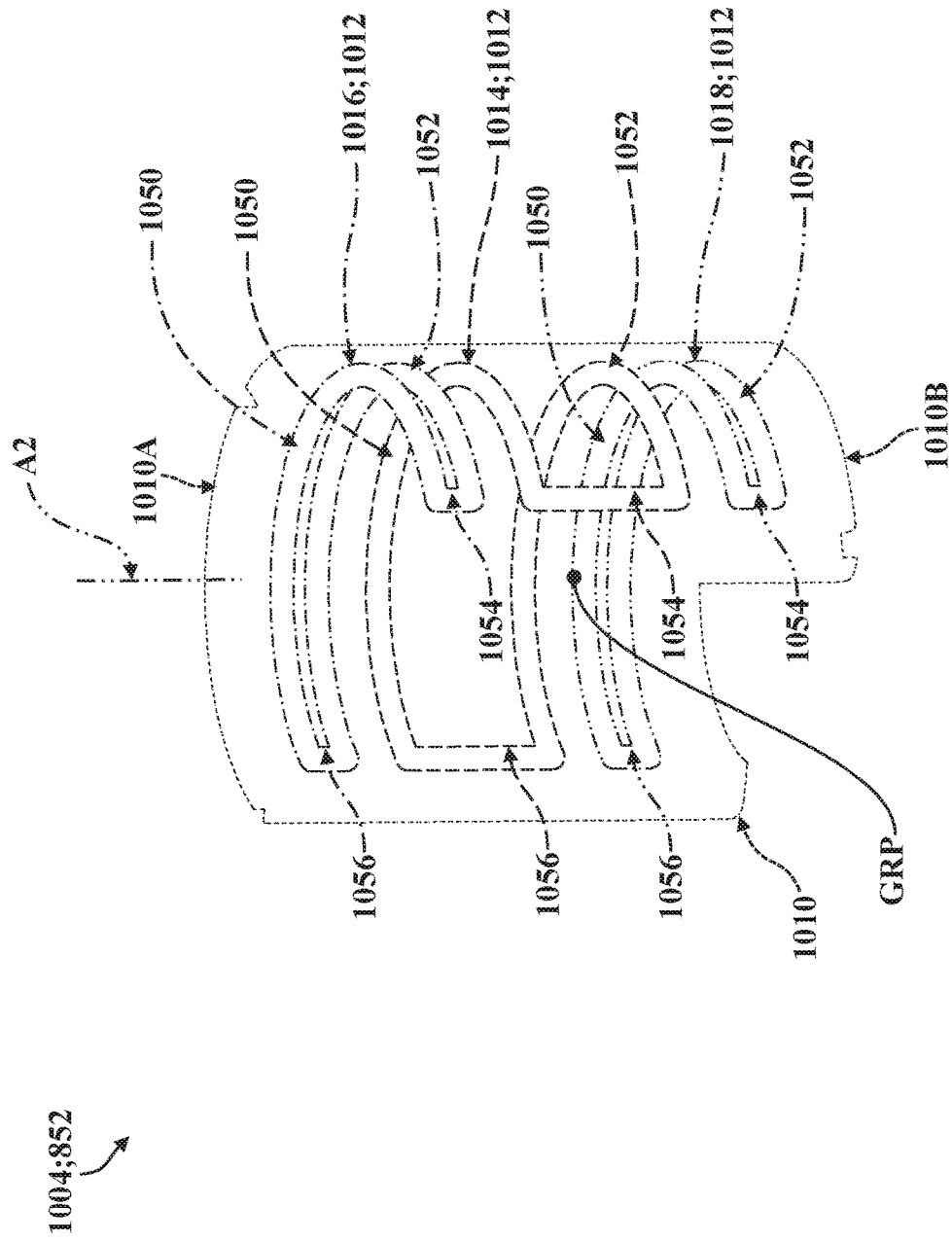
FIG. 27B is another perspective view of the coil assembly of FIG. 27A, shown from the same perspective as FIG. 27A but with the coil frame, the transmit coil, the proximal receive coil, and the distal receive coil each depicted in phantom outline for illustrative purposes.
Figure 28A:
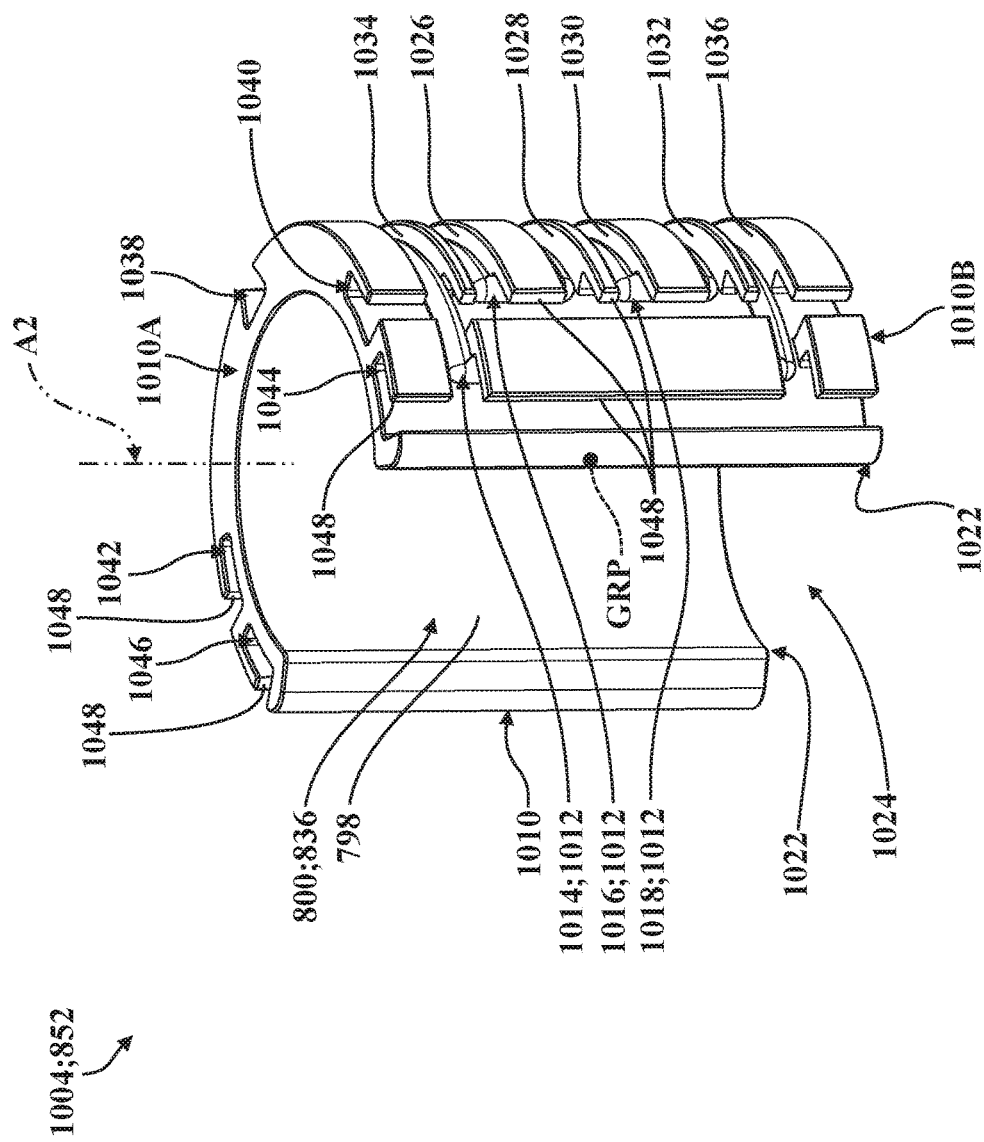
FIG. 28A is a perspective view of another embodiment of a coil assembly, shown having a coil frame supporting a generically-depicted coil arrangement comprising a proximal receive coil and a distal receive coil arranged generally within a transmit coil.
Figure 28B:
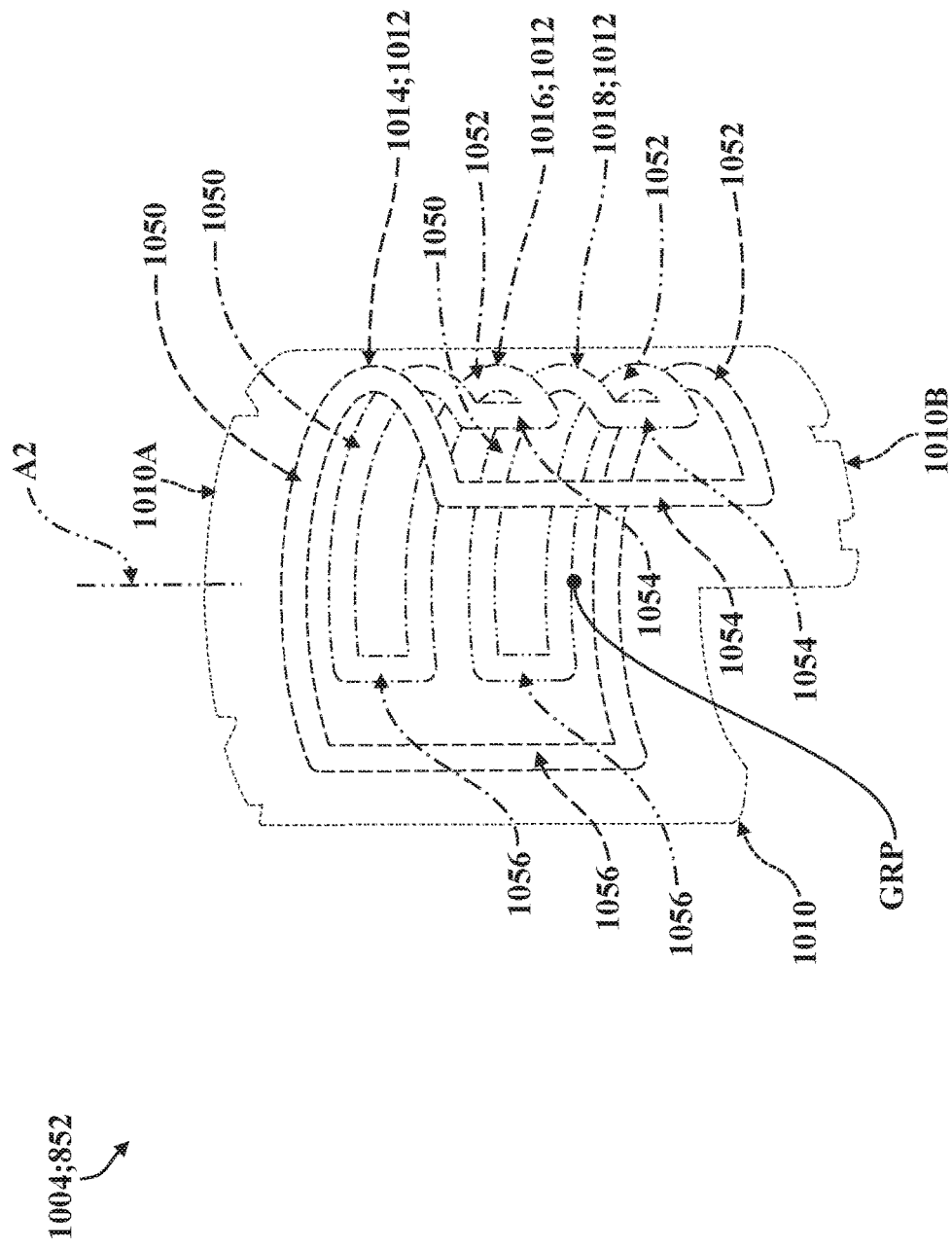
FIG. 28B is another perspective view of the coil assembly of FIG. 28A, shown from the same perspective as FIG. 28A but with the coil frame, the transmit coil, the proximal receive coil, and the distal receive coil each depicted in phantom outline for illustrative purposes.

Referring now to the LVDT coil assembly 1004 depicted in FIGS. 27A-27B, in this embodiment, the coil arrangement 1012 is configured such that the proximal receive coil 1016 is disposed adjacent to the first frame end 1010A, the distal receive coil 1018 is disposed adjacent to the second frame end 1010B, and the transmit coil 1014 is arranged vertically between the receive coils 1018. Thus, the coil frame 1010 depicted in FIG. 27A is defined with the first proximal receive winding slot 1026 being nearest to the first frame end 1010A followed, sequentially, by the second proximal receive winding slot 1028, the first transmit winding slot 1034, the second transmit winding slot 1036, the first distal receive winding slot 1030, and the second distal receive winding slot 1032.

Accordingly, for the coil arrangement 1012 depicted in FIGS. 27A-27B: the proximal receive coil 1016 is wound in a loop along the first proximal receive winding slot 1026, the first linking slot 1040, the second proximal receive winding slot 1028, the second linking slot 1042, back to the first proximal receive winding slot 1026, and so on; the transmit coil 1014 is wound in a loop along the first transmit winding slot 1034, the first linking slot 1040, the second transmit winding slot 1036, the second linking slot 1042, back to the first transmit winding slot 1034, and so on; and the distal receive coil 1018 is wound in a loop along the first distal receive winding slot 1030, the first linking slot 1040, the second distal receive winding slot 1032, the second linking slot 1042, back to the first distal receive winding slot 1030, and so on. When configured in this way, the coil arrangement 1012 depicted in FIGS. 27A-27B comprises substantially similar proximal coil portions 1050 for each of the coils 1014, 1016, 1018, as well as substantially similar distal coil portions 1052 for each of the coils 1014, 1016, 1018 that are also substantially similar to the proximal coil portions 1050. Here too, the first and second link portions 1054, 1056 of the transmit coil 1014 are substantially similar to each other, but are different from the first and second link portions 1054, 1056 of the receive coils 1016, 1018. More specifically, the first link portion 1054 of the proximal receive coil 1016 is substantially similar to its second link portion 1056, as well as to both the first and second link portions 1054, 1056 of the distal receive coil 1016.

Referring now to FIG. 27B, in this embodiment, the transmit coil 1014 is arranged substantially equidistantly between the receive coils 1016, 1018. Here, the receive coils 1016, 1018 are of substantially identical configuration to each other, but are different from the transmit coil 1014. More specifically, the coil portions 1050, 1052 of the transmit coil 1014 are spaced farther away from each other along the guide axis A2 than the coil portions 1050, 1052 of the receive coils 1016, 1018. Put differently, the link portions 1054, 1056 of the transmit coil 1014 are larger than the link portions 1054, 1056 of the receive coils 1016, 1018. As noted above, in this illustrative embodiment, the proximal and distal coil portions 1050, 1052 for each of the coils 1014, 1016, 1018 are substantially similar to each other in that they all comprise an arc-shaped profile that extends around the guide axis A2 toward the opening 796 (e.g., extending to the first and second linking slots 1040, 1042).

Referring now to the LVDT coil assembly 1004 depicted in FIGS. 28A-28B, in this embodiment, the coil arrangement 1012 is configured such that the transmit coil 1014 is disposed adjacent to the first frame end 1010A as well as the second frame end 1010B, with the receive coils 1016, 1018 arranged "within" the transmit coil 1014, with the proximal receive coil 1016 arranged closer to the first frame end 1010A than to the second frame end 1010B, and with the distal receive coil 1018 arranged closer to the second frame end 1010B than to the first frame end 1010A. Thus, the coil frame 1010 depicted in FIG. 28A is defined with the first transmit winding slot 1034 being nearest to the first frame end 1010A followed, sequentially, by the first proximal receive winding slot 1026, the second proximal receive winding slot 1028, the first distal receive winding slot 1030, the second distal receive winding slot 1032, and the second transmit winding slot 1036.

Accordingly, for the coil arrangement 1012 depicted in FIGS. 28A-28B: the proximal receive coil 1016 is wound in a loop along the first proximal receive winding slot 1026, the first linking slot 1040, the second proximal receive winding slot 1028, the second linking slot 1042, back to the first proximal receive winding slot 1026, and so on; the transmit coil 1014 is wound in a loop along the first transmit winding slot 1034, the third linking slot 1044, the second transmit winding slot 1036, the fourth linking slot 1046, back to the first transmit winding slot 1034, and so on; and the distal receive coil 1018 is wound in a loop along the first distal receive winding slot 1030, the first linking slot 1040, the second distal receive winding slot 1032, the second linking slot 1042, back to the first distal receive winding slot 1030, and so on.

When configured in this way, the coil arrangement 1012 depicted in FIGS. 28A-28B comprises substantially similar proximal coil portions 1050 for each of the receive coils 1016, 1018, as well as substantially similar distal coil portions 1052 for each of the receive coils 1016, 1018 that are also substantially similar to the proximal coil portions 1050 of the receive coils 1016, 1018. Further, the proximal coil portion 1050 of the transmit coil 1014 is substantially similar to the distal coil portion 1052 of the transmit coil 1014, but the coil portions 1050, 1052 of the transmit coil 1014 are different from the coil portions 1052 of the receive coils 1016, 1018 in this embodiment. Here too, the first and second link portions 1054, 1056 of the transmit coil 1014 are substantially similar to each other, but are different from the first and second link portions 1054, 1056 of the receive coils 1016, 1018. More specifically, the first link portion 1054 of the proximal receive coil 1016 is substantially similar to its second link portion 1056, as well as to both the first and second link portions 1054, 1056 of the distal receive coil 1016.

Referring now to FIG. 28B, in this embodiment, the transmit coil 1014 is arranged such that the receive coils 1016, 1018 are arranged "within" the transmit coil 1014, spaced substantially equidistantly from each other. Here, the proximal coil portion 1050 of the proximal receive coil 1016 spaced from the proximal coil portion 1050 of the transmit coil 1014 in a way that is substantially equal to how the distal coil portion 1052 of the distal receive coil 1018 is spaced from the distal coil portion 1052 of the transmit coil 1014. Here too, the receive coils 1016, 1018 are of substantially identical configuration to each other, but are different from the transmit coil 1014. More specifically, the coil portions 1050, 1052 of the transmit coil 1014 are spaced farther away from each other along the guide axis A2 than the coil portions 1050, 1052 of the receive coils 1016, 1018. Put differently, the link portions 1054, 1056 of the transmit coil 1014 are larger than the link portions 1054, 1056 of the receive coils 1016, 1018. However, In this illustrative embodiment, the proximal and distal coil portions 1050, 1052 for each of the receive coils 1016, 1018 are substantially similar to each other in that they all comprise an arc-shaped profile that extends around the guide axis A2 toward the opening 796 (e.g., between the first and second linking slots 1040, 1042), but are different from the proximal and distal coil portions 1050, 1052 of the transmit coil 1014. Here, the proximal and distal coil portions 1050, 1052 of the transmit coil 1014 substantially similar to each other in that they both comprise an arc-shaped profile that extends around the guide axis A2 toward the opening 796 (e.g., between the third and fourth linking slots 1044, 1046). However, because of how the third and fourth linking slots 1044, 1046 are arranged relative to the first and second linking slots 1040, 1042, the proximal and distal coil portions 1050, 1052 of the transmit coil 1014 extend farther toward the opening 796 than the proximal and distal coil portions 1050, 1052 of the receive coils 1016, 1018.

Referring, generally, to FIGS. 25A-28B, those having ordinary skill in the art will appreciate that the coils 1014, 1016, 1018 of the LVDT coil assemblies 1004 described and illustrated herein are shaped and arranged so as to extend around the guide axis A2 toward the opening 796 with arc-shaped profiles when viewed normal to the guide axis A2. Put differently, the coil portions 1050, 1052 are each arc-shaped (e.g., generally C-shaped and/or U-shaped) and are arranged so as to encompass the guide axis A2 without obstructing or traversing the opening 796. Furthermore, the link portions 1054, 1056 of each of the coils 1014, 1016, 1018 are shaped and arranged so as to extend between their respective coil portions 1050, 1052, and are illustrated as having generally cylindrical profiles for illustrative purposes only. Here, it will be appreciated that the looped wire which defines the coils 1014, 1016, 1018 may define various curved profiles as wire is looped, wound, or otherwise arranged to form the coils 1014, 1016, 1018. Accordingly, it will be appreciated that the coils 1014, 1016, 1018 could be configured in a number of different ways consistent with the present disclosure.

Irrespective of the specific configuration and arrangement of the coils 1014, 1016, 1018, the LVDT coil assembly 1004 is configured to facilitate determining the presence of the impactor assembly 802 within the channel 794 of the guide 804. More specifically, the LVDT coil assembly 1004 is configured to determine a relative axial position of the flange 812 between the first and second axial channel ends 794A, 794B of the channel 794. To this end, the sensor controller 1008 is generally disposed in electrical communication with each of the coils 1014, 1016, 1018, and may be may be configured to generate (or otherwise communicate) a transmit signal (e.g., an alternating current) to the transmit coil 1014 in order to generate an electromagnetic field that induces voltage in the receive coils 1016, 1018 to generate a receive signal (e.g., a differential voltage across the receive coils 1016, 1018) that can be monitored by the sensor controller 1008. It will be appreciated that the forgoing is an illustrative example, and other configurations are contemplated. By way of non-limiting example, a number of different components of the surgical system 30 could be utilized to generate the transmit signal and/or monitor the receive signal.

Because of how the receive coils 1016, 1018 are arranged (e.g., in the same way relative to the guide reference point GRP) and configured (e.g., having the same number of windings and being wired in series with each other), the voltage induced in each of the receive coils 1016, 1018 cancels out when a ferromagnetic object is arranged equidistantly between the receive coils 1016, 1018, but changes when that ferromagnetic object moves away from one receive coil and toward the other. Here, for example, the flange 812 of the impactor assembly 802 could be manufactured from a ferromagnetic material (or could comprise a ferromagnetic insert, not shown) and could be shaped and arranged such that voltage induced in the receive coils 1016, 1018 via the transmit coil 1014 cancels out when the flange reference point FRP is coincident with the guide reference point GRP. However, relative movement between the guide 804 and the impactor assembly 802 will necessarily bring the flange reference point FRP out of coincident alignment with the guide reference point GRP. Here, if the flange 812 moves away from the proximal receive coil 1016 and toward the distal receive coil 1018, the receive signal will change in response and in a way that correlates to the change in position of the flange 812. Likewise, if the flange 812 moves away from the distal receive coil 1018 and toward the proximal receive coil 1016, the receive signal will change in response and in a way that correlates to the change in position of the flange 812, but the receive signal will be opposite in phase. Put differently, the amplitude of the receive signal can be used to determine how far away the flange reference point FRP has moved from the guide reference point GRP, and the phase of the receive signal (e.g., compared to the phase of the transmit signal) can be used to determine which direction the flange reference point FRP has moved from the guide reference point GRP. Accordingly, the LVDT coil assembly 1004 can be utilized in order to determine the relative axial position of the flange 812 between the first and second axial channel ends 794A, 794B in ways similar to those described above in connection with the third embodiment of the end effector 440.

The present disclosure is also directed toward a method of impacting the prosthesis P at the surgical site S along the trajectory T maintained by the surgical robot 32. The method comprises different steps, including providing the impactor assembly 102, 302, 502, 802 having the head 106, 306, 506, 806, the interface 84, 284, 484, 784, the shaft 86, 286, 486, 786 extending along the impactor axis A1 between the head 106, 306, 506, 806 and the interface 84, 284, 484, 784, and the impactor engagement surface 88, 288, 488, 788. The method also includes the steps of attaching the prosthesis P to the interface 84, 284, 484, 784 of the impactor assembly 102, 302, 502, 802, and providing the guide 104, 304, 504, 804 having the mount 90, 290, 490, 790, the channel 94, 294, 494, 794 extending along the guide axis A2 and defining the opening 96, 296, 496, 796, the guide engagement surface 98, 298, 498, 798, and the limiter 100, 300, 500, 800.

The method further includes the steps of attaching the mount 90, 290, 490, 790 of the guide 104, 304, 504, 804 to the surgical robot 32, aligning and/or moving the guide 104, 304, 504, 804 with respect to the trajectory T maintained by the surgical robot 32. The method also includes the steps of positioning the impactor assembly 102, 302, 502, 802 to place the prosthesis P at the surgical site S, articulating the impactor assembly 102, 302, 502, 802 to move the shaft 86, 286, 486, 786 through the opening 96, 296, 496, 796 of the guide 104, 304, 504, 804 toward the channel 94, 294, 494, 794, and bringing the impactor engagement surface 88, 288, 488, 788 of the impactor assembly 102, 302, 502, 802 into abutment with the guide engagement surface 98, 298, 498, 798 of the guide 104, 304, 504, 804 to align the impactor axis A1 with the guide axis A2. Furthermore, the method includes the steps of moving the limiter 100, 300, 500, 800 of the guide 104, 304, 504, 804 relative to the impactor assembly 102, 302, 502, 802 to maintain coaxial alignment of the axes A1, A2 along the trajectory T with the impactor engagement surface 88, 288, 488, 788 abutting the guide engagement surface 98, 298, 498, 798, and applying impact force F to the head 106, 306, 506, 806 of the impactor assembly 102, 302, 502, 802 to impact the prosthesis P at the surgical site S.

In the method described above, it will be appreciated that certain steps may vary in sequence and/or definition based, among other things, on the specific configuration of the end effector 40, 240, 440, 740. By way of non-limiting illustration, for the first embodiment of the end effector 40 described herein, the steps of bringing the impactor engagement surface 88 into abutment with the guide engagement surface 98 and moving the limiter 100 may be further defined as moving the guide 104 along the trajectory T and away from the prosthesis P so as to bring the flange 112 into abutment with the first axial channel end 94A of the channel 94 and continuing to move the guide 104 along the trajectory T until the flange 112 is positioned within the channel 94 between the first and second axial channel ends 94A, 94B. On the other hand, these same steps may be defined differently for the second embodiment of the end effector 240 described herein, such as by pivoting the impactor assembly 302 adjacent the surgical site S to move the shaft 286 into engagement with the cam portion 384 of the latch 364 to traverse the opening 296 and bring the shaft 286 into abutment with both the guide engagement surface 298 and the retention face 382. Here, it will be appreciated that contact between the shaft 286 and the latch 364 causes the limiter 300 to move relative to the impactor assembly 302 in that the latch 364 moves sequentially from the first latch position 364A (as the shaft 286 begins to contact the cam portion 384), to the second latch position 364B (as the shaft 286 passes through the opening 296), and back to the first latch position 364A (in response to force exerted on the latch 364 from the biasing element 380). Nevertheless, it will be appreciated that other configurations are contemplated.

In this way, the methods, surgical systems 30, and end effectors 40, 240, 440, 740 described herein afford significant advantages in connection with surgical robots 32 used to carry out a broad number of surgical techniques and procedures. In particular, the alignment and releasable attachment afforded by the end effector 40, 240, 440, 740 allow the surgeon to set the trajectory T and approach the surgical site S with the prosthesis P without necessarily moving the robotic arm 36 off the trajectory T and without requiring significant manipulation of the patient's body B and/or the surgical site S itself. Furthermore, it will be appreciated that various arrangements of sensors 152, 352, 552, 852 and other components of the embodiments of the end effector 40, 240, 440, 740 and/or the surgical system 30, including without limitation the robotic control system 48, the navigation system 50, the sensor subassembly 612, 912, the follower subassembly 614, and the LVDT coil assembly 1004, can be utilized to facilitate maintaining alignment of the guide reference point GRP with the flange reference point FRP in a number of different ways. Furthermore, various aspects of the present disclosure can be employed to facilitate determining a relative axial position of the flange 112, 312, 512, 812, or another portion of the impactor assembly 102, 302, 502, 802, along the channel 94, 294, 494, 794 which, in turn, can be utilized to monitor the position of the prosthesis P relative to the surgical site S without necessitating that a tracker 60 be coupled to the impactor assembly 102, 302, 502, 802.

Moreover, while various aspects of the guides 104, 304, 504, 804 and the impactor assemblies 102, 302, 502, 802 described herein afford significant advantages for procedures involving impaction of prosthetics, those having ordinary skill in the art will appreciate that the alignment and releasable attachment advantages afforded by the end effector 40, 240, 440, 740 can be beneficial for a broad array of surgical procedures and with various types of surgical instruments, tools, and the like, in order to position, guide, control, monitor, and/or limit movement of a number of different types of prostheses P, surgical tools, instruments, workpieces, and the like.

Those having ordinary skill in the art will appreciate that aspects of the embodiments described and illustrated herein can be interchanged or otherwise combined.

It will be further appreciated that the terms "include," "includes," and "including" have the same meaning as the terms "comprise," "comprises," and "comprising." Moreover, it will be appreciated that terms such as "first," "second," "third," and the like are used herein to differentiate certain structural features and components for the non-limiting, illustrative purposes of clarity and consistency.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. An end effector assembly for impacting a prosthesis at a surgical site along a trajectory maintained by a surgical robot, said end effector assembly comprising:
   an impactor assembly comprising a head arranged to receive impact force, an interface adapted to releasably attach to the prosthesis, a shaft extending along an impactor axis between said head and said interface, and an impactor engagement surface disposed between said head and said interface; and
   a guide adapted to attach to the surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with the trajectory maintained by the surgical robot, and said guide enabling a portion of said shaft of said impactor assembly to move through said opening between said finger ends when said guide is disposed axially between said impactor engagement surface and said interface of said impactor assembly such that said portion of said shaft can enter and exit said channel.

2. The end effector assembly as set forth in claim 1, further comprising a sensor coupled to said guide to identify presence of said impactor assembly within said channel.

3. The end effector assembly as set forth in claim 2, wherein said channel of said guide extends between first and second axial channel ends; and
   wherein said sensor is further configured to determine a relative axial position of said impactor assembly between said first axial channel end and said second axial channel end.

4. The end effector assembly as set forth in claim 1, wherein said impactor assembly further comprises a flange coupled to said shaft with said flange defining said impactor engagement surface.

5. The end effector assembly as set forth in claim 2, further comprising a trigger coupled to said guide, disposed in communication with said sensor, and arranged for movement between: an extended position defined by an absence of contact between said impactor engagement surface and said guide engagement surface, and a retracted position defined by contact between said impactor engagement surface and said guide engagement surface.

6. The end effector assembly as set forth in claim 5, further comprising a pushrod interposed in force-translating relation between said trigger and said sensor to engage said sensor in response to movement of said trigger away from said extended position.

7. The end effector assembly as set forth in claim 2, wherein said sensor comprises a linear variable differential transformer (LVDT) coil assembly coupled to said guide adjacent to said channel.

8. The end effector assembly as set forth in claim 7, wherein said LVDT coil assembly comprises at least one coil with an arc-shaped profile extending through at least one of said fingers to said finger end.

9. The end effector assembly as set forth in claim 1, wherein said shaft of said impactor assembly has a first perimeter, and said impactor engagement surface has a second perimeter larger than said first perimeter.

10. The end effector assembly as set forth in claim 1, wherein said guide engagement surface is arc-shaped.

11. The end effector assembly as set forth in claim 10, wherein said arc-shaped guide engagement surface is spaced from said guide axis at a common radius.

12. The end effector assembly as set forth in claim 10, wherein said arc-shaped guide engagement surface defines a common arc having first and second arc ends each terminating at one of said finger ends, and wherein said common arc has an arc reference angle greater than 180-degrees.

13. The end effector assembly as set forth in claim 4, wherein said impactor assembly further comprises a taper arranged axially between said flange and said interface, said taper transitioning between said flange and said shaft to direct said flange into said channel of said guide in response to contact occurring between said taper and said guide.

14. The end effector assembly as set forth in claim 4, wherein said flange of said impactor assembly has a generally spherical profile.

15. The end effector assembly as set forth in claim 1, wherein said channel has a generally C-shaped profile defined by said guide engagement surface.

16. The end effector assembly as set forth in claim 1, wherein said shaft of said impactor assembly has a generally cylindrical profile.

17. The end effector assembly as set forth in claim 16, wherein said shaft of said impactor assembly defines said impactor engagement surface.

18. The end effector assembly as set forth in claim 1, wherein said guide further comprises a latch movable between:
 a first latch position to inhibit movement of said impactor assembly to exit said channel through said opening and to maintain contact between said impactor engagement surface and said guide engagement surface; and
 a second latch position to permit movement of said impactor assembly through said opening to exit said channel.

19. The end effector assembly as set forth in claim 18, wherein said latch at least partially traverses said channel of said guide in said first latch position to inhibit movement of said shaft of said impactor assembly through said opening to exit said channel.

20. The end effector assembly as set forth in claim 18, wherein said latch comprises a retention face arranged to engage said shaft of said impactor assembly in said first latch position.

21. The end effector assembly as set forth in claim 18, further comprising a biasing element interposed between said latch and said guide to urge said latch toward said first latch position.

22. The end effector assembly as set forth in claim 18, wherein said latch comprises a cam portion facing away from said guide engagement surface and arranged to abut a portion of said impactor assembly, and wherein said cam portion is configured to move said latch toward said second latch position to permit said shaft of said impactor assembly to pass through said opening of said guide to enter said channel.

23. The end effector assembly as set forth in claim 18, wherein said latch comprises a release portion arranged for actuation by a user to move said latch from said first latch position toward said second latch position to permit said shaft of said impactor assembly to pass through said opening to exit said channel of said guide.

24. The end effector assembly as set forth in claim 18, wherein said guide engagement surface has a generally U-shaped profile; and
 wherein a cylindrical portion of said shaft of said impactor assembly defines said impactor engagement surface.

25. An impactor assembly for use in impacting a prosthesis along a trajectory maintained by a surgical robot, the surgical robot having a guide comprising a body including a pair of fingers, each finger extending from the body to a finger end and the finger ends are spaced apart from one another to form an opening between the finger ends, wherein a channel extending along a guide axis is formed between the fingers, the fingers defining a guide engagement surface, said impactor assembly comprising:
 a head arranged to receive impact force;
 an interface adapted to releasably attach to the prosthesis;
 a shaft extending along an impactor axis between said head and said interface, said shaft having a first diameter sized to enable said shaft to move through the opening between the finger ends such that said shaft can enter and exit the channel; and
 a flange coupled to said shaft between said head and said interface, said flange having a second diameter that is greater than the first diameter of said shaft, said flange defining an impactor engagement surface shaped to abut and rotatably engage the guide engagement surface to simultaneously permit rotation of said impactor assembly relative to the guide and to facilitate coaxial alignment of said impactor axis with the trajectory maintained by the surgical robot.

26. A guide adapted for attachment to a surgical robot configured to support an impactor assembly along a trajectory maintained by the surgical robot, the impactor assembly comprising a head arranged to receive impact force, an interface adapted to releasably attach to a prosthesis, a shaft extending along an impactor axis between the head and the interface, and an impactor engagement surface disposed between the head and the interface, said guide comprising:
 a mount adapted to attach to the surgical robot; and
 a body operatively attached to said mount and including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with the impactor engagement surface for facilitating alignment of the impactor axis and said guide axis with the trajectory maintained by the surgical robot, and said guide enabling a portion of the shaft of the impactor assembly to move through said opening between said finger ends when said guide is disposed axially between the impactor engagement surface and the interface of the impactor assembly such that the portion of the shaft can enter and exit said channel.

27. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface; and
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends when said guide is disposed axially between said impactor engagement surface and said interface of said impactor assembly such that said portion of said shaft can enter and exit said channel.

28. A method of operating a surgical system for impacting a prosthesis at a surgical site along a planned trajectory, the surgical system comprising a surgical robot; an impactor assembly comprising a head arranged to receive impact force, an interface attached to the prosthesis, a shaft extending along an impactor axis between the head and the interface, and an impactor engagement surface disposed between the head and the interface; and a guide coupled to the surgical robot and comprising a body including a pair of fingers, each finger extending from the body to a finger end and the finger ends are spaced apart from one another to form an opening between the finger ends, wherein a channel extending along a guide axis is formed between the fingers, the fingers defining a guide engagement surface shaped to enable contact with the impactor engagement surface, and the guide enabling the shaft of the impactor assembly to move through the opening between the finger ends such that the shaft can enter and exit the channel, said method comprising:
while the impactor assembly is exited from the channel of the guide, positioning the impactor assembly to place the prosthesis at the surgical site;
while the prosthesis is placed at the surgical site, moving the shaft of the impactor assembly between the fingers, through the opening, and to enter the channel of the guide; and
with the shaft of the impactor assembly located in the channel, axially moving a position of the guide with the surgical robot for bringing the guide engagement surface into contact with the impactor engagement surface and for aligning the guide axis and the impactor axis.

29. The method of claim 28, further comprising controlling the surgical robot to move the guide for aligning the guide axis and impactor axis with the planned trajectory after bringing the guide engagement surface into contact with the impactor engagement surface.

30. The method of claim 28, further comprising controlling the surgical robot to move the guide for aligning the guide axis with the planned trajectory before bringing the guide engagement surface into contact with the impactor engagement surface.

31. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface;
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel;
a sensor coupled to said guide to identify presence of said impactor assembly within said channel; and
a trigger coupled to said guide, disposed in communication with said sensor, and arranged for movement between:
an extended position defined by an absence of contact between said impactor engagement surface and said guide engagement surface, and
a retracted position defined by contact between said impactor engagement surface and said guide engagement surface.

32. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface;
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel; and a sensor coupled to said guide to identify presence of said impactor assembly within said channel, wherein said sensor comprises a linear variable differential transformer (LVDT) coil assembly coupled to said guide adjacent to said channel, and wherein said LVDT coil assembly comprises at least one coil with an arc-shaped profile extending through at least one of said fingers to said finger end.

33. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface;
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel; and
wherein said guide engagement surface is arc-shaped.

34. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface;
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel; and
wherein said impactor assembly further comprises:
a flange coupled to said shaft with said flange defining said impactor engagement surface; and
a taper arranged axially between said flange and said interface, said taper transitioning between said flange and said shaft to direct said flange into said channel of said guide in response to contact occurring between said taper and said guide.

35. An impactor assembly for use in impacting a prosthesis along a trajectory maintained by a surgical robot, the surgical robot having a guide comprising a body including a pair of fingers, each finger extending from the body to a finger end and the finger ends are spaced apart from one another to form an opening between the finger ends, wherein a channel extending along a guide axis is formed between the fingers, the fingers defining a guide engagement surface, said impactor assembly comprising:
a head arranged to receive impact force;
an interface adapted to releasably attach to the prosthesis;
a shaft extending along an impactor axis between said head and said interface, said shaft having a first diameter sized to enable said shaft to move through the opening between the finger ends such that said shaft can enter and exit the channel;
a flange coupled to said shaft between said head and said interface, said flange having a second diameter that is greater than the first diameter of said shaft, said flange defining an impactor engagement surface shaped to engage the guide engagement surface; and
a taper arranged axially between said flange and said interface, said taper transitioning between said flange and said shaft for directing said flange into the channel of the guide in response to contact occurring between said taper and the guide.

36. A surgical system for impacting a prosthesis at a surgical site along a trajectory, said surgical system comprising:
a surgical robot;
an impactor assembly comprising a head arranged to receive impact force, an interface adapted to releasably attach to the prosthesis, a shaft extending along an impactor axis between said head and said interface, and an impactor engagement surface disposed between said head and said interface;
a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel; and
wherein said impactor assembly further comprises a flange coupled to said shaft with said flange defining said impactor engagement surface, wherein said flange has a generally spherical profile.

37. An impactor assembly for use in impacting a prosthesis along a trajectory maintained by a surgical robot, the surgical robot having a guide comprising a body including a pair of fingers, each finger extending from the body to a finger end and the finger ends are spaced apart from one another to form an opening between the finger ends, wherein a channel extending along a guide axis is formed between the fingers, the fingers defining a guide engagement surface, said impactor assembly comprising:
a head arranged to receive impact force;
an interface adapted to releasably attach to the prosthesis;
a shaft extending along an impactor axis between said head and said interface, said shaft having a first diameter sized to enable said shaft to move through the opening between the finger ends such that said shaft can enter and exit the channel; and a flange coupled to said shaft between said head and said interface, said flange having a second diameter that is greater than the first diameter of said shaft, said flange defining an impactor engagement surface shaped to engage the guide engagement surface, and wherein said flange has a generally spherical profile.

38. A surgical system for impacting a prosthesis at a surgical site along a trajectory, said surgical system comprising:

a surgical robot;

an impactor assembly comprising a head arranged to receive impact force, an interface adapted to releasably attach to the prosthesis, a shaft extending along an impactor axis between said head and said interface, and an impactor engagement surface disposed between said head and said interface;

a guide coupled to said surgical robot and comprising a body including a pair of fingers, each finger extending from said body to a finger end and said finger ends are spaced apart from one another to form an opening between said finger ends, wherein a channel extending along a guide axis is formed between said fingers, said fingers defining a guide engagement surface shaped to enable contact with said impactor engagement surface for facilitating alignment of said impactor axis and said guide axis with said trajectory maintained by said surgical robot, and said guide enabling a portion of said shaft of said impactor assembly to move through said opening between said finger ends such that said portion of said shaft can enter and exit said channel; and wherein said guide further comprises a latch movable between:

a first latch position to inhibit movement of said impactor assembly to exit said channel through said opening and to maintain contact between said impactor engagement surface and said guide engagement surface; and a second latch position to permit movement of said impactor assembly through said opening to exit said channel.

* * * * *